United States Patent
Bo et al.

(10) Patent No.: US 8,415,376 B2
(45) Date of Patent: Apr. 9, 2013

(54) INHIBITORS OF PI3 KINASE

(75) Inventors: Yunxin Y. Bo, Thousand Oaks, CA (US); Shon Booker, Thousand Oaks, CA (US); Marian Bryan, West Hills, CA (US); Holly L. Deak, Brookline, MA (US); Longbin Liu, Thousand Oaks, CA (US); Kristin Andrews, Thousand Oaks, CA (US); Nobuko Nishimura, West Hills, CA (US); Mark H. Norman, Thousand Oaks, CA (US); Kathleen Panter, Cambridge, MA (US); Laurie Schenkel, Boston, MA (US); Aaron C. Siegmund, Ventura, CA (US); Nuria A. Tamayo, Newbury Park, CA (US); Kevin Yang, San Gabriel, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 12/995,431

(22) PCT Filed: May 29, 2009

(86) PCT No.: PCT/US2009/045713
§ 371 (c)(1),
(2), (4) Date: Nov. 30, 2010

(87) PCT Pub. No.: WO2009/155121
PCT Pub. Date: Dec. 23, 2009

(65) Prior Publication Data
US 2011/0092504 A1 Apr. 21, 2011

Related U.S. Application Data

(60) Provisional application No. 61/057,745, filed on May 30, 2008.

(51) Int. Cl.
*A61K 31/47* (2006.01)
*C07D 401/02* (2006.01)
*C07D 401/14* (2006.01)

(52) U.S. Cl. .................................. 514/314; 546/167
(58) Field of Classification Search .................. 546/167; 514/314
See application file for complete search history.

(56) References Cited

U.S. PATENT DOCUMENTS

| | | |
|---|---|---|
| 2007/0225308 A1 | 9/2007 | Nakasato et al. |
| 2009/0023761 A1 | 1/2009 | Chen et al. |
| 2009/0030002 A1 | 1/2009 | Chen et al. |
| 2009/0054405 A1 | 2/2009 | Booker et al. |
| 2009/0137581 A1 | 5/2009 | Chen et al. |
| 2009/0163489 A1 | 6/2009 | Booker et al. |
| 2010/0273764 A1 | 10/2010 | Andrews et al. |
| 2010/0331293 A1 | 12/2010 | Cushing et al. |
| 2010/0331306 A1 | 12/2010 | Bui et al. |
| 2011/0092504 A1 | 4/2011 | Bo et al. |

FOREIGN PATENT DOCUMENTS

| | | |
|---|---|---|
| EP | 290153 A1 | 11/1988 |
| WO | WO03/093297 | 11/2003 |
| WO | WO2005/105801 | 11/2005 |
| WO | WO2006/046031 | 5/2006 |
| WO | WO2007/095588 | 5/2006 |
| WO | WO2007/073283 | 6/2007 |
| WO | WO2007/076092 | 7/2007 |
| WO | WO2007/117607 | 10/2007 |
| WO | WO2007/132171 | 11/2007 |
| WO | WO2007/134828 | 11/2007 |
| WO | WO2007/135398 | 11/2007 |
| WO | WO2008/012326 | 1/2008 |
| WO | WO2008/025821 | 3/2008 |
| WO | WO2008/032028 | 3/2008 |
| WO | WO2008/092831 | 8/2008 |
| WO | WO2008/118454 | 10/2008 |
| WO | WO2008/118455 | 10/2008 |
| WO | WO2008/118468 | 10/2008 |
| WO | WO2008/141065 | 11/2008 |
| WO | WO2008/144463 | 11/2008 |
| WO | WO2008/144464 | 11/2008 |
| WO | WO2008/150827 | 12/2008 |
| WO | WO2008/157191 | 12/2008 |
| WO | WO2008/157387 | 12/2008 |
| WO | WO2009/000832 | 12/2008 |
| WO | WO2009/007748 | 1/2009 |
| WO | WO2009/007750 | 1/2009 |
| WO | WO2009/007751 | 1/2009 |
| WO | WO2009/008748 | 1/2009 |

(Continued)

OTHER PUBLICATIONS

Knight et al. "Discovery of GSK2126458, a Highly Potent Inhibitor of PI3K and the Mammalian Target of Rapamycin", *ACS Medicinal Chemistry Letters*, 1: 39-43 (2010).

Hersperger et al. "Palladium-Catalyzed Cross-Coupling Reactions for the Synthesis of 6,8-Disubstituted 1,7-Naphthyridines: A Novel Class of Potent and Selective Phosphodiesterase Type 4D Inhibitors", *Journal of Medicinal Chemistry*, 43(4): 675-682 (2000).

*Primary Examiner* — Rebecca Anderson
(74) *Attorney, Agent, or Firm* — Todd M. Crissey

(57) ABSTRACT

The present invention relates to compounds of Formula (I), or a pharmaceutically acceptable salt thereof; methods of treating diseases or conditions, such as cancer, using the compounds; and pharmaceutical compositions containing the compounds, wherein Q, $X^1$, $X^2$, $R^1$ and Z are as defined herein.

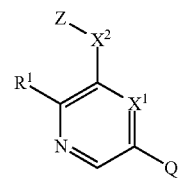

9 Claims, No Drawings

FOREIGN PATENT DOCUMENTS

| | | |
|---|---|---|
| WO | WO2009/010530 | 1/2009 |
| WO | WO2009/017822 | 2/2009 |
| WO | WO2009/021992 | 2/2009 |
| WO | WO2009/055418 | 4/2009 |
| WO | WO2009/068482 | 6/2009 |
| WO | WO2009/081105 | 7/2009 |
| WO | WO2009/085230 | 7/2009 |
| WO | WO2009/115517 | 9/2009 |
| WO | WO2009/155577 | 12/2009 |
| WO | WO2010/007099 | 1/2010 |
| WO | WO2010/007100 | 1/2010 |
| WO | WO2010/008847 | 1/2010 |
| WO | WO2010/012745 | 2/2010 |
| WO | WO2010/014939 | 2/2010 |
| WO | WO2010/030967 | 3/2010 |
| WO | WO2010/052448 | 5/2010 |
| WO | WO2010/057877 | 5/2010 |
| WO | WO2010/061180 | 6/2010 |
| WO | WO2010/096314 | 8/2010 |
| WO | WO2010/100144 | 9/2010 |
| WO | WO2010/108074 | 9/2010 |
| WO | WO2010/120987 | 10/2010 |
| WO | WO2010/126895 | 11/2010 |
| WO | WO2010/132598 | 11/2010 |
| WO | WO2010/133534 | 11/2010 |
| WO | WO2010/151601 | 12/2010 |
| WO | WO2010/151735 | 12/2010 |
| WO | WO2010/151737 | 12/2010 |
| WO | WO2010/151740 | 12/2010 |
| WO | WO2010/151791 | 12/2010 |
| WO | WO2011/051704 | 5/2011 |
| WO | WO2011/055215 | 5/2011 |
| WO | WO2011/058108 | 5/2011 |
| WO | WO2011/058113 | 5/2011 |

INHIBITORS OF PI3 KINASE

FIELD OF THE INVENTION

The present invention relates to compounds that inhibit phosphoinositide 3-kinase (PI3K); methods of treating diseases or conditions, such as cancer, using the compounds; and pharmaceutical compositions containing the compounds.

BACKGROUND OF THE INVENTION

PI3 kinases are a family of lipid kinases that have been found to play a key role in the regulation of many cellular processes including proliferation, survival, carbohydrate metabolism, and motility. PI3Ks are considered to have an important role in intracellular signal transduction. In particular, the PI3Ks generate and convey signals that have important roles in cancer. PI3Ks are ubiquitously expressed, are activated by a high proportion of cell surface receptors, especially those linked to tyrosine kinases, and influence a variety of cellular functions and events. Although some PI3K activity is likely to be essential for cellular health, PI3Ks are a diverse group of enzymes for which there is increasing evidence of functional specialization. This opens up the possibility of developing isoform-selective inhibitors that can be used to treat cancer.

The primary enzymatic activity of PI3K is the phosphorylation of inositol lipids (phosphoinositides) on the 3-position of the inositol headgroup. PI3 kinases catalyze the addition of phosphate to the 3'-OH position of the inositol ring of inositol lipids generating phosphatidyl inositol monophosphate, phosphatidyl inositol diphosphate and phosphatidyl inositol triphosphate.

There are a total of eight mammalian PI3Ks, which have been divided into three main classes on the basis of sequence homology, in vitro substrate preference, and method of activation and regulation. Enzymes of a first class (Class I) have a broad substrate specificity and phosphorylate phosphatidylinositiol (PtdIns), PtdIns(4)P and PtdIns(4,5)$P_2$. Class I PI3 kinases include mammalian p110α, p110β, p110δ and p110γ. Different members of the PI3-kinase family generate different lipid products. To date, four 3-phosphorylated inositol lipids have been identified in vivo. These lipids are bound by proteins that contain the appropriate lipid recognition module and which either act as effectors or transmit the PI3K signal onwards. The most familiar form of PI3K is a heterodimeric complex, consisting of a 110 kDa catalytic subunit now known as p110α and an 85 kDa regulatory/adapter subunit, p85α.

Phosphatidylinositol 3-kinase-alpha (PI3Kα), a dual specificity lipid and protein kinase, is composed of an 85 kDa regulatory subunit and a 110 kDa catalytic subunit. The protein includes a catalytic subunit, which uses ATP to phosphorylate PtdIns, PtdIns(4)P and PtdIns(4,5)$P_2$. PTEN, a tumor suppressor, can dephosphorylate phosphatidylinositol (3,4,5)-trisphosphate (PIP3), the major product of PI3 kinase Class I. PIP3, in turn, is required for translocation of protein kinase B (AKT1, PKB) to the cell membrane, where it is phosphorylated and activated by upstream kinases. The effect of PTEN on cell death is mediated through the PI3Kα/AKT1 pathway.

PI3Kα has been implicated in the control of cytoskeletal reorganization, apoptosis, vesicular trafficking and proliferation and differentiation processes. Increased copy number and expression of the p110α gene (PIK3CA) is associated with a number of cancers such as ovarian cancer, cervical cancer, breast cancer, colon cancer, rectal cancer, endometrial cancer, stomach cancer, liver cancer, lung cancer, thyroid cancer, acute myelogenous leukemia (AML), chronic myelogenous leukemia (CML), and glioblastomas. In view of the important role of PI3Kα in biological processes and disease states, inhibitors of this protein kinase are desirable. The present invention provides PI3K inhibitors, particularly PI3Kα inhibitors, which are useful for treating PI3Kα-mediated diseases and conditions.

SUMMARY OF THE INVENTION

The present invention provides compounds of Formula I

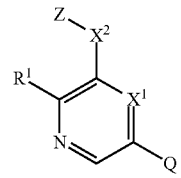

or a pharmaceutically acceptable salt thereof, wherein Q is an optionally substituted 6,6-bicyclic heteroaromatic ring selected from

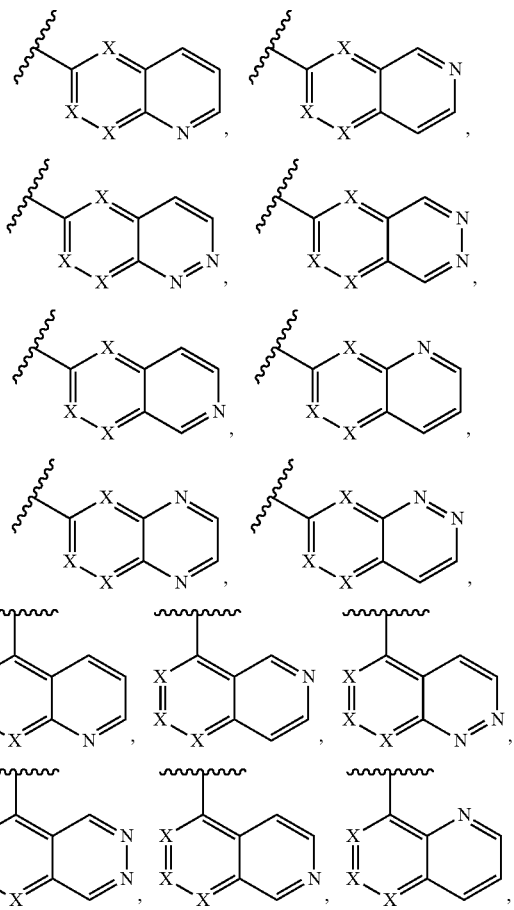

-continued

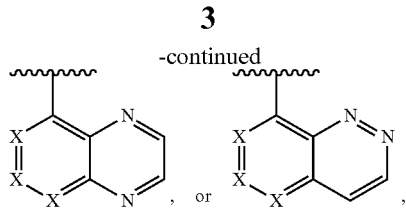

wherein the 6,6-bicyclic heteroaromatic ring has 0, 1, 2, or 3 substituents on carbon atoms that are independently selected from R;

each X is independently N or CR, provided that no more than one X is N;

$X^1$ is N or CR;

$R^1$ is halo, —$CF_3$, —$C_{1-6}$alkyl, —$C_{2-6}$alkenyl, —$C_{2-6}$alkynyl, —$OC_{1-6}$alkyl, or —CN, wherein the —$C_{1-6}$alkyl, —$C_{2-6}$alkenyl, or —$C_{2-6}$alkynyl are substituted by 0, 1, 2 or 3 substituents independently selected from —$C_{1-8}$alkyl, —$C_{2-6}$alkenyl, —$C_{2-6}$alkynyl, $C_{1-4}$haloalkyl, halo, —CN, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$, —N$R^aC_{2-6}$alkylO$R^a$, or a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, wherein the ring is further substituted by 0, 1, 2 or 3 substituents independently selected from $C_{1-8}$alkyl, —$C_{2-6}$alkenyl, —$C_{2-6}$alkynyl, $C_{1-4}$haloalkyl, halo, —CN, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$ alkylN$R^aR^a$ or —N$R^aC_{2-6}$alkylO$R^a$;

$X^2$ is —N($R^a$)S(=O)$_2$(C$R^aR^a$)$_n$—, —N($R^a$)C(=O)(C$R^aR^a$)$_n$—, —O(C$R^aR^a$)$_n$—, —(C$R^aR^a$)$_n$O—, —(C$R^aR^a$)$_n$S(=O)$_m$—, —(C$R^aR^a$)$_n$N($R^a$)—, —N($R^a$)(C$R^aR^a$)$_n$—, —S(O)$_m$(C$R^aR^a$)$_n$—, —N($R^a$)(C$R^aR^a$)$_n$—, —S(=O)$_2$N($R^a$)(C$R^aR^a$)$_n$—, —N($R^a$)C(=O)O(C$R^aR^a$)$_n$—, —N($R^a$)C(=O)N$R^a$(C$R^aR^a$)$_n$—, —N($R^a$)C(=N$R^a$)N$R^a$(C$R^aR^a$)$_n$—, —OC(=O)N$R^a$(C$R^aR^a$)$_n$—, or —N($R^a$)S(=O)$_2$N$R^a$(C$R^aR^a$)$_n$—;

Z is hydrogen, —$C_{1-6}$alkyl, —$C_{2-6}$alkenyl, —$C_{2-6}$alkynyl, —C(=O)$R^a$, or a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, wherein the —$C_{1-6}$alkyl, —$C_{2-6}$alkenyl, —$C_{2-6}$alkynyl, or ring are substituted by 0, 1, 2 or 3 substituents independently selected from $C_{1-8}$alkyl, —$C_{2-6}$alkenyl, —$C_{2-6}$alkynyl, $C_{1-4}$haloalkyl, halo, —CN, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$ alkylN$R^aR^a$ or —N$R^aC_{2-6}$alkylO$R^a$;

each R is independently hydrogen, $C_{1-4}$haloalkyl, halo, —CN, nitro, —C(=O)N$R^aR^a$, —C(=O)$R^b$, —C(=O)O$R^b$, —C(=N$R^a$)N$R^aR^a$, —O$R^a$, —OC(=O)$R^b$, —OC(=O)N$R^aR^a$, —O—$C_{1-6}$alkylN($R^a$)C(=O)O$R^b$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$, —N$R^aC_{2-6}$alkylO$R^a$, —$C_{1-6}$alkyl, —$C_{2-6}$alkenyl, —$C_{2-6}$alkynyl, or a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, wherein the —$C_{1-6}$alkyl, —$C_{2-6}$alkenyl, —$C_{2-6}$alkynyl, or ring are substituted by 0, 1, 2 or 3 substituents independently selected from $C_{1-8}$alkyl, —$C_{2-6}$alkenyl, —$C_{2-6}$alkynyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$, —N$R^aC_{2-6}$alkylO$R^a$, —N($R^a$)(C$R^aR^a$)$_n$—Y, —(C$R^aR^a$)$_n$Y, or —(C$R^aR^a$)$_n$O$R^a$;

Y is a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, which is substituted with 0, 1, or 2 substituents independently selected from $C_{1-8}$alkyl, —$C_{2-6}$alkenyl, —$C_{2-6}$alkynyl, $C_{1-4}$haloalkyl, halo, —CN, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ or —N$R^aC_{2-6}$alkylO$R^a$;

each $R^a$ is independently hydrogen or $R^b$;

each $R^b$ is independently phenyl, benzyl or $C_{1-6}$alkyl, wherein the phenyl, benzyl or $C_{1-6}$alkyl is substituted by 0, 1, 2 or 3 substituents independently selected from halo, $C_{1-4}$alkyl, $C_{1-3}$haloalkyl, —O$C_{1-4}$alkyl, —$NH_2$, —CN, —NH$C_{1-4}$alkyl, or —N($C_{1-4}$alkyl)$_2$;

each n is independently 0, 1, 2, or 3; and each m is independently 0, 1, or 2.

In an embodiment of the compounds of Formula I, or a pharmaceutically acceptable salt thereof, either separately or in combination with any of the above or below embodiments, Q is an optionally substituted 6,6-bicyclic heteroaromatic ring, wherein the ring is selected from:

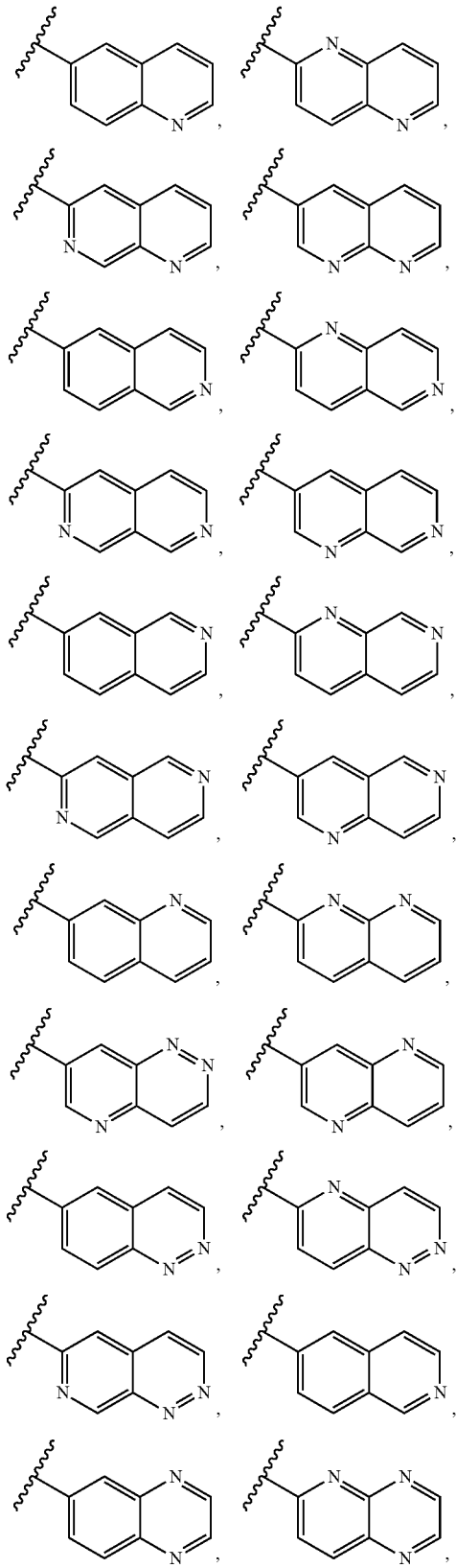

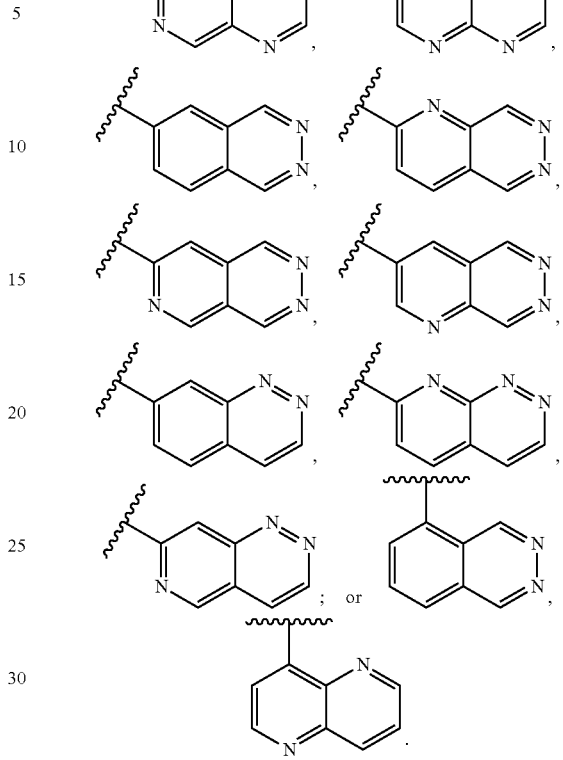

In another embodiment of the compounds of Formula I, or a pharmaceutically acceptable salt thereof, either separately or in combination with any of the above or below embodiments, $R^1$ is halo or —$CF_3$.

In another embodiment of the compounds of Formula I, or a pharmaceutically acceptable salt thereof, either separately or in combination with any of the above or below embodiments, $R^1$ is chlorine.

In another embodiment of the compounds of Formula I, or a pharmaceutically acceptable salt thereof, either separately or in combination with any of the above or below embodiments, $X^1$ is CH.

In another embodiment of the compounds of Formula I, or a pharmaceutically acceptable salt thereof, either separately or in combination with any of the above or below embodiments, $X^2$ is

—NHSO$_2$— or

—N(CH$_3$)SO$_2$—.

In another embodiment of the compounds of Formula I, or a pharmaceutically acceptable salt thereof, either separately or in combination with any of the above or below embodiments, Z is phenyl or phenyl substituted with halo or —OCH$_3$.

In another embodiment of the compounds of Formula I, or a pharmaceutically acceptable salt thereof, either separately or in combination with any of the above or below embodiments, $R^1$ is Cl; $X^1$ is CH; $X^2$ is —NHSO$_2$— and Z is fluorophenyl.

In another embodiment of the compounds of Formula I, or a pharmaceutically acceptable salt thereof, either separately or in combination with any of the above or below embodiments, Q is an optionally substituted 6,6-bicyclic heteroaromatic ring, wherein the ring is

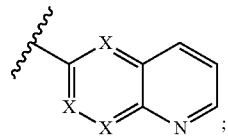

and each X is CH.

In another embodiment of the compounds of Formula I, or a pharmaceutically acceptable salt thereof, either separately or in combination with any of the above or below embodiments, Q is an optionally substituted 6,6-bicyclic heteroaromatic ring, wherein the ring is

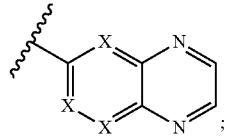

and each X is CH.

In an alternative embodiment, the present invention provides compounds of Formula I

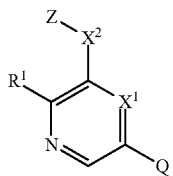

or a pharmaceutically acceptable salt thereof, wherein Q is is an optionally substituted 6,6-bicyclic heteroaromatic ring selected from

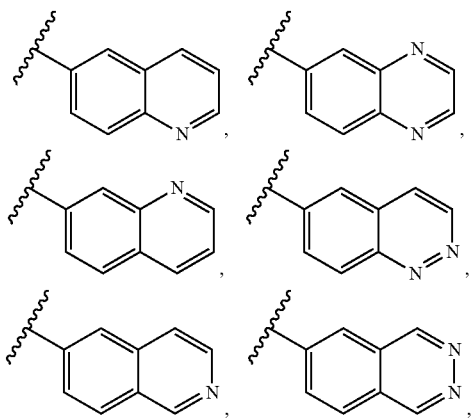

-continued wherein the 6,6-bicyclic heteroaromatic ring has 0, 1, or 2 substituents on carbon atoms that are independently selected from R;

$X^1$ is CH or N;

$R^1$ is halo, —$CF_3$ or $C_{1-6}$alkyl;

$X^2$ is —N($R^a$)S(=O)$_2$—, —(C$R^a R^a$)$_n$O—, or —(C$R^a R^a$)$_n$N($R^a$)—;

Z is hydrogen, phenyl, $C_{1-6}$alkyl, —C(=O)$R^a$, wherein the phenyl is substituted with 0, 1, 2 or 3, substituents independently selected from halo, —O$C_{1-6}$akyl, or $C_{1-6}$alkyl;

each R is independently hydrogen, $C_{1-4}$haloalkyl, halo, —CN, nitro, —C(=O)N$R^a R^a$, —C(=O)$R^b$, —C(=O)O$R^b$, —C(=N$R^a$)N$R^a R^a$, —O$R^a$, —OC(=O)$R^b$, —OC(=O)N$R^a R^a$, —O—$C_{1-6}$alkylN($R^a$)C(=O)O$R^b$, —OC(=O)N($R^a$)S(=O)$_2$$R^b$, —OC$_{2-6}$alkylN$R^a R^a$, —OC$_{2-6}$alkylO$R^a$, —S$R^a$, —S(=O)$R^b$, —S(=O)$_2$$R^b$, —S(=O)$_2$N$R^a R^a$, —S(=O)$_2$N($R^a$)C(=O)$R^b$, —S(=O)$_2$N($R^a$)C(=O)O$R^b$, —S(=O)$_2$N($R^a$)C(=O)N$R^a R^a$, —N$R^a R^a$, —N($R^a$)C(=O)$R^b$, —N($R^a$)C(=O)O$R^b$, —N($R^a$)C(=O)N$R^a R^a$, —N($R^a$)C(=N$R^a$)N$R^a R^a$, —N($R^a$)S(=O)$_2$ $R^b$, —N($R^a$)S(=O)$_2$N$R^a R^a$, —N$R^a$$C_{2-6}$alkylN$R^a R^a$, —N$R^a$$C_{2-6}$alkylO$R^a$, —$C_{1-6}$alkyl, —$C_{2-6}$alkenyl, —$C_{2-6}$alkynyl, or a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, wherein the —$C_{1-6}$alkyl, —$C_{2-6}$alkenyl, —$C_{2-6}$alkynyl, or ring are substituted by 0, 1, 2 or 3 substituents independently selected from $C_{1-8}$alkyl, —$C_{2-6}$alkenyl, —$C_{2-6}$alkynyl, $C_{1-4}$haloalkyl, halo, cyano, nitro, —C(=O)$R^b$, —C(=O)O$R^b$, —C(=O)N$R^a R^a$, —C(=N$R^a$)N$R^a R^a$, —O$R^a$, —OC(=O)$R^b$, —OC(=O)N$R^a R^a$, —OC(=O)N($R^a$)S(=O)$_2$$R^b$, —OC$_{2-6}$alkylN$R^a R^a$, —OC$_{2-6}$alkylO$R^a$, —S$R^a$, —S(=O)$R^b$, —S(=O)$_2$$R^b$, —S(=O)$_2$N$R^a R^a$, —S(=O)$_2$N($R^a$)C(=O)$R^b$, —S(=O)$_2$N($R^a$)C(=O)O$R^b$, —S(=O)$_2$N($R^a$)C(=O)N$R^a R^a$, —N$R^a R^a$, —N($R^a$)C(=O)$R^b$, —N($R^a$)C(=O)O$R^b$, —N($R^a$)C(=O)N$R^a R^a$, —N($R^a$)C(=N$R^a$)N$R^a R^a$, —N($R^a$)S(=O)$_2$$R^b$, —N($R^a$)S(=O)$_2$N$R^a R^a$, —N$R^a$$C_{2-6}$alkylN$R^a R^a$, —N$R^a$$C_{2-6}$alkylO$R^a$, —N($R^a$)(C$R^a R^a$)$_n$—Y, —(C$R^a R^a$)$_n$Y, or —(C$R^a R^a$)$_n$O$R^a$;

Y is a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, which is substituted with 0, 1, or 2 substituents independently selected from $C_{1-8}$alkyl, —$C_{2-6}$alkenyl, —$C_{2-6}$alkynyl, $C_{1-4}$haloalkyl, halo, —CN, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$ N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ or —NR$^a$C$_{2-6}$alkylOR$^a$;

each R$^a$ is independently hydrogen or R$^b$;

each R$^b$ is independently phenyl, benzyl or C$_{1-6}$alkyl, wherein the phenyl, benzyl or C$_{1-6}$alkyl is substituted by 0, 1, 2 or 3 substituents independently selected from halo, C$_{1-4}$alkyl, C$_{1-3}$haloalkyl, —OC$_{1-4}$alkyl, —NH$_2$, —CN, —NHC$_{1-4}$alkyl, or —N(C$_{1-4}$alkyl)$_2$;

each n is independently 0, 1, 2, or 3; and each m is independently 0, 1, or 2.

In the alternative embodiment of the compounds of Formula I, or a pharmaceutically acceptable salt thereof, either separately or in combination with any of the above or below embodiments, X$^1$ is CH and R$^1$ is Cl.

In the alternative embodiment of the compounds of Formula I, or a pharmaceutically acceptable salt thereof, either separately or in combination with any of the above or below embodiments, X$^2$ is —NHSO$_2$— or —N(CH$_3$)SO$_2$—.

In the alternative embodiment of the compounds of Formula I, or a pharmaceutically acceptable salt thereof, either separately or in combination with any of the above or below embodiments, Z is C$_{1-6}$alkyl or phenyl substituted with halo or —OC$_{1-6}$alkyl.

In the alternative embodiment of the compounds of Formula I, or a pharmaceutically acceptable salt thereof, either separately or in combination with any of the above or below embodiments, X$^2$ is —NHSO$_2$— or —N(CH$_3$)SO$_2$— and Z is

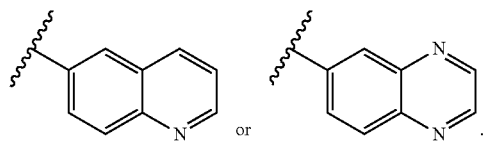

In the alternative embodiment of the compounds of Formula I, or a pharmaceutically acceptable salt thereof, either separately or in combination with any of the above or below embodiments, Q is

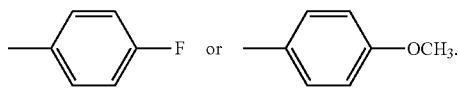

In another aspect, the present invention provides a pharmaceutical composition comprising:

A) a compound of Formula I

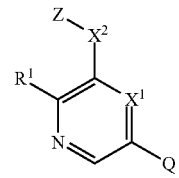

or a pharmaceutically acceptable salt thereof, wherein Q is an optionally substituted 6,6-bicyclic heteroaromatic ring selected from

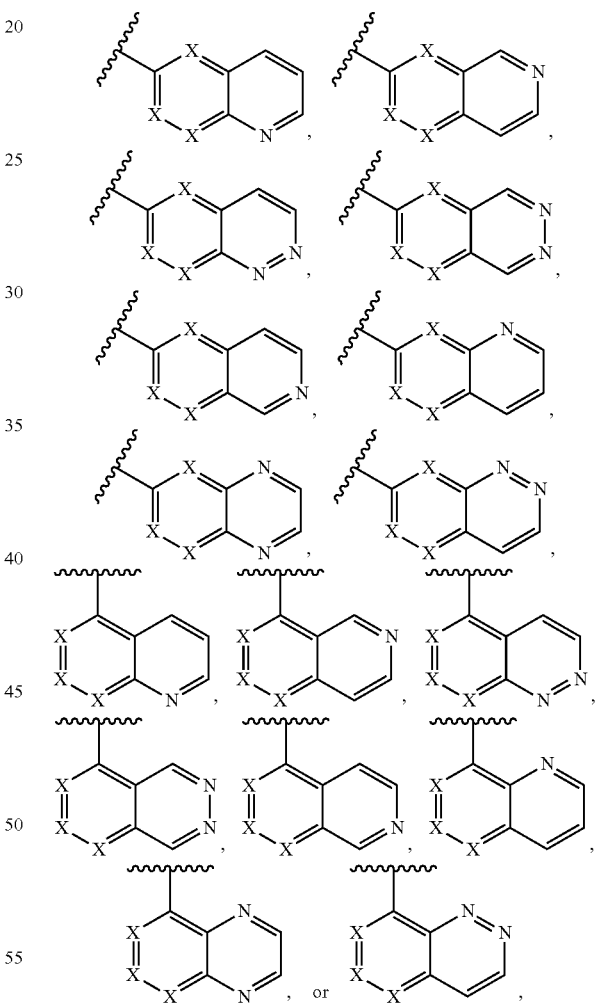

wherein the 6,6-bicyclic heteroaromatic ring has 0, 1, 2, or 3 substituents on carbon atoms that are independently selected from R;

each X is independently N or CR, provided that no more than one X is N;

X$^1$ is N or CR;

R$^1$ is halo, —CF$_3$, —C$_{1-6}$alkyl, —C$_{2-6}$alkenyl, —C$_{2-6}$alkynyl, —OC$_{1-6}$alkyl, or —CN, wherein the —C$_{1-6}$alkyl, —C$_{2-6}$alkenyl, or —C$_{2-6}$alkynyl are substituted by 0, 1, 2 or 3 substituents independently selected from —$C_{1-8}$alkyl, —$C_{2-6}$alkenyl, —$C_{2-6}$alkynyl, $C_{1-4}$haloalkyl, halo, —CN, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$, —N$R^aC_{2-6}$alkylO$R^a$, or a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, wherein the ring is further substituted by 0, 1, 2 or 3 substituents independently selected from $C_{1-8}$alkyl, —$C_{2-6}$alkenyl, —$C_{2-6}$alkynyl, $C_{1-4}$haloalkyl, halo, —CN, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ or —N$R^aC_{2-6}$alkylO$R^a$;

$X^2$ is —N($R^a$)S(=O)$_2$(C$R^aR^a$)$_n$—, —N($R^a$)C(=O)(C$R^aR^a$)$_n$—, —O(C$R^aR^a$)$_n$—, —(C$R^aR^a$)$_n$O—, —(C$R^aR^a$)$_n$S(=O)$_m$—, —(C$R^aR^a$)$_n$N($R^a$)—, —N($R^a$)(C$R^aR^a$)$_n$—, —S(O)$_m$(C$R^aR^a$)$_n$—, —N($R^a$)(C$R^aR^a$)$_n$—, —S(=O)$_2$N($R^a$)(C$R^aR^a$)$_n$—, —N($R^a$)C(=O)O(C$R^aR^a$)$_n$—, —N($R^a$)C(=O)N$R^a$(C$R^aR^a$)$_n$—, —N($R^a$)C(=N$R^a$)N$R^a$(C$R^aR^a$)$_n$—, —OC(=O)N$R^a$(C$R^aR^a$)$_n$—, or —N($R^a$)S(=O)$_2$N$R^a$(C$R^aR^a$)$_n$—;

Z is hydrogen, —$C_{1-6}$alkyl, —$C_{2-6}$alkenyl, —$C_{2-6}$alkynyl, —C(=O)$R^a$, or a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, wherein the —$C_{1-6}$alkyl, —$C_{2-6}$alkenyl, —$C_{2-6}$alkynyl, or ring are substituted by 0, 1, 2 or 3 substituents independently selected from $C_{1-8}$alkyl, —$C_{2-6}$alkenyl, —$C_{2-6}$alkynyl, $C_{1-4}$haloalkyl, halo, —CN, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ or —N$R^aC_{2-6}$alkylO$R^a$;

each R is independently hydrogen, $C_{1-4}$haloalkyl, halo, —CN, nitro, —C(=O)N$R^aR^a$, —C(=O)$R^b$, —C(=O)O$R^b$, —C(=N$R^a$)N$R^aR^a$, —O$R^a$, —OC(=O)$R^b$, —OC(=O)N$R^aR^a$, —O—$C_{1-6}$alkylN($R^a$)C(=O)O$R^b$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2$ $R^b$, —N($R^a$)S(=O)$_2$N$R^aR^a$, —N$R^aC_{2-6}$alkylN$R^aR^a$, —N$R^aC_{2-6}$alkylO$R^a$, —$C_{1-6}$alkyl, —$C_{2-6}$alkenyl, —$C_{2-6}$alkynyl, or a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, wherein the —$C_{1-6}$alkyl, —$C_{2-6}$alkenyl, —$C_{2-6}$alkynyl, or ring are substituted by 0, 1, 2 or 3 substituents independently selected from $C_{1-8}$alkyl, —$C_{2-6}$alkenyl, —$C_{2-6}$alkynyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$, —N$R^aC_{2-6}$alkylO$R^a$, —N($R^a$)(C$R^aR^a$)$_n$—Y, —(C$R^aR^a$)$_n$Y, or —(C$R^aR^a$)$_n$ O$R^a$;

Y is a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, which is substituted with 0, 1, or 2 substituents independently selected from $C_{1-8}$alkyl, —$C_{2-6}$alkenyl, —$C_{2-6}$alkynyl, $C_{1-4}$haloalkyl, halo, —CN, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$ N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ or —N$R^aC_{2-6}$alkylO$R^a$;

each $R^a$ is independently H or $R^b$;

each $R^b$ is independently phenyl, benzyl or $C_{1-6}$alkyl, wherein the phenyl, benzyl or $C_{1-6}$alkyl is substituted by 0, 1, 2 or 3 substituents independently selected from halo, $C_{1-4}$alkyl, $C_{1-3}$haloalkyl, —O$C_{1-4}$alkyl, —NH$_2$, —CN, —NH$C_{1-4}$alkyl, or —N($C_{1-4}$alkyl)$_2$;

each n is independently 0, 1, 2, or 3; and each m is independently 0, 1, or 2;

and

B) a pharmaceutically acceptable excipient.

In another embodiment of the pharmaceutical composition, in the compounds of Formula I, or a pharmaceutically acceptable salt thereof, either separately or in combination with any of the above or below embodiments, Q is an optionally substituted 6,6-bicyclic heteroaromatic ring, wherein the ring is selected from:

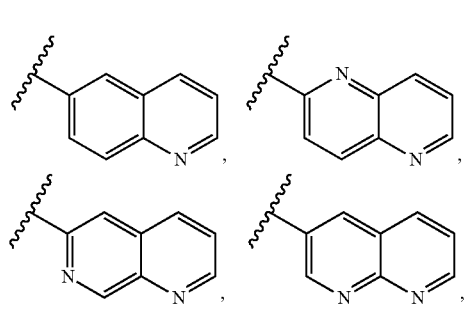

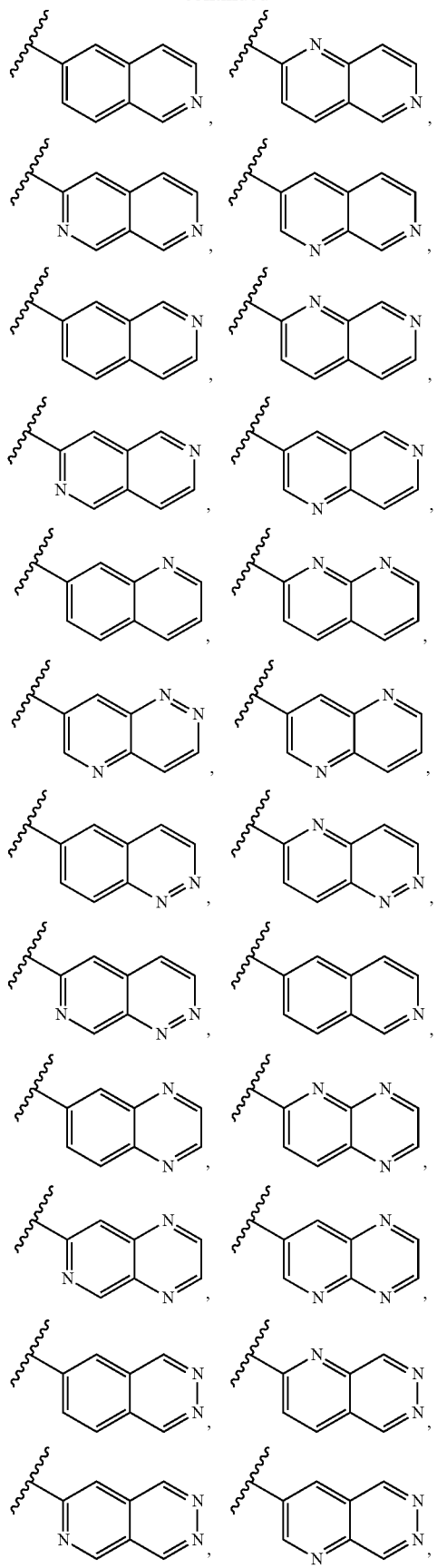

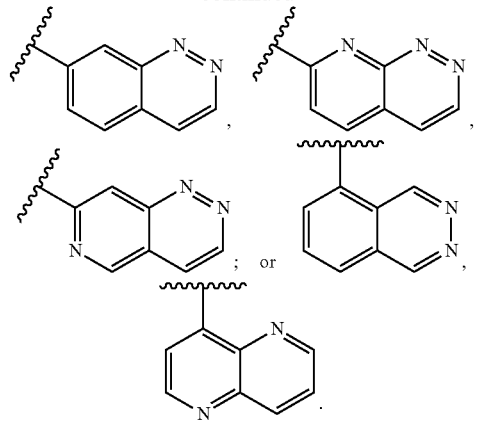

In another embodiment of the pharmaceutical composition, in the compounds of Formula I, or a pharmaceutically acceptable salt thereof, either separately or in combination with any of the above or below embodiments, $R^1$ is halo or —$CF_3$.

In another embodiment of the pharmaceutical composition, in the compounds of Formula I, or a pharmaceutically acceptable salt thereof, either separately or in combination with any of the above or below embodiments, $R^1$ is chlorine.

In another embodiment of the pharmaceutical composition, in the compounds of Formula I, or a pharmaceutically acceptable salt thereof, either separately or in combination with any of the above or below embodiments, $X^1$ is CH.

In another embodiment of the pharmaceutical composition, in the compounds of Formula I, or a pharmaceutically acceptable salt thereof, either separately or in combination with any of the above or below embodiments, $X^2$ is —$NHSO_2$— or —$N(CH_3)SO_2$—.

In another embodiment of the pharmaceutical composition, in the compounds of Formula I, or a pharmaceutically acceptable salt thereof, either separately or in combination with any of the above or below embodiments, Z is phenyl or phenyl substituted with halo or —$OCH_3$.

In another embodiment of the pharmaceutical composition, in the compounds of Formula I, or a pharmaceutically acceptable salt thereof, either separately or in combination with any of the above or below embodiments, $R^1$ is Cl; $X^1$ is CH; $X^2$ is —$NHSO_2$— and Z is fluorophenyl.

In another embodiment of the pharmaceutical composition, in the compounds of Formula I, or a pharmaceutically acceptable salt thereof, either separately or in combination with any of the above or below embodiments, Q is an optionally substituted 6,6-bicyclic heteroaromatic ring, wherein the ring is

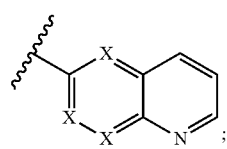

and each X is CH.

In another embodiment of the pharmaceutical composition, in the compounds of Formula I, or a pharmaceutically acceptable salt thereof, either separately or in combination with any of the above or below embodiments, Q is an optionally substituted 6,6-bicyclic heteroaromatic ring, wherein the ring is

[chemical structure of bicyclic heteroaromatic ring with X and N atoms]

and each X is CH.

In an alternative embodiment, the present invention provides a pharmaceutical composition comprising:

A) a compound of Formula I

[chemical structure of Formula I]

I or a pharmaceutically acceptable salt thereof, wherein Q is is an optionally substituted 6,6-bicyclic heteroaromatic ring selected from

[chemical structures of various bicyclic heteroaromatic rings including quinoline, quinoxaline, isoquinoline, cinnoline, phthalazine, naphthyridine variants]

, or

[additional bicyclic heteroaromatic structure];

wherein the 6,6-bicyclic heteroaromatic ring has 0, 1, or 2 substituents on carbon atoms that are independently selected from R;

$X^1$ is CH or N;

$R^1$ is halo, —$CF_3$ or $C_{1-6}$alkyl;

$X^2$ is —N($R^a$)S(=O)$_2$—, —($CR^aR^a$)$_n$O—, or —($CR^aR^a$)$_n$N($R^a$)—;

Z is hydrogen, phenyl, $C_{1-6}$alkyl, —(C=O)$R^a$, wherein the phenyl is substituted with 0, 1, 2 or 3, substituents independently selected from halo, —$OC_{1-6}$akyl, or $C_{1-6}$alkyl;

each R is independently hydrogen, $C_{1-4}$haloalkyl, halo, —CN, nitro, —C(=O)$NR^aR^a$, —C(=O)$R^b$, —C(=O)$OR^b$, —C(=$NR^a$)$NR^aR^a$, —$OR^a$, —OC(=O)$R^b$, —OC(=O)$NR^aR^a$, —O—$C_{1-6}$alkylN($R^a$)C(=O)$OR^b$, —OC(=O)N($R^a$)S(=O)$_2R^b$, —$OC_{2-6}$alkyl$NR^aR^a$, —$OC_{2-6}$alkyl$OR^a$, —$SR^a$, —S(=O)$R^b$, —S(=O)$_2R^b$, —S(=O)$_2NR^aR^a$, —S(=O)$_2$N($R^a$)C(=O)$R^b$, —S(=O)$_2$N($R^a$)C(=O)$OR^b$, —S(=O)$_2$N($R^a$)C(=O)$NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}$alkyl$NR^aR^a$, —$NR^aC_{2-6}$alkyl$OR^a$, —$C_{1-6}$alkyl, —$C_{2-6}$alkenyl, —$C_{2-6}$ alkynyl, or a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, wherein the —$C_{1-6}$alkyl, —$C_{2-6}$alkenyl, —$C_{2-6}$alkynyl, or ring are substituted by 0, 1, 2 or 3 substituents independently selected from $C_{1-8}$alkyl, —$C_{2-6}$alkenyl, —$C_{2-6}$alkynyl, $C_{1-4}$haloalkyl, halo, cyano, nitro, —C(=O)$R^b$, —C(=O)$OR^b$, —C(=O)$NR^aR^a$, —C(=$NR^a$)$NR^aR^a$, —$OR^a$, —OC(=O)$R^b$, —OC(=O)$NR^aR^a$, —OC(=O)N($R^a$)S(=O)$_2R^b$, —$OC_{2-6}$alkyl$NR^aR^a$, —$OC_{2-6}$alkyl$OR^a$, —$SR^a$, —S(=O)$R^b$, —S(=O)$_2R^b$, —S(=O)$_2NR^aR^a$, —S(=O)$_2$N($R^a$)C(=O)$R^b$, —S(=O)$_2$N($R^a$)C(=O)$OR^b$, —S(=O)$_2$N($R^a$)C(=O)$NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}$alkyl$NR^aR^a$, —$NR^aC_{2-6}$alkyl$OR^a$, —N($R^a$)($CR^aR^a$)$_n$—Y, —($CR^aR^a$)$_n$Y, or —($CR^aR^a$)$_n$$OR^a$;

Y is a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, which is substituted with 0, 1, or 2 substituents independently selected from $C_{1-8}$alkyl, —$C_{2-6}$alkenyl, —$C_{2-6}$alkynyl, $C_{1-4}$haloalkyl, halo, —CN, nitro, —C(=O)$R^b$, —C(=O)$OR^b$, —C(=O)$NR^aR^a$, —C(=$NR^a$)$NR^aR^a$, —$OR^a$, —OC(=O)$R^b$, —OC(=O)$NR^aR^a$, —OC(=O)N($R^a$)S(=O)$_2R^b$, —$OC_{2-6}$alkyl$NR^aR^a$, —$OC_{2-6}$alkyl$OR^a$, —$SR^a$, —S(=O)$R^b$, —S(=O)$_2R^b$, —S(=O)$_2NR^aR^a$, —S(=O)$_2$N($R^a$)C(=O)$R^b$, —S(=O)$_2$N($R^a$)C(=O)$OR^b$, —S(=O)$_2$N($R^a$)C(=O)$NR^aR^a$, —$NR^aR^a$, —N($R^a$)C(=O)$R^b$, —N($R^a$)C(=O)$OR^b$, —N($R^a$)C(=O)$NR^aR^a$, —N($R^a$)C(=$NR^a$)$NR^aR^a$, —N($R^a$)S(=O)$_2R^b$, —N($R^a$)S(=O)$_2NR^aR^a$, —$NR^aC_{2-6}$alkyl$NR^aR^a$ or —$NR^aC_{2-6}$alkyl$OR^a$;

each $R^a$ is independently hydrogen or $R^b$;

each $R^b$ is independently phenyl, benzyl or $C_{1-6}$alkyl, wherein the phenyl, benzyl or $C_{1-6}$alkyl is substituted by 0, 1, 2 or 3 substituents independently selected from halo, $C_{1-4}$alkyl, $C_{1-3}$haloalkyl, —$OC_{1-4}$alkyl, —$NH_2$, —CN, —$NHC_{1-4}$alkyl, or —N($C_{1-4}$alkyl)$_2$;

each n is independently 0, 1, 2, or 3; and each m is independently 0, 1, or 2; and B) a pharmaceutically acceptable excipient.

In the alternative embodiment of the pharmaceutical composition, in the compounds of Formula I, or a pharmaceutically acceptable salt thereof, either separately or in combination with any of the above or below embodiments, $X^1$ is CH and $R^1$ is Cl.

In the alternative embodiment of the pharmaceutical composition, in the compounds of Formula I, or a pharmaceutically acceptable salt thereof, either separately or in combination with any of the above or below embodiments, $X^2$ is —NHSO$_2$— or —N(CH$_3$)SO$_2$—.

In the alternative embodiment of the pharmaceutical composition, in the compounds of Formula I, or a pharmaceutically acceptable salt thereof, either separately or in combination with any of the above or below embodiments, Z is $C_{1-6}$alkyl or phenyl substituted with halo or —OC$_{1-6}$alkyl.

In the alternative embodiment of the pharmaceutical composition, in the compounds of Formula I, or a pharmaceutically acceptable salt thereof, either separately or in combination with any of the above or below embodiments, $X^2$ is —NHSO$_2$— or —N(CH$_3$)SO$_2$— and Z is

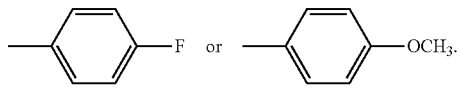

In the alternative embodiment of the pharmaceutical composition, in the compounds of Formula I, or a pharmaceutically acceptable salt thereof, either separately or in combination with any of the above or below embodiments, Q is

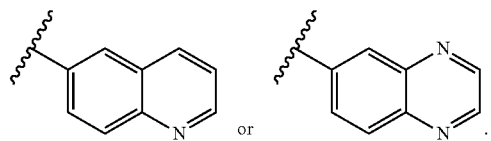 [SMILES: *c1ccc2ncccc2c1 ; *c1ccc2nccnc2c1]

In another aspect, the present invention provides methods of treating melanoma, ovarian cancer, cervical cancer, breast cancer, colon cancer, rectal cancer, endometrial cancer, pancreatic cancer, lung cancer, stomach cancer, glioblastoma, liver cancer, prostate cancer, acute lyelogeous leukemia, chronic lyelogenous leukemia, or thyroid cancer, the method comprising administering to a patient in need thereof a therapeutically effective amount of a compound of Formula I

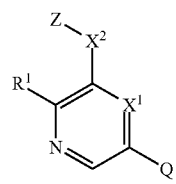

or a pharmaceutically acceptable salt thereof, wherein Q is an optionally substituted 6,6-bicyclic heteroaromatic ring selected from

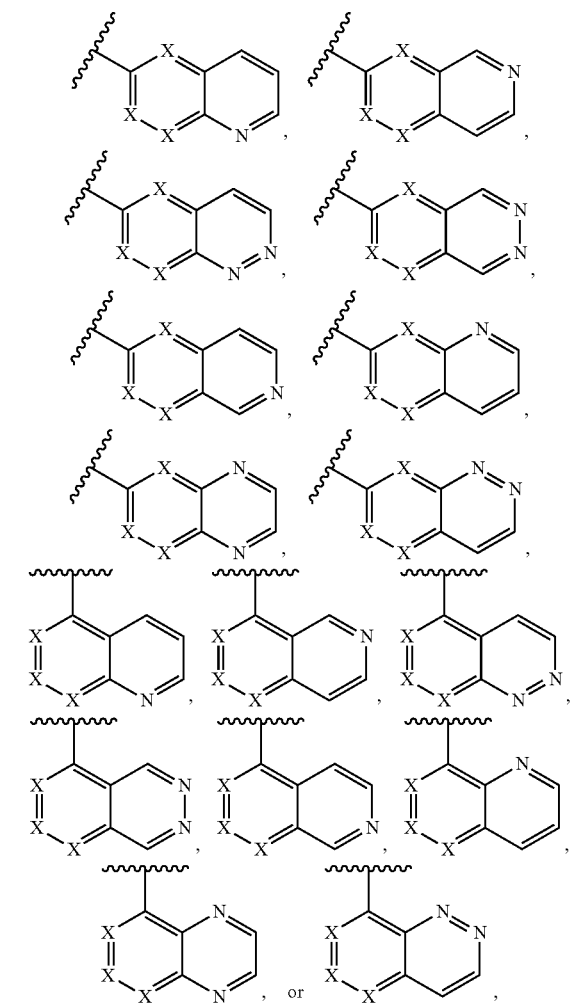

wherein the 6,6-bicyclic heteroaromatic ring has 0, 1, 2, or 3 substituents on carbon atoms that are independently selected from R;

each X is independently N or CR, provided that no more than one X is N;

$X^1$ is N or CR;

$R^1$ is halo, —CF$_3$, —C$_{1-6}$alkyl, —C$_{2-6}$alkenyl, —C$_{2-6}$alkynyl, —OC$_{1-6}$alkyl, or —CN, wherein the —C$_{1-6}$alkyl, —C$_{2-6}$alkenyl, or —C$_{2-6}$alkynyl are substituted by 0, 1, 2 or 3 substituents independently selected from —C$_{1-8}$alkyl, —C$_{2-6}$alkenyl, —C$_{2-6}$alkynyl, C$_{1-4}$haloalkyl, halo, —CN, nitro, —C(═O)R$^b$, —C(═O)OR$^b$, —C(═O)NR$^a$R$^a$, —C(═NR$^a$)NR$^a$R$^a$, —OR$^a$, —OC(═O)R$^b$, —OC(═O)NR$^a$R$^a$, —OC(═O)N(R$^a$)S(═O)$_2$R$^b$, —OC$_{2-6}$alkylNR$^a$R$^a$, —OC$_{2-6}$alkylOR$^a$, —SR$^a$, —S(═O)R$^b$, —S(═O)$_2$R$^b$, —S(═O)$_2$NR$^a$R$^a$, —S(═O)$_2$N(R$^a$)C(═O)R$^b$, —S(═O)$_2$N(R$^a$)C(═O)OR$^b$, —S(═O)$_2$N(R$^a$)C(═O)NR$^a$R$^a$, —NR$^a$R$^a$, —N(R$^a$)C(═O)R$^b$, —N(R$^a$)C(═O)OR$^b$, —N(R$^a$)C(═O)NR$^a$R$^a$, —N(R$^a$)C(═NR$^a$)NR$^a$R$^a$, —N(R$^a$)S(═O)$_2$R$^b$, —N(R$^a$)S(═O)$_2$NR$^a$R$^a$, —NR$^a$C$_{2-6}$alkylNR$^a$R$^a$, —NR$^a$C$_{2-6}$alkylOR$^a$, or a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, wherein the ring is further substituted by 0, 1, 2 or 3 substituents independently selected from C$_{1-8}$alkyl, —C$_{2-6}$alkenyl, —C$_{2-6}$alkynyl, C$_{1-4}$haloalkyl, halo, —CN, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ or —NR$^a$C$_{2-6}$alkylOR$^a$;

X$^2$ is —N(R$^a$)S(=O)$_2$(CR$^a$R$^a$)$_n$—, —N(R$^a$)C(=O)(CR$^a$R$^a$)$_n$—, —O(CR$^a$R$^a$)$_n$—, —(CR$^a$R$^a$)$_n$O—, —(CR$^a$R$^a$)$_n$S(=O)$_m$—, —(CR$^a$R$^a$)$_n$N(R$^a$)—, —N(R$^a$)(CR$^a$R$^a$)$_n$—, —S(O)$_m$(CR$^a$R$^a$)$_n$—, —N(R$^a$)(CR$^a$R$^a$)$_n$—, —S(=O)$_2$N(R$^a$)(CR$^a$R$^a$)$_n$—, —N(R$^a$)C(=O)O(CR$^a$R$^a$)$_n$—, —N(R$^a$)C(=O)NR$^a$(CR$^a$R$^a$)$_n$—, —N(R$^a$)C(=NR$^a$)NR$^a$(CR$^a$R$^a$)$_n$—, —OC(=O)NR$^a$(CR$^a$R$^a$)$_n$—, or —N(R$^a$)S(=O)$_2$NR$^a$(CR$^a$R$^a$)$_n$—;

Z is hydrogen, —C$_{1-6}$alkyl, —C$_{2-6}$alkenyl, —C$_{2-6}$alkynyl, —C(=O)R$^a$, or a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, wherein the —C$_{1-6}$alkyl, —C$_{2-6}$alkenyl, —C$_{2-6}$alkynyl, or ring are substituted by 0, 1, 2 or 3 substituents independently selected from C$_{1-8}$alkyl, —C$_{2-6}$alkenyl, —C$_{2-6}$alkynyl, C$_{1-4}$haloalkyl, halo, —CN, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ or —NR$^a$C$_{2-6}$alkylOR$^a$;

each R is independently hydrogen, C$_{1-4}$haloalkyl, halo, —CN, nitro, —C(=O)NR$^a$R$^a$, —C(=O)R$^b$, —C(=O)OR$^b$, —C(=NR$^a$)NR$^a$R$^a$, —OR$^a$, —OC(=O)R$^b$, —OC(=O)NR$^a$R$^a$, —O—C$_{1-6}$alkylN(R$^a$)C(=O)OR$^b$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$, —C$_{1-6}$alkyl, —C$_{2-6}$alkenyl, —C$_{2-6}$alkynyl, or a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, wherein the —C$_{1-6}$alkyl, —C$_{2-6}$alkenyl, —C$_{2-6}$alkynyl, or ring are substituted by 0, 1, 2 or 3 substituents independently selected from C$_{1-8}$alkyl, —C$_{2-6}$alkenyl, —C$_{2-6}$alkynyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ or —NR$^a$C$_{2-6}$alkylOR$^a$, —N(R$^a$)(CR$^a$R$^a$)$_n$—Y, —(CR$^a$R$^a$)$_n$Y, or —(CR$^a$R$^a$)$_n$OR$^a$;

Y is a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, which is substituted with 0, 1, or 2 substituents independently selected from C$_{1-8}$alkyl, —C$_{2-6}$alkenyl, —C$_{2-6}$alkynyl, C$_{1-4}$haloalkyl, halo, —CN, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ or —NR$^a$C$_{2-6}$alkylOR$^a$;

each R$^a$ is independently H or R$^b$;

each R$^b$ is independently phenyl, benzyl or C$_{1-6}$alkyl, wherein the phenyl, benzyl or C$_{1-6}$alkyl is substituted by 0, 1, 2 or 3 substituents independently selected from halo, C$_{1-4}$alkyl, C$_{1-3}$haloalkyl, —OC$_{1-4}$alkyl, —NH$_2$, —CN, —NHC$_{1-4}$alkyl, or —N(C$_{1-4}$alkyl)$_2$;

each n is independently 0, 1, 2, or 3; and each m is independently 0, 1, or 2.

In another embodiment of the methods, in the compounds of Formula I, or a pharmaceutically acceptable salt thereof, either separately or in combination with any of the above or below embodiments, Q is an optionally substituted 6,6-bicyclic heteroaromatic ring, wherein the ring is selected from:

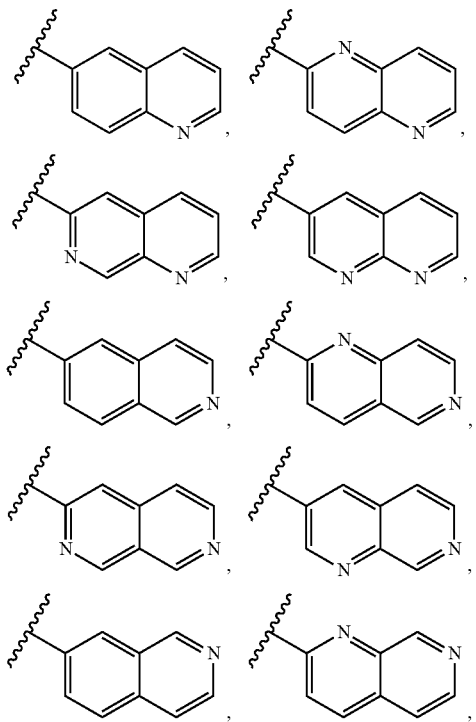

-continued

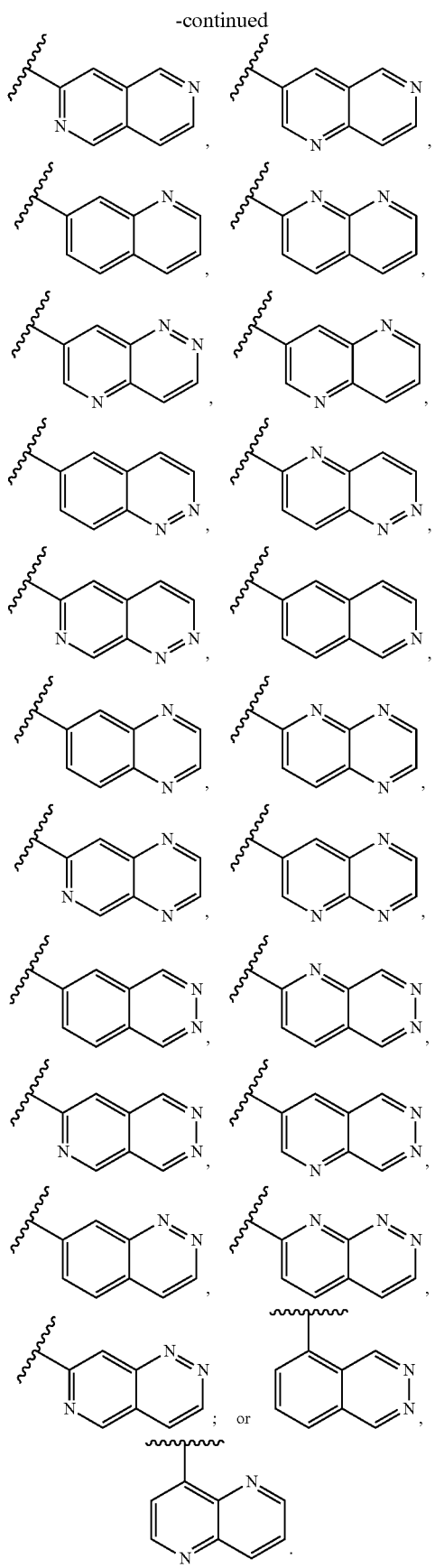

In another embodiment of the methods, in the compounds of Formula I, or a pharmaceutically acceptable salt thereof, either separately or in combination with any of the above or below embodiments, $R^1$ is halo or —$CF_3$.

In another embodiment of the methods, in the compounds of Formula I, or a pharmaceutically acceptable salt thereof, either separately or in combination with any of the above or below embodiments, $R^1$ is chlorine.

In another embodiment of the methods, in the compounds of Formula I, or a pharmaceutically acceptable salt thereof, either separately or in combination with any of the above or below embodiments, $X^1$ is CH.

In another embodiment of the methods, in the compounds of Formula I, or a pharmaceutically acceptable salt thereof, either separately or in combination with any of the above or below embodiments, $X^2$ is —$NHSO_2$— or —$N(CH_3)SO_2$—.

In another embodiment of the methods, in the compounds of Formula I, or a pharmaceutically acceptable salt thereof, either separately or in combination with any of the above or below embodiments, Z is phenyl or phenyl substituted with halo or —$OCH_3$.

In another embodiment of the methods, in the compounds of Formula I, or a pharmaceutically acceptable salt thereof, either separately or in combination with any of the above or below embodiments, $R^1$ is Cl; $X^1$ is CH; $X^2$ is —$NHSO_2$— and Z is fluorophenyl.

In another embodiment of the methods, in the compounds of Formula I, or a pharmaceutically acceptable salt thereof, either separately or in combination with any of the above or below embodiments, Q is an optionally substituted 6,6-bicyclic heteroaromatic ring, wherein the ring is

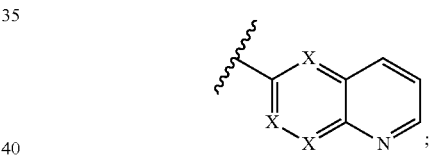

and each X is CH.

In another embodiment of the methods, in the compounds of Formula I, or a pharmaceutically acceptable salt thereof, either separately or in combination with any of the above or below embodiments, Q is an optionally substituted 6,6-bicyclic heteroaromatic ring, wherein the ring is

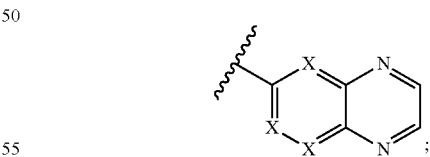

and each X is CH.

In an alternative embodiment, the present invention provides methods of treating melanoma, ovarian cancer, cervical cancer, breast cancer, colon cancer, rectal cancer, endometrial cancer, pancreatic cancer, lung cancer, stomach cancer, glioblastoma, liver cancer, prostate cancer, acute lyelogeous leukemia, chronic lyelogenous leukemia, or thyroid cancer, the method comprising administering to a patient in need thereof a therapeutically effective amount of a compound of Formula I

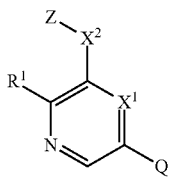

I or a pharmaceutically acceptable salt thereof
wherein Q is is an optionally substituted 6,6-bicyclic heteroaromatic ring selected from

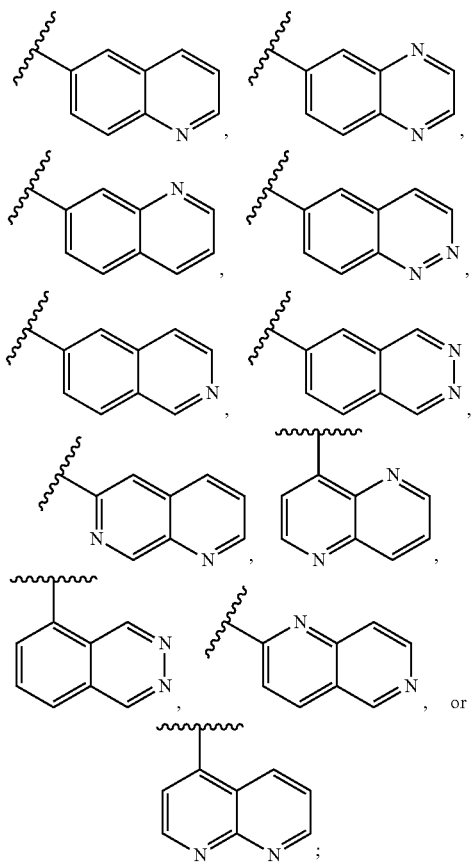

wherein the 6,6-bicyclic heteroaromatic ring has 0, 1, or 2 substituents on carbon atoms that are independently selected from R;

$X^1$ is CH or N;

$R^1$ is halo, —$CF_3$ or $C_{1-6}$alkyl;

$X^2$ is —N($R^a$)S(=O)$_2$—, —(C$R^a R^a$)$_n$O—, or —(C$R^a R^a$)$_n$N($R^a$)—;

Z is hydrogen, phenyl, $C_{1-6}$alkyl, —(C=O)$R^a$, wherein the phenyl is substituted with 0, 1, 2 or 3, substituents independently selected from halo, —O$C_{1-6}$akyl, or $C_{1-6}$alkyl;

each R is independently hydrogen, $C_{1-4}$haloalkyl, halo, —CN, nitro, —C(=O)N$R^a R^a$, —C(=O)$R^b$, —C(=O)O$R^b$, —C(=N$R^a$)N$R^a R^a$, —O$R^a$, —OC(=O)$R^b$, —OC(=O)N$R^a R^a$, —O—$C_{1-6}$alkylN($R^a$)C(=O)O$R^b$, —OC(=O)N($R^a$)S(=O)$_2 R^b$, —O$C_{2-6}$alkylN$R^a R^a$, —O$C_{2-6}$alkylO$R^a$, —S$R^a$, —S(=O)$R^b$, —S(=O)$_2 R^b$, —S(=O)$_2$N$R^a R^a$, —S(=O)$_2$N($R^a$)C(=O)$R^b$, —S(=O)$_2$N($R^a$)C(=O)O$R^b$, —S(=O)$_2$N($R^a$)C(=O)N$R^a R^a$, —N$R^a R^a$, —N($R^a$)C(=O)$R^b$, —N($R^a$)C(=O)O$R^b$, —N($R^a$)C(=O)N$R^a R^a$, —N($R^a$)C(=N$R^a$)N$R^a R^a$, —N($R^a$)S(=O)$_2 R^b$, —N($R^a$)S(=O)$_2$N$R^a R^a$, —N$R^a C_{2-6}$alkylN$R^a R^a$, —N$R^a C_{2-6}$alkylO$R^a$, —$C_{1-6}$alkyl, —$C_{2-6}$alkenyl, —$C_{2-6}$ alkynyl, or a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, wherein the —$C_{1-6}$alkyl, —$C_{2-6}$alkenyl, —$C_{2-6}$alkynyl, or ring are substituted by 0, 1, 2 or 3 substituents independently selected from $C_{1-8}$alkyl, —$C_{2-6}$alkenyl, —$C_{2-6}$alkynyl, $C_{1-4}$haloalkyl, halo, cyano, nitro, —C(=O)$R^b$, —C(=O)O$R^b$, —C(=O)N$R^a R^a$, —C(=N$R^a$)N$R^a R^a$, —O$R^a$, —OC(=O)$R^b$, —OC(=O)N$R^a R^a$, —OC(=O)N($R^a$)S(=O)$_2 R^b$, —O$C_{2-6}$alkylN$R^a R^a$, —O$C_{2-6}$alkylO$R^a$, —S$R^a$, —S(=O)$R^b$, —S(=O)$_2 R^b$, —S(=O)$_2$N$R^a R^a$, —S(=O)$_2$N($R^a$)C(=O)$R^b$, —S(=O)$_2$N($R^a$)C(=O)O$R^b$, —S(=O)$_2$N($R^a$)C(=O)N$R^a R^a$, —N$R^a R^a$, —N($R^a$)C(=O)$R^b$, —N($R^a$)C(=O)O$R^b$, —N($R^a$)C(=O)N$R^a R^a$, —N($R^a$)C(=N$R^a$)N$R^a R^a$, —N($R^a$)S(=O)$_2 R^b$, —N($R^a$)S(=O)$_2$N$R^a R^a$, —N$R^a C_{2-6}$alkylN$R^a R^a$, —N$R^a C_{2-6}$alkylO$R^a$, —N($R^a$)(C$R^a R^a$)$_n$—Y, —(C$R^a R^a$)$_n$Y, or —(C$R^a R^a$)$_n$ O$R^a$;

Y is a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, which is substituted with 0, 1, or 2 substituents independently selected from $C_{1-8}$alkyl, —$C_{2-6}$alkenyl, —$C_{2-6}$alkynyl, $C_{1-4}$haloalkyl, halo, —CN, nitro, —C(=O)$R^b$, —C(=O)O$R^b$, —C(=O)N$R^a R^a$, —C(=N$R^a$)N$R^a R^a$, —O$R^a$, —OC(=O)$R^b$, —OC(=O)N$R^a R^a$, —OC(=O)N($R^a$)S(=O)$_2 R^b$, —O$C_{2-6}$alkylN$R^a R^a$, —O$C_{2-6}$alkylO$R^a$, —S$R^a$, —S(=O)$R^b$, —S(=O)$_2 R^b$, —S(=O)$_2$N$R^a R^a$, —S(=O)$_2$ N($R^a$)C(=O)$R^b$, —S(=O)$_2$N($R^a$)C(=O)O$R^b$, —S(=O)$_2$N($R^a$)C(=O)N$R^a R^a$, —N$R^a R^a$, —N($R^a$)C(=O)$R^b$, —N($R^a$)C(=O)O$R^b$, —N($R^a$)C(=O)N$R^a R^a$, —N($R^a$)C(=N$R^a$)N$R^a R^a$, —N($R^a$)S(=O)$_2 R^b$, —N($R^a$)S(=O)$_2$N$R^a R^a$, —N$R^a C_{2-6}$alkylN$R^a R^a$ or —N$R^a C_{2-6}$alkylO$R^a$;

each $R^a$ is independently hydrogen or $R^b$;

each $R^b$ is independently phenyl, benzyl or $C_{1-6}$alkyl, wherein the phenyl, benzyl or $C_{1-6}$alkyl is substituted by 0, 1, 2 or 3 substituents independently selected from halo, $C_{1-4}$alkyl, $C_{1-3}$haloalkyl, —O$C_{1-4}$alkyl, —$NH_2$, —CN, —NH$C_{1-4}$alkyl, or —N($C_{1-4}$alkyl)$_2$;

each n is independently 0, 1, 2, or 3; and each m is independently 0, 1, or 2.

In the alternative embodiment of the methods, in the compounds of Formula I, or a pharmaceutically acceptable salt thereof, either separately or in combination with any of the above or below embodiments, $X^1$ is CH and $R^1$ is Cl.

In the alternative embodiment of the methods, in the compounds of Formula I, or a pharmaceutically acceptable salt thereof, either separately or in combination with any of the above or below embodiments, $X^2$ is

—NHSO$_2$— or

—N(CH$_3$)SO$_2$—.

In the alternative embodiment of the methods, in the compounds of Formula I, or a pharmaceutically acceptable salt thereof, either separately or in combination with any of the above or below embodiments, Z is $C_{1-6}$alkyl or phenyl substituted with halo or —O$C_{1-6}$alkyl.

In the alternative embodiment of the methods, in the compounds of Formula I, or a pharmaceutically acceptable salt thereof, either separately or in combination with any of the above or below embodiments, $X^2$ is —NHSO$_2$— or —N(CH$_3$)SO$_2$— and Z is

[Structure: 4-fluorophenyl] F or [Structure: 4-methoxyphenyl] OCH$_3$.

In the alternative embodiment of the methods, in the compounds of Formula I, or a pharmaceutically acceptable salt thereof, either separately or in combination with any of the above or below embodiments, Q is

[Structure: quinoline] or [Structure: quinoxaline].

In any of the above methods, an additional pharmaceutically active compound is administered to the patient, which compound is selected from the group consisting of antineoplastic agents; anti-angiogenic agents; chemotherapeutic agents and peptidal cancer therapy agents.

In any of the above methods, any additional pharmaceutically active agent compound is an antineoplastic agent and the antineoplastic agent is selected from the group consisting of antibiotic-type agents; alkylating agents; antimetabolite agents; hormonal agents; immunological agents; interferon-type agents; and kinase inhibitors.

Also provided by the present invention are compounds of Formula I

[Structure: Formula I showing pyridine with substituents Z-X$^2$, R$^1$, X$^1$, Q]
I or a pharmaceutically acceptable salt thereof, wherein Q is an optionally substituted 6,6-bicyclic heteroaromatic ring selected from

[Four bicyclic heteroaromatic structures with X positions and N atoms]

-continued

[Two more bicyclic heteroaromatic structures], or wherein the 6,6-bicyclic heteroaromatic ring has 0, 1, 2, or 3 substituents on carbon atoms that are independently selected from R;

each X is independently N or CR, provided that no more than one X is N;

$X^1$ is N or CR;

$R^1$ is halo, —CF$_3$, —C$_{1-6}$alkyl, —C$_{2-6}$alkenyl, —C$_{2-6}$alkynyl, —OC$_{1-6}$alkyl, or —CN, wherein the —C$_{1-6}$alkyl, —C$_{2-6}$alkenyl, or —C$_{2-6}$alkynyl are substituted by 0, 1, 2 or 3 substituents independently selected from —C$_{1-8}$alkyl, —C$_{2-6}$alkenyl, —C$_{2-6}$alkynyl, C$_{1-4}$haloalkyl, halo, —CN, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O) NR$^a$R$^a$, —NR$^a$R$^a$, —N(R$^a$)C(=O)R$^b$, —N(R$^a$)C(=O) OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$ alkylNR$^a$R$^a$, —NR$^a$C$_{2-6}$alkylOR$^a$, or a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, wherein the ring is further substituted by 0, 1, 2 or 3 substituents independently selected from C$_{1-8}$alkyl, —C$_{2-6}$alkenyl, —C$_{2-6}$alkynyl, C$_{1-4}$haloalkyl, halo, —CN, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O) NR$^a$R$^a$, —OC(=O)N(R$^a$)S(=O)$_2$R$^b$, —OC$_{2-6}$alkylN-R$^a$R$^a$, —OC$_{2-6}$alkylOR$^a$, —SR$^a$, —S(=O)R$^b$, —S(=O)$_2$ R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O) NR$^a$R$^a$, —NR$^a$R$^a$, —N(R$^a$)C(=O)R$^b$, —N(R$^a$)C(=O) OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$ alkylNR$^a$R$^a$ or —NR$^a$C$_{2-6}$ alkylOR$^a$;

$X^2$ is —N(R$^a$)S(=O)$_2$(CR$^a$R$^a$)$_n$—, —N(R$^a$)C(=O)(CR$^a$R$^a$)$_n$—, —O(CR$^a$R$^a$)$_n$—, —(CR$^a$R$^a$)$_n$O—, —(CR$^a$R$^a$)$_n$S (=O)$_m$—, —(CR$^a$R$^a$)$_n$N(R$^a$)—, —N(R$^a$)(CR$^a$R$^a$)$_n$—, —S(O)$_m$(CR$^a$R$^a$)$_n$—, —N(R$^a$)(CR$^a$R$^a$)$_n$—, —S(=O)$_2$N (R$^a$)(CR$^a$R$^a$)$_n$—, —N(R$^a$)C(=O)O(CR$^a$R$^a$)$_n$—, —N(R$^a$) C(=O)NR$^a$(CR$^a$R$^a$)$_n$—, —N(R$^a$)C(=NR$^a$)NR$^a$(CR$^a$ R$^a$)$_n$—, —OC(=O)NR$^a$(CR$^a$R$^a$)$_n$—, or —N(R$^a$)S(=O)$_2$ NR$^a$(CR$^a$R$^a$)$_n$—;

Z is hydrogen, —C$_{1-6}$alkyl, —C$_{2-6}$alkenyl, —C$_{2-6}$alkynyl, —C(=O)R$^a$, or a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, wherein the —C$_{1-6}$alkyl, —C$_{2-6}$alkenyl, —C$_{2-6}$alkynyl, or ring are substituted by 0, 1, 2 or 3 substituents independently selected from C$_{1-8}$alkyl, —C$_{2-6}$alkenyl, —C$_{2-6}$alkynyl, C$_{1-4}$haloalkyl, halo, —CN, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N (R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)

—OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ or —NR$^a$C$_{2-6}$alkylOR$^a$;

each R is independently hydrogen, C$_{1-4}$haloalkyl, halo, —CN, nitro, —C(=O)NR$^a$R$^a$, —C(=O)R$^b$, —C(=O)OR$^b$, —C(=NR$^a$)NR$^a$R$^a$, —OR$^a$, —OC(=O)R$^b$, —OC(=O)NR$^a$R$^a$, —O—C$_{1-6}$alkylN(R$^a$)C(=O)OR$^b$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$, —C$_{1-6}$alkyl, —C$_{2-6}$alkenyl, —C$_{2-6}$ alkynyl, or a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, wherein the —C$_{1-6}$alkyl, —C$_{2-6}$alkenyl, —C$_{2-6}$alkynyl, or ring are substituted by 0, 1, 2 or 3 substituents independently selected from C$_{1-8}$alkyl, —C$_{2-6}$alkenyl, —C$_{2-6}$alkynyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$, —N(R$^a$)(CR$^a$R$^a$)$_n$—Y, —(CR$^a$R$^a$)$_n$Y, or —(CR$^a$R$^a$)$_n$OR$^a$;

Y is a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, which is substituted with 0, 1, or 2 substituents independently selected from C$_{1-8}$alkyl, —C$_{2-6}$alkenyl, —C$_{2-6}$alkynyl, C$_{1-4}$haloalkyl, halo, —CN, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ or —NR$^a$C$_{2-6}$alkylOR$^a$;

each R$^a$ is independently hydrogen or R$^b$;

each R$^b$ is independently phenyl, benzyl or C$_{1-6}$alkyl, wherein the phenyl, benzyl or C$_{1-6}$alkyl is substituted by 0, 1, 2 or 3 substituents independently selected from halo, C$_{1-4}$alkyl, C$_{1-3}$haloalkyl, —OC$_{1-4}$alkyl, —NH$_2$, —CN, —NHC$_{1-4}$alkyl, or —N(C$_{1-4}$alkyl)$_2$;

each n is independently 0, 1, 2, or 3; and each m is independently 0, 1, or 2.

In an embodiment of the compounds of Formula I, or a pharmaceutically acceptable salt thereof, either separately or in combination with any of the above or below embodiments, Q is an optionally substituted 6,6-bicyclic heteroaromatic ring, wherein the ring is selected from:

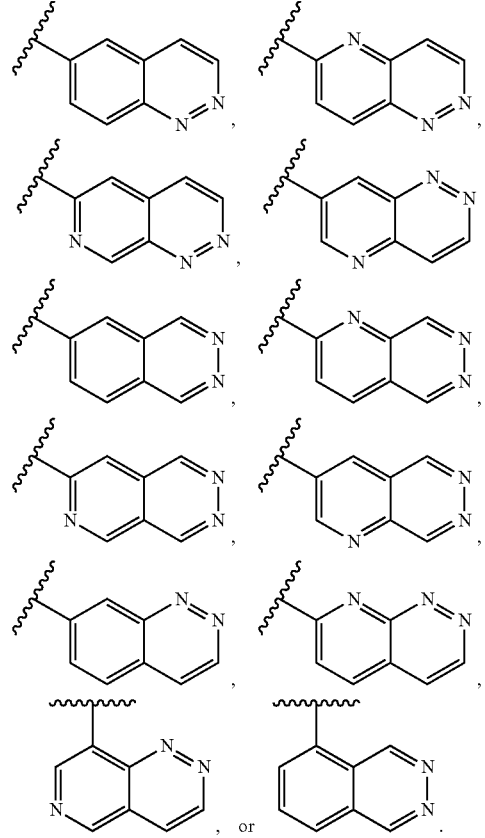

, or

.

In an embodiment of the compounds of Formula I, or a pharmaceutically acceptable salt thereof, either separately or in combination with any of the above or below embodiments, R$^1$ is halo or —CF$_3$.

In an embodiment of the compounds of Formula I, or a pharmaceutically acceptable salt thereof, either separately or in combination with any of the above or below embodiments, R$^1$ is chlorine.

In an embodiment of the compounds of Formula I, or a pharmaceutically acceptable salt thereof, either separately or in combination with any of the above or below embodiments, X$^1$ is CH.

In an embodiment of the compounds of Formula I, or a pharmaceutically acceptable salt thereof, either separately or in combination with any of the above or below embodiments, X$^2$ is

—NHSO$_2$— or

—N(CH$_3$)SO$_2$—.

In an embodiment of the compounds of Formula I, or a pharmaceutically acceptable salt thereof, either separately or in combination with any of the above or below embodiments, Z is phenyl or phenyl substituted with halo or —OCH$_3$.

In an embodiment of the compounds of Formula I, or a pharmaceutically acceptable salt thereof, either separately or in combination with any of the above or below embodiments, R$^1$ is Cl; X$^1$ is CH; X$^2$ is —NHSO$_2$— and Z is fluorophenyl.

Also provided by the present invention are compounds of Formula I

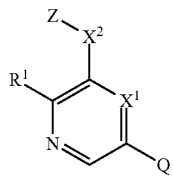

or a pharmaceutically acceptable salt thereof,
wherein Q is is an optionally substituted 6,6-bicyclic heteroaromatic ring selected from

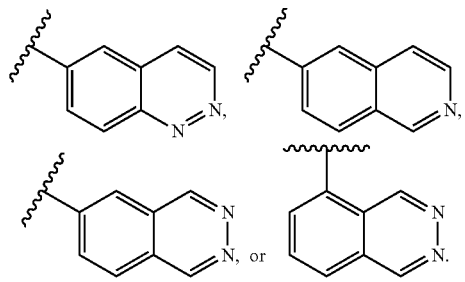

wherein the 6,6-bicyclic heteroaromatic ring has 0, 1, or 2 substituents on carbon atoms that are independently selected from R;
$X^1$ is CH or N;
$R^1$ is halo, —$CF_3$ or $C_{1-6}$alkyl;
$X^2$ is —$N(R^a)S(=O)_2$—, —$(CR^aR^a)_nO$—, or —$(CR^aR^a)_nN(R^a)$—;
Z is hydrogen, phenyl, $C_{1-6}$alkyl, —$(C=O)R^a$, wherein the phenyl is substituted with 0, 1, 2 or 3, substituents independently selected from halo, —$OC_{1-6}$akyl, or $C_{1-6}$alkyl;
each R is independently hydrogen, $C_{1-4}$haloalkyl, halo, —CN, nitro, —$C(=O)NR^aR^a$, —$C(=O)R^b$, —$C(=O)OR^b$, —$C(=NR^a)NR^aR^a$, —$OR^a$, —$OC(=O)R^b$, —$OC(=O)NR^aR^a$, —O—$C_{1-6}$alkylN($R^a$)$C(=O)OR^b$, —$OC(=O)N(R^a)S(=O)_2R^b$, —$OC_{2-6}$alkylN$R^aR^a$, —$OC_{2-6}$alkyl$OR^a$, —$SR^a$, —$S(=O)R^b$, —$S(=O)_2R^b$, —$S(=O)_2NR^aR^a$, —$S(=O)_2N(R^a)C(=O)R^b$, —$S(=O)_2N(R^a)C(=O)OR^b$, —$S(=O)_2N(R^a)C(=O)NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alkylN$R^aR^a$, —$NR^aC_{2-6}$alkyl$OR^a$, —$C_{1-6}$alkyl, —$C_{2-6}$alkenyl, —$C_{2-6}$ alkynyl, or a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, wherein the —$C_{1-6}$alkyl, —$C_{2-6}$alkenyl, —$C_{2-6}$alkynyl, or ring are substituted by 0, 1, 2 or 3 substituents independently selected from $C_{1-8}$alkyl, —$C_{2-6}$alkenyl, —$C_{2-6}$alkynyl, $C_{1-4}$haloalkyl, halo, cyano, nitro, —$C(=O)R^b$, —$C(=O)OR^b$, —$C(=O)NR^aR^a$, —$C(=NR^a)NR^aR^a$, —$OR^a$, —$OC(=O)R^b$, —$OC(=O)NR^aR^a$, —$OC(=O)N(R^a)S(=O)_2R^b$, —$OC_{2-6}$alkylN$R^aR^a$, —$OC_{2-6}$alkyl$OR^a$, —$SR^a$, —$S(=O)R^b$, —$S(=O)_2R^b$, —$S(=O)_2NR^aR^a$, —$S(=O)_2N(R^a)C(=O)R^b$, —$S(=O)_2N(R^a)C(=O)OR^b$, —$S(=O)_2N(R^a)C(=O)NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alkylN$R^aR^a$, —$NR^aC_{2-6}$alkyl$OR^a$, —$N(R^a)(CR^aR^a)_n$—Y, —$(CR^aR^a)_n$Y, or —$(CR^aR^a)_n$ $OR^a$;
Y is a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, which is substituted with 0, 1, or 2 substituents independently selected from $C_{1-8}$alkyl, —$C_{2-6}$alkenyl, —$C_{2-6}$alkynyl, $C_{1-4}$haloalkyl, halo, —CN, nitro, —$C(=O)R^b$, —$C(=O)OR^b$, —$C(=O)NR^aR^a$, —$C(=NR^a)NR^aR^a$, —$OR^a$, —$OC(=O)R^b$, —$OC(=O)NR^aR^a$, —$OC(=O)N(R^a)S(=O)_2R^b$, —$OC_{2-6}$alkylN$R^aR^a$, —$OC_{2-6}$alkyl$OR^a$, —$SR^a$, —$S(=O)R^b$, —$S(=O)_2R^b$, —$S(=O)_2NR^aR^a$, —$S(=O)_2$ $N(R^a)C(=O)R^b$, —$S(=O)_2N(R^a)C(=O)OR^b$, —$S(=O)_2N(R^a)C(=O)NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alkylN$R^aR^a$ or —$NR^aC_{2-6}$alkyl$OR^a$;
each $R^a$ is independently hydrogen or $R^b$;
each $R^b$ is independently phenyl, benzyl or $C_{1-6}$alkyl, wherein the phenyl, benzyl or $C_{1-6}$alkyl is substituted by 0, 1, 2 or 3 substituents independently selected from halo, $C_{1-4}$alkyl, $C_{1-3}$haloalkyl, —$OC_{1-4}$alkyl, —$NH_2$, —CN, —$NHC_{1-4}$alkyl, or —$N(C_{1-4}$alkyl$)_2$;
each n is independently 0, 1, 2, or 3; and
each m is independently 0, 1, or 2.

In an embodiment of the compounds of Formula I, or a pharmaceutically acceptable salt thereof, either separately or in combination with any of the above or below embodiments, $X^1$ is CH and $R^1$ is Cl.

In an embodiment of the compounds of Formula I, or a pharmaceutically acceptable salt thereof, either separately or in combination with any of the above or below embodiments, $X^2$ is

—$NHSO_2$— or

—$N(CH_3)SO_2$—.

In an embodiment of the compounds of Formula I, or a pharmaceutically acceptable salt thereof, either separately or in combination with any of the above or below embodiments, Z is $C_{1-6}$alkyl or phenyl substituted with halo or —$OC_{1-6}$alkyl.

In an embodiment of the compounds of Formula I, or a pharmaceutically acceptable salt thereof, either separately or in combination with any of the above or below embodiments. $X^2$ is —$NHSO_2$— or —$N(CH_3)SO_2$— and Z is

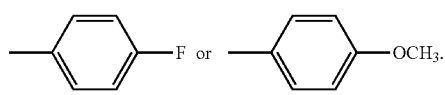

Also provided are pharmaceutical compositions comprising:
A) a compound in accordance with the above embodiments, or a pharmaceutically acceptable salt thereof; and
B) a pharmaceutically acceptable excipient.

Also provided are methods of treating melanoma, ovarian cancer, cervical cancer, breast cancer, colon cancer, rectal cancer, endometrial cancer, pancreatic cancer, lung cancer, stomach cancer, glioblastoma, liver cancer, prostate cancer, acute lyelogeous leukemia, chronic lyelogenous leukemia, or thyroid cancer, the method comprising administering to a patient in need thereof a therapeutically effective amount of a compound in accordance with the above embodiments, or a pharmaceutically acceptable salt thereof.

In the above methods, an additional pharmaceutically active compound is administered to the patient, which compound is selected from the group consisting of antineoplastic agents; anti-angiogenic agents; chemotherapeutic agents and peptidal cancer therapy agents.

In the above methods, the additional pharmaceutically active agent compound is an antineoplastic agent and the antineoplastic agent is selected from the group consisting of antibiotic-type agents; alkylating agents; antimetabolite agents; hormonal agents; immunological agents; interferon-type agents; and kinase inhibitors.

Also provided by the present invention are compounds of Formula I

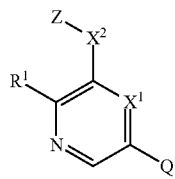

I or a pharmaceutically acceptable salt thereof,
wherein Q is a ring

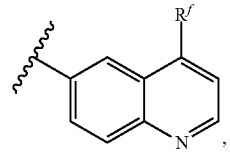

wherein the ring has 0, 1, 2, or 3 substituents on carbon atoms that are independently selected from R;
$X^1$ is N or CR;
$R^1$ is halo, —$CF_3$, —$C_{1-6}$alkyl, —$C_{2-6}$alkenyl, —$C_{2-6}$alkynyl, —$OC_{1-6}$alkyl, or —CN, wherein the —$C_{1-6}$alkyl, —$C_{2-6}$alkenyl, or —$C_{2-6}$alkynyl are substituted by 0, 1, 2 or 3 substituents independently selected from —$C_{1-8}$alkyl, —$C_{2-6}$alkenyl, —$C_{2-6}$alkynyl, $C_{1-4}$haloalkyl, halo, —CN, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$, —N$R^aC_{2-6}$alkylO$R^a$, or a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, wherein the ring is further substituted by 0, 1, 2 or 3 substituents independently selected from $C_{1-8}$alkyl, —$C_{2-6}$alkenyl, —$C_{2-6}$alkynyl, $C_{1-4}$haloalkyl, halo, —CN, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ or —N$R^aC_{2-6}$alkylO$R^a$;

$X^2$ is —N($R^a$)S(=O)$_2$(C$R^aR^a$)$_n$—, —N($R^a$)C(=O)(C$R^aR^a$)$_n$—, —O(C$R^aR^a$)$_n$—, —(C$R^aR^a$)$_n$O—, —(C$R^aR^a$)$_n$S(=O)$_m$—, —(C$R^aR^a$)$_n$N($R^a$)—, —N($R^a$)(C$R^aR^a$)$_n$—, —S(O)$_m$(C$R^aR^a$)$_n$—, —N($R^a$)(C$R^aR^a$)$_n$—, —S(=O)$_2$N($R^a$)(C$R^aR^a$)$_n$—, —N($R^a$)C(=O)O(C$R^aR^a$)$_n$—, —N($R^a$)C(=O)N$R^a$(C$R^aR^a$)$_n$—, —N($R^a$)C(=N$R^a$)N$R^a$(C$R^aR^a$)$_n$—, —OC(=O)N$R^a$(C$R^aR^a$)$_n$—, or —N($R^a$)S(=O)$_2$N$R^a$(C$R^aR^a$)$_n$—;

Z is hydrogen, —$C_{1-6}$alkyl, —$C_{2-6}$alkenyl, —$C_{2-6}$alkynyl, —C(=O)$R^a$, or a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, wherein the —$C_{1-6}$alkyl, —$C_{2-6}$alkenyl, —$C_{2-6}$alkynyl, or ring are substituted by 0, 1, 2 or 3 substituents independently selected from $C_{1-8}$alkyl, —$C_{2-6}$alkenyl, —$C_{2-6}$alkynyl, $C_{1-4}$haloalkyl, halo, —CN, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ or —N$R^aC_{2-6}$alkylO$R^a$;

each R is independently hydrogen, $C_{1-4}$haloalkyl, halo, —CN, nitro, —C(=O)N$R^aR^a$, —C(=O)$R^b$, —C(=O)O$R^b$, —C(=N$R^a$)N$R^aR^a$, —O$R^a$, —OC(=O)$R^b$, —OC(=O)N$R^aR^a$, —O—$C_{1-6}$alkylN($R^a$)C(=O)O$R^b$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$, —N$R^aC_{2-6}$alkylO$R^a$, —$C_{1-6}$alkyl, —$C_{2-6}$alkenyl, —$C_{2-6}$alkynyl, or a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, wherein the —$C_{1-6}$alkyl, —$C_{2-6}$alkenyl, —$C_{2-6}$alkynyl, or ring are substituted by 0, 1, 2 or 3 substituents independently selected from $C_{1-8}$alkyl, —$C_{2-6}$alkenyl, —$C_{2-6}$alkynyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$, —N$R^aC_{2-6}$alkylO$R^a$, —N($R^a$)(C$R^aR^a$)$_n$—Y, —(C$R^aR^a$)$_n$Y, or —(C$R^aR^a$)$_n$O$R^a$;

each $R^f$ is independently, $C_{1-4}$haloalkyl, halo, —CN, nitro, —C(=O)NR$^a$R$^a$, —C(=O)R$^b$, —C(=O)OR$^b$, —C(=NR$^a$)NR$^a$R$^a$, —OR$^a$, —OC(=O)R$^b$, —OC(=O)NR$^a$R$^a$, —O—C$_{1-6}$alkylN(R$^a$)C(=O)OR$^b$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$, —C$_{1-6}$alkyl, —C$_{2-6}$alkenyl, —C$_{2-6}$alkynyl, wherein the —C$_{1-6}$alkyl, —C$_{2-6}$alkenyl, —C$_{2-6}$alkynyl are substituted by 0, 1, 2 or 3 substituents independently selected from C$_{1-8}$alkyl, —C$_{2-6}$alkenyl, —C$_{2-6}$alkynyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$, —NR$^a$C$_{2-6}$alkylOR$^a$, —N(R$^a$)(CR$^a$R$^a$)$_n$—Y, —(CR$^a$R$^a$)$_n$Y, or —(CR$^a$R$^a$)$_n$OR$^a$;

Y is a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, which is substituted with 0, 1, or 2 substituents independently selected from C$_{1-8}$alkyl, —C$_{2-6}$alkenyl, —C$_{2-6}$alkynyl, C$_{1-4}$haloalkyl, halo, —CN, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ or —NR$^a$C$_{2-6}$alkylOR$^a$;

each $R^a$ is independently hydrogen or $R^b$;

each $R^b$ is independently phenyl, benzyl or C$_{1-6}$alkyl, wherein the phenyl, benzyl or C$_{1-6}$alkyl is substituted by 0, 1, 2 or 3 substituents independently selected from halo, C$_{1-4}$alkyl, C$_{1-3}$haloalkyl, —OC$_{1-4}$alkyl, —NH$_2$, —CN, —NHC$_{1-4}$alkyl, or —N(C$_{1-4}$alkyl)$_2$;

each n is independently 0, 1, 2, or 3; and each m is independently 0, 1, or 2.

In an embodiment of the compounds of Formula I, or a pharmaceutically acceptable salt thereof, either separately or in combination with any of the above or below embodiments, $R^1$ is halo or —CF$_3$.

In an embodiment of the compounds of Formula I, or a pharmaceutically acceptable salt thereof, either separately or in combination with any of the above or below embodiments, $R^1$ is chlorine.

In an embodiment of the compounds of Formula I, or a pharmaceutically acceptable salt thereof, either separately or in combination with any of the above or below embodiments, $X^1$ is CH.

In an embodiment of the compounds of Formula I, or a pharmaceutically acceptable salt thereof, either separately or in combination with any of the above or below embodiments, $X^2$ is

—NHSO$_2$— or

—N(CH$_3$)SO$_2$—.

In an embodiment of the compounds of Formula I, or a pharmaceutically acceptable salt thereof, either separately or in combination with any of the above or below embodiments, Z is phenyl or phenyl substituted with halo or —OCH$_3$.

In an embodiment of the compounds of Formula I, or a pharmaceutically acceptable salt thereof, either separately or in combination with any of the above or below embodiments, $R^1$ is Cl; $X^1$ is CH; $X^2$ is —NHSO$_2$— and Z is fluorophenyl.

Also provided by the present invention are compounds of Formula I

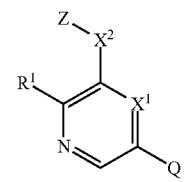

or a pharmaceutically acceptable salt thereof, wherein Q is a ring selected from

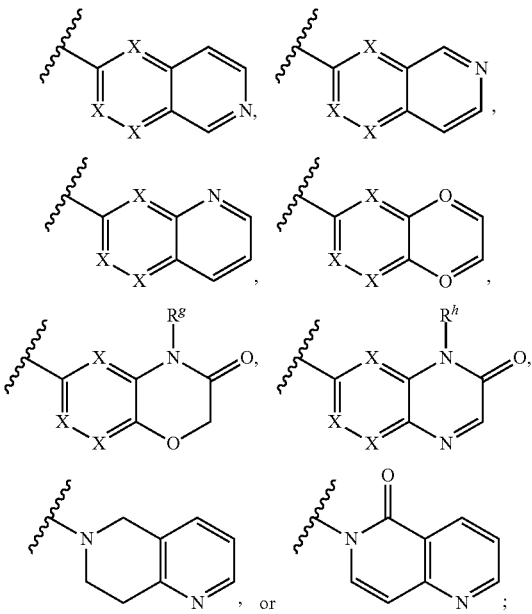

wherein the ring has 0, 1, 2, or 3 substituents on carbon atoms that are independently selected from R, provided that when Q is

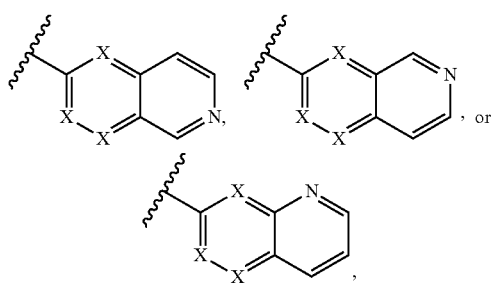

and X² is —NHSO₂—, then each R is not hydrogen;
each X is independently N or CR; provided that at least one X is N;
X¹ is N or CR;
R¹ is halo, —CF₃, —C₁₋₆alkyl, —C₂₋₆alkenyl, —C₂₋₆alkynyl, —OC₁₋₆alkyl, or —CN, wherein the —C₁₋₆alkyl, —C₂₋₆alkenyl, or —C₂₋₆alkynyl are substituted by 0, 1, 2 or 3 substituents independently selected from —C₁₋₈alkyl, —C₂₋₆alkenyl, —C₂₋₆alkynyl, C₁₋₄haloalkyl, halo, —CN, nitro, —C(=O)Rᵇ, —C(=O)ORᵇ, —C(=O)NRᵃRᵃ, —C(=NRᵃ)NRᵃRᵃ, —ORᵃ, —OC(=O)Rᵇ, —OC(=O)NRᵃRᵃ, —OC(=O)N(Rᵃ)S(=O)₂Rᵇ, —OC₂₋₆alkylNRᵃRᵃ, —OC₂₋₆alkylORᵃ, —SRᵃ, —S(=O)Rᵇ, —S(=O)₂Rᵇ, —S(=O)₂NRᵃRᵃ, —S(=O)₂N(Rᵃ)C(=O)Rᵇ, —S(=O)₂N(Rᵃ)C(=O)ORᵇ, —S(=O)2N(Rᵃ)C(=O)NRᵃRᵃ, —NRᵃRᵃ, —N(Rᵃ)C(=O)Rᵇ, —N(Rᵃ)C(=O)ORᵇ, —N(Rᵃ)C(=O)NRᵃRᵃ, —N(Rᵃ)C(=NRᵃ)NRᵃRᵃ, —N(Rᵃ)S(=O)₂Rᵇ, —N(Rᵃ)S(=O)₂NRᵃRᵃ, —NRᵃC₂₋₆alkylNRᵃRᵃ, —NRᵃC₂₋₆alkylORᵃ, or a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, wherein the ring is further substituted by 0, 1, 2 or 3 substituents independently selected from C₁₋₈alkyl, —C₂₋₆alkenyl, —C₂₋₆alkynyl, C₁₋₄haloalkyl, halo, —CN, nitro, —C(=O)Rᵇ, —C(=O)ORᵇ, —C(=O)NRᵃRᵃ, —C(=NRᵃ)NRᵃRᵃ, —ORᵃ, —OC(=O)Rᵇ, —OC(=O)NRᵃRᵃ, —OC(=O)N(Rᵃ)S(=O)₂Rᵇ, —OC₂₋₆alkylNRᵃRᵃ, —OC₂₋₆alkylORᵃ, —SRᵃ, —S(=O)Rᵇ, —S(=O)₂Rᵇ, —S(=O)₂NRᵃRᵃ, —S(=O)₂N(Rᵃ)C(=O)Rᵇ, —S(=O)₂N(Rᵃ)C(=O)ORᵇ, —S(=O)₂N(Rᵃ)C(=O)NRᵃRᵃ, —NRᵃRᵃ, —N(Rᵃ)C(=O)Rᵇ, —N(Rᵃ)C(=O)ORᵇ, —N(Rᵃ)C(=O)NRᵃRᵃ, —N(Rᵃ)C(=NRᵃ)NRᵃRᵃ, —N(Rᵃ)S(=O)₂Rᵇ, —N(Rᵃ)S(=O)₂NRᵃRᵃ, —NRᵃC₂₋₆alkylNRᵃRᵃ or —NRᵃC₂₋₆alkylORᵃ;
X² is —N(Rᵃ)S(=O)₂(CRᵃRᵃ)ₙ—, —N(Rᵃ)C(=O)(CRᵃRᵃ)ₙ—, —O(CRᵃRᵃ)ₙ—, —(CRᵃRᵃ)ₙO—, —(CRᵃRᵃ)ₙS(=O)ₘ—, —(CRᵃRᵃ)ₙN(Rᵃ)—, —N(Rᵃ)(CRᵃRᵃ)ₙ—, —S(O)ₘ(CRᵃRᵃ)ₙ—, —N(Rᵃ)(CRᵃRᵃ)ₙ—, —S(=O)₂N(Rᵃ)(CRᵃRᵃ)ₙ—, —N(Rᵃ)C(=O)O(CRᵃRᵃ)ₙ—, —N(Rᵃ)C(=O)NRᵃ(CRᵃRᵃ)ₙ—, —N(Rᵃ)C(=NRᵃ)NRᵃ(CRᵃRᵃ)ₙ—, —OC(=O)NRᵃ(CRᵃRᵃ)ₙ—, or —N(Rᵃ)S(=O)₂NRᵃ(CRᵃRᵃ)ₙ—;
Z is hydrogen, —C₁₋₆alkyl, —C₂₋₆alkenyl, —C₂₋₆alkynyl, —C(=O)Rᵃ, or a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, wherein the —C₁₋₆alkyl, —C₂₋₆alkenyl, —C₂₋₆alkynyl, or ring are substituted by 0, 1, 2 or 3 substituents independently selected from C₁₋₈alkyl, —C₂₋₆alkenyl, —C₂₋₆alkynyl, C₁₋₄haloalkyl, halo, —CN, nitro, —C(=O)Rᵇ, —C(=O)ORᵇ, —C(=O)NRᵃRᵃ, —C(=NRᵃ)NRᵃRᵃ, —ORᵃ, —OC(=O)Rᵇ, —OC(=O)NRᵃRᵃ, —OC(=O)N(Rᵃ)S(=O)₂Rᵇ, —OC₂₋₆alkylNRᵃRᵃ, —OC₂₋₆alkylORᵃ, —SRᵃ, —S(=O)Rᵇ, —S(=O)₂Rᵇ, —S(=O)₂NRᵃRᵃ, —S(=O)₂N(Rᵃ)C(=O)Rᵇ, —S(=O)₂N(Rᵃ)C(=O)ORᵇ, —S(=O)₂N(Rᵃ)C(=O)NRᵃRᵃ, —NRᵃRᵃ, —N(Rᵃ)C(=O)Rᵇ, —N(Rᵃ)C(=O)ORᵇ, —N(Rᵃ)C(=O)NRᵃRᵃ, —N(Rᵃ)C(=NRᵃ)NRᵃRᵃ, —N(Rᵃ)S(=O)₂Rᵇ, —N(Rᵃ)S(=O)₂NRᵃRᵃ, —NRᵃC₂₋₆alkylNRᵃRᵃ or —NRᵃC₂₋₆alkylORᵃ; or X²—Z together are halo;
each R is independently hydrogen, C₁₋₄haloalkyl, halo, —CN, nitro, —C(=O)NRᵃRᵃ, —C(=O)Rᵇ, —C(=O)ORᵇ, —C(=NRᵃ)NRᵃRᵃ, —ORᵃ, —OC(=O)Rᵇ, —OC(=O)NRᵃRᵃ, —O—C₁₋₆alkylN(Rᵃ)C(=O)ORᵇ, —OC(=O)N(Rᵃ)S(=O)₂Rᵇ, —OC₂₋₆alkylNRᵃRᵃ, —OC₂₋₆alkylORᵃ, —SRᵃ, —S(=O)Rᵇ, —S(=O)₂Rᵇ, —S(=O)₂NRᵃRᵃ, —S(=O)₂N(Rᵃ)C(=O)Rᵇ, —S(=O)₂N(Rᵃ)C(=O)ORᵇ, —S(=O)₂N(Rᵃ)C(=O)NRᵃRᵃ, —NRᵃRᵃ, —N(Rᵃ)C(=O)Rᵇ, —N(Rᵃ)C(=O)ORᵇ, —N(Rᵃ)C(=O)NRᵃRᵃ, —N(Rᵃ)C(=NRᵃ)NRᵃRᵃ, —N(Rᵃ)S(=O)₂ Rᵇ, —N(Rᵃ)S(=O)₂NRᵃRᵃ, —NRᵃC₂₋₆alkylNRᵃRᵃ, —NRᵃC₂₋₆alkylORᵃ, —C₁₋₆alkyl, —C₂₋₆alkenyl, —C₂₋₆alkynyl, or a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, wherein the —C₁₋₆alkyl, —C₂₋₆alkenyl, —C₂₋₆alkynyl, or ring are substituted by 0, 1, 2 or 3 substituents independently selected from C₁₋₈alkyl, —C₂₋₆alkenyl, —C₂₋₆alkynyl, C₁₋₄haloalkyl, halo, cyano, nitro, —C(=O)Rᵇ, —C(=O)ORᵇ, —C(=O)NRᵃRᵃ, —C(=NRᵃ)NRᵃRᵃ, —ORᵃ, —OC(=O)Rᵇ, —OC(=O)NRᵃRᵃ, —OC(=O)N(Rᵃ)S(=O)₂Rᵇ, —OC₂₋₆alkylNRᵃRᵃ, —OC₂₋₆alkylORᵃ, —SRᵃ, —S(=O)Rᵇ, —S(=O)₂Rᵇ, —S(=O)₂NRᵃRᵃ, —S(=O)₂N(Rᵃ)C(=O)Rᵇ, —S(=O)₂N(Rᵃ)C(=O)ORᵇ, —S(=O)₂N(Rᵃ)C(=O)NRᵃRᵃ, —NRᵃRᵃ, —N(Rᵃ)C(=O)Rᵇ, —N(Rᵃ)C(=O)ORᵇ, —N(Rᵃ)C(=O)NRᵃRᵃ, —N(Rᵃ)C(=NRᵃ)NRᵃRᵃ, —N(Rᵃ)S(=O)₂Rᵇ, —N(Rᵃ)S(=O)₂NRᵃRᵃ, —NRᵃC₂₋₆alkylNRᵃRᵃ, —NRᵃC₂₋₆alkylORᵃ, —N(Rᵃ)(CRᵃRᵃ)ₙ—Y, —(CRᵃRᵃ)ₙY, or —(CRᵃRᵃ)ₙORᵃ;
Rᵍ is hydrogen;
Rʰ is C₁₋₆alkyl; or a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, wherein the ring is substituted by 0, 1, 2 or 3 substituents independently selected from C₁₋₈alkyl, —C₂₋₆alkenyl, —C₂₋₆alkynyl, C₁₋₄haloalkyl, halo, cyano, nitro, —C(=O)Rᵇ, —C(=O)ORᵇ, —C(=O)NRᵃRᵃ, —C(=NRᵃ)NRᵃRᵃ, —ORᵃ, —OC(=O)Rᵇ, —OC(=O)NRᵃRᵃ, —OC(=O)N(Rᵃ)S(=O)₂Rᵇ, —OC₂₋₆alkylNRᵃRᵃ, —OC₂₋₆alkylORᵃ, —SRᵃ, —S(=O)Rᵇ, —S(=O)₂Rᵇ, —S(=O)₂NRᵃRᵃ, —S(=O)₂N(Rᵃ)C(=O)Rᵇ, —S(=O)₂N(Rᵃ)C(=O)ORᵇ, —S(=O)₂N(Rᵃ)C(=O)NRᵃRᵃ, —NRᵃRᵃ, —N(Rᵃ)C(=O)Rᵇ, —N(Rᵃ)C(=O)ORᵇ, —N(Rᵃ)C(=O)NRᵃRᵃ, —N(Rᵃ)C(=NRᵃ)NRᵃRᵃ, —N(Rᵃ)S(=O)₂Rᵇ, —N(Rᵃ)S(=O)₂NRᵃRᵃ, —NRᵃC₂₋₆alkylNRᵃRᵃ, —NRᵃC₂₋₆alkylORᵃ, —N(Rᵃ)(CRᵃRᵃ)ₙ—Y, —(CRᵃRᵃ)ₙY, or —(CRᵃRᵃ)ₙORᵃ;
Y is a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, which is substituted with 0, 1, or 2 substituents independently selected from C₁₋₈alkyl, —C₂₋₆alkenyl, —C₂₋₆alkynyl, C₁₋₄haloalkyl, halo, —CN, nitro, —C(=O)Rᵇ, —C(=O)ORᵇ, —C(=O)NRᵃRᵃ, —C(=NRᵃ)NRᵃRᵃ, —ORᵃ, —OC(=O)Rᵇ, —OC(=O)NRᵃRᵃ, —OC(=O)N(Rᵃ)S(=O)₂

$R^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ or —NR$^a$C$_{2-6}$alkylOR$^a$;

each R$^a$ is independently hydrogen or R$^b$;

each R$^b$ is independently phenyl, benzyl or C$_{1-6}$alkyl, wherein the phenyl, benzyl or C$_{1-6}$alkyl is substituted by 0, 1, 2 or 3 substituents independently selected from halo, C$_{1-4}$alkyl, C$_{1-3}$haloalkyl, —OC$_{1-4}$alkyl, —NH$_2$, —CN, —NHC$_{1-4}$alkyl, or —N(C$_{14}$alkyl)$_2$;

each n is independently 0, 1, 2, or 3; and each m is independently 0, 1, or 2.

In an embodiment of the compounds of Formula I, or a pharmaceutically acceptable salt thereof, either separately or in combination with any of the above or below embodiments, $R^1$ is halo or —CF$_3$.

In an embodiment of the compounds of Formula I, or a pharmaceutically acceptable salt thereof, either separately or in combination with any of the above or below embodiments, $R^1$ is chlorine.

In an embodiment of the compounds of Formula I, or a pharmaceutically acceptable salt thereof, either separately or in combination with any of the above or below embodiments, $X^1$ is CH.

In an embodiment of the compounds of Formula I, or a pharmaceutically acceptable salt thereof, either separately or in combination with any of the above or below embodiments, $X^2$ is

—NHSO$_2$— or

—N(CH$_3$)SO$_2$—.

In an embodiment of the compounds of Formula I, or a pharmaceutically acceptable salt thereof, either separately or in combination with any of the above or below embodiments, Z is phenyl or phenyl substituted with halo or —OCH$_3$.

In an embodiment of the compounds of Formula I, or a pharmaceutically acceptable salt thereof, either separately or in combination with any of the above or below embodiments, $R^1$ is Cl; $X^1$ is CH; $X^2$ is —NHSO$_2$— and Z is fluorophenyl.

Also provided are the compounds, or pharmaceutically acceptable salts thereof, selected from:

N-(2-chloro-5-(4-(4-morpholinyl)-6-quinolinyl)-3-pyridinyl)-4-fluorobenzenesulfonamide;
N-(2-chloro-5-(4-chloro-6-quinolinyl)-3-pyridinyl)-4-fluorobenzenesulfonamide;
tert-butyl (2-(((6-(6-chloro-5-(((4(4-fluorophenyl)sulfonyl)amino)-3-pyridinyl)-4-quinolinyl)oxy)ethyl)carbamate;
N-(2-chloro-5-(3-methoxy-6-quinolinyl)-3-pyridinyl)-4-fluorobenzenesulfonamide;
N-(2-chloro-5-(4-phenoxy-6-quinolinyl)-3-pyridinyl)methanesulfonamide;
N-(2-chloro-5-(6-quinoxalinyl)-3-pyridinyl)-4-fluorobenzenesulfonamide;
N-(2-chloro-5-(6-quinolinyl)-3-pyridinyl)-4-fluorobenzenesulfonamide;
N-(2-chloro-5-(4-methoxy-6-quinolinyl)-3-pyridinyl)-4-fluorobenzenesulfonamide;
N-(2-chloro-5-(4-chloro-6-quinolinyl)-3-pyridinyl)methanesulfonamide;
N-(2-chloro-5-(3-methoxy-6-quinolinyl)-3-pyridinyl)methanesulfonamide;
N-(2-chloro-5-(4-(4-morpholinyl)-6-quinolinyl)-3-pyridinyl)methanesulfonamide;
N-(2-chloro-5-(6-quinolinyl)-3-pyridinyl)methanesulfonamide;
2-chloro-N,N-dimethyl-5-(6-quinolinyl)-3-pyridinamine;
(2-chloro-5-(4-(4-morpholinyl)-6-quinolinyl)-3-pyridinyl)methanol;
(2-chloro-5-(4-(4-morpholinyl)-6-quinolinyl)-3-pyridinyl)methyl acetate;
1-(2-chloro-5-(4-(4-morpholinyl)-6-quinolinyl)-3-pyridinyl)methanamine;
N-((2-chloro-5-(4-(4-morpholinyl)-6-quinolinyl)-3-pyridinyl)methyl)-2,2-dimethylpropanamide;
N-(2-chloro-5-(7-quinolinyl)-3-pyridinyl)-4-fluorobenzenesulfonamide;
2-chloro-5-(4-(4-morpholinyl)-6-quinolinyl)-3-pyridinol;
N-(2-chloro-5-(3-(4-morpholinyl)-6-quinoxalinyl)-3-pyridinyl)-4-fluorobenzenesulfonamide;
N-(2-chloro-5-(3-(4-(1-methylethyl)-1-piperazinyl)-6-quinoxalinyl)-3-pyridinyl)-4-fluorobenzenesulfonamide;
N-(2-chloro-5-(3-hydroxy-6-quinolinyl)-3-pyridinyl)-4-fluorobenzenesulfonamide;
N-(2-chloro-5-(4-hydroxy-6-quinolinyl)-3-pyridinyl)-4-fluorobenzenesulfonamide;
N-(2-chloro-5-(4-(1-piperidinyl)-6-quinolinyl)-3-pyridinyl)-4-fluorobenzenesulfonamide;
N-(2-chloro-5-(4-(4-(1-methylethyl)-1-piperazinyl)-6-quinolinyl)-3-pyridinyl)-4-fluorobenzenesulfonamide;
N-(2-chloro-5-(4-(3-hydroxy-1-pyrrolidinyl)-6-quinolinyl)-3-pyridinyl)-4-fluorobenzenesulfonamide;
N-(2-chloro-5-(4-(4-hydroxy-1-piperidinyl)-6-quinolinyl)-3-pyridinyl)-4-fluorobenzenesulfonamide;
N-(5-(4-(4-benzyl-1-piperazinyl)-6-quinolinyl)-2-chloro-3-pyridinyl)-4-fluorobenzenesulfonamide;
N-(2-chloro-5-(4-(4-(1-phenylethyl)-1-piperazinyl)-6-quinolinyl)-3-pyridinyl)-4-fluorobenzenesulfonamide;
N-(2-chloro-5-(4-(2,6-dimethyl-4-morpholinyl)-6-quinolinyl)-3-pyridinyl)-4-fluorobenzenesulfonamide;
N-(2-chloro-5-(4-(2-methoxyethoxy)-6-quinolinyl)-3-pyridinyl)-4-fluorobenzenesulfonamide;
N-(2-chloro-5-(4-(4-morpholinyl)-6-quinolinyl)-3-pyridinyl)-2-fluorobenzenesulfonamide;
2-chloro-N-(2-chloro-5-(4-(4-morpholinyl)-6-quinolinyl)-3-pyridinyl)benzenesulfonamide;
2,6-dichloro-N-(2-chloro-5-(4-(4-morpholinyl)-6-quinolinyl)-3-pyridinyl)benzenesulfonamide;
N-(2-chloro-5-(4-(2-methoxy-3-pyridinyl)-6-quinolinyl)-3-pyridinyl)-4-fluorobenzenesulfonamide;
N-(2-chloro-5-(4-phenyl-6-quinolinyl)-3-pyridinyl)-4-fluorobenzenesulfonamide;
N-(2-chloro-5-(6-cinnolinyl)-3-pyridinyl)-4-fluorobenzenesulfonamide;
N-(2-chloro-5-(6-isoquinolinyl)-3-pyridinyl)-4-fluorobenzenesulfonamide;
N-(2-chloro-5-(5-phthalazinyl)-3-pyridinyl)-4-fluorobenzenesulfonamide;
N-(2-chloro-5-(6-phthalazinyl)-3-pyridinyl)-4-fluorobenzenesulfonamide;
N-(2-chloro-5-(1,5-naphthyridin-2-yl)-3-pyridinyl)-4-fluorobenzenesulfonamide;
N-(2-chloro-5-(1,5-naphthyridin-4-yl)-3-pyridinyl)-4-fluorobenzenesulfonamide;
N-(5-(2-amino-3-oxo-3,4-dihydro-6-quinoxalinyl)-2-chloro-3-pyridinyl)-4-fluorobenzenesulfonamide;

N-(2-chloro-5-(1,8-naphthyridin-3-yl)-3-pyridinyl)-4-fluorobenzenesulfonamide;
N-(6-(6-chloro-5-(((4-methoxyphenyl)sulfonyl)amino)-3-pyridinyl)-2-quinolinyl)acetamide;
N-(5-(2-amino-6-quinolinyl)-2-chloro-3-pyridinyl)-4-methoxybenzenesulfonamide;
N-(2-chloro-5-(6-quinolinyl)-3-pyridinyl)-4-methoxybenzenesulfonamide;
N-(2-chloro-5-(2-(methylamino)-6-quinolinyl)-3-pyridinyl)-4-methoxybenzenesulfonamide;
N-(2-chloro-5-(4-(dimethylamino)-6-quinolinyl)-3-pyridinyl)-4-methoxybenzenesulfonamide;
N-(2-chloro-5-(4-(4-methoxy-1-piperidinyl)-6-quinolinyl)-3-pyridinyl)-4-methoxybenzenesulfonamide;
2-chloro-N,N-dimethyl-5-(4-(4-morpholinyl)-6-quinolinyl)-3-pyridinamine;
2-chloro-5-(4-chloro-6-quinolinyl)-N,N-dimethyl-3-pyridinamine;
2-chloro-N,N-dimethyl-5-(4-(4-(1-phenylethyl)-1-piperazinyl)-6-quinolinyl)-3-pyridinamine;
N-(2-chloro-5-(3-(1-piperidinyl)-6-quinoxalinyl)-3-pyridinyl)-4-fluorobenzenesulfonamide;
N-(2-chloro-5-(3-((2-methoxyethyl)(methyl)amino)-6-quinoxalinyl)-3-pyridinyl)-4-fluorobenzenesulfonamide;
N-(5-(3-(4-acetyl-1-piperazinyl)-6-quinoxalinyl)-2-chloro-3-pyridinyl)-4-fluorobenzenesulfonamide;
N-(2-chloro-5-(3-((2-phenoxyethyl)amino)-6-quinoxalinyl)-3-pyridinyl)-4-fluorobenzenesulfonamide;
N-(2-chloro-5-(3-(4,4-difluoro-1-piperidinyl)-6-quinoxalinyl)-3-pyridinyl)-4-fluorobenzenesulfonamide;
tert-butyl 3-(((7-(6-chloro-5-(((4-fluorophenyl)sulfonyl)amino)-3-pyridinyl)-2-quinoxalinyl)amino)methyl)-1-piperidinecarboxylate;
N-(2-chloro-5-(3-((1-(4-fluorophenyl)ethyl)amino)-6-quinoxalinyl)-3-pyridinyl)-4-fluorobenzenesulfonamide;
N-(2-chloro-5-(3-((2-(1-piperidinyl)ethyl)amino)-6-quinoxalinyl)-3-pyridinyl)-4-fluorobenzenesulfonamide;
N-(5-(3-(3-azabicyclo[3.2.2]non-3-yl)-6-quinoxalinyl)-2-chloro-3-pyridinyl)-4-fluorobenzenesulfonamide;
N-(2-chloro-5-(3-((4-methoxybenzyl)amino)-6-quinoxalinyl)-3-pyridinyl)-4-fluorobenzenesulfonamide;
N-(2-chloro-5-(3-((2-phenylethyl)amino)-6-quinoxalinyl)-3-pyridinyl)-4-fluorobenzenesulfonamide;
N-(5-(3-(benzyl(methyl)amino)-6-quinoxalinyl)-2-chloro-3-pyridinyl)-4-fluorobenzenesulfonamide;
N-(2-chloro-5-(3-((3-methoxy-1-piperidinyl)-6-quinoxalinyl)-3-pyridinyl)-4-fluorobenzenesulfonamide;
N-(2-chloro-5-(3-(2,6-dimethyl-4-morpholinyl)-6-quinoxalinyl)-3-pyridinyl)-4-fluorobenzenesulfonamide;
N-(2-chloro-5-(3-(2-(methoxymethyl)-1-pyrrolidinyl)-6-quinoxalinyl)-3-pyridinyl)-4-fluorobenzenesulfonamide;
N-(2-chloro-5-(3-(4-methoxy-1-piperidinyl)-6-quinoxalinyl)-3-pyridinyl)-4-fluorobenzenesulfonamide;
N-(2-chloro-5-(3-((cyclohexylmethyl)amino)-6-quinoxalinyl)-3-pyridinyl)-4-fluorobenzenesulfonamide;
N-(2-chloro-5-(3-((cyanomethyl)(methyl)amino)-6-quinoxalinyl)-3-pyridinyl)-4-fluorobenzenesulfonamide;
N-(2-chloro-5-(3-(1-piperazinyl)-6-quinoxalinyl)-3-pyridinyl)-4-fluorobenzenesulfonamide;
N-(2-chloro-5-(3-((2-methoxyethyl)amino)-6-quinoxalinyl)-3-pyridinyl)-4-fluorobenzenesulfonamide;
N-(2-chloro-5-(3-((3-piperidinylmethyl)amino)-6-quinoxalinyl)-3-pyridinyl)-4-fluorobenzenesulfonamide;
N-(2-chloro-5-(1,7-naphthyridin-6-yl)pyridin-3-yl)-4-fluorobenzenesulfonamide;
N-(2-Chloro-5-(8-methoxy-1,7-naphthyridin-6-yl)pyridin-3-yl)-4-fluorobenzenesulfonamide;
N-(2-chloro-5-(4-(((5-cyclopropyl-1,2,4-oxadiazol-3-yl)methyl)(ethyl)amino)-6-quinolinyl)-3-pyridinyl)methanesulfonamide;
N-(2-chloro-5-(4-((2-cyanoethyl)(ethyl)amino)-6-quinolinyl)-3-pyridinyl)methanesulfonamide;
N-(2-chloro-5-(4-((2-methoxy-2-methylpropyl)amino)-6-quinolinyl)-3-pyridinyl)methanesulfonamide;
N-(2-chloro-5-(4-(3-(2-methylphenoxy)-1-pyrrolidinyl)-6-quinolinyl)-3-pyridinyl)methanesulfonamide;
N-(2-chloro-5-(4-(2-(methoxymethyl)-1-pyrrolidinyl)-6-quinolinyl)-3-pyridinyl)methanesulfonamide;
N-(2-chloro-5-(4-(4-phenyl-1-piperidinyl)-6-quinolinyl)-3-pyridinyl)methanesulfonamide;
N-(2-chloro-5-(4-(4-(1-phenylethyl)-1-piperazinyl)-6-quinolinyl)-3-pyridinyl)methanesulfonamide;
N-(5-(4-(4-(1,3-benzodioxol-5-ylmethyl)-1-piperazinyl)-6-quinolinyl)-2-chloro-3-pyridinyl)methanesulfonamide;
N-(2-chloro-5-(4-((3-fluorobenzyl)(methyl)amino)-6-quinolinyl)-3-pyridinyl)methanesulfonamide;
N-(2-chloro-5-(4-(5-fluoro-1,3-dihydro-2H-isoindol-2-yl)-6-quinolinyl)-3-pyridinyl)methanesulfonamide;
N-(2-chloro-5-(4-((2,5-dimethoxybenzyl)amino)-6-quinolinyl)-3-pyridinyl)methanesulfonamide;
N-(2-chloro-5-(4-(4-piperidinylamino)-6-quinolinyl)-3-pyridinyl)methanesulfonamide;
N-(2-chloro-5-(4-(4-(4-pyridinylmethyl)-1-piperazinyl)-6-quinolinyl)-3-pyridinyl)-4-fluorobenzenesulfonamide;
N-(2-chloro-5-(4-(2,2-dimethyl-4-morpholinyl)-6-quinolinyl)-3-pyridinyl)methanesulfonamide;
N-(2-chloro-5-(3-((2-(4-morpholinyl)ethyl)amino)-6-quinoxalinyl)-3-pyridinyl)-4-fluorobenzenesulfonamide;
N-(2-chloro-5-(3-(4-morpholinyl)-6-quinoxalinyl)-3-pyridinyl)methanesulfonamide;
N-(2-chloro-5-(4-(3-pyridinyl)-6-quinolinyl)-3-pyridinyl)-4-fluorobenzenesulfonamide;
N-(2-chloro-5-(4-(2-chloro-4-pyridinyl)-6-quinolinyl)-3-pyridinyl)-4-fluorobenzenesulfonamide;
N-(2-chloro-5-(4-(4-hydroxy-1-azepanyl)-6-quinolinyl)-3-pyridinyl)-4-fluorobenzenesulfonamide;
N-(2-chloro-5-(4-((2R,6S)-2,6-dimethyl-4-morpholinyl)-6-quinolinyl)-3-pyridinyl)-4-fluorobenzenesulfonamide;
N-(2-chloro-5-(4-(dimethylamino)-6-quinolinyl)-3-pyridinyl)-4-fluorobenzenesulfonamide;
N-(2-chloro-5-(4-((2-methoxyethyl)amino)-6-quinolinyl)-3-pyridinyl)-4-fluorobenzenesulfonamide;
N-(2-chloro-5-(4-((2-methoxy-1-methylethyl)amino)-6-quinolinyl)-3-pyridinyl)-4-fluorobenzenesulfonamide;
N-(2-chloro-5-(4-(tetrahydro-2H-thiopyran-4-ylmethoxy)-6-quinolinyl)-3-pyridinyl)-4-fluorobenzenesulfonamide;
N-(2-chloro-5-(4-(4-morpholinyl)-6-quinolinyl)-3-pyridinyl)-3-pyridinesulfonamide;
N-(2-chloro-5-(4-(4-(dimethylamino)phenyl)-6-quinolinyl)-3-pyridinyl)-4-fluorobenzenesulfonamide;
N-(2-chloro-5-(4-((2R,6S)-2,6-dimethyl-4-morpholinyl)-6-quinolinyl)-3-pyridinyl)methanesulfonamide;
N-(2-chloro-5-(4-(2,6-dimethyl-4-morpholinyl)-6-quinolinyl)-3-pyridinyl)methanesulfonamide;
N-(2-chloro-5-(4-(2-methyl-4-pyridinyl)-6-quinolinyl)-3-pyridinyl)methanesulfonamide;
N-(2-chloro-5-(4-(2-methoxy-4-pyridinyl)-6-quinolinyl)-3-pyridinyl)methanesulfonamide;
N-(2-chloro-5-(4-(3,6-dihydro-2H-pyran-4-yl)-6-quinolinyl)-3-pyridinyl)methanesulfonamide;
N-(2-chloro-5-(4-(tetrahydro-3-thiophenyloxy)-6-quinolinyl)-3-pyridinyl)-4-fluorobenzenesulfonamide;
N-(2-chloro-5-(4-((2S,6S)-2,6-dimethyl-4-morpholinyl)-6-quinolinyl)-3-pyridinyl)methanesulfonamide;

N-(2-chloro-5-(4-((2R,6R)-2,6-dimethyl-4-morpholinyl)-6-quinolinyl)-3-pyridinyl)methanesulfonamide;

N-(2-chloro-5-(4-(2-(trifluoromethyl)-4-pyridinyl)-6-quinolinyl)-3-pyridinyl)methanesulfonamide;

N-(2-chloro-5-(4-(6-(trifluoromethyl)-3-pyridinyl)-6-quinolinyl)-3-pyridinyl)methanesulfonamide;

N-(2-Chloro-5-(4-((tetrahydro-2H-thiopyran-1,1-dioxide-4-yl)methoxy)quinolin-6-yl)pyridin-3-yl)-4-fluorobenzenesulfonamide;

N-(2-Chloro-5-(4-(tetrahydro-2H-pyran-4-yl)quinolin-6-yl)pyridin-3-yl)methanesulfonamide;

N-(2-Chloro-5-(4-(tetrahydrothiophen-1,1-dioxide-3-yloxy)quinolin-6-yl)pyridin-3-yl)-4-fluorobenzenesulfonamide;

N-(2-Chloro-5-(4-(pyridin-3-yl)quinolin-6-yl)pyridin-3-yl)methanesulfonamide;

N-(5-(4-(Pyridin-3-yl)quinolin-6-yl)-2,3'-bipyridin-3-yl)methanesulfonamide;

N-(2-Chloro-5-(4-(pyridin-4-yl)quinolin-6-yl)pyridin-3-yl)methanesulfonamide;

N-(2-Methoxy-5-(4-morpholinoquinolin-6-yl)pyridin-3-yl)methanesulfonamide;

N-(2-Methoxy-5-(4-(pyridin-4-yl)quinolin-6-yl)pyridin-3-yl)methanesulfonamide;

N-(2-Chloro-5-(3-(pyridin-4-yl)quinoxalin-6-yl)pyridin-3-yl)-4-fluorobenzenesulfonamide;

N'-(2-Chloro-5-(4-(4-morpholinyl)-6-quinolinyl)-3-pyridinyl)-N,N-dimethylsulfamide;

N'-(2-Chloro-5-(4-(4-morpholinyl)-6-quinolinyl)-3-pyridinyl)-N-(2-methoxyethyl)-N-methylsulfamide;

N-(2-chloro-5-(4-morpholinoquinolin-6-yl)pyridin-3-yl)morpholine-4-sulfonamide;

N'-(2-chloro-5-(4-chloro-6-quinolinyl)-3-pyridinyl)-N,N-dimethylsulfamide;

N'-(2-chloro-5-(4-((2-methoxyethyl)(methyl)amino)-6-quinolinyl)-3-pyridinyl)-N-(2-methoxyethyl)-N-methylsulfamide;

N-(2-Chloro-5-(2,3-dihydrobenzo[b][1,4]dioxin-6-yl)pyridin-3-yl)-4-methoxybenzenesulfonamide;

N-(2-Chloro-5-(2,3-dihydrobenzo[b][1,4]dioxin-6-yl)pyridin-3-yl)-4-fluorobenzenesulfonamide;

N-(2-Chloro-5-(3-oxo-3,4-dihydro-2H-benzo[b][1,4]oxazin-6-yl)pyridin-3-yl)-4-fluorobenzenesulfonamide;

N-(2-chloro-5-(3-oxo-4-phenyl-3,4-dihydroquinoxalin-6-yl)pyridin-3-yl)dimethylaminosulfonamide;

N-(2-chloro-5-(3-oxo-4-phenyl-3,4-dihydroquinoxalin-6-yl)pyridin-3-yl) 2-methoxy-N-methylethanaminosulfonamide;

N-(2-chloro-5-(4-(6-methoxypyridin-3-yl)-3-oxo-3,4-dihydroquinoxalin-6-yl)pyridin-3-yl)dimethylaminosulfonamide;

N-(2-chloro-5-(3-oxo-4-(3-(trifluoromethyl)phenyl)-3,4-dihydroquinoxalin-6-yl)pyridin-3-yl)dimethylaminosulfonamide;

N-(2-chloro-5-(3-oxo-4-(3-(trifluoromethyl)phenyl)-3,4-dihydroquinoxalin-6-yl)pyridin-3-yl) 2-methoxy-N-methylethanamino sulfonamide;

N-(2-Chloro-5-(7,8-dihydro-1,6-naphthyridin-6(5H)-yl)pyridin-3-yl)-4-fluorobenzenesulfonamide;

N'-(2-Chloro-5-(4-(4-morpholinyl)-7,8-dihydro-1,6-naphthyridin-6(5H)-yl)-3-pyridinyl)-N,N-dimethylsulfamide; or N-(2-chloro-5-(5-oxo-1,6-naphthyridin-6(5H)-yl)-3-pyridinyl)-4-fluorobenzenesulfonamide.

DETAILED DESCRIPTION OF THE INVENTION

The present invention relates to compounds of Formula I

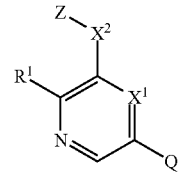

or a pharmaceutically acceptable salt thereof, as defined in the various embodiments above.

The present invention also provides pharmaceutical compositions comprising a compound of Formula I, and methods of treating diseases or conditions, such as cancer, using a compound of Formula I.

The term "alkyl" means a straight or branched chain hydrocarbon. Representative examples of alkyl groups include methyl, ethyl, propyl, isopropyl, butyl, isobutyl, tert-butyl, sec-butyl, pentyl and hexyl. Typical alkyl groups are alkyl groups having from 1 to 8 carbon atoms, which groups are commonly represented as $C_{1-8}$alkyl.

The term "alkoxy" means an alkyl group bonded to an oxygen atom. Representative examples of alkoxy groups include methoxy, ethoxy, tert-butoxy, propoxy and isobutoxy. Common alkoxy groups are $C_{1-8}$alkoxy.

The term "halogen" means chlorine, fluorine, bromine or iodine.

The term "alkenyl" means a branched or straight chain hydrocarbon having one or more carbon-carbon double bonds. Representative examples alkenyl groups include ethenyl, propenyl, allyl, butenyl and 4-methylbutenyl. Common alkenyl groups are $C_{2-8}$alkenyl.

The term "alkynyl" means a branched or straight chain hydrocarbon having one or more carbon-carbon triple bonds. Representative examples of alkynyl groups include ethynyl, propynyl (propargyl) and butynyl. Common alkynyl groups are $C_{2-8}$ alkynyl.

The term "cycloalkyl" means a cyclic, nonaromatic hydrocarbon. Examples of cycloalkyl groups include cyclopropyl, cyclobutyl, cyclopentyl, cyclohexyl and cycloheptyl. A cycloalkly group can contain one or more double bond. Examples of cycloalkyl groups that contain double bonds include cyclopentenyl, cyclohexenyl, cyclohexadienyl and cyclobutadienyl. Common cycloalkyl groups are $C_{3-8}$ cycloalkyl groups.

The term "perfluoroalkyl" means an alkyl group in which all of the hydrogen atoms have been replaced with fluorine atoms. Common perfluoroalkyl groups are $C_{1-8}$perfluoroalkyl. An example of a common perfluoroalkyl group is $CF_3$.

The term "acyl" means a group derived from an organic acid by removal of the hydroxy group (—OH). For example, the acyl group $CH_3C(\!=\!O)$— is formed by the removal of the hydroxy group from $CH_3C(\!=\!O)OH$.

The term "aryl" means a cyclic, aromatic hydrocarbon. Examples of aryl groups include phenyl and naphthyl. Common aryl groups are six to thirteen membered rings.

The term "heteroatom" as used herein means an oxygen, nitrogen or sulfur atom.

The term "heteroaryl" means a cyclic, aromatic hydrocarbon in which one or more carbon atoms of an aryl group have been replaced with a heteroatom. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, indolyl, triazolyl, pyridazinyl, indazolyl, purinyl, quinolizinyl, isoquinolyl, quinolyl, naphthyridinyl, quinoxalinyl, isothiazolyl and benzo[b]thienyl. Common heteroaryl groups are five to thirteen membered rings that contain from 1 to 4 heteroatoms. Heteroaryl groups that are five and six membered rings that contain 1 to 3 heterotaoms are particularly common.

The term "heterocycloalkyl" means a cycloalkyl group in which one or more of the carbon atoms has been replaced with a heteroatom. If the heterocycloalkyl group contains more than one heteroatom, the heteroatoms may be the same or different. Examples of heterocycloalkyl groups include tetrahydrofuryl, morpholinyl, piperazinyl, piperidinyl and pyrrolidinyl. It is also possible for the heterocycloalkyl group to have one or more double bonds, but is not aromatic. Examples of heterocycloalkyl groups containing double bonds include dihydrofuran. Common heterocycloalkyl groups are three to ten membered rings containing from 1 to 4 heteroatoms. Heterocycloalkyl groups that are five and six membered rings that contain 1 to 3 heterotaoms are particularly common.

It is also noted that the cyclic ring groups, i.e., aryl, heteroaryl, cycloalkyl, and heterocycloalkyl, can comprise more than one ring. For example, the naphthyl group is a fused bicyclic ring system. It is also intended that the present invention include ring groups that have bridging atoms, or ring groups that have a spiro orientation.

Representative examples of five to six membered aromatic rings, optionally having one or two heteroatoms, are phenyl, furyl, thienyl, pyrrolyl, oxazolyl, thiazolyl, imidazolyl, pyrazolyl, isoxazolyl, isothiazolyl, pyridinyl, pyridiazinyl, pyrimidinyl, and pyrazinyl.

Representative examples of partially saturated, fully saturated or fully unsaturated five to eight membered rings, optionally having one to three heteroatoms, are cyclopentyl, cyclohexyl, cycloheptyl, cyclooctyl and phenyl. Further exemplary five membered rings are furyl, thienyl, pyrrolyl, 2-pyrrolinyl, 3-pyrrolinyl, pyrrolidinyl, 1,3-dioxolanyl, oxazolyl, thiazolyl, imidazolyl, 2H-imidazolyl, 2-imidazolinyl, imidazolidinyl, pyrazolyl, 2-pyrazolinyl, pyrazolidinyl, isoxazolyl, isothiazolyl, 1,2-dithiolyl, 1,3-dithiolyl, 3H-1,2-oxathiolyl, 1,2,3-oxadizaolyl, 1,2,4-oxadiazolyl, 1,2,5-oxadiazolyl, 1,3,4oxadiazolyl, 1,2,3-triazolyl, 1,2,4-trizaolyl, 1,3,4-thiadiazolyl, 3H-1,2,3-dioxazolyl, 1,2,4-dioxazolyl, 1,3,2-dioxazolyl, 1,3,4-dioxazolyl, 5H-1,2,5-oxathiazolyl, and 1,3-oxathiolyl.

Further exemplary six membered rings are 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyndazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-oxathiazinyl, and 1,4,2-oxadiazinyl.

Further exemplary seven membered rings are azepinyl, oxepinyl, thiepinyl and 1,2,4-triazepinyl.

Further exemplary eight membered rings are cyclooctyl, cyclooctenyl and cyclooctadienyl.

Exemplary bicyclic rings consisting of two fused partially saturated, fully saturated or fully unsaturated five and/or six membered rings, optionally having one to four heteroatoms, are indolizinyl, indolyl, isoindolyl, indolinyl, cyclopenta(b)pyridinyl, pyrano(3,4-b)pyrrolyl, benzofuryl, isobenzofuryl, benzo(b)thienyl, benzo(c)thienyl, 1H-indazolyl, indoxazinyl, benzoxazolyl, anthranilyl, benzimidazolyl, benzthiazolyl, purinyl, quinolinyl, isoquinolinyl, cinnolinyl, phthalazinyl, quinazolinyl, quinoxalinyl, 1,8-naphthyridinyl, pteridinyl, indenyl, isoindenyl, naphthyl, tetralinyl, decalinyl, 2H-1-benzopyranyl, pyrido(3,4-b)pyridinyl, pyrido(3,2-b)pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

A cyclic ring group may be bonded to another group in more than one way. If no particular bonding arrangement is specified, then all possible arrangements are intended. For example, the term "pyridyl" includes 2-, 3-, or 4-pyridyl, and the term "thienyl" includes 2-, or 3-thienyl.

The term "substituted" means that a hydrogen atom on a molecule or group is replaced with a group or atom. Typical substituents include: halogen, $C_{1-8}$alkyl, hydroxyl, $C_{1-8}$alkoxy, —$NR^xR^x$, nitro, cyano, halo or perhalo$C_{1-8}$alkyl, $C_{2-8}$alkenyl, $C_{2-8}$alkynyl, —$SR^x$, —$S(=O)_2R^x$, —$C(=O)OR^x$, —$C(=O)R^x$, wherein each l'e is independently hydrogen or $C_1$-$C_8$ alkyl. It is noted that when the substituent is —$NR^xR^x$, the $R^x$ groups may be joined together with the nitrogen atom to form a ring.

A group or atom that replaces a hydrogen atom is also called a substituent.

Any particular molecule or group can have one or more substituent depending on the number of hydrogen atoms that can be replaced.

The symbol "—" represents a covalent bond and can also be used in a group to indicate the point of attachment to another group.

The term "therapeutically effective amount" means an amount of a compound that ameliorates, attenuates or eliminates one or more symptom of a particular disease or condition, or prevents or delays the onset of one of more symptom of a particular disease or condition.

The term "patient" means animals, such as dogs, cats, cows, horses, sheep and humans. Particular patients are mammals. The term patient includes males and females.

The term "pharmaceutically acceptable" means that the referenced substance, such as a compound of Formula I, a salt of a compound of Formula I, a formulation containing a compound of Formula I, or a particular excipient, are suitable for administration to a patient.

The terms "treating", "treat" or "treatment" and the like include preventative (e.g., prophylactic) and palliative treatment.

The term "excipient" means any pharmaceutically acceptable additive, carrier, diluent, adjuvant, or other ingredient, other than the active pharmaceutical ingredient (API), which is typically included for formulation and/or administration to a patient.

The compounds of the present invention are administered to a patient in a therapeutically effective amount. The compounds can be administered alone or as part of a pharmaceutically acceptable composition or formulation. In addition, the compounds or compositions can be administered all at once, as for example, by a bolus injection, multiple times, such as by a series of tablets, or delivered substantially uniformly over a period of time, as for example, using transdermal delivery. It is also noted that the dose of the compound can be varied over time.

In addition, the compounds of the present invention can be administered alone, in combination with other compounds of the present invention, or with other pharmaceutically active compounds. The other pharmaceutically active compounds can be intended to treat the same disease or condition as the compounds of the present invention or a different disease or condition. If the patient is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions may be different forms. For example, one or more compound may be delivered via a tablet, while another is administered via injection or orally as a syrup. All combinations, delivery methods and administration sequences are contemplated.

Since one aspect of the present invention contemplates the treatment of the disease/conditions with a combination of pharmaceutically active agents that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes and bags. Typically, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing physician or veterinarian.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc . . . Second Week, Monday, Tuesday, . . . " etc. Other variations of memory aids will be readily apparent. A "daily dose" can be a single tablet or capsule or several pills or capsules to be taken on a given day. Also, a daily dose of a compound of the present invention can consist of one tablet or capsule, while a daily dose of the second compound can consist of several tablets or capsules and vice versa. The memory aid should reflect this and aid in correct administration of the active agents.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of the present invention and other pharmaceutically active agents, if desired, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. All methods that are used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and non-aqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof In the case of capsules, and tablets, the dosage forms may also comprise buffering agents.

Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. They may also contain opacifying agents, and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferable suppositories, which can be prepared by mixing the compounds of the present invention with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

Dosage forms for topical administration of a compound of the present invention include ointments, powders, sprays and inhalants. The active compound or fit compounds are admixed under sterile condition with a physiologically acceptable carrier, and any preservatives, buffers, or propellants that may be required. Opthalmic formulations, eye ointments, powders, and solutions are also contemplated as being within the scope of this invention.

The compounds of the present invention can be administered to a patient at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that can be used depends on a number of factors, including the requirements of the patient, the severity of the condition or disease being treated, and the pharmacological activity of the compound being administered. The determination of dosage ranges and optimal dosages for a particular patient is within the ordinary skill in the art.

The compounds of the present invention can be administered as pharmaceutically acceptable salts, esters, amides or prodrugs. The term "salts" refers to inorganic and organic salts of compounds of the present invention. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," J Pharm Sci, 66: 1-19 (1977).

Examples of pharmaceutically acceptable esters of the compounds of the present invention include $C_1$-$C_8$ alkyl esters. Acceptable esters also include $C_5$-$C_7$ cycloalkyl esters, as well as arylalkyl esters such as benzyl. $C_1$-$C_4$ alkyl esters are commonly used. Esters of compounds of the present invention may be prepared according to methods that are well known in the art.

Examples of pharmaceutically acceptable amides of the compounds of the present invention include amides derived from ammonia, primary $C_1$-$C_8$ alkyl amines, and secondary $C_1$-$C_8$ dialkyl amines In the case of secondary amines, the amine may also be in the form of a 5 or 6 membered heterocycloalkyl group containing at least one nitrogen atom. Amides derived from ammonia, $C_1$-$C_3$ primary alkyl amines and $C_1$-$C_2$ dialkyl secondary amines are commonly used. Amides of the compounds of the present invention may be prepared according to methods well known to those skilled in the art.

The term "prodrug" means compounds that are transformed in vivo to yield a compound of the present invention. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

To illustrate, if the compound of the invention contains a carboxylic add functional group, a prodrug can comprise an ester formed by the replacement of the hydrogen atom of the add group with a group such as ($C_1$-$C_8$ alkyl, ($C_2$-$Cl_2$)alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)aminomethyl having from 4 to 10 carbon atoms, 3-phthalidyl, 4-crotonolactonyl, gamma-butyrolacton-4-yl, di-N, N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_2$-$_3$)alkyl.

Similarly, if a compound of the present invention comprises an alcohol functional group, a prodrug can be formed by the replacement of the hydrogen atom of the alcohol group with a group such as ($C_1$-$C_6$)alkanoyloxymethyl, 1-(($C_1$-$C_6$) alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$alkoxycarbonylaminomethyl, succinoyl, ($C_1$-$C_6$)alkanoyl, α-amino($C_1$-$C_4$)alkanoyl, arylacyl and α-aminoacyl, or α-aminoacyl-α-aminoacyl, where each α-aminoacyl group is independently selected from the naturally occurring L-amino acids, —P(O)(OH)$_2$, —P(O)(O($C_1$-$C_6$)alkyl)$_2$ or glycosyl (the radical resulting from the removal of a hydroxyl group of the hemiacetal form of a carbohydrate).

The compounds of the present invention may contain asymmetric or chiral centers, and therefore, exist in different stereoisomeric forms. It is contemplated that all stereoisomeric forms of the compounds as well as mixtures thereof, including racemic mixtures, form part of the present invention. In addition, the present invention contemplates all geometric and positional isomers. For example, if the compound contains a double bond, both the cis and trans forms (designated as S and E, respectively), as well as mixtures, are contemplated.

Mixture of stereoisomers, such as diastereomeric mixtures, can be separated into their individual stereochemical components on the basis of their physical chemical differences by known methods such as chromatography and/or fractional crystallization. Enantiomers can can also be separated by converting the enantiomeric mixture into a diasteromeric mixture by reaction with an appropriate optically active compound (e.g., an alcohol), separating the diastereomers and converting (e.g., hydrolyzing) the individual diastereomers to the corresponding pure enantiomers. Also, some compounds may be atropisomers (e.g., substituted biaryls).

The compounds of the present invention may exist in unsolvated as well as solvated forms with pharmaceutically acceptable solvents such as water (hydrate), ethanol, and the like. The present invention contemplates and encompasses both the solvated and unsolvated forms.

It is also possible that compounds of the present invention may exist in different tautomeric forms. All tautomers of compounds of the present invention are contemplated. For example, all of the tautomeric forms of the imidazole moiety are included in this invention. Also, for example, all keto-enol or imine-enamine forms of the compounds are included in this invention.

Those skilled in the art will recognize that the compound names and structures contained herein may be based on a particular tautomer of a compound. While the name or structure for only a particular tautomer may be used, it is intended that all tautomers are encompassed by the present invention, unless stated otherwise.

It is also intended that the present invention encompass compounds that are synthesized in vitro using laboratory techniques, such as those well known to synthetic chemists; or synthesized using in vivo techniques, such as through metabolism, fermentation, digestion, and the like. It is also contemplated that the compounds of the present invention may be synthesized using a combination of in vitro and in vivo techniques.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{16}O$, $^{17}O$, $^{31}P$, $^{32}P$, $^{35}S$, $^{18}F$, and $^{36}Cl$.

Compounds of the present invention that contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detection. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of this invention can generally be prepared by substituting a readily available isotopically labelled reagent for a non-isotopically labelled reagent.

The compounds of the present invention may exist in various solid states including crystalline states and as an amorphous state. The different crystalline states, also called polymorphs, and the amorphous states of the present compounds are contemplated as part of this invention.

In synthesizing compounds of the present invention, it may be desirable to use certain leaving groups. The term "leaving groups" ("LG") generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxsuccinimide, N-hydroxybenzotriazole, and the like. Examples of nucleophiles include, but are not limited to, amines, thiols, alcohols, Grignard reagents, anionic species (e.g., alkoxides, amides, carbanions) and the like.

The compounds of the present invention are useful for the treatment of PI3K mediated diseases and disorders including melanomas, carcinomas, and other cancers. In one embodiment of the invention, there is provided a method of modulating a PI3K enzyme in a patient, the method comprising administering to a patient in need thereof a therapeutically effective amount of a compound of Formula I, or a pharmaceutically acceptable salt thereof The present invention also concerns the use of a compound of Formula I, or a pharmaceutically acceptable salt thereof, for the manufacture of a medicament for the treatment of a PI3K mediated disease such as cancer.

The term "patient in need thereof" means a patient who has or is at risk of having a PI3K mediated disease or condition.

The term "cancer" means a physiological condition in mammals that is characterized by unregulated cell growth. General classes of cancers include carcinomas, lymphomas, sarcomas, and blastomas.

The compounds of the present invention can be used to treat cancer. The methods of treating a cancer comprise administering to a patient in need thereof a therapeutically effective amount of a compound of Formula I or a pharmaceutically acceptable salt thereof.

Cancers which may be treated with compounds of the present invention include, without limitation, carcinomas such as cancer of the bladder, breast, colon, rectum, kidney, liver, lung (small cell lung cancer, and non-small-cell lung cancer), esophagus, gall-bladder, ovary, pancreas, stomach, cervix, thyroid, prostate, and skin (including squamous cell carcinoma); hematopoietic tumors of lymphoid lineage (including leukemia, acute lymphocitic leukemia, chronic lyelogenous leukemia, acute lymphoblastic leukemia, B-cell lymphoma, T-cell-lymphoma, Hodgkin's lymphoma, non-Hodgkin's lymphoma, hairy cell lymphoma and Burkett's lymphoma); hematopoietic tumors of myeloid lineage (including acute and chronic myelogenous leukemias, myelodysplastic syndrome and promyelocytic leukemia); tumors of mesenchymal origin (including fibrosarcoma and rhabdomyosarcoma, and other sarcomas, e.g., soft tissue and bone); tumors of the central and peripheral nervous system (including astrocytoma, neuroblastoma, glioma and schwannomas); and other tumors (including melanoma, seminoma, teratocarcinoma, osteosarcoma, xenoderoma pigmentosum, keratoctanthoma, thyroid follicular cancer and Kaposi's sarcoma). Other cancers that can be treated with a compound of the present invention include endometrial cancer, head and neck cancer, glioblastoma, malignant ascites, and hematopoietic cancers.

The compounds of the present invention can also be used to treat hyperproliferative disorders such as thyroid hyperplasia (especially Grave's disease), and cysts (such as hypervascularity of ovarian stroma, characteristic of polycystic ovarian syndrome (Stein-Leventhal syndrome)).

The compounds of Formula I may also be administered in combination with one or more additional pharmaceutically active compounds/agents. In a particular embodiment, the additional pharmaceutically active agent is an agent that can be used to treat a cancer. For example, an additional pharmaceutically active agent can be selected from antineoplastic agents, anti-angiogenic agents, chemotherapeutic agents and peptidal cancer therapy agents. In yet another embodiment, the antineoplastic agents are selected from antibiotic-type agents, alkylating agents, antimetabolite agents, hormonal agents, immunological agents, interferon-type agents, kinase inhibitors, miscellaneous agents and combinations thereof It is noted that the additional pharmaceutically active compounds/agents may be a traditional small organic chemical molecules or can be macromolecules such as a proteins, antibodies, peptibodies, DNA, RNA or fragments of such macromolecules.

Examples of specific pharmaceutically active agents that can be used in the treatment of cancers and that can be used in combination with one or more compound of the present invention include: methotrexate; tamoxifen; fluorouracil; 5-fluorouracil; hydroxyurea; mercaptopurine; cisplatin; carboplatin; daunorubicin; doxorubicin; etoposide; vinblastine; vincristine; pacitaxel; thioguanine; idarubicin; dactinomycin; imatinib; gemcitabine; altretamine; asparaginase; bleomycin; capecitabine; carmustine; cladibrine; cyclophosphamine; cytarabine; decarazine; docetaxel; idarubicin; ifosfamide; irinotecan; fludarabine; mitosmycin; mitoxane; mitoxantrone; topotecan; vinorelbine; adriamycin; mithram; imiquimod; alemtuzmab; exemestane; bevacizumab; cetuximab; azacitidine; clofarabine; decitabine; desatinib; dexrazoxane; docetaxel; epirubicin; oxaliplatin; erlotinib; raloxifene; fulvestrant; letrozole; gefitinib; gemtuzumab; trastuzumab; gefitinib; ixabepilone; lapatinib; lenalidomide; aminolevulinic acid; temozolomide; nelarabine; sorafenib; nilotinib; pegaspargase; pemetrexed; rituximab; dasatinib; thalidomide; bexarotene; temsirolimus; bortezomib; vorinostat; capecitabine; zoledronic acid; anastrozole; sunitinib; aprepitant and nelarabine, or a pharmaceutically acceptable salt thereof Additional pharmaceutically active agents that can be used in the treatment of cancers and that can be used in combination with one or more compound of the present invention include: epoetin alfa; darbepoetin alfa; panitumumab; pegfilgrastim; palifermin; filgrastim; denosumab; ancestim; AMG 102; AMG 386; AMG 479; AMG 655; AMG 745; AMG 951; and AMG 706, or a pharmaceutically acceptable salt thereof.

The compounds of the present invention can also be used in combination with pharmaceutically active agents that treat nausea. Examples of agents that can be used to treat nausea include: dronabinol; granisetron; metoclopramide; ondansetron; and prochlorperazine; or a pharmaceutically acceptable salt thereof.

In addition, the compounds of the present invention can be used in combination with other agents that can be used to treat cancer such as acemannan; aclarubicin; aldesleukin; alitretinoin; amifostine; amrubicin; amsacrine; anagrelide; arglabin; arsenic trioxide; BAM 002 (Novelos); bicalutamide; broxuridine; celmoleukin; cetrorelix; cladribine; clotrimazole; DA 3030 (Dong-A); daclizumab; denileukin diftitox; deslorelin; dilazep; docosanol; doxercalciferol; doxifluridine; bromocriptine; cytarabine; HIT diclofenac; interferon alfa; tretinoin; edelfosine; edrecolomab; eflornithine; emitefur; epirubicin; epoetin beta; etoposide phosphate; exisulind; fadrozole; finasteride; fludarabine phosphate; formestane; fotemustine; gallium nitrate; gemtuzumab zogamicin; gimeracil/oteracil/tegafur combination; glycopine; goserelin; heptaplatin; human chorionic gonadotropin; human fetal alpha fetoprotein; ibandronic acid; interferon alfa; interferon alfa natural; interferon alfa-2; interferon alfa-2a; interferon alfa-2b; interferon alfa-N1; interferon alfa-n3; interferon alfacon-1; interferon alpha natural; interferon beta; interferon beta-1a; interferon beta-1b; interferon gamma natural; interferon gamma-1a; interferon gamma-1b; interleukin-1 beta; iobenguane; irsogladine; lanreotide; LC 9018 (Yakult); leflunomide; lenograstim; lentinan sulfate; letrozole; leukocyte alpha interferon; leuprorelin; levamisole+fluorouracil; liarozole; lobaplatin; lonidamine; lovastatin; masoprocol; melarsoprol; metoclopramide; mifepristone; miltefosine; mirimostim; mismatched double stranded RNA; mitoguazone; mitolactol; mitoxantrone; molgramostim; nafarelin; naloxone+pentazocine; nartograstim; nedaplatin; nilutamide; noscapine; novel erythropoiesis stimulating protein; NSC 631570 octreotide; oprelvekin; osaterone; paclitaxel; pamidronic acid; peginterferon alfa-2b; pentosan polysulfate sodium; pentostatin; picibanil; pirarubicin; rabbit antithymocyte polyclonal antibody; polyethylene glycol interferon alfa-2a; porfimer sodium; raltitrexed; rasburicase; rhenium Re 186 etidronate; RII retinamide; romurtide; samarium (153 Sm) lexidronam; sargramostim; sizofiran; sobuzoxane; sonermin; strontium-89 chloride; suramin; tasonermin; tazarotene; tegafur; temoporfin; teniposide; tetrachlorodecaoxide; thymalfasin; thyrotropin alfa; toremifene; tositumomab-iodine 131; treosulfan; tretinoin; trilostane; trimetrexate; triptorelin; tumor necrosis factor alpha natural; ubenimex; bladder cancer vaccine; Maruyama vaccine; melanoma lysate vaccine; valrubicin; verteporfin; virulizin; zinostatin stimalamer; abarelix; AE 941 (Aeterna); ambamustine; antisense oligonucleotide; bcl-2 (Genta); APC 8015 (Dendreon); dexaminoglutethimide; diaziquone; EL 532 (Elan); EM 800 (Endorecherche); eniluracil; etanidazole; fenretinide; filgrastim SD01 (Amgen); galocitabine; gastrin 17 immunogen; HLA-B7 gene therapy (Vical); granulocyte macrophage colony stimulating factor; histamine dihydrochloride; ibritumomab tiuxetan; ilomastat; IM 862 (Cytran); interleukin-2; iproxifene; LDI 200 (Milkhaus); leridistim; lintuzumab; CA 125 monoclonal antibody(MAb) (Biomira); cancer MAb (Japan Pharmaceutical Development); HER-2 and Fc MAb (Medarex); idiotypic 105AD7 MAb (CRC Technology); idiotypic CEA MAb (Trilex); LYM-1-iodine 131 MAb (Techniclone); polymorphic epithelial mucin-yttrium 90 MAb (Antisoma); marimastat; menogaril; mitumomab; motexafin gadolinium; MX 6 (Galderma); nolatrexed; P 30 protein; pegvisomant; porfiromycin; prinomastat; RL 0903 (Shire); rubitecan; satraplatin; sodium phenylacetate; sparfosic acid; SRL 172 (SR Pharma); SU 5416 (SUGEN); TA 077 (Tanabe); tetrathiomolybdate; thaliblastine; thrombopoietin; tin ethyl etiopurpurin; tirapazamine; cancer vaccine (Biomira); melanoma vaccine (New York University); melanoma vaccine (Sloan Kettering Institute); melanoma oncolysate vaccine (New York Medical College); viral melanoma cell lysates vaccine (Royal Newcastle Hospital); or valspodar. It is noted that the agents recited above may also be administered as pharmaceutically acceptable salts when appropriate.

The compounds of the present invention may also be used in combination with radiation therapy, hormone therapy, surgery and immunotherapy, which therapies are well know to those skilled in the art.

All patents and other publications recited herein are hereby incorporated by reference.

EXAMPLES

The examples presented below illustrate specific embodiments of the present invention. These examples are meant to be representative and are not intended to limit the scope of the claims in any manner The starting materials for the specific examples below are generally available from commercial sources, unless otherwise specified. When helpful, commercial sources may be specifically indicated.

Analytical Methods:

Unless otherwise indicated, HPLC analyses were run on an Agilent Model 1100 system with an Agilent Technologies Zorbax SB—$C_8$(5µ) reverse phase column (4.6×150 mm) run at 30° C. with a flow rate of about 1.50 mL/min (Agilent Technologies, Santa Clara, Calif.). The mobile phase used solvent A ($H_2O$/0.1% TFA) and solvent B (ACN/0.1% TFA) with a 11 min gradient from 5% to 100% ACN. The gradient was followed by a 2 mM. return to 5% ACN and about a 2.5 min. re-equilibration (flush). It is noted that all percents (%) used herein are by weight with respect to the total weight.

LC-MS Methods:

Samples were run on an Agilent model-1100 LC-MSD system with an Agilent Technologies XDB-$C_8$ (3.5µ) reverse phase column (4.6×75 mm) at 30° C. The flow rate was constant and ranged from about 0.75 mL/min to about 1.0 mL/min.

The mobile phase used a mixture of solvent A ($H_2O$/0.1% HOAc) and solvent B (ACN/0.1% HOAc) with a 9 min time period for a gradient from 10% to 90% solvent B. The gradient was followed by a 0.5 min period to return to 10% solvent B and a 2.5 min 10% solvent B re-equilibration (flush) of the column.

Preparative HPLC Methods:

Where indicated, compounds of the present invention were purified via reverse phase HPLC using a Gilson workstation (Gilson, Middleton, Wis.) utilizing one of the following two columns and methods:(A) Using a 50×100 mm column (Waters, Exterra, C18, 5µ) (Waters, Milford, Mass.) at 50 mL/min. The mobile phase used was a mixture of solvent A ($H_2O$/10 mM ammonium carbonate at pH about 10, adjusted with conc. $NH_4OH$) and solvent B (85:15 ACN/water, 10 mM ammonium carbonate at pH of about 10 adjusted with conc. $NH_4OH$). Each purification run utilized a 10 min gradient from 40% to 100% solvent B followed by a 5 mM flow of 100% solvent B. The gradient was followed by a 2 min return to 40% solvent B.

(B) Using a 20×50 mm column at 20 mL/min. The mobile phase used was a mixture of solvent A ($H_2O$/0.1% TFA) and solvent B (ACN/0.1% TFA) with a 10 min gradient from 5% to 100% solvent B. The gradient is followed by a 2 min return to 5% ACN.

Proton NMR Spectra:

Unless otherwise indicated, all $^1H$ NMR spectra were run on a Varian (Varian, Palo Alto, Calif.) series Mercury 300 MHz instrument or a Bruker (Bruker, Bilerica, Mass.) series 400 MHz instrument. Where so characterized, all observed protons are reported as parts-per-million (ppm) downfield from tetramethylsilane (TMS) or other internal reference in the appropriate solvent indicated.

Mass Spectra (MS)

Unless otherwise indicated, all mass spectral data for starting materials, intermediates and/or exemplary compounds are reported as mass/charge (m/z), having an (M+H$^+$) molecular ion. The molecular ion reported was obtained by electrospray detection method. Compounds having an isotopic atom, such as bromine and the like, are reported according to the detected isotopic pattern, as appreciated by those skilled in the art.

The following abbreviations may be used herein:
ACN acetonitrile
TFA trifluoroacetic acid
TFAA trifluoroacetic anhydride
Ts tosyl
DTT dithiothreitol
ATP adenosine 5'-triphosphate
PIP2 phosphatidylinositol bisphosphate
FBS fetal bovine serum
$Ac_2O$ acetic anhydride
DMAP dimethyl aminopyridine
rt or RT room temperature
LCMS, LC-MS or LC/MS liquid chromatography mass spectroscopy
NMR nuclear magnetic resonance
aq aqueous
py or pyr pyridine
TsCl para-toluene sulfonyl chloride
MS mass spectra
ESI electrospray ionization
m/z mass divided by charge
TS toluene sulfonyl
$iPr_2NEt$ N-ethyl diisopropylamine
HPLC high pressure liquid chromatography
TMS tetramethylsilane
iPrOH isopropyl alchohol
PG protecting group
DCM dichloromethane
DMSO dimethyl sulfoxide
DMF N,N-dimethylformamide
THF tetrahydrofuran
$Et_2O$ diethyl ether
EtOAc ethyl acetate
MeOH methyl alcohol
EtOH ethyl alcohol
MeCN acetonitrile
MeI iodomethane
NMP 1-methyl-2-pyrrolidinone
DCM dichloromethane
TFA trifuoroacetic acid
Sat. saturated
h hour
min minutes
mL milliliters
g grams
mg milligrams
HOAc acetic acid
Conc. concentrated
Pos. ion positive ion
KOAc potaisum hydroxyacetate
DME dimethyl ether
IPA or iPrOH isopropyl alcohol
Calc'd calculated
Hex hexanes
MsCl mesylchloride
$Et_3N$ triethylamine
wt weight Percents of reagents specified in the examples below are percent by volume, unless indicated otherwise General Synthetic Schemes Methods for preparing compounds of Formula I is described in Scheme 1 wherein Z, $X^2$, $X^1$, $R^1$ and Q are as defined herein. A halide such as 1 can be converted to the corresponding boronate 2, in the form of either a boronic ester or a boronic acid, when reacted with a diborane such as bis(pinacolato)diboron in the presence of a catalyst such as Pd(dppf)Cl$_2$ and a base such as KOAc in a suitable solvent, typically dioxane, DME, DMSO, or DMF at elevated temperature. The transformation 1 to 2 is similarly applicable to bromide 3 and trifluoromethanesulfonate 4 to give boronate 5. Standard Suzuki couplings (Miyaura, N.; Suzuki, A. *Chem. Rev.* 1995, 95, 2457-2483) between 2 and 3 or 4, or between 5 and 1 will give a compound of Formula I. A typical Suzuki coupling may involve agitating a mixture of the reacting partners with a catalyst such as Pd(dppf)Cl$_2$, Pd(PPh$_3$)$_4$, or mobilized palladium such as Pd-fibrecat, a base such as Na$_2$CO$_3$, in a polar solvent such as dioxane, or DME and water under an inert atmosphere. The reaction may be heated with either a conventional heating bath or under microwave irradiation.

Alternative coupling methods may be used for the synthesis of compounds of Formula I. For example, bromide 1 can be converted to a zincate either through transmetallation from the corresponding Grinard species, or by reacting with activated zinc. The resulting zincate can undergo a Negishi type of coupling (Negishi, E.-I. *Acc. Chem. Res.* 1982, 15, 340) with a bromide such as 3, in the presence of a catalyst to give a compound of Formula I.

SCHEME 1

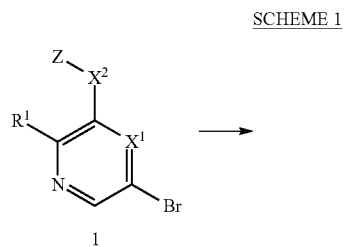

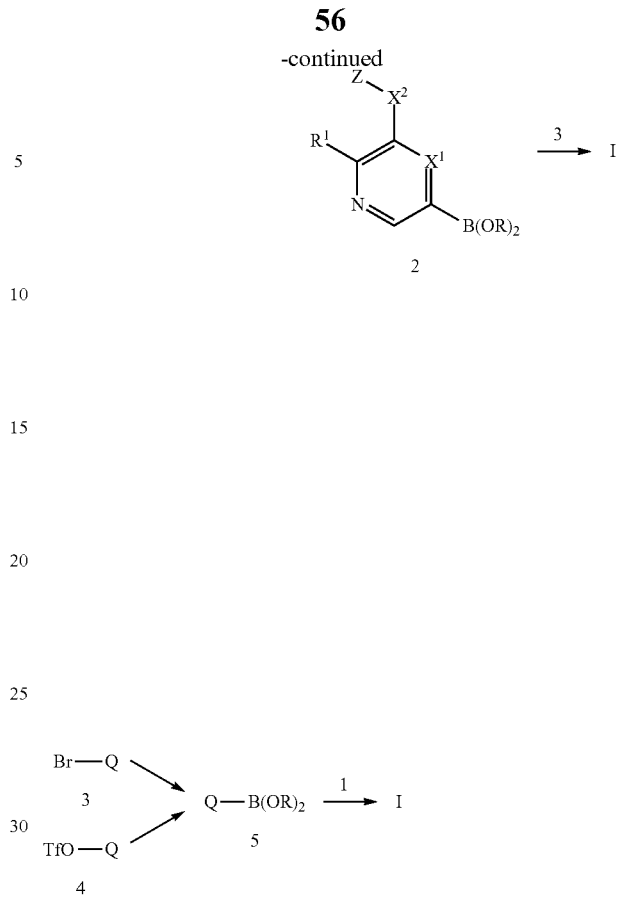

The method described in Scheme 1 may tolerate functional groups that are useful for further transformations. For example as shown in Scheme 2, an amino group such as in 1A may be present for the transformation 1A to 2A to I-A and then be functionalized as a sulfonamide such as I-B. Similarly, 6-bromo-4-chloroquinoline (3A) undergoes boronation selectively at the C—Br bond to give 3B without compromising the C—Cl bond. The C—Cl bond can withstand the subsequent Suzuki coupling leading to I-C and finally can be converted to I-D under another Suzuki condition. Alternatively, 3A can react with nucleophiles such as morpholine at the C—Cl bond to give a functionalized bromide 3C which can then be subjected to Suzuki coupling with 2.

SCHEME 2

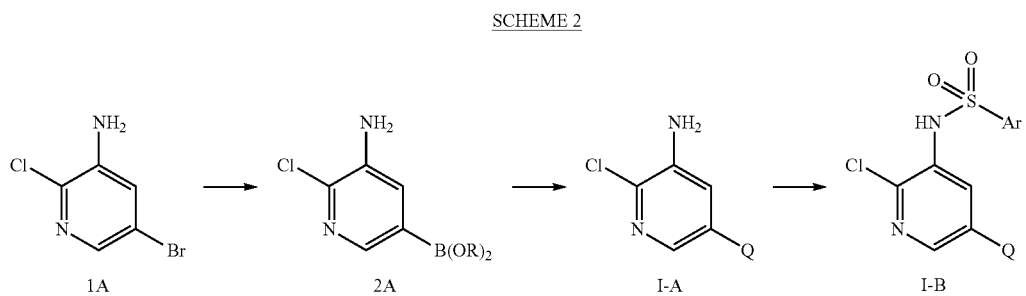

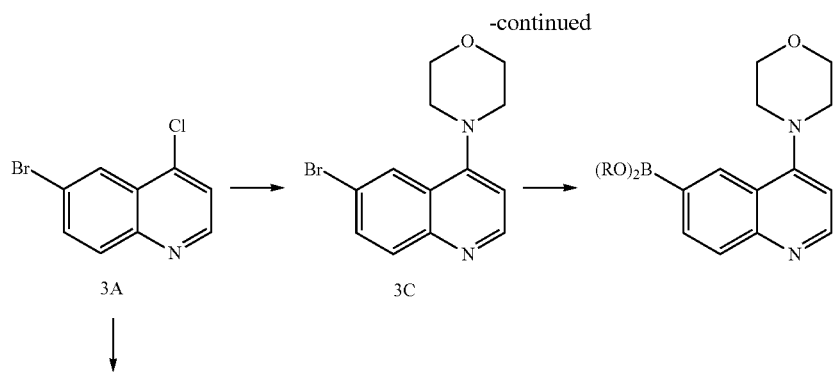

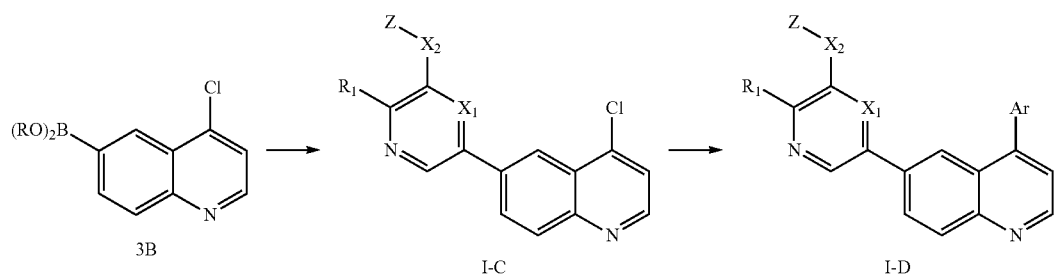

A compound of Formula I may be prepared in several methods from commercially available pyridine or pyrazine derivatives. As shown in Scheme 3, one method involves an electrophilic halogenation (e.g. chlorination) of compound 6 where the function Z—$X^2$ may be ether OH, OR, $NH_2$, or NHR that directs ortho substitution at the pyridine or pyrazine ring to give 7. Further conversion of the chloride can be achieved through reaction with a suitable nucleophiles such as an alkoxide to give 1. Compound 7 may be directly converted to a compound of Formula I ($R^1$=Cl) as described in Scheme 1, and the chloride can then be further functionalized through transition metal catalyzed cross-coupling reactions such as Suzuki or Negishi reaction. Alternatively, a phenol such as 8 can undergo electrophilic substitutions such as nitration to give 9. The latter can be reduced to aniline derivative 10 and subsequently functionalized at the 2-OH position. The 2-hydroxyl group of 9 may be converted to halide 11 and the resulting 2-halo-3-nitro compound can undergo nucleophilic substitution at the halogen to give 12.

SCHEME 3

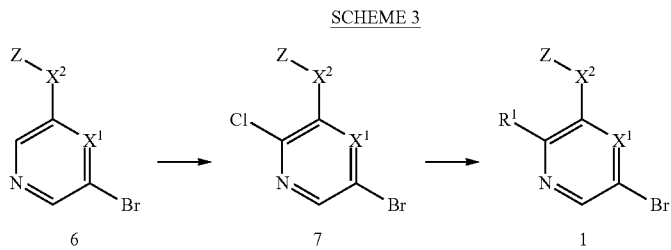

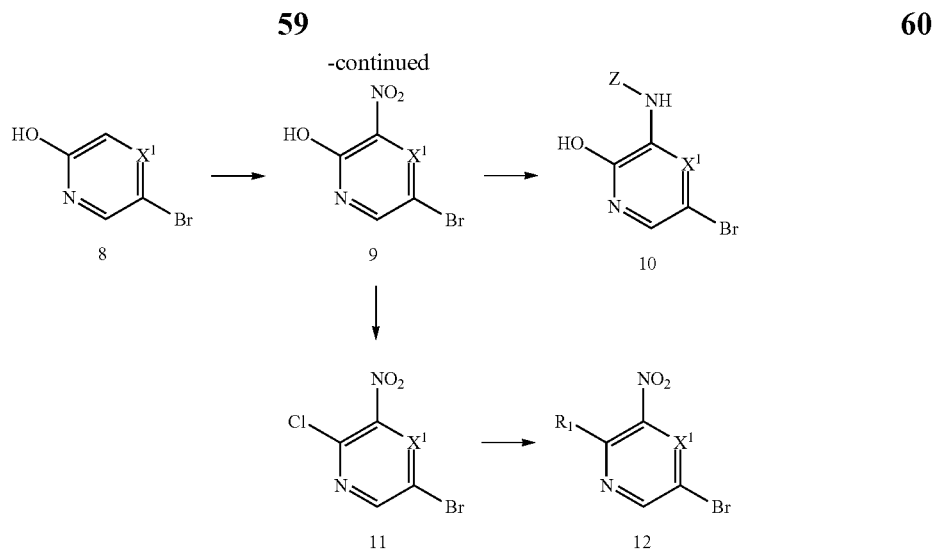

Many procedures describing the synthesis of heterocyclic [6,6]-ring systems are known in the literature. These methods are applicable for the preparation of suitably functionalized structures defined by Q in Formula I. A method of ring construction is illustrated for the synthesis of quinoline 15 (Scheme 4). For example, aniline 13 (L=Br) is heated with ethoxymethylene malonate to give enamine 14, which then cyclized to give, after decarboxylation, the 4-hydroxyquinoline derivative 15 (c.f., Lin, A. J.; Loo, T. L. *J. Med. Chem.* 1978, 21, 268). In this example E is —CO$_2$Et, but can be other appropriate functional groups.

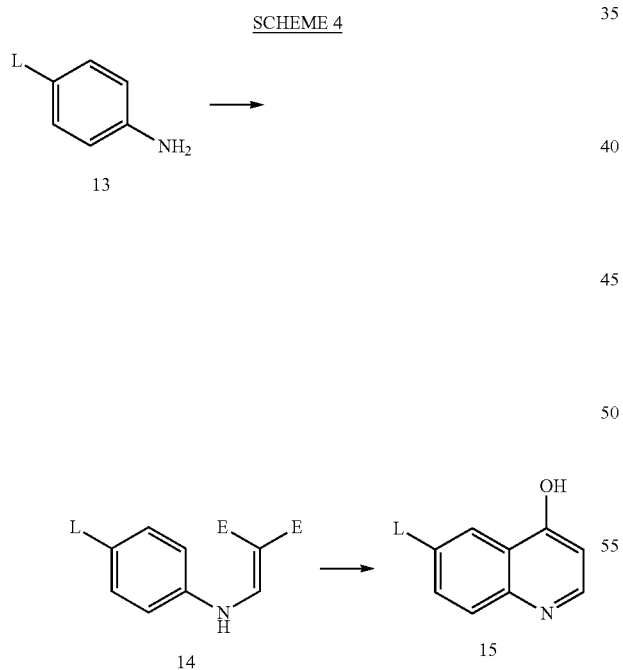

A method of functionalization of a heterocyclic [6,6]-ring system is illustrated by the synthesis of 7-bromoquinoxalin-2-ol 18 (Scheme 5). Ortho-phenylene diamine 16 cyclizes with a glyoxylate to give 17, which then can be selectively brominated at the 7-position (Lumma, W. C. et al., *J. Med. Chem.* 1981, 24, 93).

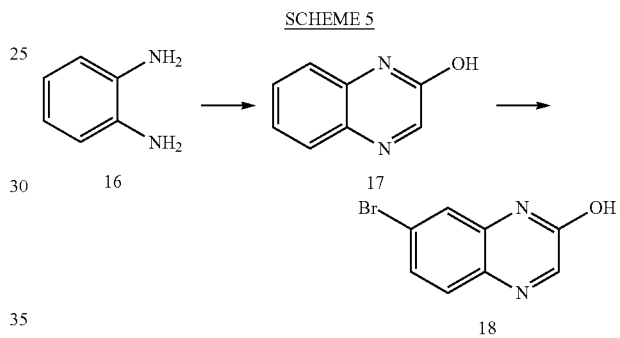

A method for the synthesis and functionalization of a heterocyclic [6,6]-ring is illustrated in Scheme 6. 3-(Cyanomethyl)picolinonitrile 19 cyclizes under basic conditions to give 20 (c.f., Hersperger, R. et al. *Bioorg. Med. Chem. Lett.* 2002, 12, 233). The latter can be converted to 8-methoxy-1,7-naphthyridin-6-yl trifluoromethanesulfonate (21) via diazonium chemistry.

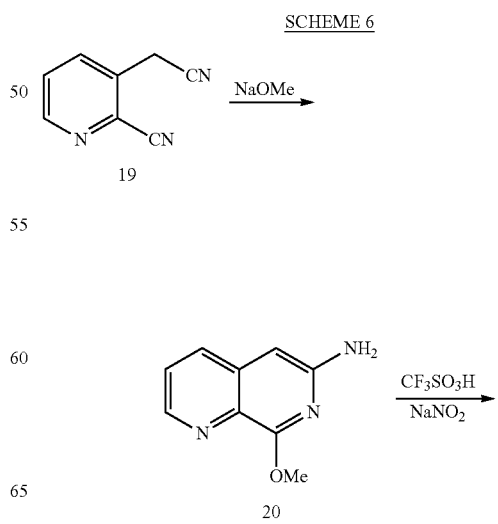

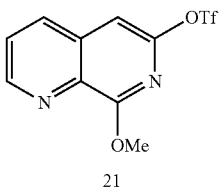

21

A useful method for the synthesis of intermediate 6 (Scheme 3) starts with the halogenation of phenol 8 followed by conventional derivatization at the OH group to structure 22 (Scheme 7). The C—X bond in 22 is particularly suitable for metal catalyzed C-heteroatom bond formation such that amides ($X^2$=(CO)NH), sulfanamides ($X^2$=(SO$_2$)NH) and other C—O, C—S bonds may be constructed.

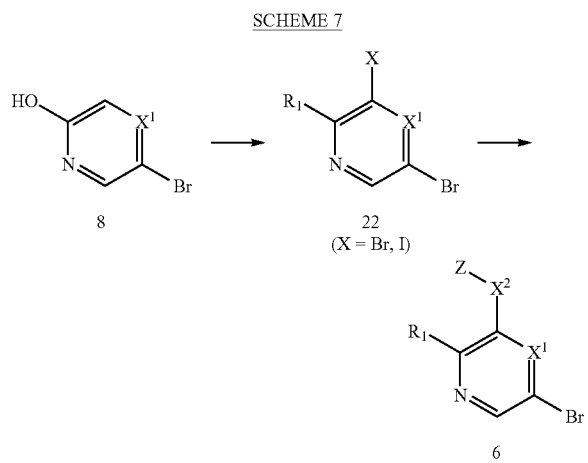

A particular class of compounds, sulfamide I-E, may be synthesized from bromide 23. The latter is best prepared by the addition of thionyl chloride, cooled at —40° C., to a pre-cooled (—30° C.) mixture of 1A, an amine $R^aR^aNH$, and a catalytic amount of DMAP, in pyridine (Scheme 8).

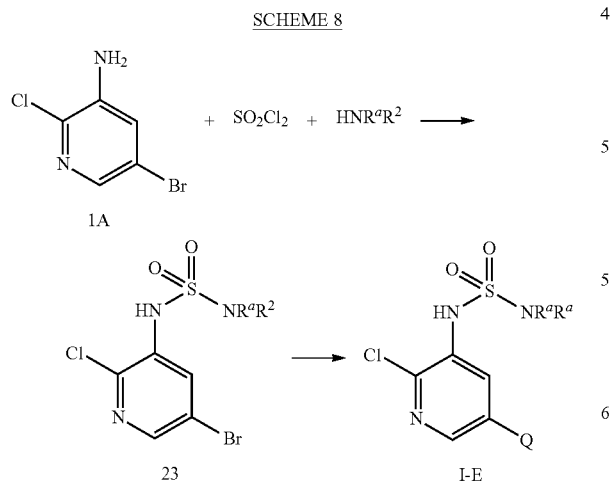

As an extension from Scheme 5, quinoxolin-2-one 17 may be further functionalized at N-1 position to quinoxolinone 23 (Scheme 9). For example, alkylation of 17 with alkyl halides in the presence of NaH may give rise to the N-alkylated product as the major regioisomer. Alternatively, Cu(II) catalyzed N-arylation with aryl boronic acids will result in the N-aryl derivative.

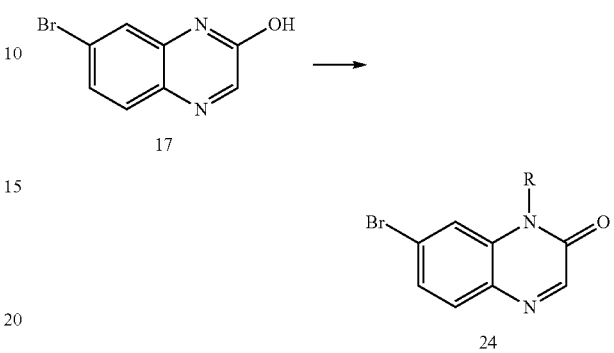

In Scheme 10, a method for the synthesis of I-F where Q is attached to the pyridine ring via a N atom is illustrated. Thus enamine formation between ketone 25 (E is a protecting group such as ethoxycarbonyl) and amine 26 (E' is an ester group) is effected in the presence of a strong acid at elevated temperature in a suitable solvent to provide 27. The latter can be cyclized at high temperature in a solvent such as diphenyl ether to give the naphthyridine derivative 28. Traditional decarboxylation of the latter after saponification, and dehydrohalogenation will give 29 (X is Cl) which can then be deprotected to amine 30. Metal catalyzed amination with a suitable partner will give rise to I-F.

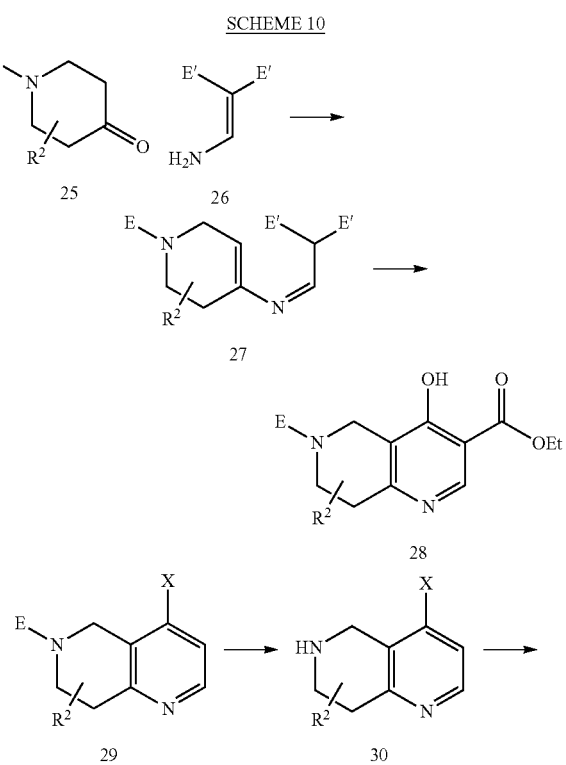

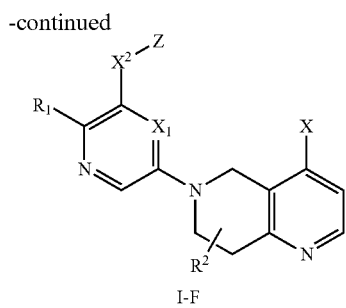

I-F

Example 1

N-(2-chloro-5-(4-(4-morpholinyl)-6-quinolinyl)-3-pyridinyl)-4-fluorobenzenesulfonamide (1) N-(5-bromo-2-chloropyridin-3-yl)-4-fluorobenzenesulfonamide: (Some starting materials may be obtained from Combi Blocks, San Diego, Calif.) A suspension of 5-bromo-2-chloropyridin-3-amine (10.0 g, 48 mmol), para-fluorobenzene sulfonyl chloride (20 g, 101 mmol), and pyridine (97 mL, 1205 mmol) was stirred at 23° C. for 24 hours. The solvent volume was then reduced by 50% under reduced pressure and the resulting solid collected by filtration, and was then washed with IPA (2×25 mL) followed by diethyl ether (20 mL). MS (ESI pos. ion) m/z calc'd for $C_{17}H_{10}BrClF_2N_2O_4S_2$: 521.9/523.9; found 522.8/524.8.

A suspension of the above product (8.70 g, 17 mmol) and sodium methoxide, 25 wt. % in methanol (9 mL, 166 mmol) in MeOH (100 mL) were then stirred at 23° C. for 45 minutes. The reaction was then concentrated to a solid under reduced pressure followed by partitioning between $CHCl_3$ (80 mL) and 2 M HCl (100 mL). The aqueous layer was then adjusted to pH 7 with 5% $NaHCO_3$. The separated organic phase was then dried over $MgSO_4$ and concentrated to a solid under reduced pressure. The solid was then suspended in hot EtOAc (20 mL), cooled, and isolated by filtration. MS (ESI pos. ion) m/z calc'd for $C_{11}H_7BrClFN_2O_2S$: 364.9/366.9; found 365.9/367.9. $^1$H NMR (400 MHz, DMSO-$d_6$) δ ppm 7.37-7.50 (m, 2 H) 7.77-7.86 (m, 2 H) 7.94 (d, J=2.35 Hz, 1 H) 8.43 (d, J=2.15 Hz, 1 H) 10.64 (br. s., 1 H).

(2) 6-bromo-4-morpholinoquinoline: A suspension of 6-bromo-4-chloroquinoline (725 mg, 2990 μmol) and morpholine (651 μL, 7474 μmol) in DMF (4 mL) was heated to 90° C. for 90 minutes. The reaction was then partitioned between EtOAc (30 mL) and water (30 mL). The separated organic was then dried over $MgSO_4$ and concentrated to an oil under reduced pressure. MS (ESI pos. ion) m/z calc'd for $C_{13}H_{13}BrN_2O$: 292.0/294.0; found 293.0/295.0.

$^1$H NMR (400 MHz, CHLOROFORM-d) δ ppm 3.17-3.25 (m, 4 H) 3.95-4.02 (m, 4 H) 6.87 (d, J=5.02 Hz, 1 H) 7.73 (dd, J=8.78, 2.26 Hz, 1 H) 7.93 (d, J=9.03 Hz, 1 H) 8.16 (d, J=2.01 Hz, 1 H) 8.75 (d, J=4.52 Hz, 1 H).

(3) 4-morpholino-6-(4,4,5,5-tetramethyl-1,3,2-dioxaborolan-2-yl)quinoline: A suspension of 6-bromo-4-morpholinoquinoline (750 mg, 2558 μmol), bis(pinacolato)diboron (650 mg, 2558 μmol), dichloro[1,1'bis(diphenylphoshino)ferrocene] palladium(II)dichloromethane adduct (140 mg, 192 μmol), and potassium acetate (502 mg, 5117 μmol) in 1,4-dioxane (4 mL) was sparged with argon for 5 minutes, sealed

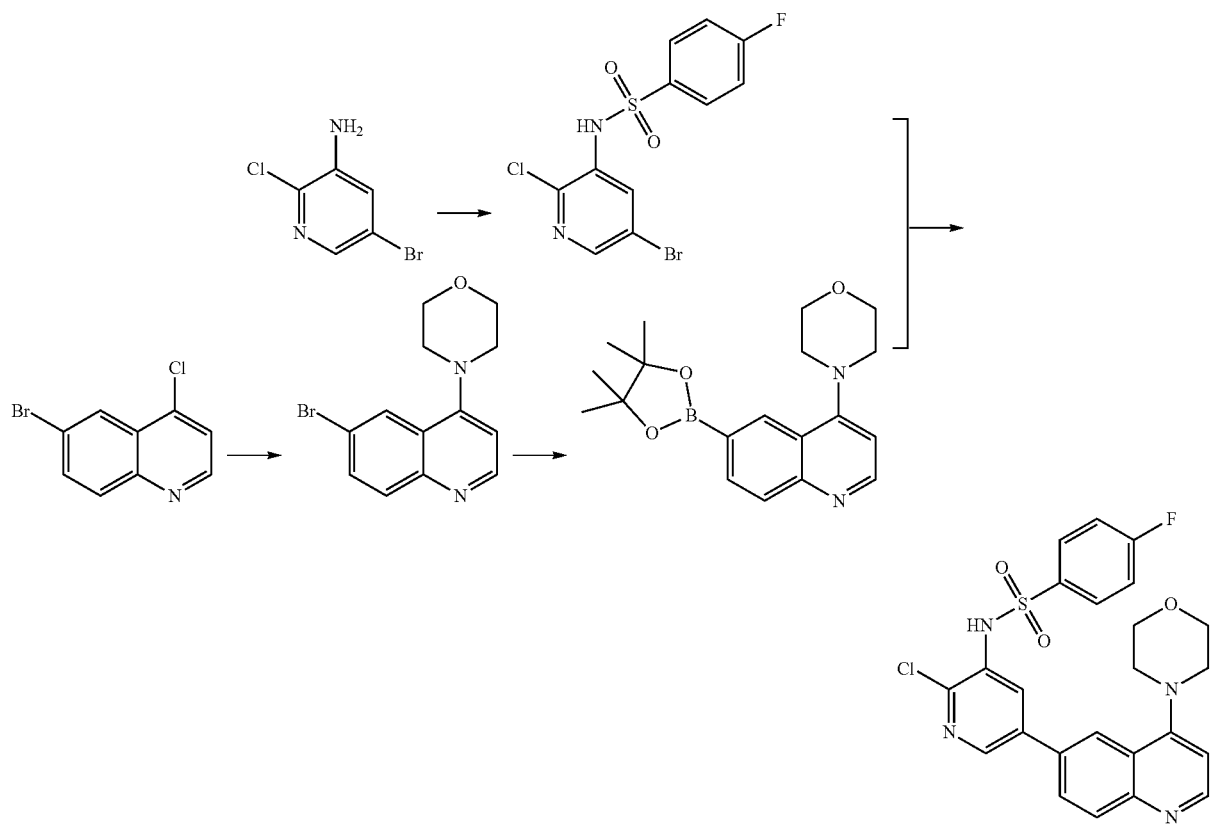

appropriately, then heated to 120° C. for 15 minutes. The reaction was then partitioned between EtOAc (30 mL) and 5% NaHCO$_3$ (10 mL). The separated organic layer was dried over MgSO$_4$, concentrated under reduced pressure, and then purified on silica (40 g) eluting with from 20 to 100% EtOAc/Hex. MS (ESI pos. ion) m/z calc'd for boronic acid as C$_{13}$H$_{15}$BN$_2$O$_3$: 258.1; found 259.1.

(4) N-(2-chloro-5-(4-(4-morpholinyl)-6-quinolinyl)-3-pyridinyl)-4-fluorobenzenesulfonamide: A suspension of N-(5-bromo-2-chloropyridin-3-yl)-4-fluorobenzenesulfonamide (159 mg, 435 μmol), 4-morpholino-6-(4,4,5,5-tetramethyl-1,3,2-dioxaborolan-2-yl)quinoline (148 mg, 435 μmol), dichloro[1,1'bis(diphenylphoshino)ferrocene]palladium(II) dichloromethane adduct (24 mg, 33 μmol), and Na$_2$CO$_3$ (184 mg, 1740 μmol) in 1,4-dioxane (2 mL) and water (1 mL) was sparged with argon for 5 minutes, then heated to 100° C. for 15 minutes. The reaction was then partitioned between 9:1 CHCl$_3$/IPA (30 mL) and 5% NaHCO$_3$ (10 mL). The separated organic was dried over MgSO$_4$, concentrated onto dry silica (5 g), and then purified on silica (40 g) eluting with from 1.5 to 3% of (2 M NH$_3$ in MeOH)/DCM. Product was isolated as an off white solid. MS (ESI pos. ion) m/z calc'd for C$_{24}$H$_{20}$ClFN$_4$O$_3$S: 498.1; found 499.0. $^1$H NMR (400 MHz, DMSO-d$_6$) δ ppm 3.27-3.33 (m, 4 H) 3.87-3.93 (m, 4 H) 7.09 (d, J=5.28 Hz, 1 H) 7.42 (t, J=8.80 Hz, 2 H) 7.79-7.87 (m, 2 H) 7.99-8.04 (m, 1 H) 8.06-8.12 (m, 2 H) 8.21 (d, J=1.76 Hz, 1 H) 8.65 (d, J=2.15 Hz, 1 H) 8.75 (d, J=5.28 Hz, 1 H) 10.87 (br. s., 1 H).

Example 2

N-(2-chloro-5-(4-chloro-6-quinolinyl)-3-pyridinyl)-4-fluorobenzenesulfonamide

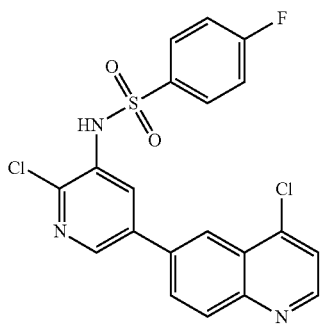 [SMILES: O=S(=O)(Nc1cc(-c2ccc3nccc(Cl)c3c2)cnc1Cl)c1ccc(F)cc1]

(1) 4-chloro-6-(4,4,5,5-tetramethyl-1,3,2-dioxaborolan-2-yl)quinoline: A suspension of 6-bromo-4-chloroquinoline (1050 mg, 4330 μmol), bis(pinacolato)diboron (1155 mg, 4546 μmol), dichloro[1,1'bis(diphenylphoshino)ferrocene] palladium(ii)dichloromethane adduct (158 mg, 216 μmol), potassium acetate (541 μl, 8660 μmol) in 1,4-dioxane (7.5 mL) was sparged with argon for 5 minutes, sealed appropriately, then heated to 120° C. for 30 minutes. The reaction was then partitioned between EtOAc (30 mL) and 5% NaHCO$_3$ (15 mL). The organic layer was separated, dried over MgSO4, concentrated under reduced pressure, and then purified on silica (40 g) eluting with from 10 to 30% of EtOAc/hex. MS(ESI pos. ion) m/z calc'd for boron acid as C$_{15}$H$_{17}$BClNO$_2$: 207.0; found 208.4. $^1$H NMR (400 MHz, CHLOROFORM-d) δ ppm 1.40 (s, 12 H) 7.49 (d, J=4.70 Hz, 1 H) 8.06-8.12 (m, 1 H) 8.12-8.17 (m, 1 H) 8.72 (s, 1 H) 8.80 (d, J=4.70 Hz, 1 H).

(2) N-(2-chloro-5-(4-chloro-6-quinolinyl)-3-pyridinyl)-4-fluorobenzenesulfonamide: Prepared in a similar manner as described in step 4/Example 1. MS (ESI pos. ion) m/z calc'd for C$_{20}$H$_{12}$Cl$_2$FN$_3$O$_2$S: 447.0; found 448.0. $^1$H NMR (400 MHz, DMSO-d$_6$) δ ppm 7.46 (t, J=8.80 Hz, 2 H) 7.79-7.90 (m, 3 H) 8.07 (d, J=2.35 Hz, 1 H) 8.16-8.27 (m, 2 H) 8.32 (d, J=1.56 Hz, 1 H) 8.78 (d, J=2.15 Hz, 1 H) 8.91 (d, J=4.69 Hz, 1 H) 10.57 (s, 1 H).

Example 3 tert-butyl(2-((6-(6-chloro-5-(((4-fluorophenyl)sulfonyl)amino)-3-pyridinyl)-4-quinolinyl)oxy)ethyl)carbamate

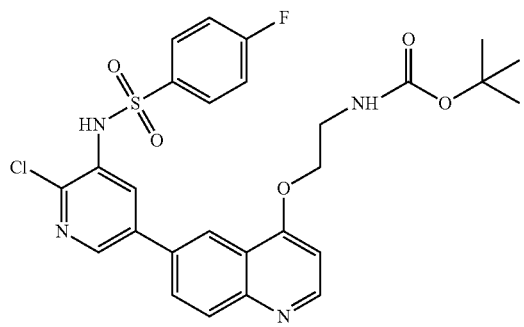 [SMILES: CC(C)(C)OC(=O)NCCOc1ccnc2ccc(-c3cnc(Cl)c(NS(=O)(=O)c4ccc(F)cc4)c3)cc12]

(1) tert-butyl 2-(6-bromoquinolin-4-yloxy)ethylcarbamate: A suspension of 6-bromo-4-chloroquinoline (1000 mg, 4124 μmol), tert-butyl n-(2-hydroxyethyl)carbamate (2327 μl, 14433 μmol), and cesium carbonate (825 μl, 10309 μmol) in DMF (5 mL) was stirred at 37° C. for 18 hours. The reaction was then partitioned between EtOAc (40 mL) and water (60 mL). The separated organic was dried over MgSO$_4$, concentrated under reduced pressure with toluene, and then purified on silica (80 g) eluting with from 20 to 90% of EtOAc/Hexanes. MS (ESI pos. ion) m/z calc'd for C$_{16}$H$_{19}$BrN$_2$O$_3$: 366.1/368.1; found 367.1/369.1. $^1$H NMR (400 MHz, CHLOROFORM-d) δ ppm 1.47 (s, 9 H) 3.70 (d, J=5.02 Hz, 2 H) 4.26 (t, J=5.02 Hz, 2 H) 5.06 (br. s., 1 H) 6.75 (d, J=5.02 Hz, 1 H) 7.76 (dd, J=9.03, 2.01 Hz, 1 H) 7.91 (d, J=9.03 Hz, 1 H) 8.33 (s, 1 H) 8.74 (d, J=5.02 Hz, 1 H).

(2) tert-butyl (2-((6-(6-chloro-5-(((4-fluorophenyl)sulfonyl)amino)-3-pyridinyl)-4-quinolinyl)oxy)ethyl)carbamate: Prepared in a similar manner as described in step 4/Example 1. MS (ESI pos. ion) m/z calc'd for C$_{27}$H$_{26}$ClFN$_4$O$_5$S: 572.1; found 573.1.

Example 4

N-(2-chloro-5-(3-methoxy-6-quinolinyl)-3-pyridinyl)-4-fluorobenzenesulfonamide

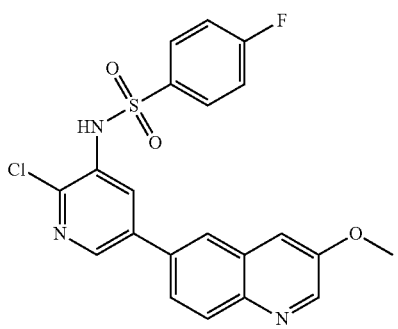 [SMILES: COc1cnc2ccc(-c3cnc(Cl)c(NS(=O)(=O)c4ccc(F)cc4)c3)cc2c1]

(1) 6-bromo-3-methoxyquinoline: A mixture of 6-bromoquinolin-3-ol (2000 mg, 8926 μmol), methanol (361 μl, 8926 μmol), triphenylphosphine (2068 μl, 8926 μmol), and diisopropyl azodicarboxylate (1805 μl, 8926 μmol) in THF (20 mL) was stirred at 23° C. for 18 hours. The reaction was first concentrated under reduced pressure then partitioned between EtOAc (60 mL) and 5% NaHCO$_3$ (30 mL). The separated organic layer was dried over MgSO$_4$, concentrated under reduced pressure, and then purified on silica (120 g) eluting with 10% isocratic EtOAc/Hex. MS (ESI pos. ion) m/z calc'd for C$_{10}$H$_8$BrNO: 238.0/240.0; found 237.0/239.0. $^1$H NMR (400 MHz, CHLOROFORM-d) δ ppm 3.95 (s, 3 H) 7.26 (s, 1 H) 7.62 (dd, J=8.90, 2.25 Hz, 1 H) 7.87-7.93 (m, 2 H) 8.66 (d, J=2.74 Hz, 1 H).

(2) N-(2-chloro-5-(3-methoxy-6-quinolinyl)-3-pyridinyl)-4-fluorobenzenesulfonamide: Prepared in a similar manner as described in step 4/Example 1. MS (ESI pos. ion) m/z calc'd for C$_{21}$H$_{15}$ClFN$_3$O$_3$S: 443.0; found 444.0. $^1$H NMR (400 MHz, DMSO-d$_6$) δ ppm 3.97 (s, 3 H) 7.44 (t, J=8.78 Hz, 2 H) 7.80-7.90 (m, 4 H) 8.08 (d, J=9.03 Hz, 1 H) 8.12 (d, J=2.01 Hz, 1 H) 8.23 (s, 1 H) 8.67-8.71 (m, 2 H) 10.56 (br. s., 1 H).

Example 5

N-(2-chloro-5-(4-phenoxy-6-quinolinyl)-3-pyridinyl)methanesulfonamide

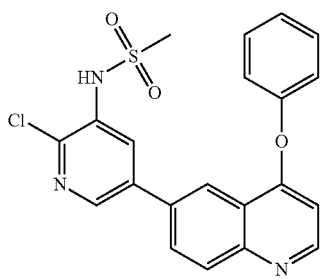 [SMILES: CS(=O)(=O)Nc1cc(-c2ccc3nccc(Oc4ccccc4)c3c2)cnc1Cl]

(1) 6-bromo-4-phenoxyquinoline: A suspension of 6-bromo-4-chloroquinoline (787 mg, 3245 μmol), phenol (611 mg, 6491 μmol), and cesium carbonate (779 μl, 9736 μmol) in DMF (8 mL) was heated to 50° C. with stirring for 72 hours. The reaction was then partitioned between EtOAc (30 mL) and 1 M NaOH (30 mL). The separated organic layer was dried over MgSO$_4$ and then concentrated to a solid under reduced pressure from toluene. MS (ESI pos. ion) m/z calc'd for C$_{15}$H$_{10}$BrNO: 299.0/301.0; found 300.0/302.0. $^1$H NMR (400 MHz, CHLOROFORM-d) δ ppm 6.56 (d, J=5.02 Hz, 1 H) 7.15-7.23 (m, 2 H) 7.48 (t, J=8.03 Hz, 2 H) 7.82 (dd, J=9.03, 2.01 Hz, 1 H) 7.97 (d, J=9.03 Hz, 1 H) 8.55 (d, J=2.01 Hz, 1 H) 8.66 (d, J=5.52 Hz, 1 H).

(2) N-(2-chloro-5-(4-phenoxy-6-quinolinyl)-3-pyridinyl)methanesulfonamide: Prepared in a similar manner as described in step 4/Example 1. MS (ESI pos. ion) m/z calc'd for C$_{21}$H$_{16}$ClN$_3$O$_3$S: 425.1; found 426.0. $^1$H NMR (400 MHz, DMSO-d$_6$) δ ppm 3.19 (s, 3 H) 6.66 (d, J=5.28 Hz, 1 H) 7.31-7.43 (m, 3 H) 7.57 (t, J=7.92 Hz, 2 H) 8.14-8.23 (m, 2 H) 8.26 (d, J=2.35 Hz, 1 H) 8.60 (s, 1 H) 8.71-8.79 (m, 2 H) 9.88 (s, 1 H).

Example 6

N-(2-chloro-5-(6-quinoxalinyl)-3-pyridinyl)-4-fluorobenzenesulfonamide

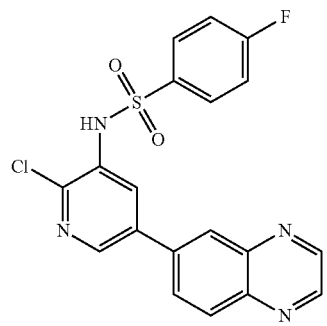 [SMILES: O=S(=O)(Nc1cc(-c2ccc3nccnc3c2)cnc1Cl)c1ccc(F)cc1]

(Some starting materials may be obtained from Carbocore, Woodlands, Tex.) Prepared in a similar manner as described in step 4/Example 1. MS (ESI pos. ion) m/z calc'd for C$_{19}$H$_{12}$ClFN4O$_2$S: 414.0; found 415.0. $^1$H NMR (400 MHz, DMSO-d$_6$) δ ppm 7.44 (t, J=8.78 Hz, 2 H) 7.84 (dd, J=8.78, 5.27 Hz, 2 H) 8.13-8.29 (m, 3 H) 8.42 (s, 1 H) 8.83 (s, 1 H) 9.03 (d, J=11.04 Hz, 2 H) 10.58 (s, 1 H).

Example 7

N-(2-chloro-5-(6-quinolinyl)-3-pyridinyl)-4-fluorobenzenesulfonamide

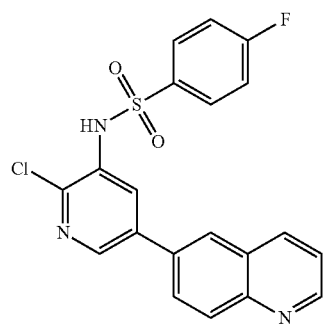 [SMILES: O=S(=O)(Nc1cc(-c2ccc3ncccc3c2)cnc1Cl)c1ccc(F)cc1]

(Some starting materials may be obtained from TCI, Portland, Oreg.) Prepared in a similar manner as described in step 4/Example 1. MS (ESI pos. ion) m/z calc'd for C$_{20}$H$_{13}$ClFN$_3$O$_2$S: 413.0; found 414.0. $^1$H NMR (400 MHz, DMSO-d$_6$) δ ppm 7.45 (t, J=8.80 Hz, 2 H) 7.62 (dd, J=8.22, 4.11 Hz, 1 H) 7.84 (dd, J=8.61, 5.09 Hz, 2 H) 8.05-8.11 (m, 1 H) 8.12-8.20 (m, 2 H) 8.35 (s, 1 H) 8.47 (d, J=8.02 Hz, 1 H) 8.76 (d, J=1.96 Hz, 1 H) 8.97 (d, J=4.11 Hz, 1 H) 10.54 (s, 1 H).

Example 8

N-(2-chloro-5-(4-methoxy-6-quinolinyl)-3-pyridinyl)-4-fluorobenzenesulfonamide

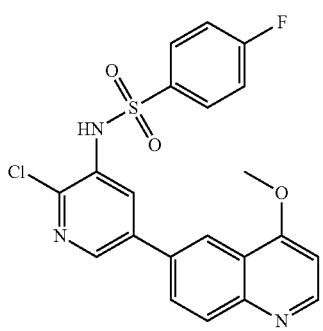 [SMILES: COc1ccnc2ccc(-c3cnc(Cl)c(NS(=O)(=O)c4ccc(F)cc4)c3)cc12]

(Some starting materials may be obtained from ECA International, Palatine, Ill.) Prepared in a similar manner as described in step 4/Example 1. MS (ESI pos. ion) m/z calc'd for C$_{21}$H$_{15}$ClFN$_3$O$_3$S: 443.0; found 444.0. $^1$H NMR (400 MHz, DMSO-d$_6$) δ ppm 4.12 (s, 3 H) 7.13 (d, J=5.52 Hz, 1 H) 7.46 (t, J=8.78 Hz, 2 H) 7.84 (dd, J=8.78, 5.27 Hz, 2 H) 7.99 (d, J=2.01 Hz, 1 H) 8.02-8.13 (m, 2 H) 8.28 (s, 1 H) 8.70 (s, 1 H) 8.81 (d, J=5.52 Hz, 1 H) 10.65 (br. s., 1 H).

Example 9

N-(2-chloro-5-(4-chloro-6-quinolinyl)-3-pyridinyl)methanesulfonamide

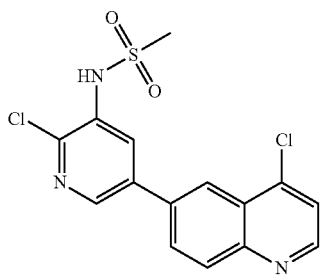 [SMILES: CS(=O)(=O)Nc1cc(-c2ccc3nccc(Cl)c3c2)cnc1Cl]

(Some starting materials may be obtained from ECA International, Palatine, Ill.) Prepared in a similar manner as described in step 4/Example 1. MS (ESI pos. ion) m/z calc'd for C$_{15}$H$_{11}$Cl$_2$N$_3$O$_2$S: 367.0; found 368.0. $^1$H NMR (400 MHz, DMSO-d$_6$) δ ppm 3.21 (s, 3 H) 7.85 (d, J=4.69 Hz, 1 H) 8.22-8.29 (m, 3 H) 8.45 (s, 1 H) 8.77 (d, J=2.35 Hz, 1 H) 8.90 (d, J=4.70 Hz, 1 H) 9.91 (s, 1 H).

Example 10

N-(2-chloro-5-(3-methoxy-6-quinolinyl)-3-pyridinyl)methanesulfonamide

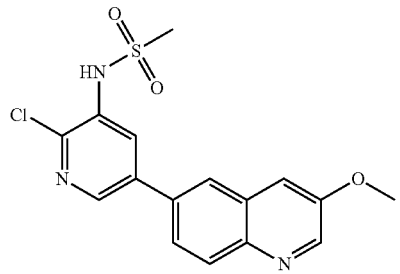 [SMILES: COc1cnc2ccc(-c3cnc(Cl)c(NS(C)(=O)=O)c3)cc2c1]

(Some starting materials may be obtained from BioBlocks, San Diego, Calif.) Prepared in a similar manner as described in step 4/Example 1. MS (ESI pos. ion) m/z calc'd for C$_{16}$H$_{14}$ClN$_3$O$_3$S: 363.0; found 364.1. $^1$H NMR (400 MHz, DMSO-d$_6$) δ ppm 3.22 (s, 3 H) 3.96 (s, 3 H) 7.86 (d, J=2.74 Hz, 1 H) 7.95 (dd, J=8.80, 2.15 Hz, 1 H) 8.08 (d, J=8.80 Hz, 1 H) 8.23 (d, J=2.35 Hz, 1 H) 8.29 (d, J=1.96 Hz, 1 H) 8.69 (d, J=2.93 Hz, 1 H) 8.73 (d, J=2.35 Hz, 1 H) 9.90 (s, 1 H).

Example 11

N-(2-chloro-5-(4-(4-morpholinyl)-6-quinolinyl)-3-pyridinyl)methanesulfonamide

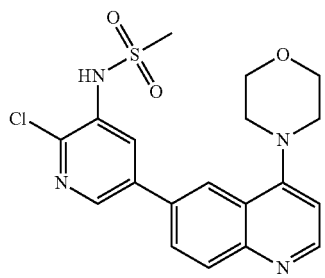 [SMILES: CS(=O)(=O)Nc1cc(-c2ccc3nccc(N4CCOCC4)c3c2)cnc1Cl]

Prepared in a similar manner as described in step 4/Example 1. MS (ESI pos. ion) m/z calc'd for C$_{19}$H$_{19}$ClN$_4$O$_3$S: 418.1; found 419.1. $^1$H NMR (400 MHz, DMSO-d$_6$) δ ppm 3.21 (s, 3 H) 3.22-3.28 (m, 4 H) 3.86-3.94 (m, 4 H) 7.07 (d, J=5.09 Hz, 1 H) 8.09 (d, J=0.98 Hz, 2 H) 8.20-8.26 (m, 2 H) 8.71 (d, J=2.35 Hz, 1 H) 8.75 (d, J=5.09 Hz, 1 H) 9.96 (br. s., 1 H).

Example 12

N-(2-chloro-5-(6-quinolinyl)-3-pyridinyl)methanesulfonamide

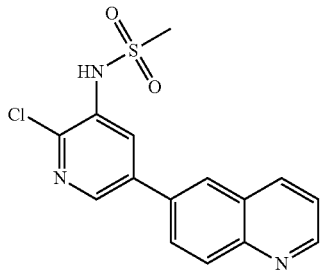 [SMILES: CS(=O)(=O)Nc1cc(-c2ccc3ncccc3c2)cnc1Cl]

Prepared in a similar manner as described in step 4/Example 1. MS (ESI pos. ion) m/z calc'd for $C_{15}H_{12}ClN_3O_2S$: 333.0; found 334.0. $^1$H NMR (400 MHz, DMSO-$d_6$) δ ppm 3.21 (s, 3 H) 7.61 (dd, J=8.28, 4.27 Hz, 1 H) 8.15 (s, 2 H) 8.26 (d, J=2.01 Hz, 1 H) 8.41 (s, 1 H) 8.47 (d, J=8.03 Hz, 1 H) 8.76 (d, J=2.51 Hz, 1 H) 8.96 (d, J=4.02 Hz, 1 H) 9.90 (s, 1 H).

Example 13

2-chloro-N,N-dimethyl-5-(6-quinolinyl)-3-pyridinamine

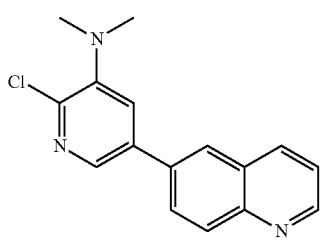 [SMILES: CN(C)c1cc(-c2ccc3ncccc3c2)cnc1Cl]

Prepared in a similar manner as described in step 4/Example 1. MS (ESI pos. ion) m/z calc'd for $C_{16}H_{14}ClN_3$: 283.1; found 284.1. $^1$H NMR (400 MHz, CHLOROFORM-d) δ ppm 2.95 (s, 6 H) 7.47 (dd, J=8.31, 4.21 Hz, 1 H) 7.59 (d, J=2.15 Hz, 1 H) 7.92 (dd, J=8.71, 2.05 Hz, 1 H) 7.99 (d, J=1.76 Hz, 1 H) 8.23 (t, J=9.10 Hz, 2 H) 8.35 (d, J=2.15 Hz, 1 H) 8.96 (dd, J=4.11, 1.56 Hz, 1 H).

Example 14

(2-chloro-5-(4-(4-morpholinyl)-6-quinolinyl)-3-pyridinyl)methanol

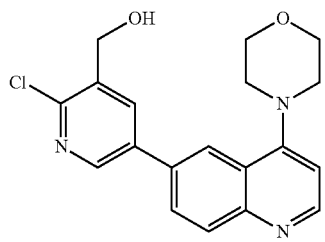 [SMILES: OCc1cc(-c2ccc3nccc(N4CCOCC4)c3c2)cnc1Cl]

(Some starting materials may be obtained from Adesis Inc., New Castle, Del.) A mixture of 4-morpholinoquinolin-6-yl-boronic acid (500 mg, 1937 μmol), PdCl$_2$(dppf) (70.9 mg, 96.9 μmol), Na$_2$CO$_3$ (616 mg, 5812 μmol) and (5-bromo-2-chloropyridin-3-yl)methanol (431 mg, 1937 μmol) in DME (8 mL) and water (3 mL) was heated to 95° C. under nitrogen. After 2 h, the mixture was concentrated and the residue was partitioned between water and DCM containing $^i$PrOH (1%). The aqueous layer was extracted several times with DCM containing $^i$PrOH (1%). The combined organic phase was concentrated and suspended in DMSO-MeOH (1:1). This mixture was then filtered, washed with MeOH to give the desired product (230 mg, 94% pure based on LCMS). The filtrate was purified with HPLC and concentrated to an oil. This was partitioned between DCM and saturated NaHCO$_3$. The organic phase was dried over Na$_2$SO$_4$ and concentrated to a white solid (100 mg). LCMS (ESI, pos. ion): calc'd for $C_{19}H_{18}ClN_3O_2$: 355.1; found: 356.1 (M+1). $^1$H NMR (400 MHz, CHLOROFORM-d) δ ppm 2.19-2.39 (m, 1 H) 3.21-3.33 (m, 4 H) 3.95-4.06 (m, 4 H) 4.91 (d, J=5.02 Hz, 2 H) 6.93 (d, J=4.52 Hz, 1 H) 7.88 (d, J=9.03 Hz, 1 H) 8.13-8.27 (m, 3 H) 8.63 (d, J=2.01 Hz, 1 H) 8.79 (d, J=5.02 Hz, 1 H)

Example 15

(2-chloro-5-(4-(4-morpholinyl)-6-quinolinyl)-3-pyridinyl)methyl acetate

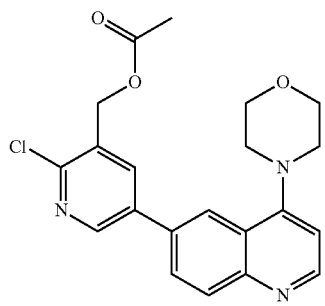 [SMILES: CC(=O)OCc1cc(-c2ccc3nccc(N4CCOCC4)c3c2)cnc1Cl]

(Some starting materials may be obtained from Adesis Inc., New Castle, Del.) A mixture of (2-chloro-5-(4-morpholino-quinolin-6-yl)pyridin-3-yl)methanol (63 mg, 177 μmol), Hunig's Base (300 μl, 1718 μmol), and Ac$_2$O (17 μl, 177

μmol) in DCM (10 mL) was stirred at rt. A small amount of DMF (10 drops) was added. After 2 h, a tiny amount of DMAP was added. After an additional 1 h, the solvent was removed under vacuum and the residue was treated with water. The slurry was extracted with DCM containing MeOH (2%). The organic phase was dried over Na$_2$SO$_4$, concentrated, and purified on silica using 1% MeOH in DCM to give a film (70 mg). LCMS (ESI, pos. ion): calc'd for C$_{21}$H$_{20}$ClN$_3$O$_3$: 397.1; found: 398.1 (M+1). $^1$H NMR (400 MHz, TFA-CHLOROFORM-d) δ ppm 2.26 (s, 3 H) 3.97 (d, J=4.02 Hz, 4 H) 4.11 (d, J=4.52 Hz, 4 H) 5.39 (s, 2 H) 7.10 (d, J=7.03 Hz, 1 H) 8.10-8.19 (m, 1 H) 8.17-8.28 (m, 2 H) 8.33 (s, 1 H) 8.60 (d, J=6.52 Hz, 1 H) 8.91 (d, J=2.01 Hz, 1 H) 13.20 (s, 1 H)

Example 16

1-(2-chloro-5-(4-(4-morpholinyl)-6-quinolinyl)-3-pyridinyl)methanamine

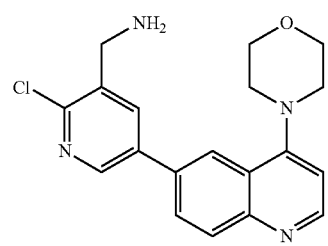 [SMILES: NCc1cc(-c2ccc3nccc(N4CCOCC4)c3c2)cnc1Cl]

(Some starting materials may be obtained from Adesis Inc., New Castle, Del.) (1) To a mixture of (2-chloro-5-(4-morpholinoquinolin-6-yl)pyridin-3-yl)methanol (125 mg, 351 μmol), Hunig's Base (150 μl, 859 μmol) in THF (5 mL), cooled in an ice bath, was added MsCl (55 μL, 703 μmol). The cooling bath was removed. After 20 min, the reaction mixture was cooled with an ice bath. Aqueous ammonia (4000 μl, 68113 μmol) was added. The mixture was stirred at rt overnight. The mixture was purified on HPLC and the product fraction was concentrated to dryness and dissolved in saturated NaHCO$_3$ (20 mL). Upon sitting at rt for 1 h, solid separated out. The mixture was filtered and washed with water to give a white solid (70 mg, 56% two steps). LCMS (ESI, pos. ion): calc'd for C$_{19}$H$_{19}$ClN$_4$O:354.2; found: 355.2 (M+1).

$^1$H NMR (400 MHz, TFA-DMSO-d$_6$) δ ppm 3.87 (d, J=4.30 Hz, 4 H) 3.97 (d, J=4.30 Hz, 4 H) 4.30 (q, J=5.74 Hz, 2 H) 7.34 (d, J=7.04 Hz, 1 H) 8.16 (d, J=8.80 Hz, 1 H) 8.33 (dd, J=9.00, 1.56 Hz, 1 H) 8.39 (s, 1 H) 8.45 (d, J=2.15 Hz, 1 H) 8.75 (d, J=7.04 Hz, 1 H) 8.95 (d, J=2.35 Hz, 1 H)

Example 17

N-((2-chloro-5-(4-(4-morpholinyl)-6-quinolinyl)-3-pyridinyl)methyl)-2,2-dimethylpropanamide

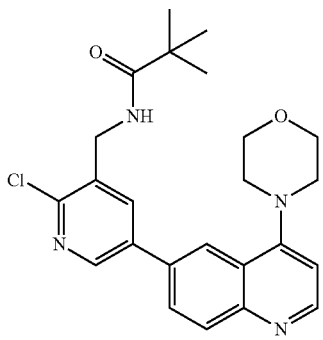 [SMILES: CC(C)(C)C(=O)NCc1cc(-c2ccc3nccc(N4CCOCC4)c3c2)cnc1Cl]

(Some starting materials may be obtained from Adesis Inc., New Castle, Del.) To a mixture of (2-chloro-5-(4-morpholinoquinolin-6-yl)pyridin-3-yl)methanamine (50 mg, 141 μmol) and Et$_3$N (300 μl, 2152 μmol) in DCM (5 mL) was added pivaloyl chloride (100 μL, 813 μmol). The solution was stirred at rt for 1 h. The mixture was partitioned between DCM (10 mL) and aqueous NaHCO$_3$ (20 mL). The organic layer was dried over Na$_2$SO$_4$ and concentrated. The residue was purified on silica with 1-5% (2N NH$_3$-MeOH) in DCM to give the product as a yellow solid after concentration (20 mg, 32%). LCMS (ESI, pos. ion): calc'd for C$_{24}$H$_{27}$ClN$_4$O$_2$: 438.2; found: 439.2 (M+1). $^1$H NMR (400 MHz, CHLOROFORM-d) d ppm 1.21-1.28 (m, 12 H) 3.19-3.35 (m, 4 H) 3.95-4.08 (m, 4 H) 4.58 (d, J=6.06 Hz, 2 H) 6.37 (br. s., 1 H) 6.93 (d, J=4.89 Hz, 1 H) 7.83 (dd, J=8.90, 1.66 Hz, 1 H) 8.00 (d, J=2.15 Hz, 1 H) 8.10-8.25 (m, 5 H) 8.61 (d, J=2.15 Hz, 2 H) 8.79 (d, J=4.89 Hz, 2 H)

Example 18

N-(2-chloro-5-(7-quinolinyl)-3-pyridinyl)-4-fluorobenzenesulfonamide

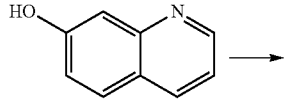

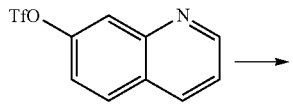

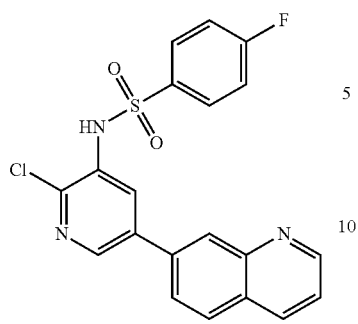

1) Quinolin-7-yl trifluoromethanesulfonate. (Some starting materials may be obtained from Adesis Inc., New Castle, Del.) To a suspension of 7-hydroxyquinoline (0.47 g, 3.2 mmol) in DCM (7 mL) at 0° C. under a nitrogen atmosphere was added pyridine (0.34 mL, 4.23 mmol), followed by trifluoromethanesulfonic anhydride (0.57 mL, 3.4 mmol The mixture was stirred for 30 min at 0° C. and 1 h at rt. The reaction mixture was diluted with EtOAc, washed with water, brine, dried over $Na_2SO_4$, and concentrated in vacuum. The title compound was obtained as an off-white solid. MS (ESI pos. ion) m/z: calc'd for $C_{10}H_6F_3NO_3S$: 277.0; found: 278.0 (M+1).

(2) N-(2-chloro-5-(7-quinolinyl)-3-pyridinyl)-4-fluorobenzenesulfonamide. A 15-mL reaction vial was charged with N-(2-chloro-5-(4,4,5,5-tetramethyl-1,3,2-dioxaborolan-2-yl)pyridin-3-yl)-4-fluorobenzenesulfonamide (0.20 g, 0.48 mmol), quinolin-7-yl trifluoromethanesulfonate (0.12 g, 0.43 mmol), sodium carbonate (0.14 g, 1.3 mmol), 1,1'-bis(diphenylphosphino)ferrocene palladium dichloride (23 mg, 0.03 mmol), dioxane (2 mL) and water (1 mL). The vial was sealed, purged with nitrogen and heated at 100° C. for 2 h. After cooling to rt, it was diluted with EtOAc and washed with water and brine. Purification by silica gel chromatography (MeOH in DCM: 0-4%) gave the title compound as a tan solid. MS (ESI pos. ion) m/z: calc'd for $C_{20}H_{13}ClFN_3O_2S$: 413.0; found: 414.0 (M+1). $^1H$ NMR (300 MHz, DMSO-$d_6$) δ: 0.57 (br s, 1H) 9.00 (d, J=3.2 Hz, 1H) 8.80 (d, J=1.9 Hz, 1H) 8.45 (J=8.5 Hz, 1H) 8.32 (s, 1H), 8.18-8.13 (m, 2H) 7.94 (dd, J=8.1 Hz, 1.4 Hz, 1H) 7.87-7.81 (m, 2H) 7.60 (dd, J=8.1 Hz, 4.3 Hz, 1H) 7.49-7.41 (m, 2H).

Example 19

2-chloro-5-(4-(4-morpholinyl)-6-quinolinyl)-3-pyridinol

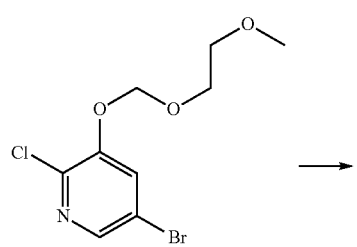

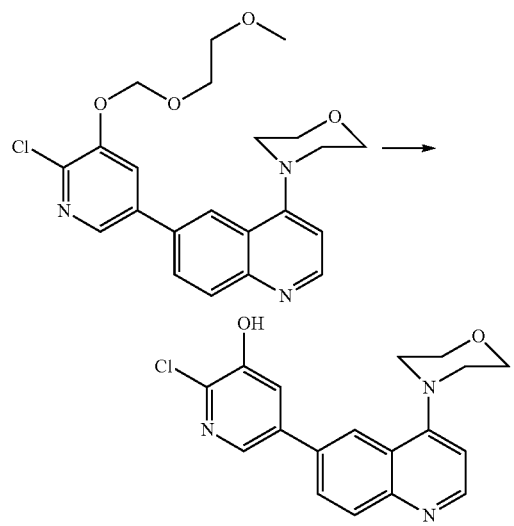

(1) 6-(6-chloro-5-((2-methoxyethoxy)methoxy)pyridin-3-yl)-4-morpholinoquinoline: (Some starting materials may be obtained from Adesis, New Castle, Del.) To a microwave vial (5 mL), 4-morpholino-6-(4,4,5,5-tetramethyl-1,3,2-dioxaborolan-2-yl)quinoline (0.0429 g, 0.126 mmol), 5-bromo-2-chloro-3-((2-methoxyethoxy)methoxy)pyridine (0.0400 g, 0.135 mmol), $PdCl_2$ (dppf)-$CH_2Cl_2$ adduct (0.0109 g, 0.00126 mmol) and potassium carbonate (2.0 M, 0.158 mL, 0.315 mmol) were mixed into 1,4-dioxane (3 mL). The mixture was degassed by bubbling argon through for 10 min. The tube was irradiated with microwave at 100° C. for 10 min two times. The reaction mixture was cooled to RT then partitioned between water (20 mL) and EtOAc (20 mL). The aqueous phase was extracted with EtOAc (2×20 mL). The combined organic phases were washed with saturated aqueous NaCl (50 mL). The organic phase was dried over sodium sulfate, filtered and concentrated in vacuo to afford a brown solid (0.0826 g). The crude product was purified by column chromatography (eluent: acetone in $CHCl_3$ 30% -60%) to afford a light brown solid (0.0328 g). m/z calc'd for $C_{22}H_{24}ClN_3O_4$: 429.1, found 430.1 (M+1). $^1H$ NMR (300 MHz, CHLOROFORM-d) δ ppm 3.22-3.31 (m, 4 H), 3.35 (s, 3 H), 3.54-3.63 (m, 2 H), 3.86-4.06 (m, 6 H), 5.46 (s, 2 H), 6.92 (d, J=5.0 Hz, 1 H), 7.81-7.90 (m, 2 H). 8.14-8.23 (m, 2 H), 8.37 (d, J=2.0 Hz, 1 H), 8.78 (d, J=5.0 Hz, 1 H).

(2) 2-chloro-5-(4-(4-morpholinyl)-6-quinolinyl)-3-pyridinol: To a microwave vial (2 mL), 6-(6-chloro-5-((2-methoxyethoxy)methoxy)pyridin-3-yl)-4-morpholinoquinoline (0.0328 g, 0.0763 mmol) was dissolved into DCM (1 mL). Trifluoroacetic acid (1 mL, 13.0 mmol) was added and the brown solution was stirred at RT for 2 h then the mixture was heated at 60° C. for 1.5 h. The solvent was evaporated and the brown residue was taken into methanol. The crude product was purified by preparative HPLC to afford 0.020 g of pale yellow solid. This solid was treated with a few mL of saturated aqueous $NaHCO_3$ and extracted with EtOAc (10 mL). The organic phase was dried over sodium sulfate, evaporate in vacuo, then dried in vacuum oven for overnight to afford a pale yellow solid (0.0150 g) as the desired product. m/z calc'd for $C_{18}H_{16}ClN_3O_2$: 341.1; found 342.0 (M+1). $^1H$ NMR (300 MHz, DMSO-$d_6$) δ ppm 3.36-3.42 (m, 4 H), 3.84-3.96 (m, 4 H), 7.11 (d, J=5.4 Hz, 1 H), 7.71 (d, J=2.2 Hz, 1 H), 8.01-8.12

(m, 2 H), 8.20 (d, J=1.0 Hz, 1 H), 8.33 (d, J=2.2 Hz, 1 H), 8.73 (d, J=5.4 Hz, 1 H), 11.04 (s, 1 H).

Example 20

N-(2-chloro-5-(3-(4-morpholinyl)-6-quinoxalinyl)-3-pyridinyl)-4-fluorobenzenesulfonamide

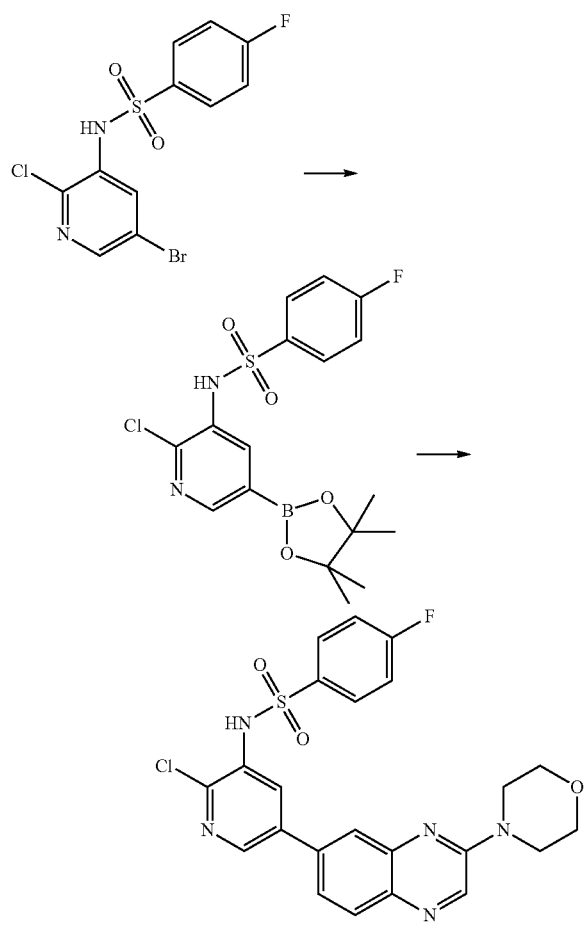

(1) N-(2-chloro-5-(4,4,5,5-tetramethyl-1,3,2-dioxaborolan-2-yl)pyridin-3-yl)-4-fluorobenzenesulfonamide: (Some starting materials may be obtained from Aldrich, St. Louis, Mo.) To a microwave vial (20 mL) was added N-(5-bromo-2-chloropyridin-3-yl)-4-fluorobenzenesulfonamide (2.01 g, 5.51 mmol), 4,4,5,5-tetramethyl-2-(4,4,5,5-tetramethyl-1,3,2-dioxaborolan-2-yl)-1,3,2-dioxaborolane (1.56 g, 6.12 mmol), potassium acetate (1.11 g, 11.3 mmol) and PdCl$_2$(dppf)-CH$_2$Cl$_2$ adduct (0.236 g, 0.288 mmol) in 1,4-dioxane (10 mL). The mixture was degassed by bubbling nitrogen through for 5 min. The tube was irradiated with microwave at 120° C., 15 min then again at 120° C. for 10 min. The reaction mixture was cooled to RT then partitioned between water (100 mL) and EtOAc (100 mL). The aqueous phase was extracted with EtOAc (100 mL). The combined organic phases were washed with saturated aqueous NaCl (200 mL). The organic phase was dried over sodium sulfate, filtered and concentrated in vacuo to afford 3.56 g of brown residue. The crude product was purified by column chromatography (eluent: EtOAc in hexanes from 0% to 50%) to afford a clear sticky oil (1.53 g) which solidified upon standing as the desired product. m/z: calc'd for boronic acid C$_{11}$H$_9$BClFN$_2$O$_4$S: 330.0; found 331.0 (boronic acid M+1). $^1$H NMR (300 MHz, CHLOROFORM-d) δ ppm 1.33-1.41 (m, 12 H), 6.88 (s, 1 H), 7.10-7.19 (m, 2 H), 7.75-7.83 (m, 2 H), 8.31 (d, J=1.6 Hz, 1 H), 8.46 (d, J=1.6 Hz, 1 H).

(2) 7-bromo-2-morpholinoquinoxaline: To a microwave vial (5 mL), 7-bromo-2-chloroquinoxaline (0.201 g, 0.826 mmol) and morpholine (0.200 mL, 2.29 mmol) were dissolved into DMF (4 mL). The reaction mixture was stirred at 90° C. for 2 h. The mixture was cooled to RT then partitioned between water (50 mL) and EtOAc (30 mL). The aqueous phase was extracted with EtOAc (2×20 mL). The combined organic phases were dried over sodium sulfate, filtered and concentrated in vacuo to afford 0.451 g of yellow solid. Recrystalization from DCM afforded a light yellow crystal (0.124 g) as the desired product. m/z: calc'd for C$_{12}$H$_{12}$BrN$_3$O: 293.0; found 294.0 (M+1). $^1$H NMR (300 MHz, CHLOROFORM-d) δ ppm 3.72-3.83 (m, 4 H), 3.83-3.93 (m, 4 H), 7.49 (dd, J=8.8, 2.2 Hz, 1 H), 7.75 (d, J=8.6 Hz, 1 H), 7.88 (d, J=2.0 Hz, 1 H), 8.55 (s, 1 H).

(3) N-(2-chloro-5-(3-(4-morpholinyl)-6-quinoxalinyl)-3-pyridinyl)-4-fluorobenzenesulfonamide: To a microwave vial (5 mL) was added N-(2-chloro-5-(4,4,5,5-tetramethyl-1,3,2-dioxaborolan-2-yl)pyridin-3-yl)-4-fluorobenzenesulfonamide (0.123 g, 0.298 mmol), 7-bromo-2-morpholinoquinoxaline (0.0777 g, 0.264 mmol), PdCl$_2$(dppf)-CH$_2$Cl$_2$ adduct (0.0108 g, 0.0132 mmol) and potassium carbonate (2.0 M, 0.330 mL, 0.660 mmol) in 1,4-dioxane (3 mL). The mixture was degassed by bubbling nitrogen through for 10 min. The tube was irradiated with microwave at 100° C. for 10 min. The reaction mixture was cooled to RT then partitioned between water (30 mL) and EtOAc (30 mL). The aqueous phase was extracted with EtOAc (30 mL), then with 25% isopropanol in CHCl$_3$+1% NH$_4$OH (30 mL). The combined organic phases were dried over sodium sulfate, filtered and concentrated in vacuo to yield 0.125 g of crude product. This crude product and a crude from another batch of reaction was combined and purified by column chromatography (eluent: EtOAc in hexanes from 0% to 100%), then washed with hexanes and DCM to afford a pale yellow solid (0.144 g) as the desired product. m/z: calc'd for C$_{23}$H$_{19}$ClFN$_5$O$_3$S: 499.1; found 500.0 (M+1). $^1$H NMR (300 MHz, DMSO-d$_6$) δ ppm 3.67-3.91 (m, 8 H), 7.37-7.52 (m, 2 H), 7.70 (dd, J=8.6, 2.0 Hz, 1 H), 7.76-7.89 (m, 3 H), 7.96 (d, J=8.5 Hz, 1 H), 8.06 (d, J=2.3 Hz, 1 H), 8.72 (d, J=2.2 Hz, 1 H), 8.87 (s, 1 H), 10.53 (s, 1 H).

Example 21

N-(2-chloro-5-(3-(4-(1-methylethyl)-1-piperazinyl)-6-quinoxalinyl)-3-pyridinyl)-4-fluorobenzenesulfonamide

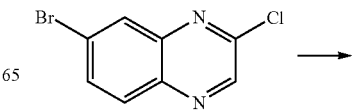

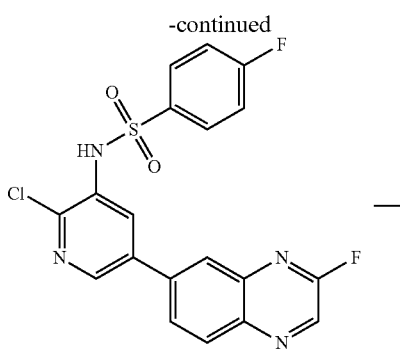

→

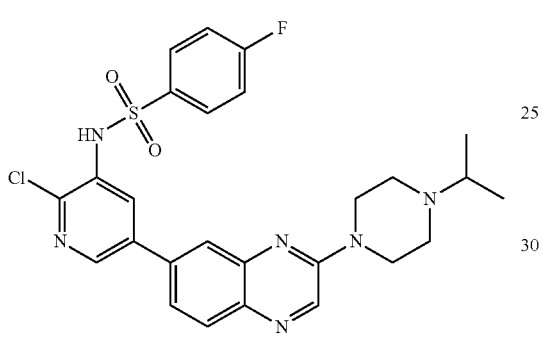

(1) 7-bromo-2-fluoroquinoxaline: (Some starting materials may be obtained from Aldrich, St. Louis, Mo.) To a round-bottomed flask (150 mL), 7-bromo-2-chloroquinoxaline (1.73 g, 7.12 mmol) was suspended into DMSO (20 mL). Tetrabutylammonium fluoride (1.0 M in THF, 8.55 mL, 8.55 mmol) was added. The reaction was stirred at RT for 1.5 h. Water (100 mL) was added and the resulting solid was collected, washed with water and air dried to obtain a cream color solid (1.54 g) as the desired product. This compound does not ionize. $^1$H NMR (300 MHz, DMSO-$d_6$) δ ppm 7.92-8.41 (m, 3 H), 8.90-9.14 (m, 1 H).

(2) N-(2-chloro-5-(3-fluoro quinoxalin-6-yl)pyridin-3-yl)-4-fluorobenzenesulfonamide: To a microwave vial (20 mL) was added N-(2-chloro-5-(4,4,5,5-tetramethyl-1,3,2-dioxaborolan-2-yl)pyridin-3-yl)-4-fluorobenzenesulfonamide (1.64 g, 3.97 mmol), 7-bromo-2-fluoroquinoxaline (0.998 g, 4.40 mmol), PdCl$_2$(dppf)-CH$_2$Cl$_2$ adduct (0.169 g, 0.207 mmol) and potassium carbonate (2.0 M, 4.97 mL, 9.94 mmol) in 1,4-dioxane (15 mL). The mixture was degassed by bubbling nitrogen through for 10 min. The tube was irradiated with microwave at 100° C. for 10 min. The reaction mixture was cooled to RT then partitioned between water (50 mL) and EtOAc (50 mL). The aqueous phase was extracted with EtOAc (2×50 mL). The combined organic phases were washed with saturated aqueous NaCl (100 mL). The organic phase was dried over sodium sulfate, filtered and concentrated in vacuo to afford a brown/black residue. The crude product was purified by column chromatography (eluent: EtOAc in hexanes 10% -50%) to afford a waxy solid (1.12 g) as the desired product. m/z: calc'd for $C_{19}H_{11}ClF_2N_4O_2S$: 432.0; found 432.9 (M+1). $^1$H NMR (300 MHz, CHLOROFORM-d) δ ppm 7.05-7.14 (m, 1 H), 7.15-7.24 (m, 2 H), 7.82-7.92 (m, 2 H), 7.96 (dd, J=8.6, 2.0 Hz, 1 H), 8.16 (d, J=1.8 Hz, 1 H), 8.31 (d, J=8.6 Hz, 1 H), 8.35 (d, J=2.3 Hz, 1 H), 8.52 (d, J=2.3 Hz, 1 H), 8.77 (d, J=7.9 Hz, 1 H).

(3) N-(2-chloro-5-(3-(4-(1-methylethyl)-1-piperazinyl)-6-quinoxalinyl)-3-pyridinyl)-4-fluorobenzenesulfonamide: To a microwave vial (5 mL), N-(2-chloro-5-(3-fluoroquinoxalin-6-yl)pyridin-3-yl)-4-fluorobenzenesulfonamide (0.0313 g, 0.0723 mmol) and 1-isopropylpiperazine (0.0259 mL, 0.181 mmol) were dissolved in DMF (1 mL). The yellow solution was stirred at 60° C. for 1.5 h. The reaction mixture was cooled to RT then partitioned between water (10 mL) and EtOAc (10 mL). The aqueous phase was extracted with 10% isopropanol in CHCl$_3$+1% NH$_4$OH (2×10 mL). The combined organic phases were dried over sodium sulfate, filtered and concentrated in vacuo to afford a crude product 0.0307 g). The crude product was purified by column chromatography (eluent: iPrOH (w/10% NH$_4$OH) in CHCl$_3$ from 0% to 12.5%) to afford a pale yellow solid (0.0210 g) as the desired product. m/z: calc'd for $C_{26}H_{26}ClFN_6O_2S$: 540.2; found 541.1 (M+1). $^1$H NMR (300 MHz, DMSO-$d_6$) δ 1.18 (d, J=6.6 Hz, 6 H), 3.04 (s, 4 H), 3.14-3.23 (m, 1 H), 4.00 (s, 4 H), 7.32 (t, J=8.8 Hz, 2 H), 7.61 (dd, J=8.5, 1.9 Hz, 1 H), 7.71 (d, J=1.8 Hz, 1 H), 7.75-7.86 (m, 2 H), 7.85-7.97 (m, 2 H), 8.26 (s, 1 H), 8.88 (s, 1 H).

Example 22

N-(2-chloro-5-(3-hydroxy-6-quinolinyl)-3-pyridinyl)-4-fluorobenzenesulfonamide

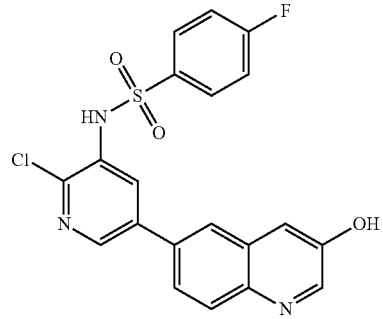 [SMILES: O=S(=O)(Nc1cc(-c2ccc3ncc(O)cc3c2)cnc1Cl)c1ccc(F)cc1]

To a microwave vial (5 mL) was added N-(2-chloro-5-(4,4,5,5-tetramethyl-1,3,2-dioxaborolan-2-yl)pyridin-3-yl)-4-fluorobenzenesulfonamide (0.129 g, 0.312 mmol), 6-bromoquinolin-3-ol (Li et. Al, Bioorganic & Medicinal Chemistry Letters (2006), 16(7), 2000-2007) (0.0703 g, 0.314 mmol), PdCl$_2$(dppf)-CH$_2$Cl$_2$ adduct (0.0128 g, 0.0156 mmol) and potassium carbonate (2.0 M, 0.390 mL, 0.781 mmol) in 1,4-dioxane (3 mL). The mixture was degassed by bubbling nitrogen through for 10 min. The tube was irradiated with microwave at 100° C. for 10 min. The reaction mixture was cooled to RT then partitioned between water (10 mL) and EtOAc (10 mL). The product went into aqueous almost exclusively. The aqueous phase was passed through BE-SCX column (Varian, Palo Alto, Calif., 10 gm) then eluted with MeOH. MeOH fraction contains the product. MeOH was evaporated and yielded a brown solid (0.0846 g) as the desired product. m/z: calc'd for $C_{20}H_{13}ClFN_3O_3S$: 429.0; found 430.0 (M+1). $^1$H NMR (300 MHz, DMSO-$d_6$) δ ppm 7.21-7.35 (m, 2 H), 7.52-7.65 (m, 2 H), 7.74-7.86 (m, 3 H), 7.89 (d, J=1.8 Hz, 1 H), 7.96 (d, J=8.6 Hz, 1 H), 8.03-8.15 (m, 1 H), 8.58 (d, J=2.8 Hz, 1 H), 10.40 (s, 1 H).

Example 23

N-(2-chloro-5-(4-hydroxy-6-quinolinyl)-3-pyridinyl)-4-fluorobenzenesulfonamide

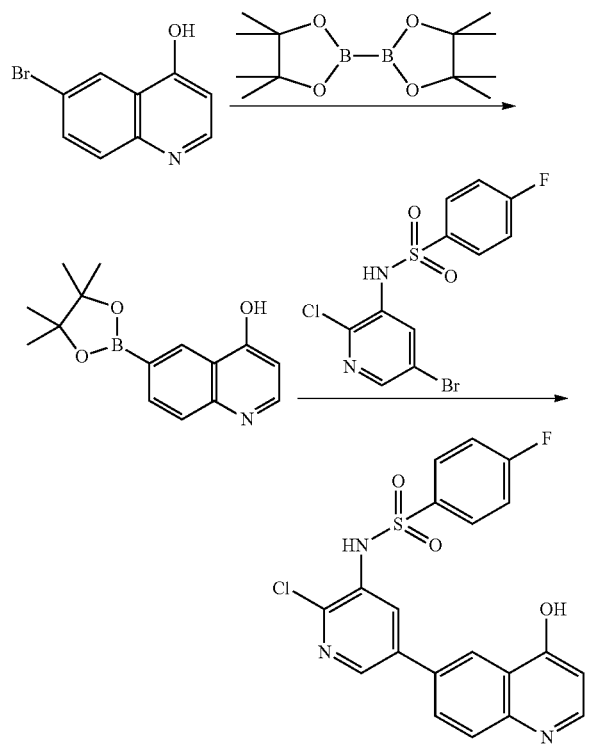

(1) 6-(4,4,5,5-tetramethyl-1,3,2-dioxaborolan-2-yl)quinolin-4-ol. (Some starting materials may be obtained from BioBlocks, San Diego, Calif. and Small Molecule, Inc., Hoboken, N.J.) To a suspension of 6-bromoquinolin-4-ol (0.2 g, 0.9 mmol) in dioxane (10 mL) was added bis(pinacolato) diboron (0.3 g, 1 mmol), potassium acetate (0.4 g, 4 mmol), and 1,1'-bis(diphenylphosphino)ferrocene]dichloride palladium(II) (0.05 g, 0.07 mmol) in order. The reaction mixture was then heated at 90° C. under $N_2$ for 3 h. LC/MS showed no sign of starting material mass. Reaction mixture was cooled to rt. The solvent was separated from the inorganic solid by filtration. The filtrate was concentrated to driness. The crude product was purified using $SiO_2$ (12 g) chromatography with DCM:MeOH=95%:5% as the solvent system to afford the product as brownish solid. (50 mg) MS (ESI pos. ion) m/z: calc'd for $C_{15}H_{18}BNO_3$: 271.1; found: 272.3 (M+1). $^1$H NMR (300 MHz, CHLOROFORM-d) δ ppm 1.34 (s, 12 H) 6.34 (d, J=7.31 Hz, 1 H) 7.53 (d, J=8.33 Hz, 1 H) 7.69-7.85 (m, 1 H) 7.99 (d, J=9.50 Hz, 1 H) 8.89 (s, 1 H) 10.78 (br. s., 1 H).

(2) N-(2-chloro-5-(4-hydroxy-6-quinolinyl)-3-pyridinyl)-4-fluorobenzenesulfonamide. To a 5 mL CEM microwave tube was added 6-(4,4,5,5-tetramethyl-1,3,2-dioxaborolan-2-yl)quinolin-4-ol (0.045 g, 0.2 mmol), N-(5-bromo-2-chloropyridin-3-yl)-4-fluorobenzenesulfonamide (0.06 g, 0.2 mmol), sodium carbonate (0.2 mL, 0.5 mmol), Pd fibrecat PPh (20% wt, 15 mg), and dioxane (3 mL). The vial was sealed and placed into CEM microwave (CEM Corp., Matthews, N.C.) for 20 min. at 120° C., with 100 watts of power. LC/MS showed a desired product mass as a major peak. The reaction mixture was partitioned between DCM/water. The aqueous layer was extracted with DCM (2×10 mL). The combined organic layers were washed with water, brine, dried over $MgSO_4$ and concentrated. The crude product was purified using $SiO_2$ (12 g) chromatography with DCM:EtOAc:MeOH=85%:10%:5% as the solvent system to afford the product as light yellow solid (15 mg). The aqueous layer was loaded in the cation exchange resin (Varian Mega Be-SCX, 10 gm 60 mL). The resin was eluted first with water, then MeOH and finally with MeOH containing $NH_3$ (2M). The fractions containing the product were combined and concentrated. The crude product was purified using $SiO_2$ (12 g) chromatography with DCM:EtOAc:MeOH=85%:10%:5% as the solvent system to afford the product as light yellow solid (50.0 mg). MS (ESI pos. ion) m/z: calc'd for $C_{20}H_{13}ClFN_3O_3S$: 429.2; found: 430.3 (M+1). $^1$H NMR (300 MHz, DMSO-$d_6$) δ ppm 6.10 (d, J=7.45 Hz, 1 H) 7.42 (t, J=8.84 Hz, 2 H) 7.67 (d, J=8.62 Hz, 1 H) 7.81 (dd, J=8.84, 5.19 Hz, 2 H) 7.90-8.02 (m, 3 H) 8.28 (s, 1 H) 8.58 (s, 1 H) 10.51 (br. s., 1 H) 11.91 (br. s., 1 H).

Example 24

N-(2-chloro-5-(4-(1-piperidinyl)-6-quinolinyl)-3-pyridinyl)-4-fluorobenzenesulfonamid

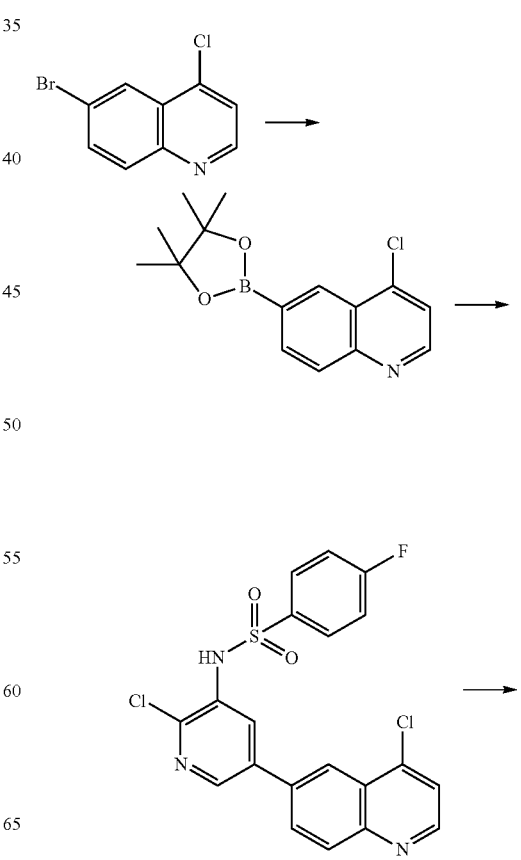

-continued

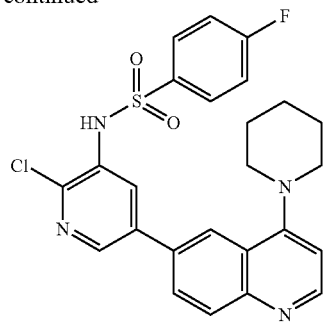

(1) 4-chloro-6-(4,4,5,5-tetramethyl-1,3,2-dioxaborolan-2-yl)quinoline. (Some starting materials may be obtained from Aldrich, St. Louis, Mo.) To a suspension of 6-bromo-4-chloroquinoline (1.5 g, 6.2 mmol) in dioxane (40 mL) was added bis(pinacolato)diboron (2.4 g, 9.3 mmol), potassium acetate (2.4 g, 25 mmol), and 1,1'-bis(diphenylphosphino)ferrocene] dichloride palladium(II) (0.34 g, 0.47 mmol) in order. The reaction mixture was then heated at 90° C. under $N_2$ for 3 h. The reaction was cooled to rt and the solvent was removed. The residue was partitioned between EtOAc/water. The aqueous layer was extracted more with EtOAc (2×15 mL). The combined organic layers were dried over $MgSO_4$ and concentrated. The crude product was purified using $SiO_2$ chromatography with DCM:EtOAc:MeOH=85%:10%:5% solvent system to afford the product as brown solid (1.45 g). MS (ESI pos. ion) m/z: calc'd for $C_{15}H_{17}BClNO_2$: 289.1; found: 290.3 (M+1). $^1$H NMR (300 MHz, CHLOROFORM-d) δ ppm 1.41 (s, 12 H) 7.51 (d, J=4.82 Hz, 1 H) 8.05-8.12 (m, 1 H) 8.14 (s, 1 H) 8.73 (s, 1 H) 8.81 (d, J=4.68 Hz, 1 H).

(2) N-(5-bromo-2-chloropyridin-3-yl)-4-fluorobenzenesulfonamide. To a solution of 3-amino-5-bromo-2-chloropyridine (10.0 g, 48 2 mmol) in pyridine (100 mL) was added 4-fluorobenzenesulfonyl chloride (18.8 g, 96.4 mmol). The resulting mixture was heated to 100° C. under $N_2$ for 6 h then stirred at rt for 20 h. Pyridine was removed as much as possible. The residue was partitioned between EtOAc/water. The aqueous layer was extracted with EtOAc. The combined organic layers were dried over $MgSO_4$ and concentrated. The crude product was suspended in DCM. The solid was then collected by filtration. The solid was then dried on the air for couple of hours. NMR and LC/MS showed it was the desired product (6.3 g). The filtrate was then purified using $SiO_2$ (330 g) chromatography with hexanes:acetone=80%:20% as the solvent system to afford the product as light yellow solid (4.8 g). The total combined weight was 11.1 g. MS (ESI pos. ion) m/z: calc'd for $C_{11}H_7BrClFN_2O_2S$: 363.7; found: 364.3 (M+1). $^1$H NMR (300 MHz, MeOH) δ ppm 7.26 (t, J=8.77 Hz, 2 H) 7.77-7.87 (m, 2 H) 8.10 (d, J=2.34 Hz, 1 H) 8.26 (d, J=2.34 Hz, 1 H).

(3) N-(2-chloro-5-(4-chloroquinolin-6-yl)pyridin-3-yl)-4-fluorobenzenesulfonamide. To a 5 mL CEM microwave tube was added N-(5-bromo-2-chloropyridin-3-yl)-4-fluorobenzenesulfonamide (0.4 g, 1 mmol), 4-chloro-6-(4,4,5,5-tetramethyl-1,3,2-dioxaborolan-2-yl)quinoline (0.4 g, 1 mmol), sodium carbonate (2 mL, 3 mmol), Pd fibrecat PPh (Sigma-Aldrich, St. Lois, Mo.) (20% wt, 80 mg) and dioxane (3 mL). The vial was sealed and placed into CEM microwave for 20 min. at 120° C., with 100 Watts of power via Powermax. LC/MS showed a desired product mass as the major peak. The reaction mixture was partitioned between DCM/water. The aqueous layer was extracted with DCM (3×10 mL). The combined organic layers were washed with water, brine, dried over $MgSO_4$ and concentrated. The crude product was purified using $SiO_2$ (120 g) chromatography with hexanes:acetone=80%:20% as the solvent system to afford the product as light yellow solid (270 mg). MS (ESI pos. ion) m/z: calc'd for $C_{20}H_{12}Cl_2FN_3O_2S$: 447.5; found: 448.3 (M+1). $^1$H NMR (300 MHz, CHLOROFORM-d) δ ppm 6.99 (br. s., 1 H) 7.13-7.24 (m, 2 H) 7.60 (d, J=4.68 Hz, 1 H) 7.88 (dd, J=8.99, 4.90 Hz, 2 H) 7.97 (dd, J=8.77, 2.05 Hz, 1 H) 8.28 (d, J=8.77 Hz, 1 H) 8.33 (d, J=2.19 Hz, 1 H) 8.38 (d, J=1.90 Hz, 1 H) 8.52 (d, J=2.34 Hz, 1 H) 8.87 (d, J=4.68 Hz, 1 H).

(4) N-(2-chloro-5-(4-(1-piperidinyl)-6-quinolinyl)-3-pyridinyl)-4-fluorobenzenesulfonamide. To a solution of N-(2-chloro-5-(4-chloroquinolin-6-yl)pyridin-3-yl)-4-fluorobenzenesulfonamide (0.07 g, 0.2 mmol) in DMF (5 mL) was added piperidine (0.05 ml, 0.5 mmol). The reaction mixture was heated to 100° C. under $N_2$ for 20 h. The reaction was stop and cooled to rt. The reaction mixture was partitioned between DCM/water. The organic layer was washed more with water, dried over $MgSO_4$ and removed solvent. The crude product was purified using $SiO_2$ (12 g) chromatography with hexanes:acetone=80%:20% as the solvent system to afford the product as white solid. (40 mg). MS (ESI pos. ion) m/z: calc'd for $C_{25}H_{22}ClFN_4O_2S$: 496.1; found: 497.5 (M+1). $^1$H NMR (300 MHz, CHLOROFORM-d) δ ppm 1.75 (d, J=5.26 Hz, 2 H) 1.90 (d, J=4.97 Hz, 4 H) 3.17-3.32 (m, 4 H) 6.90 (d, J=4.97 Hz, 1 H) 7.11-7.23 (m, 2 H) 7.76-7.92 (m, 3 H) 8.17 (d, J=8.77 Hz, 1 H) 8.23 (s, 1 H) 8.36 (d, J=2.34 Hz, 1 H) 8.51 (d, J=2.19 Hz, 1 H) 8.76 (d, J=5.12 Hz, 1 H).

Example numbers 25-30 were prepared according to the procedure described in Example 24.

Example 25

N-(2-chloro-5-(4-(4-(1-methylethyl)-1-piperazinyl)-6-quinolinyl)-3-pyridinyl)-4-fluorobenzenesulfonamide

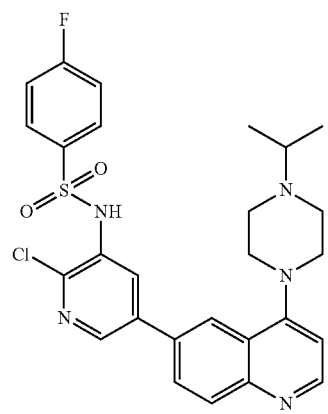 [SMILES: CC(C)N1CCN(c2ccnc3ccc(-c4cnc(Cl)c(NS(=O)(=O)c5ccc(F)cc5)c4)cc23)CC1]

(Some starting materials may be obtained from Aldrich, St. Louis, Mo.) MS (ESI pos. ion) m/z: calc'd for $C_{27}H_{27}ClFN_5O_2S$: 539.2; found: 540.3 (M+1). $^1$H NMR (300 MHz, CHLOROFORM-d) δ ppm 1.15 (d, J=6.58 Hz, 6 H) 2.75-2.95 (m, 5 H) 3.27-3.39 (m, 4 H) 6.93 (d, J=4.97 Hz, 1 H) 7.18 (t, J=8.55 Hz, 2 H) 7.77-7.92 (m, 3 H) 8.19 (d, J=8.62 Hz, 1 H) 8.27 (d, J=1.90 Hz, 1 H) 8.37 (d, J=2.34 Hz, 1 H) 8.51 (d, J=2.34 Hz, 1 H) 8.79 (d, J=4.97 Hz, 1 H).

Example 26

N-(2-chloro-5-(4-(3-hydroxy-1-pyrrolidinyl)-6-quinolinyl)-3-pyridinyl)-4-fluorobenzenesulfonamide

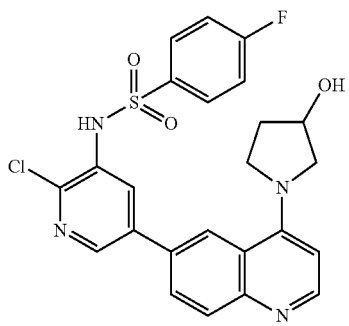 [SMILES: O=S(=O)(Nc1cc(-c2ccc3nccc(N4CCC(O)C4)c3c2)cnc1Cl)c1ccc(F)cc1]

(Some starting materials may be obtained from TCI, Portland, Oreg.) MS (ESI pos. ion) m/z: calc'd for $C_{24}H_{20}ClFN_4O_3S$: 498.1; found: 499.3 (M+1). $^1$H NMR (300 MHz, CHLOROFORM-d) δ ppm 2.18-2.23 (m, 2 H) 3.41 (q, J=2.05 Hz, 1 H) 3.68-3.77 (m, 2 H) 3.94-4.10 (m, 2 H) 4.66 (d, J=3.22 Hz, 1 H) 6.51 (d, J=5.85 Hz, 1 H) 7.10-7.21 (m, 2 H) 7.75 (d, J=8.77 Hz, 1 H) 7.82 (dd, J=8.92, 4.97 Hz, 2 H) 8.03 (d, J=8.77 Hz, 1 H) 8.21 (d, J=2.19 Hz, 1 H) 8.32-8.39 (m, 2 H) 8.43 (d, J=5.70 Hz, 1 H).

Example 27

N-(2-chloro-5-(4-(4-hydroxy-1-piperidinyl)-6-quinolinyl)-3-pyridinyl)-4-fluorobenzenesulfonamide

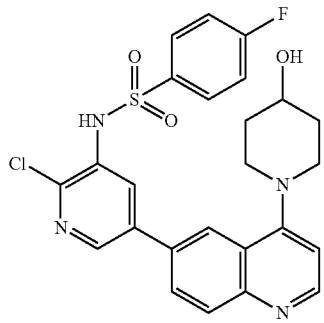 [SMILES: O=S(=O)(Nc1cc(-c2ccc3nccc(N4CCC(O)CC4)c3c2)cnc1Cl)c1ccc(F)cc1]

(Some starting materials may be obtained from Aldrich, St. Louis, Mo.) MS (ESI pos. ion) m/z: calc'd for $C_{25}H_{22}ClFN_4O_3S$: 493.1; found: 494.3 (M+1). $^1$H NMR (300 MHz, CHLOROFORM-d) δ ppm 1.83-2.02 (m, 2 H) 2.21 (ddd, J=6.58, 3.22, 3.07 Hz, 2 H) 3.20-3.38 (m, 2 H) 3.56-3.78 (m, 2 H) 4.12 (ddd, J=8.26, 5.85, 2.85 Hz, 1 H) 6.96 (d, J=5.55 Hz, 1 H) 7.19 (t, J=8.55 Hz, 2 H) 7.85 (dd, J=9.06, 4.97 Hz, 3 H) 7.88-7.94 (m, 1 H) 8.19 (s, 1 H) 8.34 (d, J=2.19 Hz, 1 H) 8.49 (d, J=2.34 Hz, 1 H) 8.71 (d, J=5.70 Hz, 1 H).

Example 28

N-(5-(4-(4-benzyl-1-piperazinyl)-6-quinolinyl)-2-chloro-3-pyridinyl)-4-fluorobenzenesulfonamide

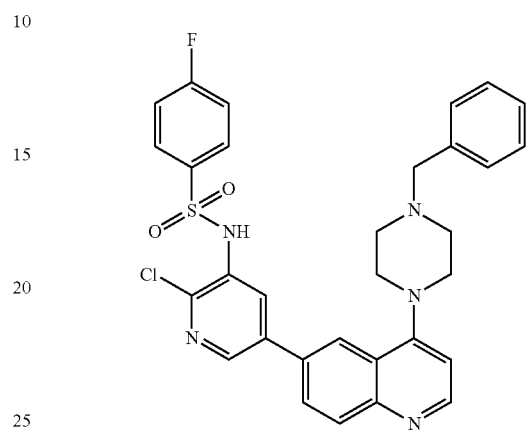

(Some starting materials may be obtained from Aldrich, St. Louis, Mo.) MS (ESI pos. ion) m/z: calc'd for $C_{31}H_{27}ClFN_5O_2S$: 587.2; found: 588.3 (M+1). $^1$H NMR (300 MHz, CHLOROFORM-d) δ ppm 2.81 (br. s., 4 H) 3.33 (br. s., 4 H) 3.67 (s, 2 H) 6.92 (d, J=5.12 Hz, 1 H) 7.17 (t, J=8.48 Hz, 2 H) 7.29-7.44 (m, 5 H) 7.85 (dd, J=8.92, 4.82 Hz, 3 H) 8.18 (d, J=8.77 Hz, 1 H) 8.25 (s, 1 H) 8.35 (d, J=2.34 Hz, 1 H) 8.50 (d, J=2.34 Hz, 1 H) 8.78 (d, J=4.97 Hz, 1 H).

Example 29

N-(2-chloro-5-(4-(4-(1-phenylethyl)-1-piperazinyl)-6-quinolinyl)-3-pyridinyl)-4-fluorobenzenesulfonamide

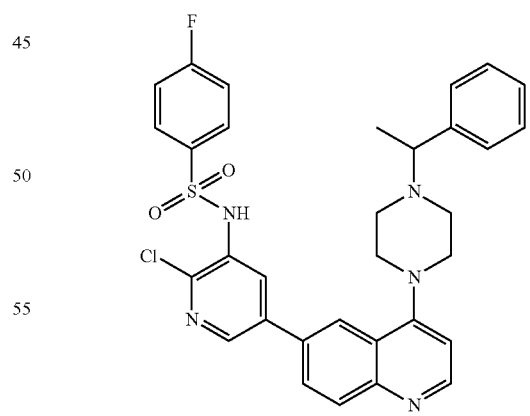

(Some starting materials may be obtained from Chess GmbH, Mannheim, Germany) MS (ESI pos. ion) m/z: calc'd for $C_{32}H_{29}ClFN_5O_2S$: 601.2; found: 602.5 (M+1). $^1$H NMR (400 MHz, CHLOROFORM-d) δ ppm 1.46 (d, J=6.65 Hz, 3 H) 2.74 (br. s., 2 H) 2.85 (br. s., 2 H) 3.30 (br. s., 4 H) 3.53 (d, J=6.46 Hz, 1 H) 6.91 (d, J=5.09 Hz, 1 H) 7.16 (t, J=8.51 Hz, 2 H) 7.21-7.27 (m, 2 H) 7.33 (t, J=7.53 Hz, 2 H) 7.35-7.40 (m, 2 H) 7.84 (dd, J=8.90, 4.99 Hz, 3 H) 8.17 (d, J=8.80 Hz, 1 H) 8.21 (d, J=1.96 Hz, 1 H) 8.33 (d, J=2.35 Hz, 1 H) 8.48 (s, 1 H) 8.77 (d, J=4.89 Hz, 1 H).

Example 30

N-(2-chloro-5-(4-(2,6-dimethyl-4-morpholinyl)-6-quinolinyl)-3-pyridinyl)-4-fluorobenzenesulfonamide

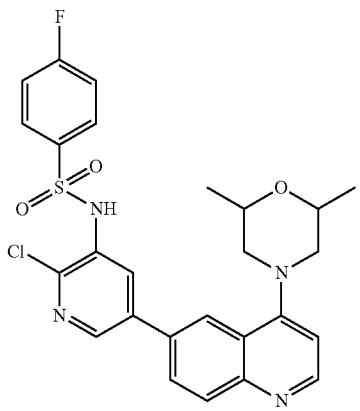 [SMILES: CC1CN(c2ccnc3ccc(-c4cnc(Cl)c(NS(=O)(=O)c5ccc(F)cc5)c4)cc23)CC(C)O1]

(Some starting materials may be obtained from Fluka Chemie, St. Louis, Mo.) MS (ESI pos. ion) m/z: calc'd for C$_{26}$H$_{24}$ClFN$_4$O$_3$S: 526.2; found: 527.5 (M+1). $^1$H NMR (300 MHz, CHLOROFORM-d) δ ppm 1.29 (t, J=7.45 Hz, 6 H) 2.62-2.78 (m, 1 H) 2.97-3.11 (m, 1 H) 3.28 (d, J=11.69 Hz, 1 H) 3.47 (d, J=11.69 Hz, 1 H) 4.01-4.17 (m, 1 H) 4.35 (t, J=6.28 Hz, 1 H) 6.93 (d, J=4.97 Hz, 1 H) 7.18 (t, J=8.55 Hz, 2 H) 7.75-7.93 (m, 3 H) 8.21 (d, J=10.82 Hz, 2 H) 8.30-8.39 (m, 1 H) 8.49 (d, J=2.34 Hz, 1 H) 8.80 (d, J=4.97 Hz, 1 H).

Example 31

N-(2-chloro-5-(4-(2-methoxyethoxy)-6-quinolinyl)-3-pyridinyl)-4-fluorobenzenesulfonamide

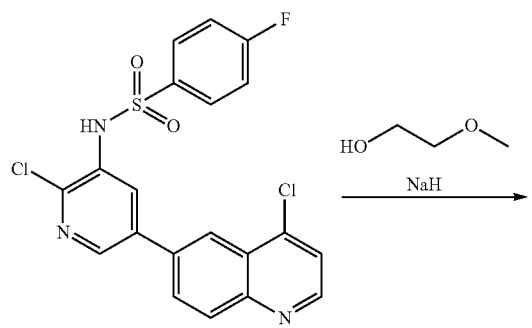

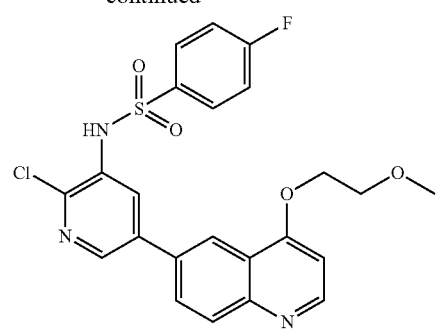

(Some starting materials may be obtained from Aldrich, St. Louis, Mo.) To a solution of 2-methoxyethanol (0.2 mL, 2 mmol) in DMF (10 mL) at 0° C. was added sodium hydride, 60% dispersion in mineral oil (0.09 mL, 2 mmol). After the addition, the ice bath was removed. The reaction mixture was warmed up to rt and continued to stir at rt. After 20 min, N-(2-chloro-5-(4-chloroquinolin-6-yl)pyridin-3-yl)-4-fluorobenzenesulfonamide (0.1 g, 0.2 mmol) was added. It was continued to stir for 20 h. LC/MS showed total conversion. Reaction was quenched with water. The resulting mixture was partitioned between EtOAc/water. The organic layer was washed with water, brine, dried over MgSO$_4$ and concentrated. The crude product was purified using SiO$_2$ (12 g) chromatography with hexanes:acetone=80%:20% as the solvent system to afford the desired product as light yellow solid (25 mg). A peak at 28 min was collected. The solvent was removed in vacuo to afford the desired product as light yellow solid (80.0 mg). MS (ESI pos. ion) m/z: calc'd for C$_{23}$H$_{19}$ClFN$_3$O$_4$S: 487.1; found: 488.4 (M+1). $^1$H NMR (300 MHz, CHLOROFORM-d) δ ppm 3.53 (s, 3 H) 3.90-4.00 (m, 2 H) 4.35-4.49 (m, 2 H) 6.84 (d, J=5.26 Hz, 1 H) 7.19 (t, J=8.55 Hz, 2 H) 7.88 (ddd, J=8.62, 4.17, 3.87 Hz, 3 H) 8.17 (d, J=8.77 Hz, 1 H) 8.33 (d, J=2.34 Hz, 1 H) 8.43 (d, J=1.90 Hz, 1 H) 8.50 (d, J=2.34 Hz, 1 H) 8.81 (d, J=5.26 Hz, 1 H).

Example 32

N-(2-chloro-5-(4-(4-morpholinyl)-6-quinolinyl)-3-pyridinyl)-2-fluorobenzenesulfonamide

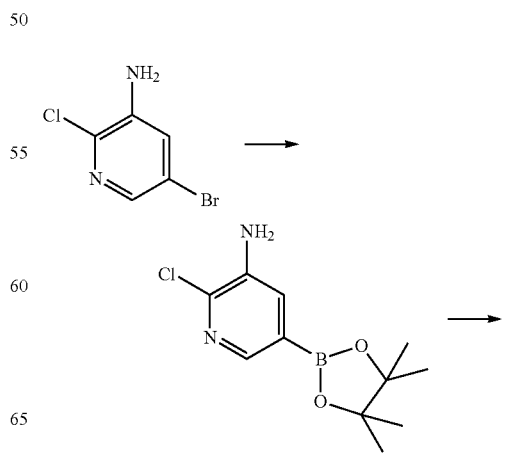

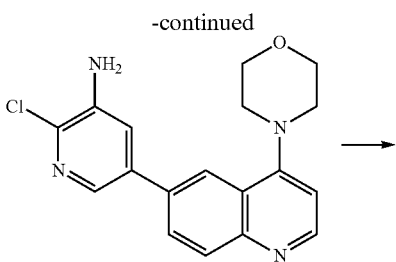

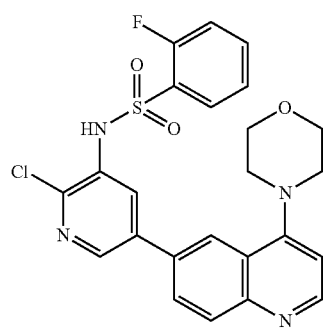 [SMILES: O=S(=O)(Nc1cc(-c2ccc3nccc(N4CCOCC4)c3c2)cnc1Cl)c1ccccc1Cl]

(1) 2-chloro-5-(4,4,5,5-tetramethyl-1,3,2-dioxaborolan-2-yl)pyridin-3-amine. (Some starting materials may be obtained from Aldrich, St. Louis, Mo.) To a 5 mL microwave tube was added 5-bromo-2-chloropyridin-3-amine (0.1 g, 0.5 mmol), bis(pinacolato)diboron (0.2 g, 0.7 mmol), potassium acetate (0.2 g, 2 mmol), 1,1'-bis(diphenylphosphino)ferrocene]dichloride palladium(ii) (0.03 g, 0.04 mmol), and dioxane (3 mL). The vial was sealed and placed in Biotage Initiator microwave (Biotage, Charlottesville, Va.) for 20 min at 110° C. LC/MS showed no sign of starting material. Dioxane was removed in vacuo. The residue was partitioned between EtOAc/water. The organic layer was washed with water, brine, dried over MgSO$_4$ and removed solvent. The crude product was purified using SiO$_2$ (12 g) chromatography with hexanes:acetone=85%:15% as the solvent system to afford the desired product as light yellow solid (75 mg). A peak at 38 min was collected. The solvent was concentrated to afford the desired product as light yellow solid (75 mg). MS (ESI pos. ion) m/z: calc'd for C$_{11}$H$_{16}$BClN$_2$O$_2$: 254.1; found: 255.3 (M+1). $^1$H NMR (300 MHz, CHLOROFORM-d) δ ppm 1.35 (s, 12 H) 4.03 (br. s., 2 H) 7.40 (d, J=1.61 Hz, 1 H) 8.14 (d, J=1.61 Hz, 1 H).

(2) 2-chloro-5-(4-morpholinoquinolin-6-yl)pyridin-3-amine. To a 5 mL CEM microwave tubes was added 2-chloro-5-(4,4,5,5-tetramethyl-1,3,2-dioxaborolan-2-yl)pyridin-3-amine (0.3 g, 1 mmol), 6-bromo-4-morpholinoquinoline (0.32 g, 1.5 mmol), sodium carbonate (1 mL, 2.5 mmol), Pd-fibrecat (20% wt, 60 mg), and dioxane (3 mL). The tube was sealed and placed into CEM microwave for 20 min. at 130° C., with 100 Watts of power via powermax. LC/MS showed a desired product mass as a major peak. The reaction mixture was partitioned between DCM/water. The aqueous layer was extracted with DCM (2×10 mL). The organic layer was dried over MgSO$_4$ and concentrated. The crude product was purified using SiO$_2$ (40 g) chromatography with DCM:EtOAc:MeOH=70%:26%:4% as the solvent system to afford the desired product as light yellow solid (250 mg). MS (ESI pos. ion) m/z: calc'd for C$_{18}$H$_{17}$ClN$_4$O: 340.1; found: 341.4 (M+1). $^1$H NMR (300 MHz, CHLOROFORM-d) δ ppm 3.22-3.33 (m, 4 H) 3.96-4.06 (m, 4 H) 4.25 (br. s., 2 H) 6.93 (d, J=4.97 Hz, 1 H) 7.31 (d, J=2.19 Hz, 1 H) 7.83 (dd, J=8.77, 2.05 Hz, 1 H) 8.15 (td, J=6.14, 2.48 Hz, 3 H) 8.79 (d, J=4.97 Hz, 1 H).

(3) N-(2-chloro-5-(4-(4-morpholinyl)-6-quinolinyl)-3-pyridinyl)-2-fluorobenzenesulfonamide. To a solution of 2-chloro-5-(4-morpholinoquinolin-6-yl)pyridin-3-amine (0.07 g, 0.2 mmol) in pyridine (8 mL) was added 2-fluorobenzenesulfonyl chloride (0.3 ml, 2 mmol). The resulting mixture was heated to 100° C. under N$_2$ 20 h. Pyridine was removed as much as possible. The residue was partitioned between EtOAc/water. The aqueous layer was extracted with EtOAc (3×10 mL). The combined organic layers were dried over MgSO$_4$ and concentrated. The crude product was purified using SiO$_2$ (12 g) chromatography starting with hexane:acetone=70%:30%, then DCM:EtOAc:MeOH=80%:15%:5%, The peaks at 22 and 25 min were collected and combined. The solvent was removed in vacuo. These mono and bis mixtures were dissolved in MeOH and treated with K$_2$CO$_3$. After stirred for 20 min at rt, the solvent was concentrated. The residue was dissolved in water and neutralized to pH ~7. The resulting mixture was extracted with CHCl$_3$ (3×15 mL). The combined organic layers were dried in MgSO$_4$ and concentrated to afford the desired product as light yellow solid (50 mg). MS (ESI pos. ion) m/z: calc'd for C$_{24}$H$_{20}$ClFN$_4$O$_3$S: 498.1; found: 499.5 (M+1). $^1$H NMR (300 MHz, CHLOROFORM-d) δ ppm 6.95 (d, J=5.12 Hz, 1 H) 7.20-7.33 (m, 2 H) 7.57-7.69 (m, 1 H) 7.79-7.95 (m, 2 H) 8.15-8.26 (m, 2 H) 8.34 (d, J=2.19 Hz, 1 H) 8.45 (d, J=2.34 Hz, 1 H) 8.81 (d, J=4.97 Hz, 1 H).

Examples 33 and 34 were prepared according to the procedure described in example 32.

Example 33

2-chloro-N-(2-chloro-5-(4-(4-morpholinyl)-6-quinolinyl)-3-pyridinyl)benzenesulfonamide

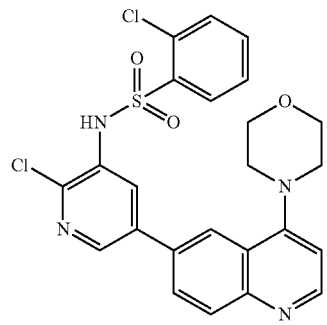

(Some starting materials may be obtained from Avocado Research, Ward Hills, Mass.) MS (ESI pos. ion) m/z: calc'd for C$_{24}$H$_{20}$Cl$_2$N$_4$O$_3$S: 514.1; found: 515.5 (M+1). $^1$H NMR (300 MHz, CHLOROFORM-d) δ ppm 6.95 (d, J=5.12 Hz, 1 H) 7.20-7.33 (m, 2 H) 7.57-7.69 (m, 1 H) 7.79-7.95 (m, 2 H) 8.15-8.26 (m, 2 H) 8.34 (d, J=2.19 Hz, 1 H) 8.45 (d, J=2.34 Hz, 1 H) 8.81 (d, J=4.97 Hz, 1 H).

Example 34

2,6-dichloro-N-(2-chloro-5-(4-(4-morpholinyl)-6-quinolinyl)-3-pyridinyl)benzenesulfonamide

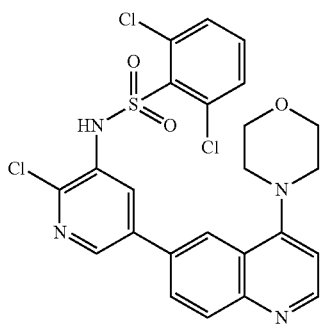 [SMILES: O=S(=O)(Nc1cc(-c2ccc3nccc(N4CCOCC4)c3c2)cnc1Cl)c1c(Cl)cccc1Cl]

(Some starting materials may be obtained from Alfa Aesar, Ward Hills, Mass.) To a flame-dry 50 mL rb flask was added 2-chloro-5-(4-morpholinoquinolin-6-yl)pyridin-3-amine (0.07 g, 0.2 mmol) and THF (8 mL). The reaction mixture was cooled to 0° C. followed by adding sodium bis(trimethylsilyl) amide, 1.0 m solution in tetrahydrofuran (0.4 mL, 0.4 mmol). After the addition, it was continued to stir at 0° C. under $N_2$. After 30 min, 2,6-dichlorobenzene-1-sulfonyl chloride (0.07 g, 0.3 mmol) was added into the reaction mixture. After the addition, it was continued to stir at 0° C. then slowly warmed up to rt overnight. The reaction was quenched with water. The solvent was concentrated. The residue was partitioned between EtOAc/water. The organic layer was washed with brine, dried over $MgSO_4$ and concentrated. The crude product was purified using $SiO_2$ (12 g) chromatography with DCM:EtOAc:MeOH=70%:26%:4% as the solvent system to afford the desired product as light yellow solid (63.0 mg). MS (ESI pos. ion) m/z: calc'd for $C_{24}H_{19}Cl_3N_4O_3S$: 548.1; found: 549.4 (M+1). $^1$H NMR (300 MHz, CHLOROFORM-d) δ ppm 3.21-3.38 (m, 4 H) 3.93-4.11 (m, 4 H) 6.94 (d, J=4.97 Hz, 1 H) 7.33-7.44 (m, 1 H) 7.45-7.55 (m, 2 H) 7.85 (dd, J=8.77, 2.05 Hz, 1 H) 8.18 (d, J=8.77 Hz, 1 H) 8.25 (d, J=1.90 Hz, 1 H) 8.39-8.50 (m, 2 H) 8.81 (d, J=4.97 Hz, 1 H).

Example 35

N-(2-chloro-5-(4-(2-methoxy-3-pyridinyl)-6-quinolinyl)-3-pyridinyl)-4-fluorobenzenesulfonamide

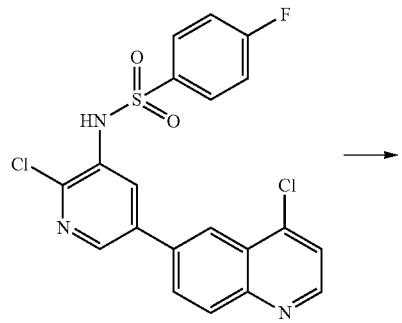

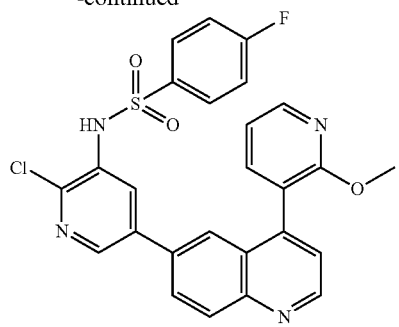

(Some starting materials may be obtained from Frontier Scientific, Inc., Logan, Utah) To a 5 mL CEM microwave tube was added N-(2-chloro-5-(4-chloroquinolin-6-yl)pyridin-3-yl)-4-fluorobenzenesulfonamide (0.07 g, 0.2 mmol), 2-methoxypyridine-3-boronic acid hydrate (0.07 g, 0.5 mmol), sodium carbonate (0.2 mL, 0.5 mmol), Pd fibrecat PPh (20% wt, 15 mg), and dioxane (3 mL). The vial was sealed and placed into CEM microwave for 20 min. at 120° C., with 100 watts of power. LC/MS showed a desired product mass as a major peak. The reaction mixture was partitioned between DCM/water. The aqueous layer was extracted with DCM (2×10 mL). The combined organic layers were washed with water, brine, dried over $MgSO_4$ and concentrated. The crude product was purified using $SiO_2$ (12 g) chromatography with hexanes:acetone=80%:20% as the solvent system to afford the desired product as light yellow solid (25 mg). MS (ESI pos. ion) m/z: calc'd for $C_{26}H_{18}ClFN_4O_3S$: 520.1; found: 521.3 (M+1). $^1$H NMR (300 MHz, CHLOROFORM-d) δ ppm 3.95 (s, 3 H) 7.06-7.19 (m, 3 H) 7.42 (d, J=4.53 Hz, 1 H) 7.67 (dd, J=7.31, 1.90 Hz, 1 H) 7.72 (d, J=1.90 Hz, 1 H) 7.75-7.82 (m, 2 H) 7.90 (dd, J=8.77, 2.05 Hz, 1 H) 8.20 (d, J=2.34 Hz, 1 H) 8.31 (d, J=8.77 Hz, 1 H) 8.34 (d, J=2.19 Hz, 1 H) 8.40 (dd, J=5.04, 1.97 Hz, 1 H) 9.03 (d, J=4.38 Hz, 1 H).

Example 36

N-(2-chloro-5-(4-phenyl-6-quinolinyl)-3-pyridinyl)-4-fluorobenzenesulfonamide

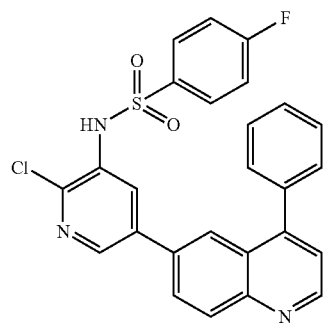 [SMILES: O=S(=O)(Nc1cc(-c2ccc3nccc(-c4ccccc4)c3c2)cnc1Cl)c1ccc(F)cc1]

(Some starting materials may be obtained from Sigma, St. Louis, Mo.) MS (ESI pos. ion) m/z: calc'd for $C_{26}H_{17}ClFN_4O_3S$: 489.1; found: 490.3 (M+1). $^1$H NMR (300 MHz, CHLOROFORM-d) δ ppm 7.01-7.12 (m, 2 H) 7.44 (d, J=4.53 Hz, 1 H) 7.54-7.64 (m, 5 H) 7.78 (dd, J=9.06, 4.97 Hz, 2 H) 7.92 (dd, J=8.77, 2.19 Hz, 1 H) 8.08 (d, J=1.75

Hz, 1)8.20 (d, J=2.34 Hz, 1 H) 8.32 (d, J=8.62 Hz, 1 H) 8.37 (d, J=2.19 Hz, 1 H) 9.02 (d, J=4.53 Hz, 1 H).

Example 37

N-(2-chloro-5-(6-cinnolinyl)-3-pyridinyl)-4-fluorobenzenesulfonamide

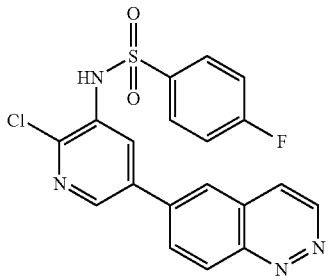 [SMILES: O=S(=O)(Nc1cc(-c2ccc3nnccc3c2)cnc1Cl)c1ccc(F)cc1]

(Some starting materials may be obtained from Inogent Laboratories Private Lmited, Begumpet Hyerabad, India) A glass microwave reaction vessel was charged with 6-bromo-cinnoline (150 mg, 0.7 mmol), N-(2-chloro-5-(4,4,5,5-tetramethyl-1,3,2-dioxaborolan-2-yl)pyridin-3-yl)-4-fluorobenzenesulfonamide (296 mg, 0.7 mmol), anhydrous sodium carbonate (228 mg, 2.2 mmol), 1,1'-bis(diphenylphosphino)ferrocene-palladium dichloride (37 mg, 0.05 mmol) and dioxane-$H_2O$ (2:1, 3 mL). The reaction vessel was sealed and the mixture was stirred and heated at 100° C. for 1 h. Water was added in, and the suspension was filtered, the solid was air-dried. The crude was purified through a Redi-Sep® (Teledyne ISCO, Lincoln, Nebr.) pre-packed silica gel column (40 g), eluting with a gradient of 2% to 5% MeOH in $CH_2Cl_2$ to provide N-(2-chloro-5-(cinnolin-6-yl)pyridin-3-yl)-4-fluorobenzenesulfonamide (15 mg, 5.0% yield) as a yellow solid. MS (ESI pos. ion) m/z: calc'd for $C_{19}H_{12}ClFN_4O_2S$:414.8.0; found: 415.0 (MH+). $^1$H NMR (400 MHz, DMSO-$d_6$) δ ppm 7.44(t, J=8.78 Hz, 2 H) 7.83 (dd, J=8.78, 5.27 Hz, 2 H) 8.24 (s, 1 H) 8.28-8.31 (m, 2 H) 8.46 (s, 1 H) 8.60 (d, J=9.03 Hz, 1 H) 8.79 (s, 1 H) 9.46 (d, J=5.52 Hz, 1 H) 10.60 (s, 1 H).

Example 38

N-(2-chloro-5-(6-isoquinolinyl)-3-pyridinyl)-4-fluorobenzenesulfonamide

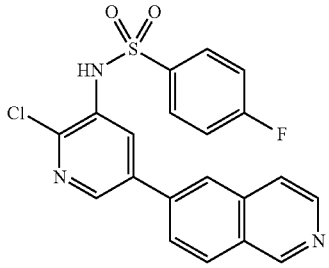 [SMILES: O=S(=O)(Nc1cc(-c2ccc3cnccc3c2)cnc1Cl)c1ccc(F)cc1]

(Some starting materials may be obtained from Kalexsyn, Kalamazoo, Mich.) A glass microwave reaction vessel was charged with 6-bromoisoquinoline (120 mg, 0.58 mmol), N-(2-chloro-5-(4,4,5,5-tetramethyl-1,3,2-dioxaborolan-2-yl)pyridin-3-yl)-4-fluorobenzenesulfonamide (262 mg, 0.6 mmol), 1,1'-bis(diphenylphosphino)ferrocene-palladium dichloride (32 mg, 0.04 mmol), sodium carbonate (183 mg, 1.730 mmol), and dioxane-$H_2O$ (2:1, 3 mL). The reaction mixture was sealed and heated at 100° C. for 1 h. Water was added in, and the suspension was filtered, the solid was air-dry. The crude product was chromatographed through a Redi-Sep® pre-packed silica gel column (40 g), eluting with a gradient of 2% to 5% MeOH in $CH_2Cl_2$ to provide N-(2-chloro-5-(isoquinolin-6-yl)pyridin-3-yl)-4-fluorobenzenesulfonamide (20 mg, 8.4% yield) as a white solid. MS (ESI pos. ion) m/z: calc'd for $C_{20}H_{13}ClFN_3O_2S$:413.0; found: 414.0(MH+). $^1$H NMR (400 MHz, DMSO-$d_6$) δ ppm 7.44(t, J=8.80 Hz, 2 H) 7.82-7.85 (m, 2 H) 7.93 (d, J=5.87 Hz, 1 H) 8.00 (dd, J=8.61, 1.37 Hz, 1 H) 8.16 (d, J=2.15 Hz, 1 H) 8.29 (d, J=8.61 Hz, 1 H) 8.33 (s, 1 H) 8.58 (d, J=5.67 Hz, 1 H) 8.75 (s, 1 H) 9.40 (s, 1 H) 10.58 (s, 1 H).

Example 39

N-(2-chloro-5-(5-phthalazinyl)-3-pyridinyl)-4-fluorobenzenesulfonamide

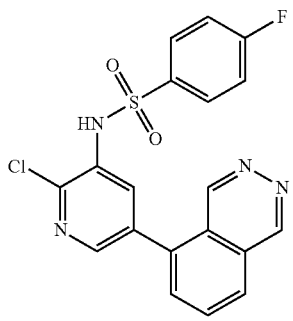 [SMILES: O=S(=O)(Nc1cc(-c2cccc3cnncc23)cnc1Cl)c1ccc(F)cc1]

(1) 5-bromophthalazine: A mixture of aluminum tribromide (37 mL, 0.37 mol), aluminum trichloride (98 g, 0.74 mol) and (1E,2E)-1,2-bis(4-bromobenzylidene)hydrazine (Dimmock, J. R. et al., Eur. J. Med. Chem. 1995, 30, 287-301) (18 g, 49 mmol)was stirred at 190° C. for 1 hour. After cooling to room temperature, the reaction mixture was treated with water (200 mL, 49 mmol) and 5% solution of hydrochloric acid (100 mL). The mixture was then basified with 15% potassium hydroxide and extracted thoroughly with DCM. The combined organics were dried over $Na_2SO_4$ and concentrated under reduced pressure to afford a (aprox. 4:1) mixture of 5- and 6-bromophthalazine.

They were separated by preparative reverse-phase liquid chromatography eluting with 10->50% of (ACN, 0.1% TFA)/ $H_2O$, 0.1% TFA. MS (ESI pos. ion) m/z calc'd for $C_8H_5BrN_2$: 207.9/209.9; found 208.9/210.9. $^1$H NMR (400 MHz, DMSO-$d_6$) δ ppm 7.98 (t, J=7.8 Hz, 1 H) 8.24 (d, J=8.0 Hz, 1 H), 8.36 (d, J=7.6 Hz, 1 H) 9.74 (d, J=5.1 Hz, 2 H). 6-bromophthalazine: MS (ESI pos. ion) m/z calc'd for $C_8H_5BrN_2$: 207.9/209.9; found 208.9/210.9. $^1$H NMR (400 MHz, DMSO-$d_6$) ppm 8.14 (d, J=8.5 Hz, 1 H) 8.20 (dd, J=8.5, 1.7 Hz, 1 H) 8.49 (d, J=1.4 Hz, 1 H) 9.69 (d, J=19.4 Hz, 2 H).

(2) N-(2-chloro-5-(5-phthalazinyl)-3-pyridinyl)-4-fluorobenzenesulfonamide: A suspension of N-(2-chloro-5-(4,4,5,5-tetramethyl-1,3,2-dioxaborolan-2-yl)pyridin-3-yl)-4-fluorobenzenesulfonamide (149 mg, 362 μmol), 5-bromophthalazine (63 mg, 301 μmol), dichloro[1,1'bis (diphenylphoshino)ferrocene]palladium(II)dichloromethane adduct (17 mg, 23 μmol), and Na$_2$CO$_3$ (96 mg, 904 μmol) in 1,4-dioxane (2 mL) and water (1 mL) was spurged with nitrogen for 5 minutes, then heated to 100° C. for 2 hours. The reaction was then partitioned between 9:1 CHCl$_3$/IPA (30 mL) and 5% NaHCO$_3$ (10 mL). The separated organic was dried over Na$_2$SO$_4$, concentrated onto dry silica, and then purified on silica eluting with 1->4% of MeOH/DCM. Product was isolated as light yellow solid. MS (ESI pos. ion) m/z calc'd for C$_{19}$H$_{12}$ClFN$_4$O$_2$S: 414.0; found 415.0. $^1$H NMR (400 MHz, DMSO-d$_6$) δ ppm 7.44 (t, J=8.7 Hz, 2 H) 7.83-7.90 (m, 2 H) 7.96 (d, J=2.1 Hz, 1 H) 8.04 (d, J=7.0 Hz, 1 H) 8.15 (t, J=7.7 Hz, 1 H) 8.30 (d, J=8.0 Hz, 1 H) 8.51 (d, J=2.0 Hz, 1 H) 9.43 (s, 1 H) 9.79 (d, J=1.2 Hz, 1 H) 10.61 (s, 1 H).

Example 40

N-(2-chloro-5-(6-phthalazinyl)-3-pyridinyl)-4-fluorobenzenesulfonamide

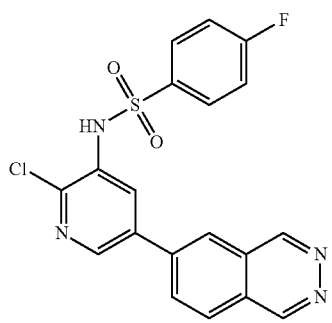 [SMILES: O=S(=O)(Nc1cc(-c2ccc3cnncc3c2)cnc1Cl)c1ccc(F)cc1]

A suspension of N-(2-chloro-5-(4,4,5,5-tetramethyl-1,3,2-dioxaborolan-2-yl)pyridin-3-yl)-4-fluorobenzenesulfonamide (102 mg, 247 μmol), 6-bromophthalazine (43 mg, 206 μmol), dichloro[1,1'bis(diphenylphoshino)ferrocene]palladium(II)dichloromethane adduct (11 mg, 15 μmol), and Na$_2$CO$_3$ (65 mg, 617 μmol) in 1,4-dioxane (2 mL) and water (1 mL) was sparged with nitrogen for 5 minutes, then heated to 100° C. for 2 hours. The reaction was then partitioned between 9:1 CHCl$_3$/IPA (30 mL) and 5% NaHCO$_3$ (10 mL). The separated organic was dried over Na$_2$SO$_4$, concentrated onto dry silica, and then purified on silica eluting with 2→5% of MeOH/DCM. Product was isolated as light yellow solid. MS (ESI pos. ion) m/z calc'd for C$_{19}$H$_{12}$ClFN$_4$O$_2$S: 414.0; found 415.0. $^1$H NMR (400 MHz, DMSO-d$_6$) δ 7.44 (t, J=8.8 Hz, 2 H) 7.80-7.87 (m, 2 H) 8.24 (d, J=2.1 Hz, 1 H) 8.32 (d, J=8.4 Hz, 1 H) 8.38 (dd, J=8.7, 2.0 Hz, 1 H) 8.54 (s, 1 H) 8.79 (d, J=2.1 Hz, 1 H) 9.76 (s, 2 H) 10.60 (s, 1 H).

Example 41

N-(2-chloro-5-(1,5-naphthyridin-2-yl)-3-pyridinyl)-4-fluorobenzenesulfonamide

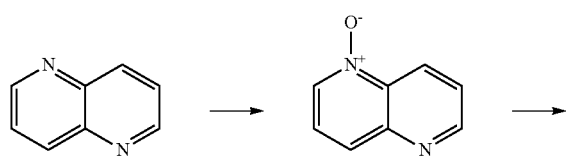

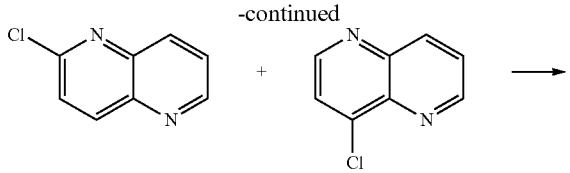

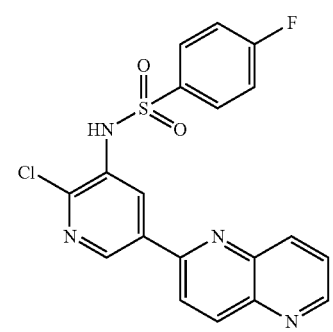

(1) 1,5-naphthyridine N (1)-oxide. (Some starting materials may be obtained from Aldrich, St. Louis, Mo.) To a 100 mL round-bottomed flask was added 1,5-naphthyridine (260 mg, 1998 μmol), CH$_2$Cl$_2$ (10 mL), 3-chloroperoxybenzoic acid (517 mg, 2997 μmol). The reaction mixture was stirred at room temperature for overnight (ca 16 h). The solvent was removed in vacuo and the residue was purified by silica gel chromatography, eluting with 20% MeOH/EtOAc to give the product (223 mg, 76.4% yield). MS (ESI pos. ion) m/z calc'd for C$_8$H$_6$N$_2$O: 146.0; found 147.0. $^1$H NMR (300 MHz, MeOD) δ ppm 7.81 (dd, J=8.77, 6.14 Hz, 1 H) 7.91 (dd, J=8.92, 4.24 Hz, 1 H) 8.24 (d, J=8.77 Hz, 1 H) 8.76 (dd, J=6.14, 0.88 Hz, 1 H) 9.04 (d, J=9.94 Hz, 1 H) 9.12 (dd, J=4.24, 1.61 Hz, 1 H)

(2) 2-chloro-1,5-naphthyridine. To a 50 mL round-bottomed flask was added 1,5-naphthyridine N-oxide (198 mg, 1355 μmol), phosphorus oxychloride (2 mL, 21457 μmol). The reaction mixture was stirred at 100° C. for 8 h. The solvent was removed in vacuo. The reaction mixture was diluted with NaHCO$_3$ (2 mL) and extracted with EtOAc (2×20 mL). The organic extract was washed with saturated NaCl (2 mL), dried over Na$_2$SO$_4$, filtered and concentrated in vacuo and the residue was purified by silica gel chromatography, eluting with 60% EtOAc/hexanes to give 2-chloro-1,5-naphthyridine (78 mg, 35% yield), MS (ESI pos. ion) m/z calc'd for C$_8$H$_5$ClN$_2$: 164.0; found 165.0. $^1$H NMR (300 MHz, CHLOROFORM-d)δ ppm 7.64 (d, J=8.77 Hz, 1 H) 7.66-7.72 (m, J=4.38 Hz, 1 H) 8.35 (t, J=8.77 Hz, 2) 8.99 (dd, J=4.17, 1.68 Hz, 1 H)

4-chloro-1,5-naphthyridine (86 mg, 39% yield), MS (ESI pos. ion) m/z calc'd for C$_8$H$_5$ClN$_2$: 164.0; found 165.0. $^1$H NMR (300 MHz, CHLOROFORM-d) δ ppm 7.75 (dd, J=8.55, 4.17 Hz, 1 H) 7.79 (d, J=4.68 Hz, 1 H) 8.47 (dd, J=8.62, 1.61 Hz, 1 H) 8.87 (d, J=4.68 Hz, 1 H) 9.11 (dd, J=4.09, 1.61 Hz, 1 H)

(3) N-(2-chloro-5-(1,5-naphthyridin-2-yl)-3-pyridinyl)-4-fluorobenzenesulfonamide. To a 50 mL round-bottomed flask was added 2-chloro-1,5-naphthyridine (54 mg, 328 μmol), N-(2-chloro-5-(4,4,5,5-tetramethyl-1,3,2-dioxaborolan-2-yl)pyridin-3-yl)-4-fluorobenzenesulfonamide (135 mg, 328 μmol), tetrakis(triphenylphosphine)palladium (38 mg, 33 μmol), sodium carbonate (70 mg, 656 μmol), dioxane (3 mL). The reaction mixture was stirred at 100° C. for 30 min. The mixture was cooled down to room temperature. The reaction mixture was diluted with water (3 mL) and extracted with EtOAc (2×30 mL). The organic extract was washed with saturated NaCl (2 mL), dried over Na$_2$SO$_4$, filtered and concentrated in vacuo and the residue was purified by silica gel chromatography, eluting with 80% EtOAc/hexanes to give N-(2-chloro-5-(1,5-naphthyridin-2-yl)pyridin-3-yl)-4-fluorobenzenesulfonamide (78 mg, 57% yield) as a white solid. MS (ESI pos. ion) m/z calc'd for C$_{19}$H$_{12}$ClFN$_4$O$_2$S: 414.0; found 415.0. $^1$H NMR (300 MHz, CHLOROFORM-d) δ ppm 7.07 (s, 1 H) 7.16 (t, J=8.55 Hz, 2 H) 7.73 (dd, J=8.55, 4.17 Hz, 1 H) 7.88 (dd, J=8.92, 4.97 Hz, 2 H) 8.11 (d, J=8.77 Hz, 1 H) 8.49 (d, J=8.48 Hz, 1 H) 8.55 (d, J=8.77 Hz, 1 H) 8.83 (d, J=2.19 Hz, 1 H) 8.94 (d, J=2.19 Hz, 1 H) 9.03 (dd, J=4.09, 1.61 Hz, 1 H)

Example 42

N-(2-chloro-5-(1,5-naphthyridin-4-yl)-3-pyridinyl)-4-fluorobenzenesulfonamide

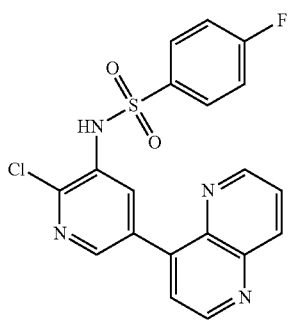 [SMILES: O=S(=O)(Nc1cc(-c2ccnc3cccnc23)cnc1Cl)c1ccc(F)cc1]

(Some starting materials may be obtained from Aldrich, St. Louis, Mo.) To a 50 mL round-bottomed flask was added 4-chloro-1,5-naphthyridine (40 mg, 243 μmol), N-(2-chloro-5-(4,4,5,5-tetramethyl-1,3,2-dioxaborolan-2-yl)pyridin-3-yl)-4-fluorobenzenesulfonamide (100 mg, 243 μmol), tetrakis(triphenylphosphine)palladium (28 mg, 24 μmol), sodium carbonate (243 μl, 486 μmol), dioxane (2 mL). The reaction mixture was stirred at 100° C. for 5 h. The mixture was cooled down to room temperature. The reaction mixture was diluted with water (3 mL) and extracted with EtOAc (2×30 mL). The organic extract was washed with saturated NaCl (3 mL), dried over Na$_2$SO$_4$, filtered and concentrated in vacuo and the residue was purified by silica gel chromatography, eluting with 70% EtOAc/hexanes to give N-(2-chloro-5-(1,5-naphthyridin-4-yl)pyridin-3-yl)-4-fluorobenzenesulfonamide (46 mg, 46% yield) as a white solid. MS (ESI pos. ion) m/z calc'd for C$_{19}$H$_{12}$ClFN$_4$O$_2$S: 414.0; found 415.0. $^1$H NMR (300 MHz, CHLOROFORM-d) δ ppm 7.09 (s, 1 H) 7.13-7.23 (m, J=8.33 Hz, 2 H) 7.68 (d, J=4.38 Hz, 1 H) 7.75 (dd, J=8.55, 4.17 Hz, 1 H) 7.97 (dd, J=8.99, 4.90 Hz, 2 H) 8.49-8.56 (m, J=2.85, 2.85 Hz, 2 H) 8.58 (d, J=2.05 Hz, 1 H) 9.01 (dd, J=4.17, 1.68 Hz, 1 H) 9.10 (d, J=4.38 Hz, 1 H)

Example 43

N-(5-(2-amino-3-oxo-3,4-dihydro-6-quinoxalinyl)-2-chloro-3-pyridinyl)-4-fluorobenzenesulfonamide

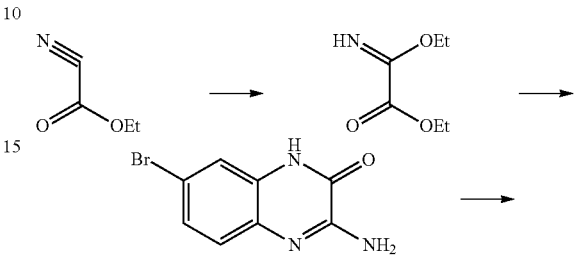

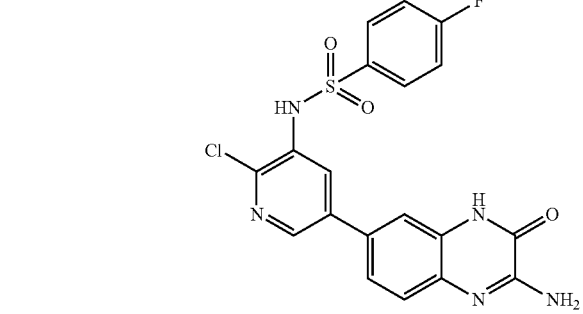

(1) Ethyl 2-ethoxy-2-iminoacetate. (Some starting materials may be obtained from Aldrich, St. Louis, Mo.) To a 100 mL round-bottomed flask was added ethyl cyanoformate (8 mL, 83 mmol), EtOH (10 mL, 171 mmol), pentane (30 mL). Anhydous HCl gas was bubbled to the solution at −15° C. for three hours. The solid was filtered out and washed with EtOH, ether. After the drying, the solid was suspended in Et$_2$O (60 mL), Et$_3$N (12 mL) was then added. The mixture was stirred at room temperature for 2 hours. The solid was filtered out and washed with Et$_2$O. The solvent was removed in vacuo to give ethyl 2-ethoxy-2-iminoacetate (7.2 g, 60% yield) as a crude product which was used for the next step reaction without further purification.

(2) 3-amino-7-bromoquinoxalin-2(1H)-one. To a 100 mL round-bottomed flask was added 4-bromobenzene-1,2-diamine (1.87 g, 10.00 mmol), ethyl 2-ethoxy-2-iminoacetate (1.60 g, 11.0 mmol), EtOH (20 mL). The reaction mixture was stirred at 100° C. for 2 h. The mixture was cooled down to room temperature. The solid was filtered out and washed with EtOH to give 3-amino-7-bromoquinoxalin-2(1H)-one (1.43 g, 59.6% yield). MS (ESI pos. ion) m/z calc'd for C$_8$H$_6$BrN$_3$O: 239, 241 found: 240, 242. $^1$H NMR (300 MHz, DMSO-d$_6$) δ ppm 7.07 (d, J=8.48 Hz, 1 H) 7.12-7.33 (m, 3 H) 7.40 (d, J=2.05 Hz, 1 H) 12.16 (s, 1 H)

(3) N-(5-(2-amino-3-oxo-3,4-dihydro-6-quinoxalinyl)-2-chloro-3-pyridinyl)-4-fluorobenzenesulfonamide. To a 50 mL round-bottomed flask was added 3-amino-7-bromoquinoxalin-2(1H)-one (120 mg, 501 µmol), N-(2-chloro-5-(1,5-dimethyl-2,4-dioxa-bicyclo[3.1.0]hexan-3-yl)pyridin-3-yl)-4-fluorobenzenesulfonamide (200 mg, 501 µmol), tetrakis(triphenylphosphine)palladium (58 mg, 50 µmol), sodium carbonate (501 µl, 1003 µmol), dioxane (3 mL). The reaction mixture was stirred at 100° C. for overnight. The mixture was cooled down to room temperature and was diluted with water (2 mL) and extracted with CH$_2$Cl$_2$ (4×20 mL). The organic extract was washed with saturated NaCl (1 mL), dried over Na$_2$SO$_4$, filtered and concentrated in vacuo and the residue was purified by silica gel chromatography, eluting with 10% MeOH/CH$_2$Cl$_2$ to give N-(5-(2-amino-3-oxo-3,4-dihydroquinoxalin-6-yl)-2-chloropyridin-3-yl)-4-fluorobenzenesulfonamide (38 mg, 17% yield). MS (ESI pos. ion) m/z calc'd for C$_{19}$H$_{13}$ClFN$_5$O$_3$S: 445.0; found 446.0. $^1$H NMR (300 MHz, DMSO) δ ppm 12.28 (s,1H), 10.55 (s, 1H), 8.52 (s, 1H), 7.93 (s, 1H), 7.80-7.90(m, 3H), 7.43-7.48 (m, 2H), 7.38-7.41 (m, 2H)

Example 44

N-(2-chloro-5-(1,8-naphthyridin-3-yl)-3-pyridinyl)-4-fluorobenzenesulfonamide

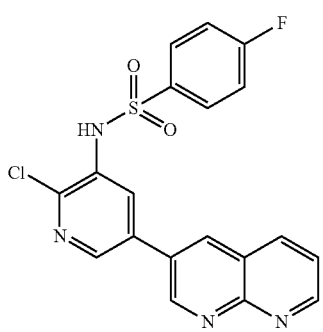 [SMILES: O=S(=O)(Nc1cc(-c2cnc3ncccc3c2)cnc1Cl)c1ccc(F)cc1]

(Some starting materials may be obtained from Princeton Biomolecular Research, Inc., Monmouth Junction, N.J.) To a 50 mL round-bottomed flask was added 3-bromo-1,8-naphthyridine (73 mg, 351 µmol), N-(2-chloro-5-(1,5-dimethyl-2,4-dioxa-bicyclo[3.1.0]hexan-3-yl)pyridin-3-yl)-4-fluorobenzenesulfonamide (140 mg, 351 µmol), tetrakis(triphenylphosphine)palladium (41 mg, 35 µmol), sodium carbonate (351 µl, 702 µmol), dioxane (3 mL). The reaction mixture was stirred at 100° C. for 5 h. The mixture was cooled down to room temperature. The reaction mixture was diluted with water (1 mL) and extracted with CH$_2$Cl$_2$ (5×20 mL). The organic extract was washed with saturated NaCl (2 mL), dried over Na$_2$SO$_4$, filtered and concentrated in vacuo and the residue was purified by silica gel chromatography, eluting with 10% MeOH/CH$_2$Cl$_2$ to give N-(2-chloro-5-(1,8-naphthyridin-3-yl)pyridin-3-yl)-4-fluorobenzenesulfonamide (98 mg, 67% yield) as a white solid. MS (ESI pos. ion) m/z calc'd for C$_{19}$H$_{12}$ClFN$_4$O$_2$S: 414.0; found 415.0. $^1$H NMR (300 MHz, MeOD) δ ppm 7.30 (t, J=8.77 Hz, 2 H) 7.76 (dd, J=8.18, 4.38 Hz, 1 H) 7.89 (dd, J=8.99, 5.04 Hz, 2 H) 8.44 (d, J=2.34 Hz, 1 H) 8.62 (dd, J=8.18, 1.90 Hz, 1 H) 8.70 (d, J=2.34 Hz, 1 H) 8.79 (d, J=2.48 Hz, 1 H) 9.15 (dd, J=4.38, 1.90 Hz, 1 H) 9.39 (d, J=2.48 Hz, 1 H)

Example 45

N-(6-(6-chloro-5-(((4-methoxyphenyl)sulfonyl)amino)-3-pyridinyl)-2-quinolinyl)acetamide

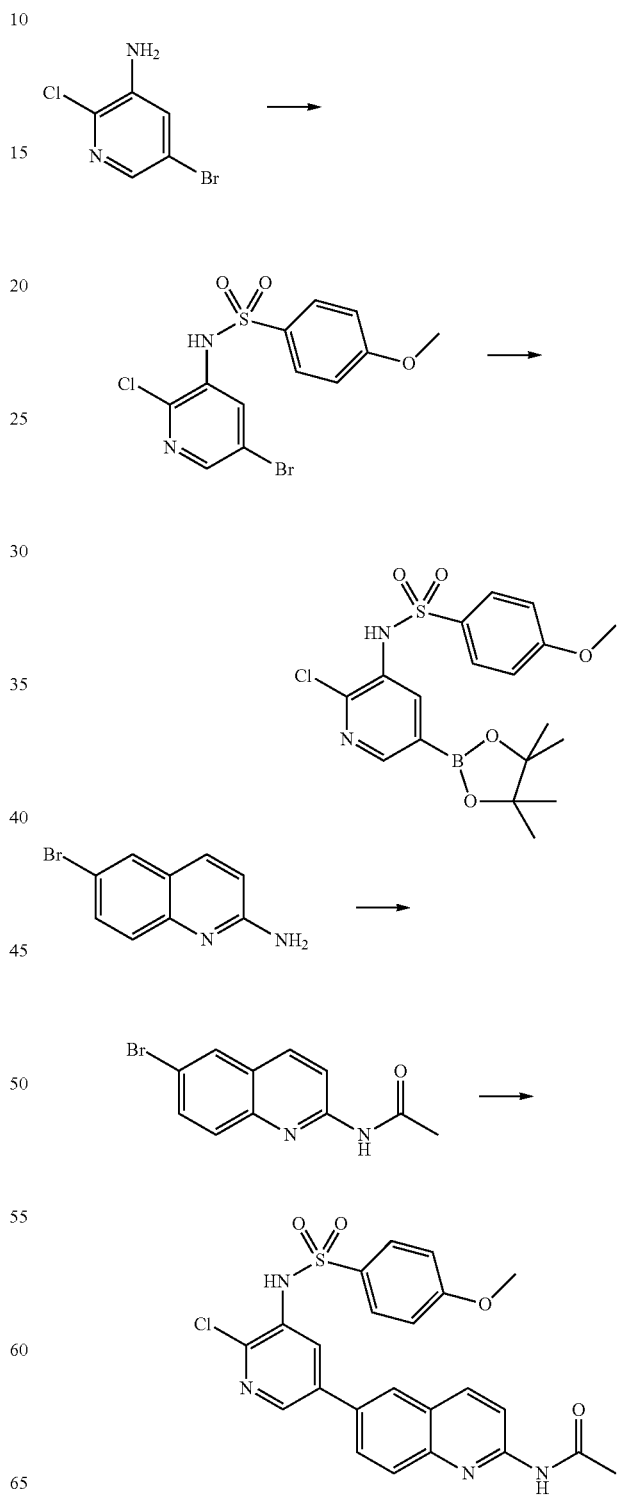

(1) N-(5-bromo-2-chloropyridin-3-yl)-4-methoxybenzenesulfonamide. (Some starting materials may be obtained from Aldrich, St. Louis, Mo. and Fluka Chemie, Buchs, Switzerland) A round bottom flask was charged with 5-bromo-2-chloropyridin-3-amine (2.50 g, 12.1 mmol) and 24 mL THF and the solution was cooled to −78° C. under nitrogen. 1.0 M LiHMDS (24.1 mL, 24.1 mmol) was added slowly and the solution was stirred for 10 min at −78° C. 4-methoxybenzene-1-sulfonyl chloride (3.49 g, 16.9 mmol) dissolved in a minimum amount of THF (~5 mL) was added slowly, and the cooling bath was removed after 10 min. The reaction was stirred at room temperature overnight and was quenched with saturated NH$_4$Cl. The layers were separated, and the organic portion was diluted with CH$_2$Cl$_2$, washed with 1 N HCl and brine. The organic portion was dried with MgSO$_4$, filtered and concentrated. The crude material was dissolved in CH$_2$Cl$_2$ (~20 mL) and ether was added (~40 mL) in portions over 15 min. After allowing to stand in the freezer for 1 h, the solids were filtered and washed with ether. N-(5-bromo-2-chloropyridin-3-yl)-4-methoxybenzenesulfonamide (3.127 g, 68.7% yield) was isolated as a white crystalline solid. MS (ESI pos. ion) m/z calc'd for C$_{12}$H$_{10}$BrClN$_2$O$_3$S: 377.6; found 378.8.

(2) N-(2-chloro-5-(4,4,5,5-tetramethyl-1,3,2-dioxaborolan-2-yl)pyridin-3-yl)-4-methoxybenzenesulfonamide. A pressure bottle was charged with potassium acetate (2.43 g, 24.8 mmol), bis(pinacalato)diboron (3.15 g, 12.4 mmol), PdCl$_2$(dppf)-CH$_2$Cl$_2$ (0.675 g, 0.826 mmol), N-(5-bromo-2-chloropyridin-3-yl)-4-methoxybenzenesulfonamide (3.12 g, 8.26 mmol) and 15.7 mL dioxane. The bottle was flushed with argon and sealed, and the mixture was heated at 90° C. for 4 h. LCMS showed desired as major (mass observed=boronic acid). The mixture was diluted with EtOAc and washed with water. The organic portion was dried with MgSO$_4$, filtered and concentrated. The crude material was purified by silica gel chromatography 0-50% EtOAc/Hex to provide N-(2-chloro-5-(4,4,5,5-tetramethyl-1,3,2-dioxaborolan-2-yl)pyridin-3-yl)-4-methoxybenzenesulfonamide (3.023 g, 86.2% yield) as a white waxy solid after drying in vacuo. MS (ESI pos. ion) m/z calc'd for C$_{18}$H$_{22}$BClN$_2$O$_5$S: 424.7; found 342.9 (M+1 boronic acid).

(3) N-(6-bromoquinolin-2-yl)acetamide. A pyrex reaction tube was charged with 6-bromoquinolin-2-amine (200 mg, 897 µmol) and acetic anhydride (1692 µl, 17932 µmol). The tube was sealed and the mixture was heated at 45° C. After 3 h, LCMS showed no conversion. Catalytic DMAP was added, and heating was continued for 2 h. Trace conversion was observed. The temperature was increased to 100° C. and the reaction was stirred overnight. LCMS showed complete conversion in the morning. The mixture was cooled to 0° C. and the solids were filtered and rinsed with ether to provide N-(6-bromoquinolin-2-yl)acetamide (150 mg, 63.1% yield) as a brown solid. MS (ESI pos. ion) m/z calc'd for C$_{11}$H$_9$BrN$_2$O: 265.1/267.1; found 264.9/267.0.

(4) N-(6-(6-chloro-5-(((4-methoxyphenyl)sulfonyl)amino)-3-pyridinyl)-2-quinolinyl)acetamide. A reaction tube was charged with 2.0 M aqueous sodium carbonate (356 µl, 713 µmol), Pd(Ph$_3$P)$_4$ (16 mg, 14 µmol), N-(2-chloro-5-(4,4,5,5-tetramethyl-1,3,2-dioxaborolan-2-yl)pyridin-3-yl)-4-methoxybenzenesulfonamide (111 mg, 261 µmol), N-(6-bromoquinolin-2-yl)acetamide (63 mg, 238 µmol) and 1.2 mL EtOH. The tube was sealed and the mixture was heated at 90° C. for 2 h. The mixture was diluted with CH$_2$Cl$_2$ and water, and the aqueous portion was brought to pH 7-8 with 2 N HCl. The layers were separated, the aqueous was extracted with additional CH$_2$Cl$_2$, and the combined organics were dried with MgSO$_4$, filtered and concentrated. The crude material was purified by silica gel chromatography using a CH$_2$Cl$_2$ in 90/10/1 CH$_2$Cl$_2$/MeOH/NH$_4$OH gradient. This material was further purified by trituration in MeOH. Filtration of the solids, followed by washing with MeOH and drying provided N-(6-(6-chloro-5-(4-methoxyphenylsulfonamido)pyridin-3-yl)quinolin-2-yl)acetamide (35 mg, 30% yield) as an off-white solid. MS (ESI pos. ion) m/z calc'd for C$_{23}$H$_{19}$ClN$_4$O$_4$S: 482.9/484.9; found 483.0/485.0. $^1$H NMR (400 MHz, DMSO-d$_6$) δ ppm 2.18 (s, 3 H), 3.84 (s, 3H), 7.10-7.14 (m, 2 H), 7.71-7.75 (m, 2 H), 7.90-7.92 (m, 1 H), 7.97-8.00 (m, 1 H), 8.07-8.08 (m, 1 H), 8.22-8.23 (m, 1 H), 8.35-8.44 (m, 2 H), 8.69-8.70 (m, 1 H), 10.27 (br s, 1 H), 10.90 (br s, 1 H).

Example 46

N-(5-(2-amino-6-quinolinyl)-2-chloro-3-pyridinyl)-4-methoxybenzenesulfonamide

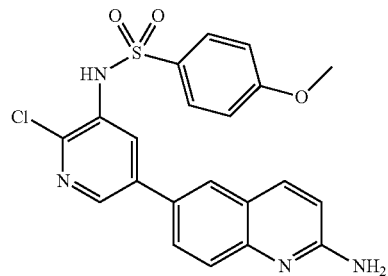 [SMILES: COc1ccc(S(=O)(=O)Nc2cc(-c3ccc4nc(N)ccc4c3)cnc2Cl)cc1]

A reaction tube was charged with sodium carbonate (353 µl, 706 µmol), Pd(Ph$_3$P)$_4$ (16 mg, 14 µmol), N-(2-chloro-5-(4,4,5,5-tetramethyl-1,3,2-dioxaborolan-2-yl)pyridin-3-yl)-4-methoxybenzenesulfonamide (100 mg, 235 µmol), 6-bromoquinolin-2-amine (53 mg, 235 µmol) and 1.2 mL EtOH. The tube was sealed and the mixture was heated at 90° C. for 2 h. The mixture was diluted with CH$_2$Cl$_2$ and washed with water. The organic portion was dried with MgSO$_4$, filtered and concentrated. The crude material was dissolved in MeOH/DMSO and purified by reverse phase chromatography, 10-90% ACN/0.1% TFA in water over 15 min. The aqueous portion was brought to ~pH 7 and extracted. The organic portion was dried, filtered and concentrated to provide N-(5-(2-aminoquinolin-6-yl)-2-chloropyridin-3-yl)-4-methoxybenzenesulfonamide (12 mg, 12% yield) as a light yellow solid. MS (ESI pos. ion) m/z calc'd for C$_{21}$H$_{17}$ClN$_4$O$_3$S: 440.9/442.9; found 441.0/443.0. $^1$H NMR (400 MHz, DMSO-d$_6$) δ ppm 3.88 (s, 3 H), 6.88 (br s, 2 H), 6.89 (d, 1 H, J=8), 7.15-7.18 (m, 2 H), 7.61 (d, 1 H, J=8), 7.75-7.80 (m, 3 H), 7.97-8.00 (m, 2 H), 8.03-8.06 (m, 1 H), 8.62-8.63 (m, 1 H), 10.46 (br, s, 1 H).

Example 47

N-(2-chloro-5-(6-quinolinyl)-3-pyridinyl)-4-methoxybenzenesulfonamide

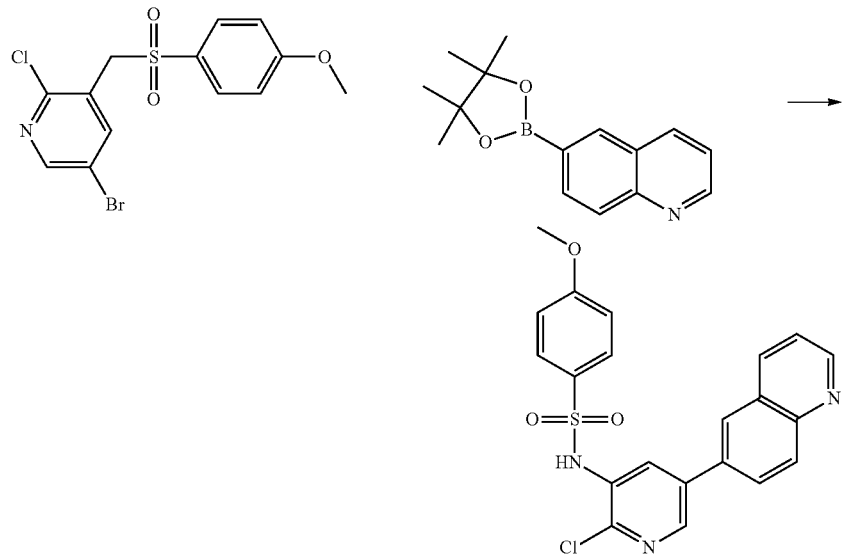

(Some starting materials may be obtained from AstaTech, Inc. Princeton, N.J.) A 15 mL sealed pressure tube was charged with N-(5-bromo-2-chloropyridin-3-yl)-4-methoxybenzenesulfonamide (120 mg, 0.318 mmol), 6-(4,4,5,5-tetramethyl-1,3,2-dioxaborolan-2-yl)quinoline (90 mg, 0.350 mmol) in ethanol (1.5 mL). To this was added 5 mol % of Pd(PPh$_3$)$_4$ (18 mg, 0.016 mmol) and Na$_2$CO$_3$ (2M, 0.4 mL). The flask was flushed with argon, sealed and stirred at 90° C. for 4 hours. The crude mixture was partitioned between water and ethyl acetate, extracted with ethyl acetate (3x), dried over Na$_2$SO$_4$ and concentrated in vacuo. The Solids were taken up in minimal methylene chloride and purified via ISCO, 40 g RediSep® (Teledyne ISCO, Lincoln, Nebr.) column with a 20-100% gradient of ethyl acetate in hexanes, to afford the desired material. MS (ESI pos. ion) m/z calc'd for C$_{21}$H$_{16}$ClN$_3$O$_3$S: 425.1; found 426.1 (M+1). $^1$H NMR (400 MHz, DMSO-d$_6$) δ ppm 3.83 (s, 3 H) 7.12 (d, J=8.80 Hz, 2 H) 7.63 (dd, J=8.36, 4.25 Hz, 1 H) 7.72 (d, J=8.61 Hz, 2 H) 8.05 (dd, J=8.95, 1.81 Hz, 1 H) 8.10 (d, J=1.96 Hz, 1 H) 8.13-8.19 (m, 1 H) 8.32 (d, J=1.76 Hz, 1 H) 8.47 (d, J=8.51 Hz, 1 H) 8.72 (d, J=1.76 Hz, 1 H) 8.97 (dd, J=4.16, 1.32 Hz, 1 H) 10.32 (s, 1 H)

Example 48

N-(2-chloro-5-(2-(methylamino)-6-quinolinyl)-3-pyridinyl)-4-methoxybenzenesulfonamide

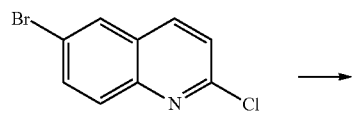

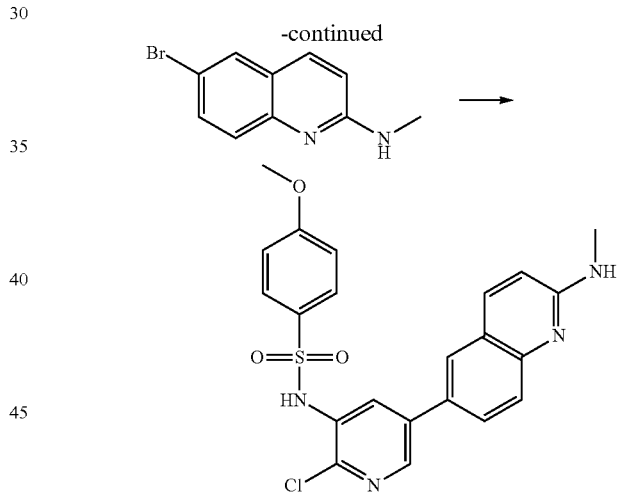

(1) 6-bromo-N-methylquinolin-2-amine: To a solution of 6-bromo-2-chloroquinoline (200 mg, 0.825 mmol) in ethanol (1.5 mL) was added methylamine (192 mg, 2.474 mmol). The reaction was irradiated in the microwave at 100° C. for 90 minutes. The crude material was cooled to ambient temperature, partitioned between water and methylene chloride and extracted with 15 mL of methylene chloride (3x). The organic layer was dried over MgSO$_4$, filtered and concentrated under reduced pressure. The resulting solid was purified by ISCO with a 10-40% gradient of ethyl acetate in hexanes to afford the desired product.

(2) N-(2-chloro-5-(2-(methylamino)-6-quinolinyl)-3-pyridinyl)-4-methoxybenzenesulfonamide: In a 15 mL sealed-pressure tube was added N-(2-chloro-5-(4,4,5,5-tetramethyl-1,3,2-dioxaborolan-2-yl)pyridin-3-yl)-4-methoxybenzenesulfonamide (140 mg, 0.329 mmol), 6-bromo-N-methylquinolin-2-amine (65 mg, 0.274 mmol), sodium carbonate (2M, 0.4 mL) and 8 mol % of Pd(PPh$_3$)$_4$ (25 mg, 0.022 mmol), in ethanol (1.5 mL). The reaction was stirred at 75° C. for 16 hours. Desired material was isolated by Gilson reverse phase HPLC (Gilson, Middleton, Wis.) with a 15-90% gradient of ACN in water with 0.1% TFA as a modifier. Following basification with saturated sodium bicarbonate and extraction with methylene chloride, the organic layer was dried over $Na_2SO_4$, filtered and concentrated in vacuo to afford the desired product. MS (ESI pos. ion) m/z calc'd for $C_{22}H_{19}ClN_4O_3S$: 454.9; found 455.9 (M+1). $^1$HNMR (400 MHz, DMSO-$d_6$) δ ppm 2.93 (d, J=4.69 Hz, 3 H) 3.83 (s, 3 H) 6.82 (d, J=9.00 Hz, 1 H) 7.11 (d, J=9.00 Hz, 2 H) 7.28 (d, J=4.11 Hz, 1 H) 7.62 (d, J=8.71 Hz, 1 H) 7.68-7.77 (m, 3 H) 7.89-7.99 (m, 3 H) 8.59 (d, J=2.35 Hz, 1 H) 10.30 (s, 1 H)

Example 49

N-(2-chloro-5-(4-(dimethylamino)-6-quinolinyl)-3-pyridinyl)-4-methoxybenzenesulfonamide

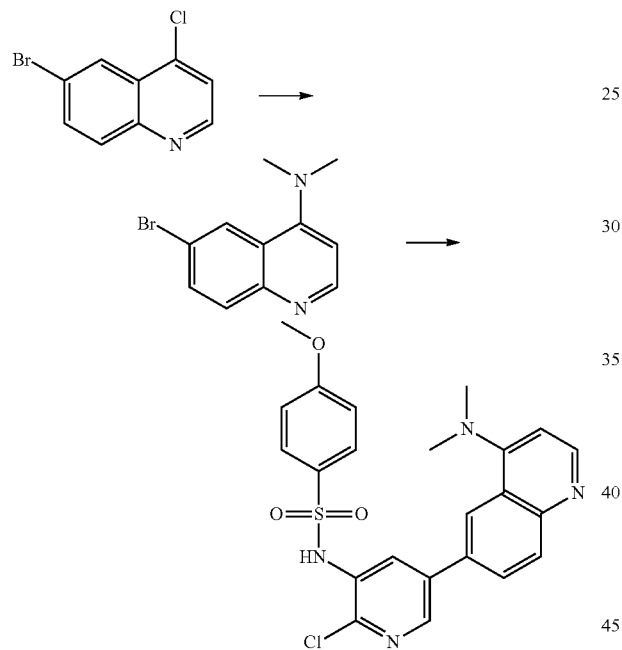

(1) 6-bromo-N,N-dimethylquinolin-4-amine: In a 5 mL microwave tube was added 6-bromo-4-chloroquinoline (180 mg, 0.742 mmol), dimethylamine (40% Wt in water, 0.7 mL)) in EtOH (0.8 mL). The tube was sealed and irradiated at 120° C. for 30 minutes. The crude was cooled to ambient temperature, partitioned between water and methylene chloride, and extracted with DCM (3×). Organic layer was dried over $Na_2SO_4$ and concentrated to afford the desired material. The material was carried forward as is.

(2) N-(2-chloro-5-(4-(dimethylamino)-6-quinolinyl)-3-pyridinyl)-4-methoxybenzenesulfonamide: In a 15 mL sealed-pressure tube was added 6-bromo-N,N-dimethylquinolin-4-amine (80 mg, 0.319 mmol), N-(2-chloro-5-(3,3,4,4-tetramethylborolan-1-yl)pyridin-3-yl)-4-methoxybenzenesulfonamide (189 mg, 0.446 mmol), sodium carbonate (2M, 0.5 mL) and 8 mol % Pd(PPh$_3$)$_4$ in EtOH (2.0 mL). The tube was purged with argon for 10 minutes, backfilled with argon, sealed and placed in a pre-heated oil bath for 6 hours. The crude was partitioned between equal parts water and methylene chloride, extracted with 20 mL of methylene chloride (3×), washed with brine, dried over $Na_2SO_4$, filtered and concentrated in vacuo. Resulting solids were taken up in equal parts MeOH and DMSO and purified by Gilson reverse phase HPLC with a 15-90% gradient of ACN in water with 0.1% TFA as a modifier. Following basification with saturated sodium bicarbonate and extraction with methylene chloride (3×, 10 mL), the organic layer was dried over $Na_2SO_4$, filtered and concentrated in vacuo to afford the desired material. MS (ESI pos. ion) m/z calc'd for $C_{23}H_{21}ClN_4O_3S$: 469.0; found 469.0 (M+1). $^1$HNMR (400 MHz, DMSO-$d_6$) δ ppm 3.13 (s, 6 H) 3.81 (s, 3 H) 6.94 (d, J=5.48 Hz, 1 H) 7.06-7.11 (m, 2 H) 7.69-7.75 (m, 2 H) 7.93-7.98 (m, 2 H) 7.99-8.04 (m, 1 H) 8.21 (d, J=1.96 Hz, 1 H) 8.53 (d, J=2.25 Hz, 1 H) 8.61 (d, J=5.48 Hz, 1 H) 10.88 (s, 1 H)

Example 50

N-(2-chloro-5-(4-(4-methoxy-1-piperidinyl)-6-quinolinyl)-3-pyridinyl)-4-methoxybenzenesulfonamide

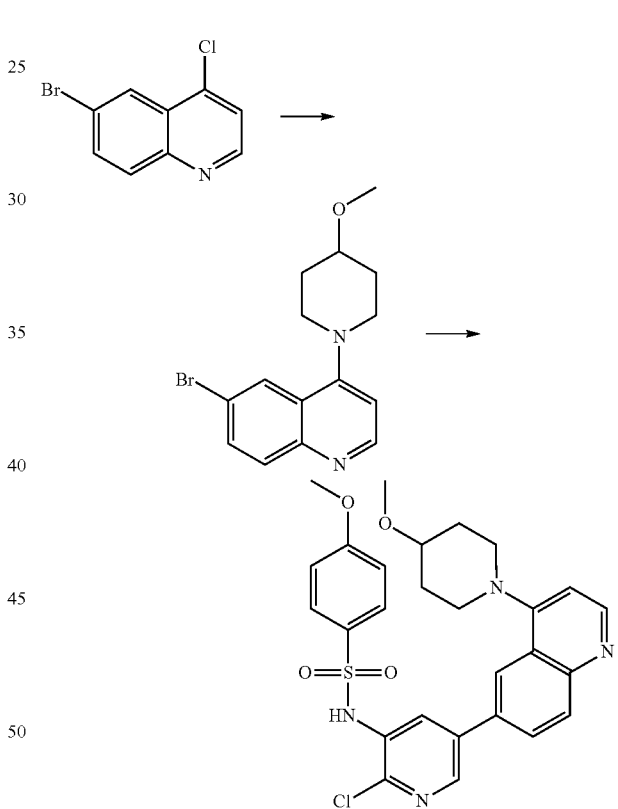

(1) 6-bromo-4-(4-methoxypiperidin-1-yl)quinoline: (Some starting materials may be obtained from Oakwood Products Inc., Columbia, S.C., BioBlocks, San Diego, Calif. and Aldrich, St. Louis, Mo.) A 5 mL microwave tube was charged with 6-bromo-4-chloroquinoline (150 mg, 0.619 mmol) and 4-methoxypiperidine (712 mg, 6.186 mmol), in EtOH (0.8 mL). The tube was irradiated at 135° C. for 3 hours. The crude material was concentrated in vacuo, diluted with EtOAc, washed with 0.1 N HCl and extracted with EtOAc (2×, 15 mL) and concentrated under reduced pressure to afford the desired material.

(2) N-(2-chloro-5-(4-(4-methoxy-1-piperidinyl)-6-quinolinyl)-3-pyridinyl)-4-methoxybenzenesulfonamide: In a 15 mL sealed-pressure tube was added 6-bromo-4-(4-methoxypiperidin-1-yl)quinoline (54 mg, 0.168 mmol), N-(2-chloro-5-(3,3,4,4-tetramethylborolan-1-yl)pyridin-3-yl)-4-methoxybenzenesulfonamide (100 mg, 0.235 mmol), sodium carbonate (2M, 0.3 mL) and 8 mol% Pd(PPh$_3$)$_4$ in EtOH (2.0 mL). The tube was purged with argon for 10 minutes, backfilled with argon, sealed and placed in a pre-heated oil bath for 3 hours. The crude was partitioned between equal parts water and DCM and extracted with DCM (3×, 20 mL). Organics were washed with brine, dried over Na$_2$SO$_4$, filter and concentrated in vacuo. Resulting solids were taken up in equal parts MeOH and DMSO and purified by Gilson reverse phase HPLC with a 20-95% gradient of ACN in water with 0.1% TFA as a modifier. Following basification with saturated sodium bicarbonate and extraction with methylene chloride (3×, 10 mL), the organic layer was dried over Na$_2$SO$_4$, filtered and concentrated in vacuo to afford desired product. MS (ESI pos. ion) m/z calc'd for C$_{27}$H$_{27}$ClN$_4$O$_4$S: 539.0; found 539.2 (M+1). $^1$HNMR (400 MHz, DMSO-d$_6$) δ ppm 1.99-2.11 (m, 2 H) 2.29-2.42 (m, 2 H) 3.32 (dd, 2 H) 3.57 (s, 3 H) 3.67-3.78 (m, 3 H) 4.05 (s, 3 H) 7.27-7.36 (m, 3 H) 7.96 (d, J=9.00 Hz, 2 H) 8.19-8.25 (m, 1 H) 8.28-8.33 (m, 2 H) 8.39 (d, J=1.96 Hz, 1 H) 8.85 (d, J=1.56 Hz, 1 H) 8.94 (d, J=5.09 Hz, 1 H) 10.71 (s, 1 H)

Example 51

2-chloro-N,N-dimethyl-5-(4-(4-morpholinyl)-6-quinolinyl)-3-pyridinamine

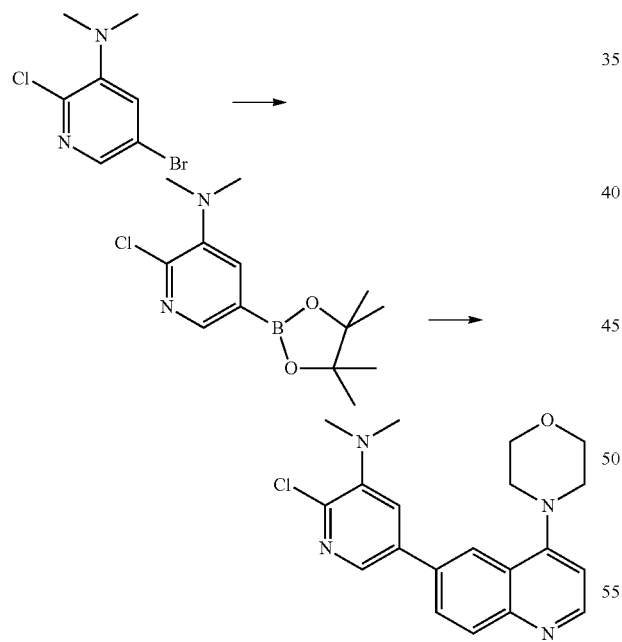

(1) 2-chloro-N,N-dimethyl-5-(4,4,5,5-tetramethyl-1,3,2-dioxaborolan-2-yl)pyridin-3-amine: (Some starting materials may be obtained from Small Molcule, Inc., Hoboken, N.J.) To a microwave vial (5 mL), 5-bromo-2-chloro-N,N-dimethylpyridin-3-amine (0.504 g, 2.14 mmol), 4,4,5,5-tetramethyl-2-(4,4,5,5-tetramethyl-1,3,2-dioxaborolan-2-yl)-1,3,2-dioxaborolane (0.606 g, 2.39 mmol), potassium acetate (0.536 g, 5.46 mmol) and PdCl$_2$(dppf)-CH$_2$Cl$_2$ adduct (0.0887 g, 0.109 mmol) were added in 1,4-dioxane (5 mL). The mixture was degassed by bubbling nitrogen through for 5 min. The tube was irradiated with microwave at 120° C. for 15 min then again at 120° C. for 10 min. The reaction was quenched by adding water (40 mL). The aqueous phase was extracted with EtOAc (3×20 mL). The combined organic phases were washed with saturated aqueous NaCl (50 mL). The organic phase was dried over sodium sulfate, filtered and concentrated in vacuo to afford a crude product. The crude product was purified by column chromatography (eluent: EtOAc in hexanes 0% -20%) to afford the title compound as a cream solid (0.364 g). m/z: calc'd for boronic acid C$_7$H$_{10}$BClN$_2$O$_2$; 200.0, found: 201.1 (M+1). $^1$H NMR (300 MHz, CHLOROFORM-d) δ ppm 1.36 (s, 12 H), 2.86 (s, 6 H), 7.67 (d, J=1.6 Hz, 1 H), 8.35 (d, J=1.6 Hz, 1 H).

(2) 2-chloro-N,N-dimethyl-5-(4-(4-morpholinyl)-6-quinolinyl)-3-pyridinamine: To a microwave vial (5 mL), 2-chloro-N,N-dimethyl-5-(4,4,5,5-tetramethyl-1,3,2-dioxaborolan-2-yl)pyridin-3-amine (0.102 g, 0.362 mmol), 6-bromo-4-morpholinoquinoline (0.112 g, 0.382 mmol), PdCl$_2$(dppf)-CH$_2$Cl$_2$ adduct (0.0149 g, 0.0182 mmol) and potassium carbonate (0.500 mL, 1.00 mmol) were added in 2.5 mL of 1,4-dioxane. The mixture was degassed by bubbling nitrogen through for 10 min. The tube was irradiated with microwave at 100° C. for 10 min. The reaction was cooled to rt then partitioned between water (20 mL) and EtOAc (20 mL). The aqueous phase was extracted with EtOAc (2×20 mL). The combined organic phases were washed with saturated aqueous NaCl (40 mL). The organic phase was dried over sodium sulfate, filtered and concentrated in vacuo. The crude product was purified by column chromatography (eluent: isopropanol in CHCl$_3$ 0% -10%) to afford the title compound as a light yellow solid (0.0864 g). m/z: calc'd for C$_{20}$H$_{21}$ClN$_4$O; 368.1, found: 369.1 (M+1). $^1$H NMR (300 MHz, CHLOROFORM-d) δ ppm 2.96 (s, 6 H), 3.24-3.34 (m, 4 H), 3.95-4.07 (m, 4 H), 6.94 (d, J=5.0 Hz, 1 H), 7.57 (d, J=2.2 Hz, 1 H), 7.87 (dd, J=8.8, 2.0 Hz, 1 H), 8.18 (dd, J=5.5, 3.1 Hz, 2 H), 8.33 (d, J=2.2 Hz, 1 H), 8.80 (d, J=5.0 Hz, 1 H).

Example 52

2-chloro-5-(4-chloro-6-quinolinyl)-N,N-dimethyl-3-pyridinamine

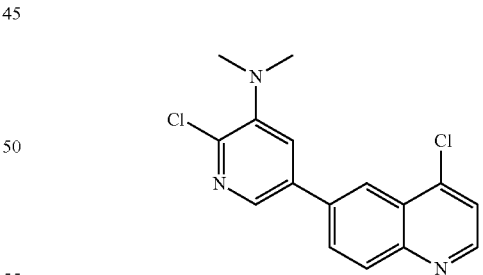

(Some starting materials may be obtained from ECA International, Palatine, Ill.) To a microwave vial (5 mL), 2-chloro-N,N-dimethyl-5-(4,4,5,5-tetramethyl-1,3,2-dioxaborolan-2-yl)pyridin-3-amine (0.110 g, 0.390 mmol), 6-bromo-4-chloroquinoline (0.102 g, 0.419 mmol), PdCl$_2$ (dppf)-CH$_2$Cl$_2$ adduct (0.0183 g, 0.0224 mmol) and potassium carbonate (0.500 mL, 1.00 mmol) were added into 1,4-dioxane (3 mL). The mixture was degassed by bubbling nitrogen through for 10 min. The tube was irradiated with microwave at 100° C. for 10 min. The reaction was cooled to RT then partitioned between water (20 mL) and EtOAc (20 mL). The aqueous phase was extracted with EtOAc (2×20 mL). The combined organic phases were washed with saturated aqueous NaCl (40 mL). The organic phase was dried over sodium sulfate, filtered and concentrated in vacuo. The crude product was purified by column chromatography (eluent: acetone in hexanes 0% -30%) to afford the title compound as a white solid (0.0884 g). m/z: calc'd for $C_{16}H_{13}Cl_2N_3$; 317.0, found: 318.1 (M+1). $^1$H NMR (300 MHz, CHLOROFORM-d) δ ppm 2.97 (s, 6 H), 7.55-7.63 (m, 2 H), 7.98 (dd, J=8.8, 2.0 Hz, 1 H), 8.25 (d, J=8.8 Hz, 1 H), 8.38 (dd, J=5.3, 2.0 Hz, 2 H), 8.84 (d, J=4.7 Hz, 1 H).

Example 53

2-chloro-N,N-dimethyl-5-(4-(4-(1-phenylethyl)-1-piperazinyl)-6-quinolinyl)-3-pyridinamine

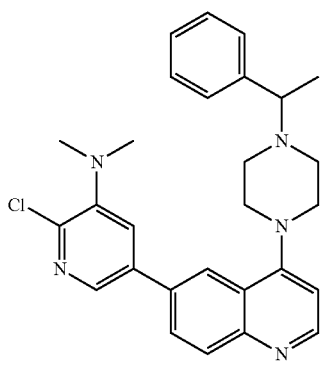 [SMILES: CC(c1ccccc1)N1CCN(c2ccnc3ccc(-c4cnc(Cl)c(N(C)C)c4)cc23)CC1]

(Some starting materials may be obtained from Chess GmbH, Mannnheim, Germany) To a microwave vial (5 mL), 2-chloro-5-(4-chloroquinolin-6-yl)-N,N-dimethylpyridin-3-amine (0.0846 g, 0.266 mmol) and 1-(1-phenylethyl)-piperazine (0.125 mL, 0.665 mmol) were added into DMSO (4 mL). The mixture was stirred at 90 $_o$C for 2.5 h, at 110° C. for 3 h, then at RT for overnight. The reaction was partitioned between water (20 mL) and EtOAc (20 mL). The aqueous phase was extracted with EtOAc (2×20 mL). The combined organic phases were washed with saturated aqueous NaCl (40 mL). The organic phase was dried over sodium sulfate, filtered and concentrated in vacuo. The crude product was purified by column chromatography (eluent: acetone in hexanes 0% -50%) to afford the title compound as a white solid (0.0886 g). m/z: calc'd for $C_{28}H_{30}ClN_5$; 471.2, found: 472.2 (M+1). $^1$H NMR (300 MHz, CHLOROFORM-d) δ ppm 1.46 (d, J=6.6 Hz, 3 H), 2.63-2.89 (m, 4 H), 2.94 (s, 6 H), 3.29 (t, J=4.4 Hz, 4 H), 3.51 (d, J=6.7 Hz, 1 H), 6.88 (d, J=5.0 Hz, 1 H), 7.28-7.42 (m, 5 H), 7.56 (d, J=2.2 Hz, 1 H), 7.84 (dd, J=8.7, 2.1 Hz, 1 H), 8.10-8.20 (m, 2 H), 8.33 (d, J=2.2 Hz, 1 H), 8.75 (d, J=5.0 Hz, 1 H).

Representative synthesis of 3-amino substituted quinoxaline derivatives:

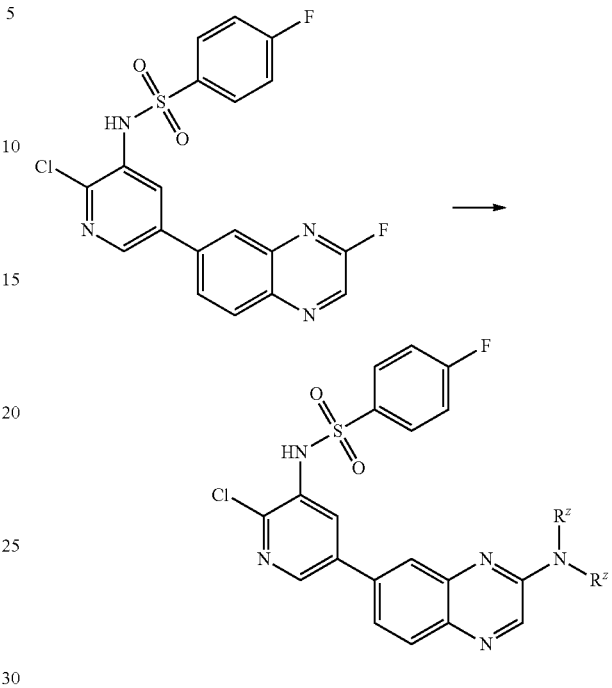

To a solution of N-(2-chloro-5-(3-fluoroquinoxalin-6-yl)pyridin-3-yl)-4-fluorobenzenesulfonamide (40 mg, 92 µmol) in DMSO (1 mL) was added the amine (1M in DMF, 231 µl, 231 µmol) and DMSO (0.57 mL). The reaction was heated to 60° C. for 24 h. The reaction was then cooled to 23° C. and submitted to mass-directed purification to give the product as a yellow solid. $R^z$s are typical substituents on amines and can taken together with the nitrogen atom to form a ring.

Example 54

N-(2-chloro-5-(3-(1-piperidinyl)-6-quinoxalinyl)-3-pyridinyl)-4-fluorobenzenesulfonamide

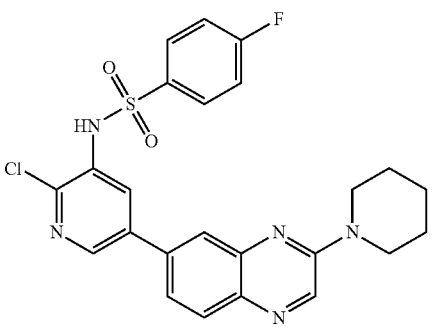 [SMILES: O=S(=O)(Nc1cc(-c2ccc3ncc(N4CCCCC4)nc3c2)cnc1Cl)c1ccc(F)cc1]

(Some starting materials may be obtained from Aldrich, St. Louis, Mo.) MS (ESI pos. ion) m/z calc'd for $C_{24}H_{21}ClFN_5O_2S$: 497.1; found 498.0. $^1$H NMR (300 MHz, CDCl$_3$) δ ppm 1.75 (m, 6 H) 3.83-3.84 (m, 4 H) 7.07 (s, 1 H) 7.14-7.16 (m, 2 H) 7.51-7.54 (m, 1 H) 7.82-7.86 (m, 3 H)

7.95-7.98 (d, J=9 Hz, 1 H) 8.32-8.33 (d, J=3 Hz, 1 H) 8.49-8.50 (d, J=3 Hz, 1 H) 8.62 (s, 1 H)

Example 55

N-(2-chloro-5-(3-((2-methoxyethyl)(methyl)amino)-6-quinoxalinyl)-3-pyridinyl)-4-fluorobenzenesulfonamide

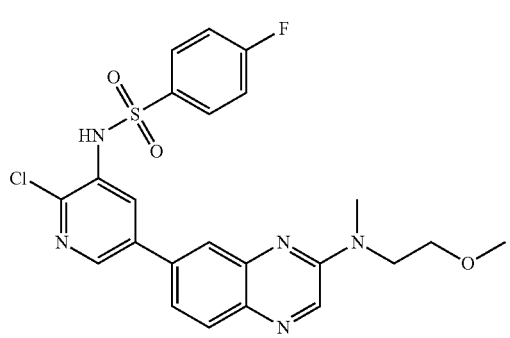 [SMILES: COCCN(C)c1cnc2ccc(-c3cnc(Cl)c(NS(=O)(=O)c4ccc(F)cc4)c3)cc2n1]

(Some starting materials may be obtained from Aldrich or Sigma, St. Louis, Mo.) MS (ESI pos. ion) m/z calc'd for $C_{23}H_{21}ClFN_5O_3S$: 501.1; found 502.0. $^1$H NMR (300 MHz, CDCl$_3$) δ ppm 3.35-3.38 (d, J=8.04 Hz, 6 H) 3.69-3.72 (t, 5.33 Hz, 2 H) 3.93 (t, J=5.33 Hz, 2 H) 7.01 (s, 1 H) 7.13-7.25 (m, 2 H) 7.52 (dd, J=8.48, 2.05 Hz, 1 H) 7.81-7.88 (m, 3 H) 7.98 (d, J=8.48 Hz, 1 H) 8.32 (d, J=2.19 Hz, 1 H) 8.50 (d, J=2.34 Hz, 1 H) 8.60 (s, 1 H)

Example 56

N-(5-(3-(4-acetyl-1-piperazinyl)-6-quinoxalinyl)-2-chloro-3-pyridinyl)-4-fluorobenzenesulfonamide

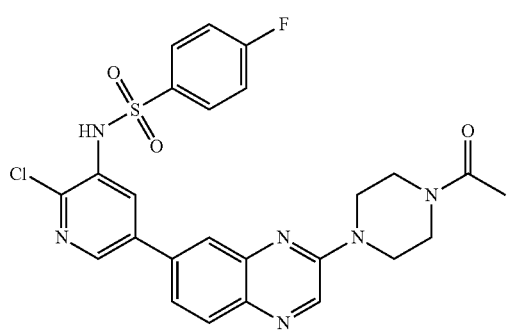 [SMILES: CC(=O)N1CCN(c2cnc3ccc(-c4cnc(Cl)c(NS(=O)(=O)c5ccc(F)cc5)c4)cc3n2)CC1]

(Some starting materials may be obtained from Aldrich, St. Louis, Mo.) MS (ESI pos. ion) m/z calc'd for $C_{23}H_{21}ClFN_5O_3S$: 540.1; found 541.2. $^1$H NMR (300 MHz, CDCl$_3$) δ ppm 2.21 (s, 3 H) 3.67-3.76 (m, 2 H) 3.85 (m, 4 H) 3.89-3.98 (m, 2 H) 7.06 (s, 1 H) 7.13-7.25 (m, 2 H) 7.62 (dd, J=8.55, 2.12 Hz, 1 H) 7.81-7.92 (m, 3 H) 8.03 (d, J=8.62 Hz, 1 H) 8.34 (d, J=2.19 Hz, 1 H) 8.50 (d, J=2.34 Hz, 1 H) 8.65 (s, 1 H)

Example 57

N-(2-chloro-5-(3-((2-phenoxyethyl)amino)-6-quinoxalinyl)-3-pyridinyl)-4-fluorobenzenesulfonamide

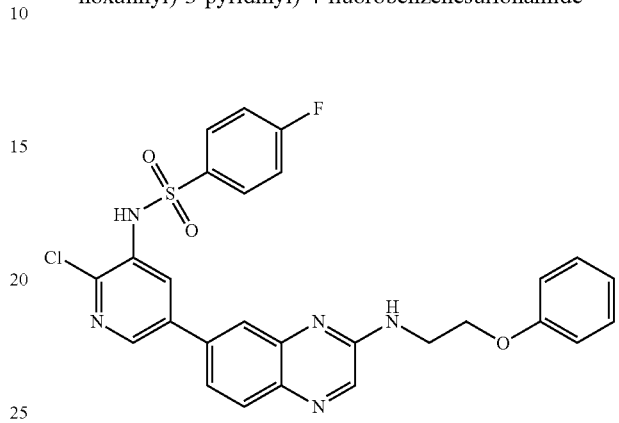

(Some starting materials may be obtained from Aldrich, St. Louis, Mo.) MS (ESI pos. ion) m/z calc'd for $C_{27}H_{21}ClFN_5O_3S$: 549.1; found 550.0. $^1$H NMR (300 MHz, CDCl$_3$) δ ppm 4.01-4.08 (m, 2 H) 4.28 (t, J=4.97 Hz, 2 H) 6.94-7.05 (m, 4 H) 7.17 (t, J=8.55 Hz, 2 H) 7.27-7.35 (m, 2 H) 7.56 (dd, J=8.48, 2.05 Hz, 1 H) 7.81-7.91 (m, 3 H) 7.99 (d, J=8.48 Hz, 1 H) 8.27-8.35 (m, 2 H) 8.51 (d, J=2.34 Hz, 1 H)

Example 58

N-(2-chloro-5-(3-(4,4-difluoro-1-piperidinyl)-6-quinoxalinyl)-3-pyridinyl)-4-fluorobenzenesulfonamide

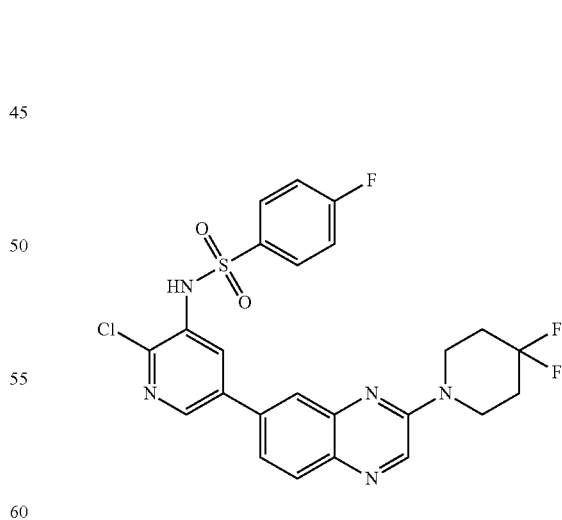

(Some starting materials may be obtained from Aldrich, St. Louis, Mo.) MS (ESI pos. ion) m/z calc'd for $C_{24}H_{19}ClF_3N_5O_2S$: 533.1; found 534.0. $^1$H NMR (300 MHz, CDCl$_3$) δ ppm 2.15 (m, 4 H) 3.97-4.03 (m, 4 H) 7.01 (s, 1 H)

7.14-7.25 (m, 2 H) 7.58-7.63 (m, 1 H) 7.81-7.90 (m, 3 H) 8.02 (d, J=8.48 Hz, 1 H) 8.34 (d, J=2.34 Hz, 1 H) 8.50 (d, J=2.34 Hz, 1 H) 8.67 (s, 1 H)

Example 59 tert-butyl 3-(((7-(6-chloro-5-(((4-fluorophenyl)sulfonyl)amino)-3-pyridinyl)-2-quinoxalinyl)amino)methyl)-1-piperidinecarboxylate

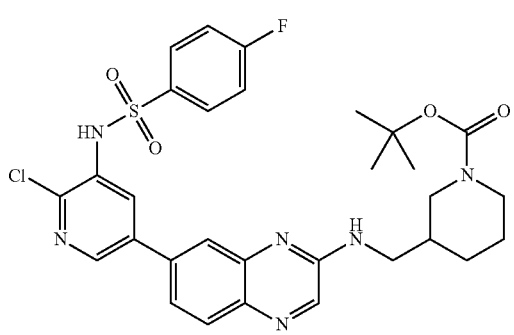 [SMILES: CC(C)(C)OC(=O)N1CCCC(CNc2cnc3ccc(-c4cnc(Cl)c(NS(=O)(=O)c5ccc(F)cc5)c4)cc3n2)C1]

(Some starting materials may be obtained from. Asta Tech, Inc., Princeton, N.J.) MS (ESI pos. ion) m/z calc'd for $C_{30}H_{32}ClFN_6O_4S$: 626.2; found 626.8. $^1$H NMR (300 MHz, CDCl$_3$) δ ppm 1.41-1.51 (m, 9 H) 1.71 (m, 2 H) 1.92-2.09 (m, 2 H) 3.05 (m, 2 H) 3.27-3.59 (m, 4 H) 3.93 (m, 1 H) 7.09-7.25 (m, 3 H) 7.61 (m, 1 H) 7.81-7.94 (m, 3 H) 8.04 (d, J=8.62 Hz, 1 H) 8.22-8.30 (m, 1 H) 8.41-8.54 (m, 2 H)

Example 60

N-(2-chloro-5-(3-((1-(4-fluorophenyl)ethyl)amino)-6-quinoxalinyl)-3-pyridinyl)-4-fluorobenzenesulfonamide

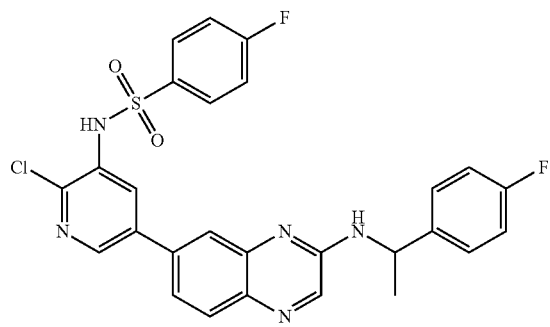 [SMILES: CC(Nc1cnc2ccc(-c3cnc(Cl)c(NS(=O)(=O)c4ccc(F)cc4)c3)cc2n1)c1ccc(F)cc1]

(Some starting materials may be obtained from Aldrich, St. Louis, Mo.) MS (ESI pos. ion) m/z calc'd for $C_{27}H_{20}ClF_2N_5O_2S$: 551.1; found 552.0. $^1$H NMR (300 MHz, CDCl$_3$) δ ppm 1.68 (d, J=6.72 Hz, 3 H) 5.33 (d, J=7.02 Hz, 1 H) 6.99-7.25 (m, 5 H) 7.39-7.48 (m, 2 H) 7.55 (dd, J=8.48, 1.90 Hz, 1 H) 7.80-7.89 (m, 3 H) 7.97 (d, J=8.33 Hz, 1 H) 8.22-8.32 (m, 2 H) 8.47 (d, J=2.19 Hz, 1 H)

Example 61

N-(2-chloro-5-(3-((2-(1-piperidinyl)ethyl)amino)-6-quinoxalinyl)-3-pyridinyl)-4-fluorobenzenesulfonamide

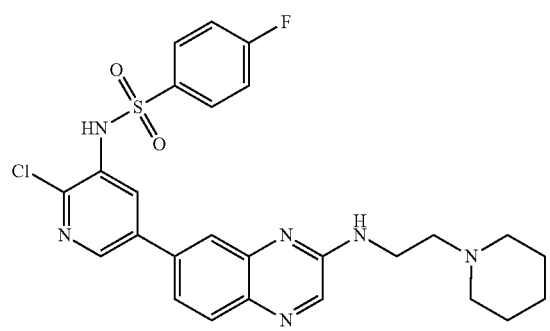 [SMILES: O=S(=O)(Nc1cc(-c2ccc3ncc(NCCN4CCCCC4)nc3c2)cnc1Cl)c1ccc(F)cc1]

(Some starting materials may be obtained from Aldrich, St. Louis, Mo.) MS (ESI pos. ion) m/z calc'd for $C_{26}H_{26}ClFN_6O_2S$: 540.2; found 540.8. $^1$H NMR (300 MHz, CDCl$_3$) δ ppm 1.93-2.14 (m, 8 H) 2.76 (m, 2 H) 3.43 (m, 2 H) 4.08 (m, 2 H) 7.05 (br. s., 1 H) 7.13-7.25 (m, 2 H) 7.58 (dd, J=8.48, 2.05 Hz, 1 H) 7.80-7.90 (m, 3 H) 8.01 (d, J=8.48 Hz, 1 H) 8.32-8.44 (m, 2 H) 8.49 (d, J=2.34 Hz, 1 H)

Example 62

N-(5-(3-(3-azabicyclo[3.2.2]non-3-yl)-6-quinoxalinyl)-2-chloro-3-pyridinyl)-4-fluorobenzenesulfonamide

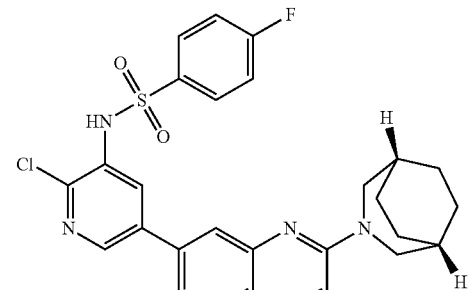

MS (ESI pos. ion) m/z calc'd for $C_{27}H_{25}ClFN_5O_2S$: 537.1; found 538.0. $^1$H NMR (300 MHz, CDCl$_3$) δ ppm 1.76 (t, J=1.75 Hz, 8 H) 2.29 (br. s., 2 H) 4.02 (d, J=4.09 Hz, 4 H) 7.00 (s, 1 H) 7.12-7.25 (m, 2 H) 7.51 (dd, J=8.48, 2.05 Hz, 1 H)

7.81-7.91 (m, 3 H) 7.97 (d, J=8.48 Hz, 1 H) 8.33 (d, J=2.34 Hz, 1 H) 8.50 (d, J=2.34 Hz, 1 H) 8.69 (s, 1 H)

Example 63

N-(2-chloro-5-(3-((4-methoxybenzyl)amino)-6-quinoxalinyl)-3-pyridinyl)-4-fluorobenzenesulfonamide

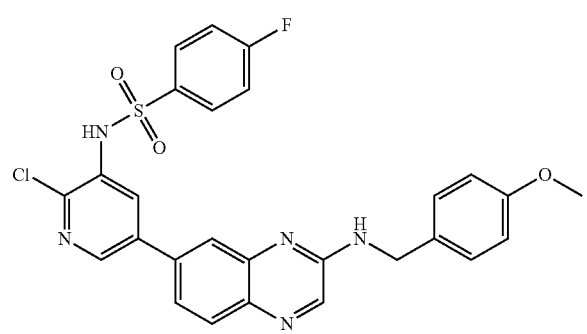 [SMILES: COc1ccc(CNc2cnc3ccc(-c4cnc(Cl)c(NS(=O)(=O)c5ccc(F)cc5)c4)cc3n2)cc1]

(Some starting materials may be obtained from Aldrich, St. Louis, Mo.) MS (ESI pos. ion) m/z calc'd for $C_{27}H_{21}ClFN_5O_3S$: 549.1; found 550.0. $^1$H NMR (300 MHz, CDCl$_3$) δ ppm 3.82 (s, 3 H) 4.73 (m, 2H), 6.92 (m, 3 H) 7.17 (m, 2H) 7.38 (m, 2 H) 7.85-8.00 (m, 3 H) 8.23 (br. s., 1H) 8.33 (d, J=2.19 Hz, 1 H) 8.50 (d, J=2.19 Hz, 1 H)

Example 64

N-(2-chloro-5-(3-((2-phenylethyl)amino)-6-quinoxalinyl)-3-pyridinyl)-4-fluorobenzenesulfonamide

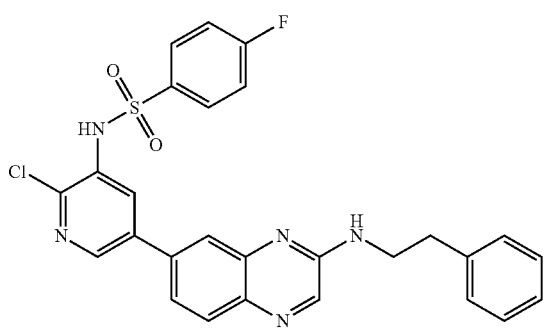 [SMILES: O=S(=O)(Nc1cc(-c2ccc3ncc(NCCc4ccccc4)nc3c2)cnc1Cl)c1ccc(F)cc1]

(Some starting materials may be obtained from Fluka Chemie, Buchs, Switzerland) MS (ESI pos. ion) m/z calc'd for $C_{27}H_{21}ClFN_5O_2S$: 533.1; found 534.0. $^1$H NMR (300 MHz, CDCl$_3$) δ ppm 3.10 (t, J=6.87 Hz, 2 H) 3.89 (d, J=4.97 Hz, 2 H) 7.07-7.25 (m, 3 H) 7.27-7.36 (m, 5 H) 7.61 (dd, J=8.48, 1.90 Hz, 1 H) 7.83-7.94 (m, 3 H) 8.00 (d, J=8.48 Hz, 1 H) 8.21-8.30 (m, 2 H) 8.45 (d, J=2.19 Hz, 1 H)

Example 65

N-(5-(3-(benzyl(methyl)amino)-6-quinoxalinyl)-2-chloro-3-pyridinyl)-4-fluorobenzenesulfonamide

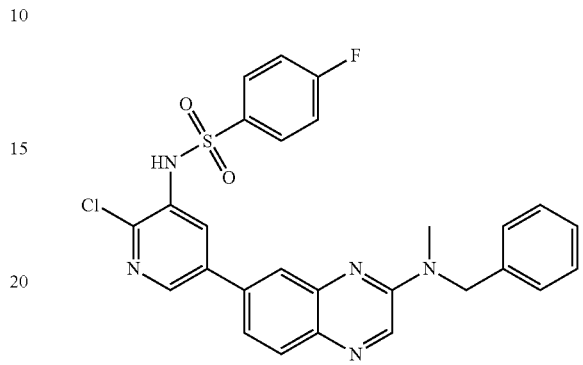

(Some starting materials may be obtained from Aldrich, St. Louis, Mo.) MS (ESI pos. ion) m/z calc'd for $C_{27}H_{21}ClFN_5O_2S$: 533.1; found 534.0. $^1$H NMR (300 MHz, CDCl$_3$) δ ppm 3.33 (s, 3 H) 4.99 (s, 2 H) 7.01 (s, 1 H) 7.11-7.25 (m, 2 H) 7.27-7.38 (m, 5 H) 7.54 (dd, J=8.48, 2.05 Hz, 1 H) 7.81-7.92 (m, 3 H) 7.99 (d, J=8.48 Hz, 1 H) 8.32 (d, J=2.19 Hz, 1 H) 8.48-8.57 (m, 2 H)

Example 66

N-(2-chloro-5-(3-((3-methoxy-1-piperidinyl)-6-quinoxalinyl)-3-pyridinyl)-4-fluorobenzenesulfonamide

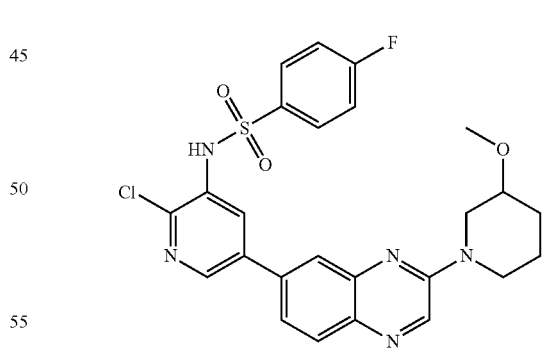

(Some starting materials may be obtained from Alfa Aesar, Ward Hill, Mass.) MS (ESI pos. ion) m/z calc'd for $C_{25}H_{23}ClFN_5O_3S$: 527.1; found 528.0. $^1$H NMR (300 MHz, CDCl$_3$) δ ppm 1.66-1.95 (m, 4 H) 3.44 (br. s., 4 H) 3.60-3.74 (m, 2 H) 3.91 (br. s., 1 H) 4.13-4.21 (m, 1 H) 7.01 (s, 1 H) 7.13-7.25 (m, 2 H) 7.54 (dd, J=8.48, 2.05 Hz, 1 H) 7.80-7.89

(m, 3 H) 7.98 (d, J=8.48 Hz, 1 H) 8.32 (d, J=2.34 Hz, 1 H) 8.48-8.51 (m, 1 H) 8.65 (s, 1 H)

Example 67

N-(2-chloro-5-(3-(2,6-dimethyl-4-morpholinyl)-6-quinoxalinyl)-3-pyridinyl)-4-fluorobenzenesulfonamide

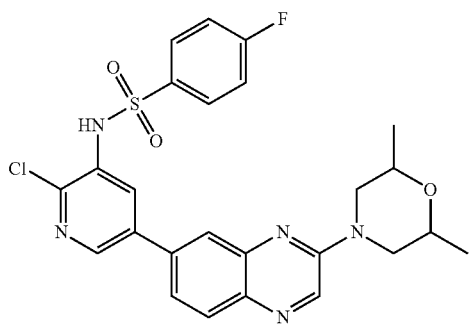 [SMILES: CC1CN(c2cnc3ccc(-c4cnc(Cl)c(NS(=O)(=O)c5ccc(F)cc5)c4)cc3n2)CC(C)O1]

(Some starting materials may be obtained from Fluka Chemie, Buchs, Switzerland) MS (ESI pos. ion) m/z calc'd for $C_{25}H_{23}ClFN_5O_3S$: 527.1; found 528.0. $^1$H NMR (300 MHz, CDCl$_3$) δ ppm 1.25-1.38 (m, 6 H) 2.79 (dd, J=13.01, 10.67 Hz, 1.5 H) 3.52 (dd, J=13.01, 6.58 Hz, 0.5 H) 3.69-3.84 (m, 1.5 H) 3.98 (dd, J=12.93, 3.29 Hz, 0.5 H) 4.17-4.27 (m, 0.5H) 4.40 (d, J=11.69 Hz, 1.5H) 7.03 (s, 1 H) 7.13-7.25 (m, 2 H) 7.55-7.61 (m, 1 H) 7.80-7.91 (m, 3 H) 8.01 (d, J=8.48 Hz, 1 H) 8.34 (d, J=2.34 Hz, 1 H) 8.50 (d, J=2.19 Hz, 1 H) 8.61 (s, 1 H)

Example 68

N-(2-chloro-5-(3-(2-(methoxymethyl)-1-pyrrolidinyl)-6-quinoxalinyl)-3-pyridinyl)-4-fluorobenzenesulfonamide

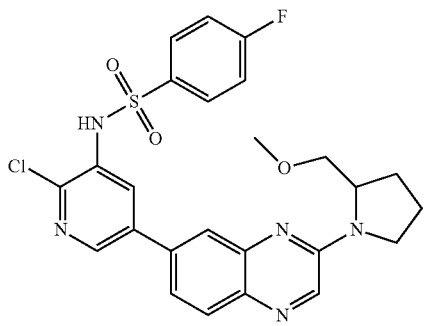 [SMILES: COCC1CCCN1c1cnc2ccc(-c3cnc(Cl)c(NS(=O)(=O)c4ccc(F)cc4)c3)cc2n1]

(Some starting materials may be obtained from ACB Blocks, Ltd., Moscow, Russia) MS (ESI pos. ion) m/z calc'd for $C_{25}H_{23}ClFN_5O_3S$: 527.1; found 528.0. $^1$H NMR (300 MHz, CDCl$_3$) δ ppm 2.20 (m, 4 H) 3.38 (s, 3 H) 3.53-3.66 (m, 1 H) 3.97 (br. s., 1) 4.65 (m, 3 H) 7.04-7.25 (m, 3 H) 7.60 (dd, J=8.48, 1.90 Hz, 1 H) 7.81-7.88 (m, 2 H) 8.01-8.10 (m, 2 H) 8.29 (d, J=2.34 Hz, 1 H) 8.48 (d, J=2.34 Hz, 1 H) 8.70 (s, 1 H)

Example 69

N-(2-chloro-5-(3-(4-methoxy-1-piperidinyl)-6-quinoxalinyl)-3-pyridinyl)-4-fluorobenzenesulfonamide

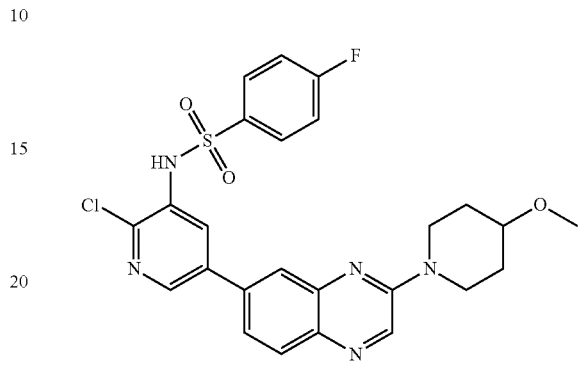

(Some starting materials may be obtained from Aldrich, St. Louis, Mo.) MS (ESI pos. ion) m/z calc'd for $C_{25}H_{23}ClFN_5O_3S$: 527.1; found 528.0. $^1$H NMR (300 MHz, CDCl$_3$) δ ppm 1.77 (m, 2 H) 2.02 (m, 2 H) 3.43 (s, 3 H) 3.58 (m, 3 H) 4.14 (m, 2 H) 7.00 (d, J=9.21 Hz, 1 H) 7.13-7.25 (m, 2 H) 7.55 (dd, J=8.55, 1.97 Hz, 1 H) 7.80-7.89 (m, 3 H) 7.98 (d, J=8.48 Hz, 1 H) 8.33 (d, J=2.34 Hz, 1 H) 8.50 (d, J=2.19 Hz, 1 H) 8.65 (s, 1 H)

Example 70

N-(2-chloro-5-(3-((cyclohexylmethyl)amino)-6-quinoxalinyl)-3-pyridinyl)-4-fluorobenzenesulfonamide

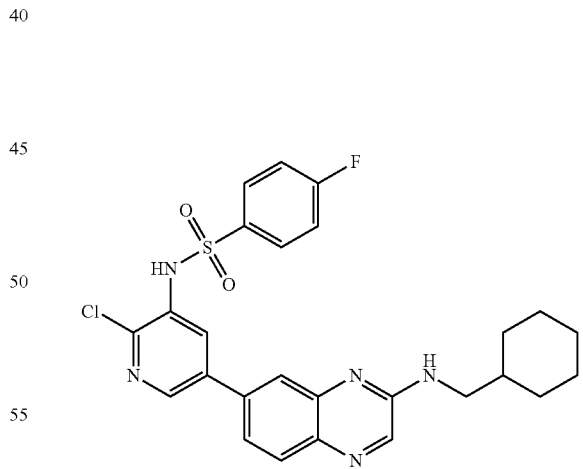

(Some starting materials may be obtained from Aldrich, St. Louis, Mo.) MS (ESI pos. ion) m/z calc'd for $C_{26}H_{25}ClFN_5O_2S$: 525.1; found 526.0. $^1$H NMR (300 MHz, CDCl$_3$) δ ppm 1.01-1.34 (m, 4 H) 1.63-1.94 (m, 7 H) 3.45 (t, J=6.21 Hz, 2 H) 6.98-7.25 (m, 3 H) 7.55 (dd, J=8.48, 2.05 Hz, 1 H) 7.82-7.90 (m, 3 H) 7.98 (d, J=8.48 Hz, 1 H) 8.31 (d, J=2.19 Hz, 2 H) 8.48 (d, J=2.19 Hz, 1 H)

Example 71

N-(2-chloro-5-(3-((cyanomethyl)(methyl)amino)-6-quinoxalinyl)-3-pyridinyl)-4-fluorobenzenesulfonamide

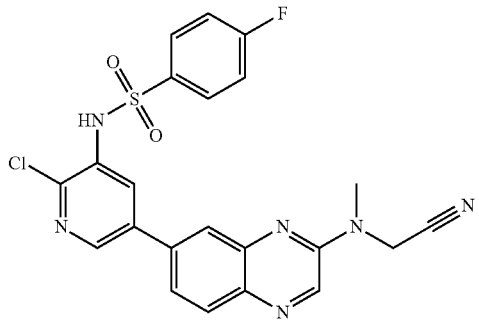 [SMILES: CN(CC#N)c1cnc2ccc(-c3cnc(Cl)c(NS(=O)(=O)c4ccc(F)cc4)c3)cc2n1]

(Some starting materials may be obtained from Sigma, St. Louis, Mo.) MS (ESI pos. ion) m/z calc'd for $C_{22}H_{16}ClFN_6O_2S$: 482.1; found 483.2. $^1$H NMR (300 MHz, CDCl$_3$) δ ppm 3.53-3.56 (m, 3 H) 4.05-4.13 (m, 2 H) 7.03 (br. s., 2 H) 7.50 (m, 1 H) 7.68 (m, 2 H) 7.93 (m, 1 H) 8.24 (br. s., 2 H) 8.47 (m, 1 H) 9.16 (m, 2 H)

Example 72

N-(2-chloro-5-(3-(1-piperazinyl)-6-quinoxalinyl)-3-pyridinyl)-4-fluorobenzenesulfonamide

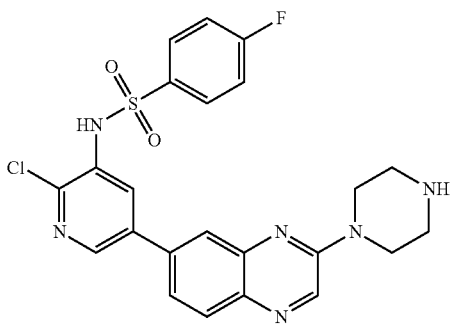 [SMILES: O=S(=O)(Nc1cc(-c2ccc3ncc(N4CCNCC4)nc3c2)cnc1Cl)c1ccc(F)cc1]

(Some starting materials may be obtained from Aldrich, St. Louis, Mo.) MS (ESI pos. ion) m/z calc'd for $C_{23}H_{20}ClFN_6O_2S$: 498.1; found 499.2. $^1$H NMR (300 MHz, CDCl$_3$) δ ppm 3.12 (m, 4 H) 3.92 (d, J=5.12 Hz, 4 H) 6.97 (t, J=8.62 Hz, 2 H) 7.50 (dd, J=8.62, 2.05 Hz, 1 H) 7.60-7.66 (m, 2 H) 7.73 (d, J=1.75 Hz, 1 H) 7.82 (d, J=8.48 Hz, 1 H) 8.10 (d, J=2.34 Hz, 1 H) 8.29 (d, J=2.19 Hz, 1 H) 8.49 (s, 1 H)

Example 73

N-(2-chloro-5-(3-((2-methoxyethyl)amino)-6-quinoxalinyl)-3-pyridinyl)-4-fluorobenzenesulfonamide

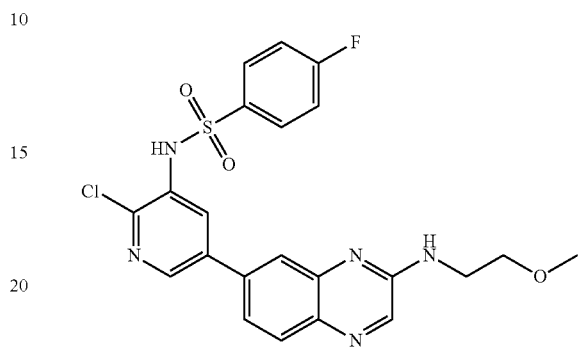

(Some starting materials may be obtained from Aldrich, St. Louis, Mo.) MS (ESI pos. ion) m/z calc'd for $C_{22}H_{19}ClFN_5O_3S$: 487.1; found 488.0. $^1$H NMR (300 MHz, CDCl$_3$) δ ppm 3.44 (s, 3 H) 3.70-3.81 (m, 4 H) 7.14-7.19 (m, 3 H) 7.61 (m, 1 H) 7.83-7.87 (m, 3 H) 7.96-7.99 (m, 1 H) 8.25 (s, 1 H) 8.32 (m, 1 H) 8.49 (s, 1 H)

Example 74

N-(2-chloro-5-(3-((3-piperidinylmethyl)amino)-6-quinoxalinyl)-3-pyridinyl)-4-fluorobenzenesulfonamide

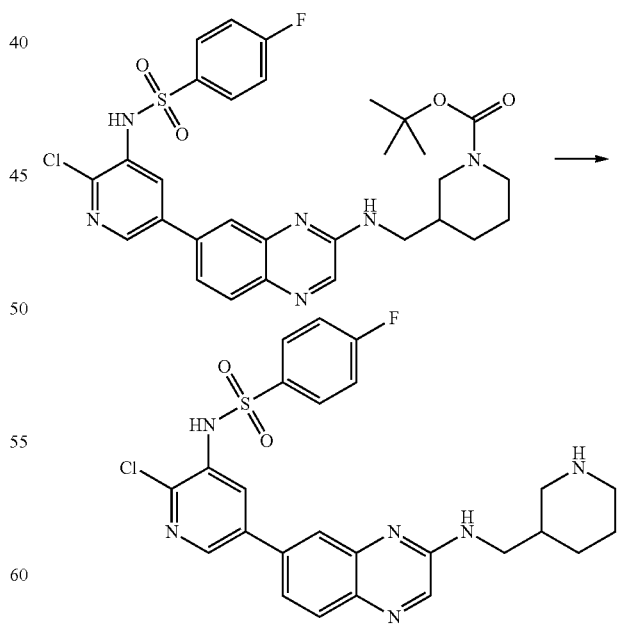

(Some starting materials may be obtained from Asta Tech, Inc., Princeton, N.J.) To a solution of tert-butyl 3-((7-(6-chloro-5-(4-fluorophenylsulfonamido)pyridin-3-yl)quinoxalin-2-ylamino)methyl)piperidine-1-carboxylate (5 mg, 8 µmol) in DCM (1 mL) was added TFA (1 mL) and the reaction was stirred at 23° C. for 15 min. The reaction was then concentrated in vacuo and coevaporated with DCM (3×; 1 ml) to give the desired product as a yellow film. MS (ESI pos. ion) m/z calc'd for $C_{25}H_{24}ClFN_6O_2S$: 526.1; found 527.0. $^1$H NMR (300 MHz, CDCl$_3$) δ ppm 1.23-1.38 (m, 2 H) 1.78 (m, 1 H) 1.89 (m, 2 H) 2.22 (br. s., 1 H) 2.66 (t, J=11.84 Hz, 1 H) 2.79 (d, J=3.07 Hz, 1 H) 3.36-3.52 (m, 3 H) 7.05-7.12 (m, 2 H) 7.48 (dd, J=8.48, 2.05 Hz, 1 H) 7.71-7.88 (m, 4 H) 8.19-8.23 (m, 2 H) 8.38-8.41 (m, 1 H)

Example 75

N-(2-chloro-5-(1,7-naphthyridin-6-yl)pyridin-3-yl)-4-fluorobenzenesulfonamide

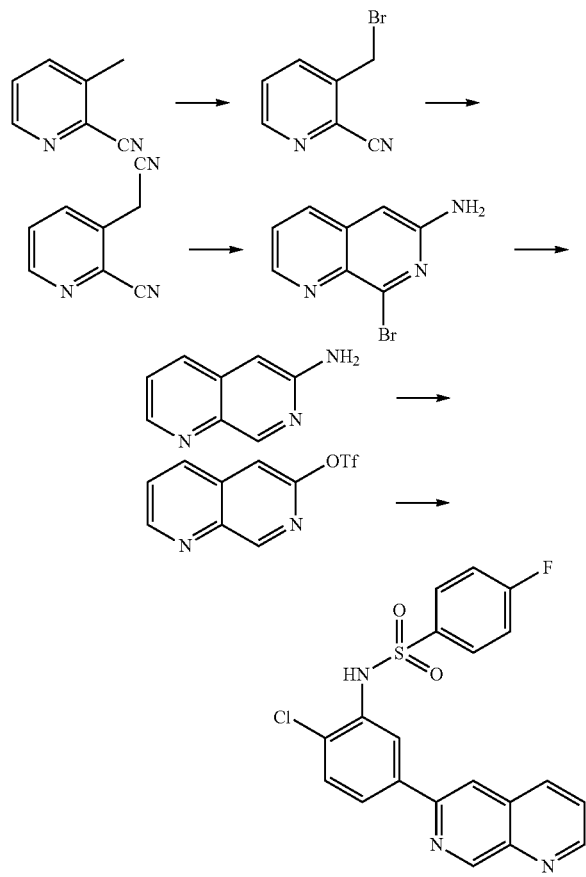

(1) 3-(bromomethyl)picolinonitrile. (Some starting materials may be obtained from TCI America, Wellesley, Mass.) To a 100 mL round-bottomed flask was added 3-methylpicolinonitrile (2.36 g, 20.0 mmol), NBS (7.82 g, 43.9 mmol), and CCl$_4$ (50 mL). The reaction mixture was stirred at reflux for 16 h. The mixture was cooled to room temperature. The solid was filtered and washed with 50% EtOAc/hexanes. The solvent was removed in vacuo and the residue was purified by silica gel chromatography, eluting with 30% EtOAc/hexane to give 3-(bromomethyl)picolinonitrile (2.56 g, 65.0% yield). MS (ESI pos. ion) m/z calc'd for $C_7H_5BrN_2$: 196.0, 198.0; found 197.0, 199.0. $^1$H NMR (300 MHz, CHLOROFORM-d) δ ppm 4.64 (s, 2 H) 7.54 (dd, J=8.04, 4.68 Hz, 1 H) 7.92 (dd, J=8.04, 1.61 Hz, 1 H) 8.66 (dd, J=4.75, 1.53 Hz, 1 H)

(2) 3-(cyanomethyl)picolinonitrile. To a 100 mL round-bottomed flask was added 3-(bromomethyl)picolinonitrile (1.56 g, 7917 µmol), potassium cyanide (509 µL, 11876 µmol), MeOH (50 mL). The reaction mixture was stirred at room temperature for 6 h. the solvent was removed in vacuo and the residue was dissolved in EtOAc (50 mL), washed with water (10 mL), saturated NaCl (10 mL), dried over Na$_2$SO$_4$, filtered and concentrated in vacuo. The residue was purified by silica gel chromatography, eluting with 40% EtOAc/hexanes to give 3-(cyanomethyl)picolinonitrile (328 mg, 28.9% yield). MS (ESI pos. ion) m/z calc'd for $C_8H_5N_3$: 143.0; found 144.0. $^1$H NMR (300 MHz, CHLOROFORM-d) δ ppm 4.06 (s, 2 H) 7.63 (dd, J=8.11, 4.75 Hz, 1 H) 8.01-8.08 (m, J=0.73 Hz, 1 H) 8.73 (dd, J=4.75, 1.39 Hz, 1 H)

(3) 8-bromo-1,7-naphthyridin-6-amine. To a 50 mL round-bottomed flask was added hydrobromic acid, 30% in acetic acid (317 µl, 5868 µmol). 3-(cyanomethyl)picolinonitrile (280 mg, 1956 µmol) in AcOH (0.5 mL) was then added at 0° C. The reaction mixture was stirred at 0° C. for 30 min. The solid was filtered out and washed with 50% EtOAc/hexanes. The solid was treated with sat. NaHCO$_3$ (5 mL) and the mixture was extracted with EtOAc (2×50 mL). The organic extract was washed with satd NaCl (5 mL), dried over Na$_2$SO$_4$, filtered and concentrated in vacuo and the residue was purified by silica gel chromatography, eluting with 40% EtOAc/hexanes to give 8-bromo-1,7-naphthyridin-6-amine (312 mg, 71% yield). MS (ESI pos. ion) m/z calc'd for $C_8H_6BrN_3$: 223.0, 225.0; found 224.0, 226.0. $^1$H NMR (300 MHz, CHLOROFORM-d) δ ppm 4.63 (s, 2 H) 6.61 (s, 1 H) 7.42 (dd, J=8.48, 4.09 Hz, 1 H) 7.85 (dd, J=8.48, 1.61 Hz, 1 H) 8.78 (dd, J=3.95, 1.61 Hz, 1 H)

(4) 1,7-naphthyridin-6-amine. To a 50 mL round-bottomed flask was added 8-bromo-1,7-naphthyridin-6-amine (224 mg, 1000 µmol), potassium hydroxide (67.3 mg, 1200 µmol), 10% palladium on carbon (10.6 mg, 100.0 µmol), EtOH (2 mL). The mixture was hydrogenated for 4 h under a hydrogen balloon. The catalyst was filtered through a pad of Celite® (diatomaceous earth) and washed with EtOAc. The solvent was removed in vacuo and the residue was purified by silica gel chromatography, eluting with EtOAc to give 1,7-naphthyridin-6-amine (108 mg, 74.4% yield). MS (ESI pos. ion) m/z calc'd for $C_8H_7N_3$: 145.0; found 146.0. $^1$H NMR (300 MHz, CHLOROFORM-d) δ ppm 4.56 (s, 2 H) 6.66 (s, 1 H) 7.38 (dd, J=8.48, 4.09 Hz, 1 H) 7.81-7.91 (m, J=7.16 Hz, 1 H) 8.68 (dd, J=4.02, 1.53 Hz, 1 H) 9.12 (s, 1 H)

(5) 1,7-naphthyridin-6-yl trifluoromethanesulfonate. To a 50 mL round-bottomed flask was added 1,7-naphthyridin-6-amine (102 mg, 703 µmol), sodium nitrite (0.04 mL, 1405 µmol), DMF (1.6 mL), trifluoromethanesulfonic acid (0.8 mL, 9041 µmol). The reaction mixture was stirred at room temperature for 2 h. The mixture was diluted with EtOAc (40 mL) and washed with water (5 mL), saturated NaHCO$_3$ (5 mL), and saturated NaCl (5 mL), dried over Na$_2$SO$_4$, filtered and concentrated in vacuo and the residue was purified by silica gel chromatography, eluting with 50% EtOAc/hexanes to give 1,7-naphthyridin-6-yl trifluoromethanesulfonate (138 mg, 71% yield) as a yellow solid. MS (ESI pos. ion) m/z calc'd for $C_9H_5F_3N_2O_3S$: 278.0; found 279.0. $^1$H NMR (300 MHz, CHLOROFORM-d) δ ppm 7.61 (s, 1 H) 7.71 (dd, J=8.48, 4.24 Hz, 1 H) 8.21-8.30 (m, J=0.58 Hz, 1 H) 9.12 (dd, J=4.24, 1.61 Hz, 1 H) 9.36 (s, 1 H)

(6) N-(2-chloro-5-(1,7-naphthyridin-6-yl)pyridin-3-yl)-4-fluorobenzenesulfonamide. To a 50 mL round-bottomed flask was added 1,7-naphthyridin-6-yl trifluoromethanesulfonate (42 mg, 151 µmol), N-(2-chloro-5-(4,4,5,5-tetramethyl-1,3,2-dioxaborolan-2-yl)pyridin-3-yl)-4-fluorobenzenesulfonamide (62 mg, 151 µmol), tetrakis(triphenylphosphine)palladium (17 mg, 15 µmol), sodium carbonate (151 µl, 302 µmol), dioxane (1 mL). The reaction mixture was stirred at 100° C. for 1 h. The mixture was cooled down to room temperature. The reaction mixture was diluted with water (5 mL) and extracted with EtOAc (2×40 mL). The organic extract was washed with saturated NaCl (5 mL), dried over $Na_2SO_4$, filtered and concentrated in vacuo and the residue was purified by silica gel chromatography, eluting with 70% EtOAc/hexanes to give N-(2-chloro-5-(1,7-naphthyridin-6-yl)pyridin-3-yl)-4-fluorobenzenesulfonamide (46 mg, 73% yield) as a white solid. MS (ESI pos. ion) m/z calc'd for $C_{19}H_{12}ClFN_4O_2S$: 414.0; found 415.0. $^1$H NMR (300 MHz, CHLOROFORM-d) δ ppm 7.01 (s, 1 H) 7.10-7.21 (m, J=8.18 Hz, 2 H) 7.68 (dd, J=8.33, 4.24 Hz, 1 H) 7.82-7.91 (m, 2 H) 8.11 (d, J=0.73 Hz, 1 H) 8.27 (d, J=7.75 Hz, 1 H) 8.78 (d, J=2.19 Hz, 1 H) 8.95 (d, J=2.19 Hz, 1 H) 9.08 (dd, J=4.17, 1.68 Hz, 1 H) 9.62 (s, 1 H)

Example 76

N-(2-Chloro-5-(8-methoxy-1,7-naphthyridin-6-yl)pyridin-3-yl)-4-fluorobenzenesulfonamide

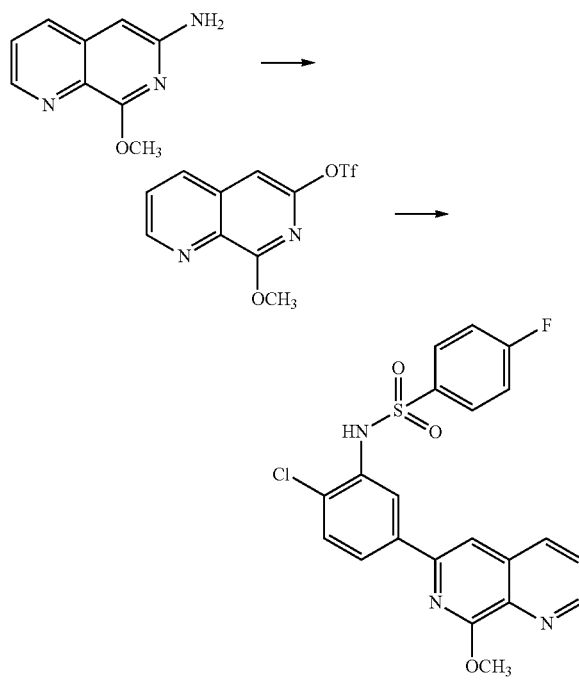

(1) 8-methoxy-1,7-naphthyridin-6-yl trifluoromethanesulfonate. (Some starting materials may be obtained from Parkway Scientific, NY, N.Y.) To a 50 mL round-bottomed flask was added 8-methoxy-1,7-naphthyridin-6-amine (175 mg, 999 µmol), DMF (1.6 mL), trifluoromethane sulfonic acid (0.8 mL, 9041 µmol), sodium nitrite (0.06 mL, 1998 µmol). The reaction mixture was stirred at room temperature for 2 h. The reaction mixture was diluted with water (10 mL) and extracted with EtOAc (2×40 mL). The organic extract was washed with water (10 mL), satd NaCl (10 mL), dried over $Na_2SO_4$, filtered and concentrated in vacuo and the residue was purified by silica gel chromatography, eluting with 60% EtOAc/hexanes to give 8-methoxy-1,7-naphthyridin-6-yl trifluoromethanesulfonate (126mg, 41% yield). MS (ESI pos. ion) m/z calc'd for $C_{10}H_7F_3N_2O_4S$: 308.0; found 309.0. $^1$H NMR (300 MHz, CHLOROFORM-d) δ ppm 4.25 (s, 3 H) 7.13 (s, 1 H) 7.70 (dd, J=8.33, 4.24 Hz, 1 H) 8.19 (dd, J=8.40, 1.53 Hz, 1 H) 9.04 (dd, J=4.24, 1.61 Hz, 1 H)

(2) N-(2-chloro-5-(8-methoxy-1,7-naphthyridin-6-yl)pyridin-3-yl)-4-fluorobenzenesulfonamide. To a 50 mL round-bottomed flask was added 8-methoxy-1,7-naphthyridin-6-yl trifluoromethanesulfonate (46 mg, 149 µmol), N-(2-chloro-5-(4,4,5,5-tetramethyl-1,3,2-dioxaborolan-2-yl)pyridin-3-yl)-4-fluorobenzenesulfonamide (62 mg, 149 µmol), tetrakis(triphenylphosphine)palladium (17 mg, 15 µmol), sodium carbonate (149 µl, 298 µmol), and dioxane (1 mL). The reaction mixture was stirred at 100° C. for 1 h. The mixture was cooled down to room temperature. The reaction mixture was diluted with saturated $NH_4Cl$ (5 mL) and extracted with EtOAc (2×30 mL). The organic extract was washed with water (5 mL), saturated NaCl (5 mL), dried over $Na_2SO_4$, filtered and concentrated in vacuo nad the residue was purified by silica gel chromatography, eluting with 30% EtOAc/$CH_2Cl_2$ to give N-(2-chloro-5-(8-methoxy-1,7-naphthyridin-6-yl)pyridin-3-yl)-4-fluorobenzenesulfonamide (42 mg, 63% yield) as a white solid. MS (ESI pos. ion) m/z calc'd for $C_{20}H_{14}ClFN_4O_3S$: 444.0; found 445.0. $^1$H NMR (300 MHz, CHLOROFORM-d) δ ppm 4.34 (s, 3 H) 7.10-7.21 (m, 2 H) 7.66 (dd, J=8.33, 4.24 Hz, 1 H) 7.72 (s, 1 H) 7.81-7.91 (m, 2 H) 8.20 (dd, J=8.33, 1.61 Hz, 1 H) 8.78 (d, J=2.19 Hz, 1 H) 8.91 (d, J=2.19 Hz, 1 H) 9.01 (dd, J=4.24, 1.61 Hz, 1 H)

| Example | Name | Prepared analogous to example number | MS (M + 1) |
|---|---|---|---|
| 77 | N-(2-chloro-5-(4-(((5-cyclopropyl-1,2,4-oxadiazol-3-yl)methyl)(ethyl)amino)-6-quinolinyl)-3-pyridinyl)methanesulfonamide | 24 | 499.0 |
| 78 | N-(2-chloro-5-(4-((2-cyanoethyl)(ethyl)amino)-6-quinolinyl)-3-pyridinyl)methanesulfonamide | 24 | 429.9 |
| 79 | N-(2-chloro-5-(4-((2-methoxy-2-methylpropyl)amino)-6-quinolinyl)-3-pyridinyl)methanesulfonamide | 24 | 434.9 |
| 80 | N-(2-chloro-5-(4-(3-(2-methylphenoxy)-1-pyrrolidinyl)-6-quinolinyl)-3-pyridinyl)methanesulfonamide | 24 | 508.9 |
| 81 | N-(2-chloro-5-(4-(2-(methoxymethyl)-1-pyrrolidinyl)-6-quinolinyl)-3-pyridinyl)methanesulfonamide | 24 | 446.9 |
| 82 | N-(2-chloro-5-(4-(4-phenyl-1-piperidinyl)-6-quinolinyl)-3-pyridinyl)methanesulfonamide | 24 | 493.0 |
| 83 | N-(2-chloro-5-(4-(4-(1-phenylethyl)-1-piperazinyl)-6-quinolinyl)-3-pyridinyl)methanesulfonamide | 24 | 522.0 |
| 84 | N-(5-(4-(4-(1,3-benzodioxol-5-ylmethyl)-1-piperazinyl)-6-quinolinyl)-2-chloro-3-pyridinyl)methanesulfonamide | 24 | 552.0 |
| 85 | N-(2-chloro-5-(4-((3-fluorobenzyl)(methyl)amino)-6-quinolinyl)-3-pyridinyl)methanesulfonamide | 24 | 471.0 |
| 86 | N-(2-chloro-5-(4-(5-fluoro-1,3-dihydro-2H-isoindol-2-yl)-6-quinolinyl)-3-pyridinyl)methanesulfonamide | 24 | 469.0 |

| Example | Name | Prepared analogous to example number | MS (M + 1) |
|---|---|---|---|
| 87 | N-(2-chloro-5-(4-((2,5-dimethoxybenzyl)amino)-6-quinolinyl)-3-pyridinyl)methanesulfonamide | 24 | 499.0 |
| 88 | N-(2-chloro-5-(4-(4-piperidinylamino)-6-quinolinyl)-3-pyridinyl)methanesulfonamide | 24 | 432.0 |
| 89 | N-(2-chloro-5-(4-(4-(4-pyridinylmethyl)-1-piperazinyl)-6-quinolinyl)-3-pyridinyl)-4-fluorobenzenesulfonamide | 1 | 589.1 |
| 90 | N-(2-chloro-5-(4-(2,2-dimethyl-4-morpholinyl)-6-quinolinyl)-3-pyridinyl)methanesulfonamide | 11 | 447.0 |
| 91 | N-(2-chloro-5-(3-((2-(4-morpholinyl)ethyl)amino)-6-quinoxalinyl)-3-pyridinyl)-4-fluorobenzenesulfonamide | 20 | 543.0 |
| 92 | N-(2-chloro-5-(3-(4-morpholinyl)-6-quinoxalinyl)-3-pyridinyl)methanesulfonamide | 20 | 419.9 |
| 93 | N-(2-chloro-5-(4-(3-pyridinyl)-6-quinolinyl)-3-pyridinyl)-4-fluorobenzenesulfonamide | 35 | 490.8 |
| 94 | N-(2-chloro-5-(4-(2-chloro-4-pyridinyl)-6-quinolinyl)-3-pyridinyl)-4-fluorobenzenesulfonamide | 35 | 524.9 |
| 95 | N-(2-chloro-5-(4-(4-hydroxy-1-azepanyl)-6-quinolinyl)-3-pyridinyl)-4-fluorobenzenesulfonamide | 26 | 527.0 |
| 96 | N-(2-chloro-5-(4-((2R,6S)-2,6-dimethyl-4-morpholinyl)-6-quinolinyl)-3-pyridinyl)-4-fluorobenzenesulfonamide | 26 | 527.0 |
| 97 | N-(2-chloro-5-(4-(dimethylamino)-6-quinolinyl)-3-pyridinyl)-4-fluorobenzenesulfonamide | 1 | 457.0 |
| 98 | N-(2-chloro-5-(4-((2-methoxyethyl)amino)-6-quinolinyl)-3-pyridinyl)-4-fluorobenzenesulfonamide | 1 | 487.0 |
| 99 | N-(2-chloro-5-(4-((2-methoxy-1-methylethyl)amino)-6-quinolinyl)-3-pyridinyl)-4-fluorobenzenesulfonamide | 1 | 501.0 |
| 100 | N-(2-chloro-5-(4-(tetrahydro-2H-thiopyran-4-ylmethoxy)-6-quinolinyl)-3-pyridinyl)-4-fluorobenzenesulfonamide | 1 | 544.0 |
| 101 | N-(2-chloro-5-(4-(4-morpholinyl)-6-quinolinyl)-3-pyridinyl)-3-pyridinesulfonamide | 32 | 481.9 |
| 102 | N-(2-chloro-5-(4-(4-(dimethylamino)phenyl)-6-quinolinyl)-3-pyridinyl)-4-fluorobenzenesulfonamide | 35 | 532.9 |
| 103 | N-(2-chloro-5-(4-((2R,6S)-2,6-dimethyl-4-morpholinyl)-6-quinolinyl)-3-pyridinyl)methanesulfonamide | 24 | 446.9 |
| 104 | N-(2-chloro-5-(4-(2,6-dimethyl-4-morpholinyl)-6-quinolinyl)-3-pyridinyl)methanesulfonamide | 24 | 446.9 |
| 105 | N-(2-chloro-5-(4-(2-methyl-4-pyridinyl)-6-quinolinyl)-3-pyridinyl)methanesulfonamide | 116 | 424.9 |
| 106 | N-(2-chloro-5-(4-(2-methoxy-4-pyridinyl)-6-quinolinyl)-3-pyridinyl)methanesulfonamide | 116 | 440.9 |
| 107 | N-(2-chloro-5-(4-(3,6-dihydro-2H-pyran-4-yl)-6-quinolinyl)-3-pyridinyl)methanesulfonamide | 116 | 415.9 |
| 108 | N-(2-chloro-5-(4-(tetrahydro-3-thiophenyloxy)-6-quinolinyl)-3-pyridinyl)-4-fluorobenzenesulfonamide | 1 | 515.8 |
| 109 | N-(2-chloro-5-(4-((2S,6S)-2,6-dimethyl-4-morpholinyl)-6-quinolinyl)-3-pyridinyl)methanesulfonamide | 104* | 446.9 |
| 110 | N-(2-chloro-5-(4-((2R,6R)-2,6-dimethyl-4-morpholinyl)-6-quinolinyl)-3-pyridinyl)methanesulfonamide | 104* | 446.9 |
| 111 | N-(2-chloro-5-(4-(2-(trifluoromethyl)-4-pyridinyl)-6-quinolinyl)-3-pyridinyl)methanesulfonamide | 116 | 478.8 |
| 112 | N-(2-chloro-5-(4-(6-(trifluoromethyl)-3-pyridinyl)-6-quinolinyl)-3-pyridinyl)methanesulfonamide | 116 | 478.8 |

*Enantiomers were separated on Chiralpak AD-H (2 × 25 cm) SN 08-9743 using 25% ethanol (0.1% DEA)/CO$_2$, 100 bar at 75 mL/min with detection at 220 nm.

| Example | Structure |
|---|---|
| 77 | 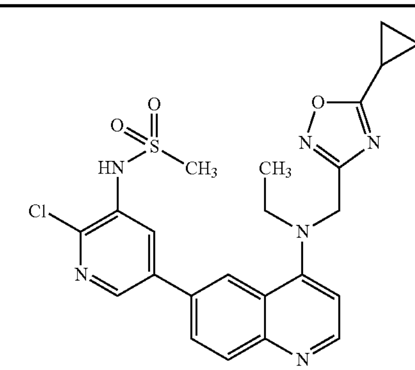 |
| 78 | 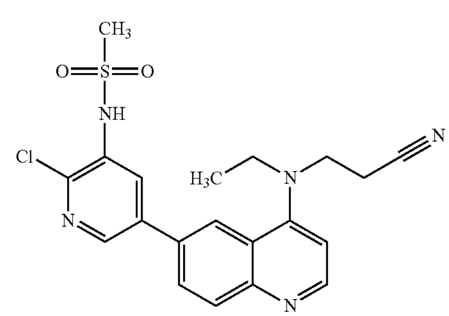 [SMILES: CCN(CCC#N)c1ccnc2ccc(-c3cnc(Cl)c(NS(C)(=O)=O)c3)cc12] |

| Example | Structure |
|---|---|
| 79 | 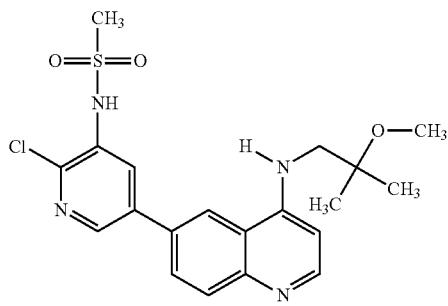 [SMILES: COC(C)(C)CNc1ccnc2ccc(-c3cnc(Cl)c(NS(C)(=O)=O)c3)cc12] |
| 80 | 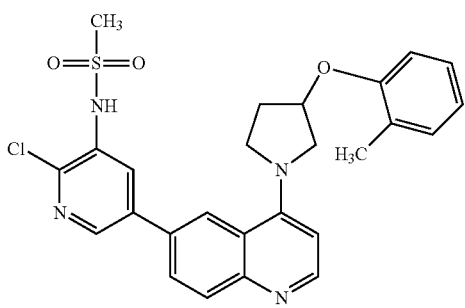 [SMILES: Cc1ccccc1OC1CCN(c2ccnc3ccc(-c4cnc(Cl)c(NS(C)(=O)=O)c4)cc23)C1] |
| 81 | 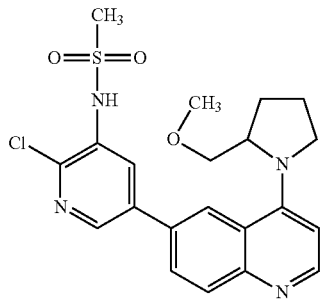 [SMILES: COCC1CCCN1c1ccnc2ccc(-c3cnc(Cl)c(NS(C)(=O)=O)c3)cc12] |
| 82 | 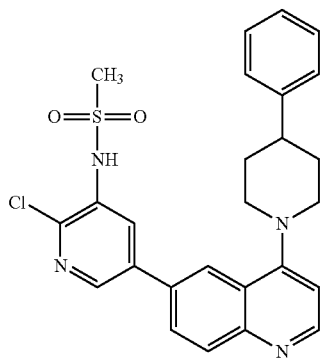 [SMILES: CS(=O)(=O)Nc1cc(-c2ccc3nccc(N4CCC(c5ccccc5)CC4)c3c2)cnc1Cl] |
| Example | Structure |
|---|---|
| 83 | 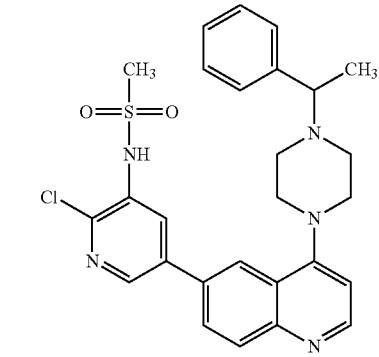 [SMILES: CC(c1ccccc1)N1CCN(c2ccnc3ccc(-c4cnc(Cl)c(NS(C)(=O)=O)c4)cc23)CC1] |
| 84 | 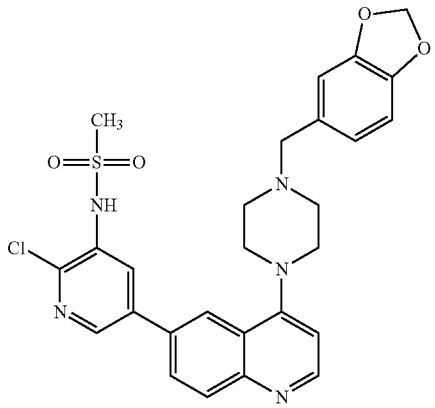 [SMILES: CS(=O)(=O)Nc1cc(-c2ccc3nccc(N4CCN(Cc5ccc6c(c5)OCO6)CC4)c3c2)cnc1Cl] |
| 85 | 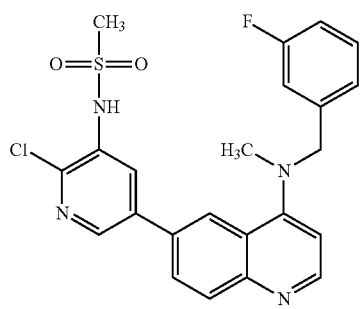 [SMILES: CN(Cc1cccc(F)c1)c1ccnc2ccc(-c3cnc(Cl)c(NS(C)(=O)=O)c3)cc12] |
| 86 | 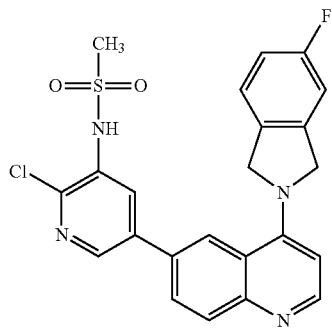 [SMILES: CS(=O)(=O)Nc1cc(-c2ccc3nccc(N4Cc5ccc(F)cc5C4)c3c2)cnc1Cl] |

-continued
| Example | Structure |
|---|---|
| 87 | 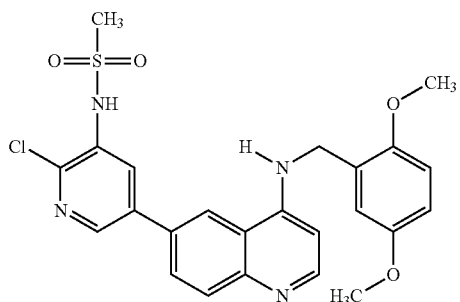 |
| 88 | 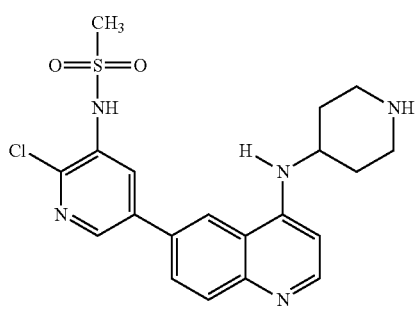 [SMILES: CS(=O)(=O)Nc1cc(-c2ccc3nccc(NC4CCNCC4)c3c2)cnc1Cl] |
| 89 | 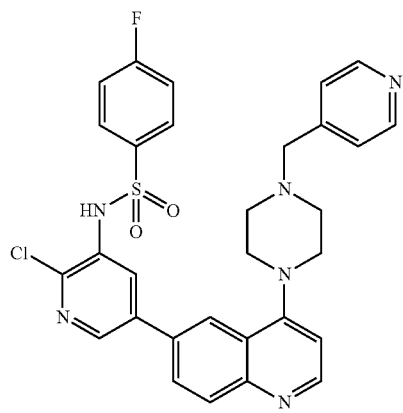 [SMILES: O=S(=O)(Nc1cc(-c2ccc3nccc(N4CCN(Cc5ccncc5)CC4)c3c2)cnc1Cl)c1ccc(F)cc1] |
| 90 | 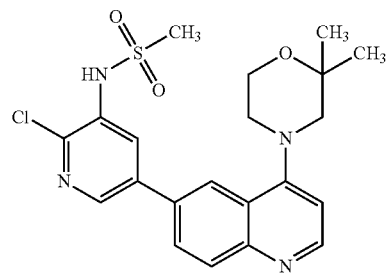 [SMILES: CC1(C)CN(c2ccnc3ccc(-c4cnc(Cl)c(NS(C)(=O)=O)c4)cc23)CCO1] |
| 91 | 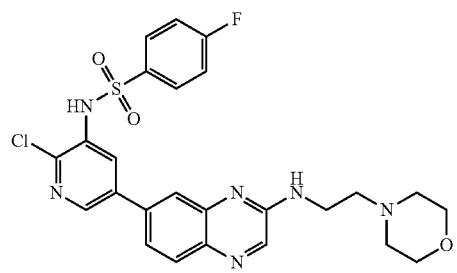 [SMILES: O=S(=O)(Nc1cc(-c2ccc3ncc(NCCN4CCOCC4)nc3c2)cnc1Cl)c1ccc(F)cc1] |
-continued
| Example | Structure |
|---|---|
| 92 | 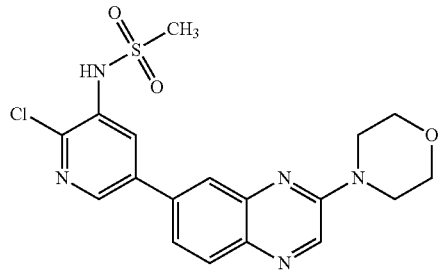 [SMILES: CS(=O)(=O)Nc1cc(-c2ccc3ncc(N4CCOCC4)nc3c2)cnc1Cl] |
| 93 | 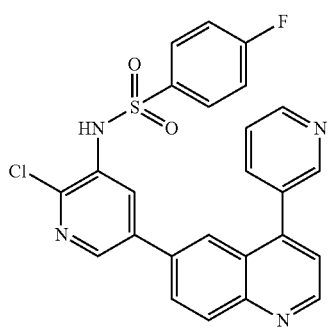 [SMILES: O=S(=O)(Nc1cc(-c2ccc3nccc(-c4cccnc4)c3c2)cnc1Cl)c1ccc(F)cc1] |
| 94 | 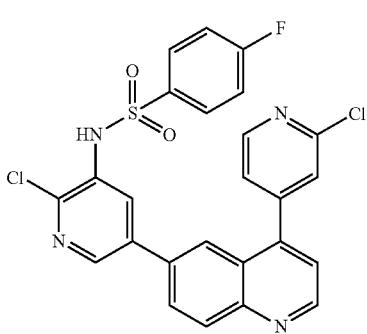 [SMILES: O=S(=O)(Nc1cc(-c2ccc3nccc(-c4ccnc(Cl)c4)c3c2)cnc1Cl)c1ccc(F)cc1] |
| 95 | 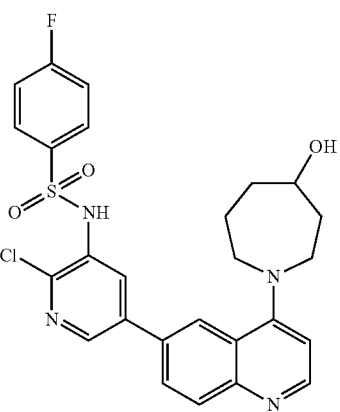 [SMILES: O=S(=O)(Nc1cc(-c2ccc3nccc(N4CCCC(O)CC4)c3c2)cnc1Cl)c1ccc(F)cc1] |

-continued
| Example | Structure |
|---------|-----------|
| 96 | 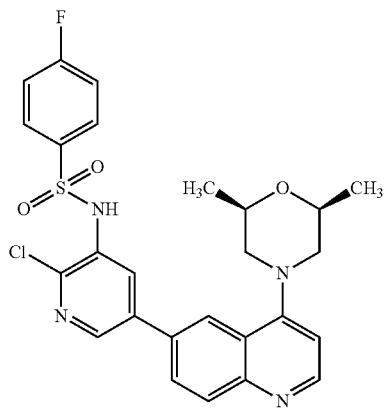 [SMILES: C[C@@H]1CN(c2ccnc3ccc(-c4cnc(Cl)c(NS(=O)(=O)c5ccc(F)cc5)c4)cc23)C[C@H](C)O1] |
| 97 | 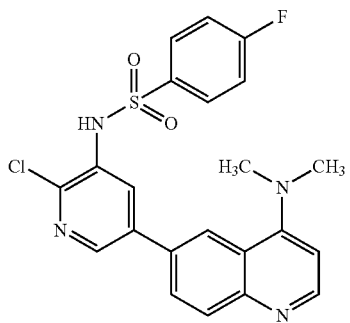 [SMILES: CN(C)c1ccnc2ccc(-c3cnc(Cl)c(NS(=O)(=O)c4ccc(F)cc4)c3)cc12] |
| 98 | 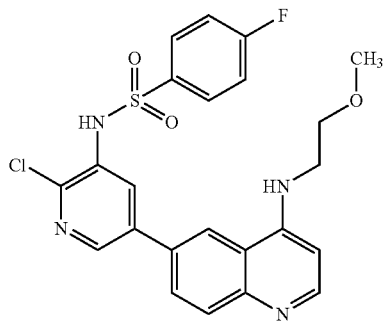 [SMILES: COCCNc1ccnc2ccc(-c3cnc(Cl)c(NS(=O)(=O)c4ccc(F)cc4)c3)cc12] |
| 99 | 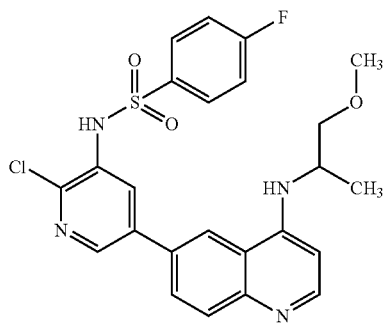 [SMILES: COCC(C)Nc1ccnc2ccc(-c3cnc(Cl)c(NS(=O)(=O)c4ccc(F)cc4)c3)cc12] |
-continued
| Example | Structure |
|---------|-----------|
| 100 | 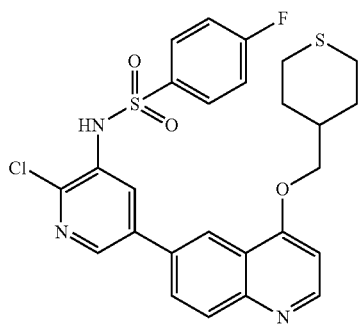 [SMILES: O=S(=O)(Nc1cc(-c2ccc3nccc(OCC4CCSCC4)c3c2)cnc1Cl)c1ccc(F)cc1] |
| 101 | 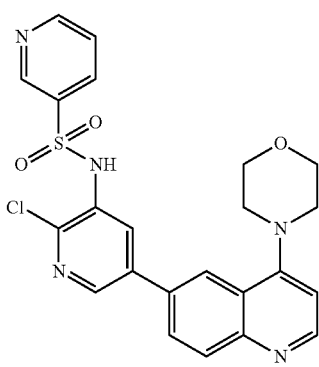 [SMILES: O=S(=O)(Nc1cc(-c2ccc3nccc(N4CCOCC4)c3c2)cnc1Cl)c1cccnc1] |
| 102 | 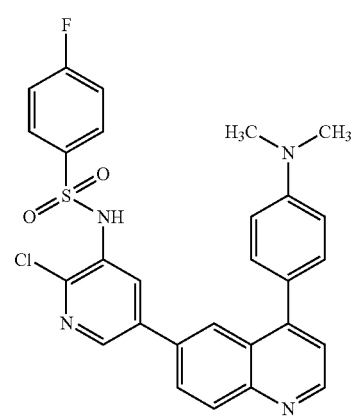 [SMILES: CN(C)c1ccc(-c2ccnc3ccc(-c4cnc(Cl)c(NS(=O)(=O)c5ccc(F)cc5)c4)cc23)cc1] |
| 103 | 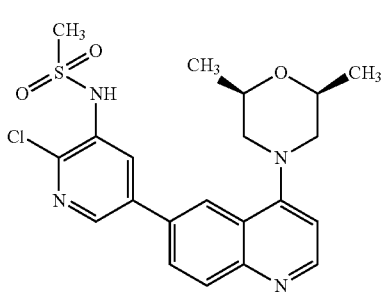 [SMILES: C[C@@H]1CN(c2ccnc3ccc(-c4cnc(Cl)c(NS(C)(=O)=O)c4)cc23)C[C@H](C)O1] |

-continued
| Example | Structure |
|---|---|
| 104 | 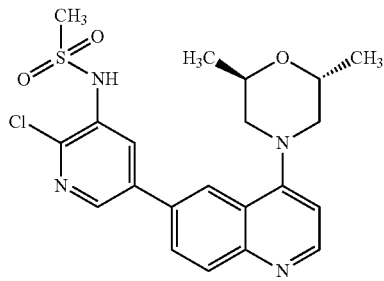 [SMILES: C[C@@H]1CN(c2ccnc3ccc(-c4cnc(Cl)c(NS(C)(=O)=O)c4)cc23)C[C@@H](C)O1] |
| 105 | 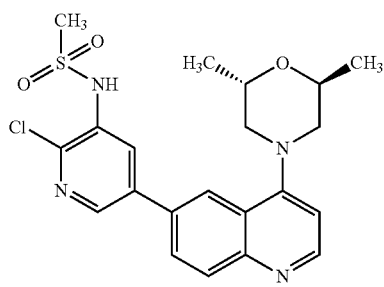 [SMILES: C[C@H]1CN(c2ccnc3ccc(-c4cnc(Cl)c(NS(C)(=O)=O)c4)cc23)C[C@H](C)O1] |
| 106 | 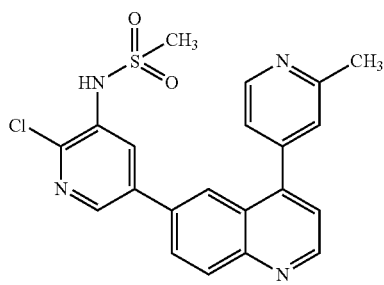 [SMILES: Cc1cc(-c2ccnc3ccc(-c4cnc(Cl)c(NS(C)(=O)=O)c4)cc23)ccn1] |
| 107 | 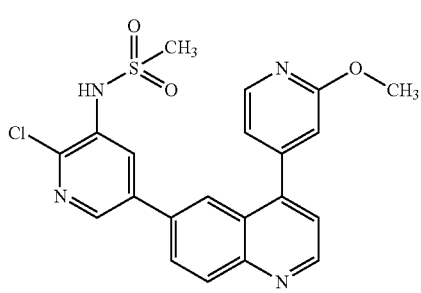 [SMILES: COc1cc(-c2ccnc3ccc(-c4cnc(Cl)c(NS(C)(=O)=O)c4)cc23)ccn1] |
| | 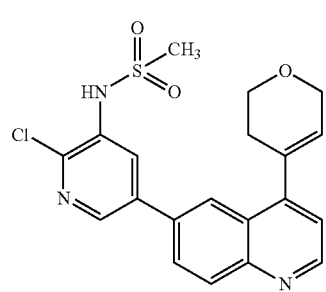 [SMILES: CS(=O)(=O)Nc1cc(-c2ccc3nccc(C4=CCOCC4)c3c2)cnc1Cl] |
-continued
| Example | Structure |
|---|---|
| 108 | 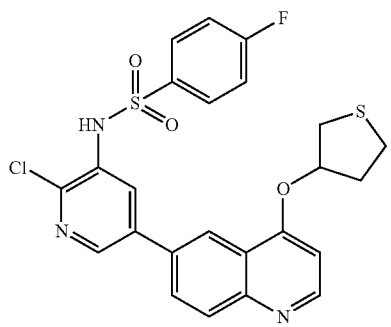 [SMILES: O=S(=O)(Nc1cc(-c2ccc3nccc(OC4CCSC4)c3c2)cnc1Cl)c1ccc(F)cc1] |
| 109 | 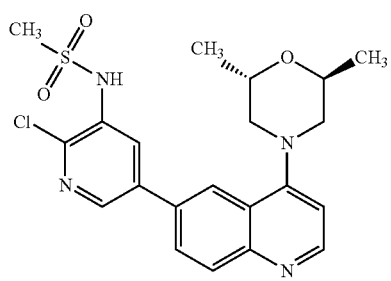 |
| 110 | 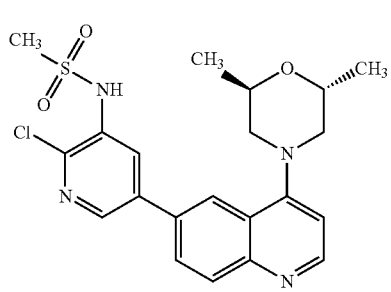 |
| 111 | 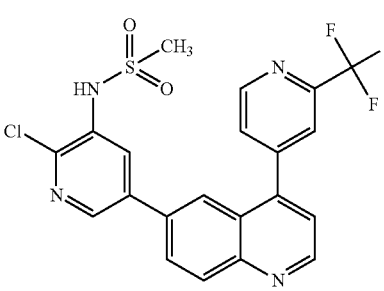 |
| 112 | 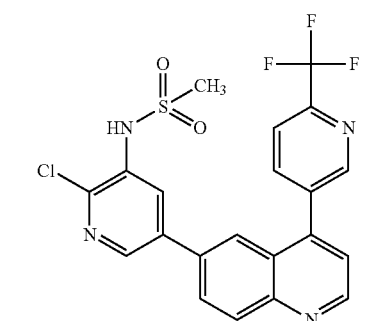 |

Example 113

N-(2-Chloro-5-(4-((tetrahydro-2H-thiopyran-1,1-dioxide-4-yl)methoxy)quinolin-6-yl)pyridin-3-yl)-4-fluorobenzenesulfonamide

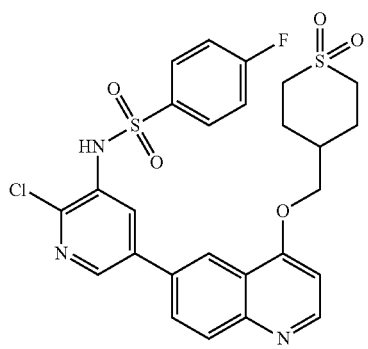 [SMILES: O=S1(=O)CCC(COc2ccnc3ccc(-c4cnc(Cl)c(NS(=O)(=O)c5ccc(F)cc5)c4)cc23)CC1]

To a solution of N-(2-chloro-5-(4-((tetrahydro-2H-thiopyran-4-yl)methoxy)quinolin-6-yl)pyridin-3-yl)-4-fluorobenzenesulfonamide (0.060 g, 0.11 mmol) in MeOH (8 mL) and water (2 mL) was added sodium periodate (0.071 g, 0.33 mmol). The reaction mixture was heated at 60° C. for 20 h. The reaction mixture was partitioned between water and DCM. The aqueous layer was extracted with DCM (2×10 mL). The combined organic layers were dried over MgSO$_4$ and concentrated. The crude product was purified by column chromatography (12 g, 5% MeOH and 20% EtOAc in DCM) to afford the desired product as a white solid (25.0 mg). MS (ESI pos. ion) m/z: calcd for $C_{26}H_{23}ClFN_3O_5S_2$: 575.1; found: 575.8 [M+1]. $^1$H NMR (300 MHz, CHLOROFORM-d) δ ppm 2.18 (s, 2 H) 2.29 (s, 1 H) 2.41 (s, 2 H) 3.17 (s, 4 H) 4.18 (d, J=6.28 Hz, 2 H) 6.83 (d, J=5.26 Hz, 1 H) 7.13-7.23 (m, 2 H) 7.76-7.87 (m, 2 H) 7.93 (dd, J=8.84, 2.12 Hz, 1 H) 8.23 (d, J=8.77 Hz, 1 H) 8.32-8.40 (m, 2 H) 8.52 (d, J=2.19 Hz, 1 H) 8.84 (d, J=5.26 Hz, 1 H).

EXAMPLE 114

N-(2-Chloro-5-(4-(tetrahydro-2H-pyran-4-yl)quinolin-6-yl)pyridin-3-yl)methanesulfonamide

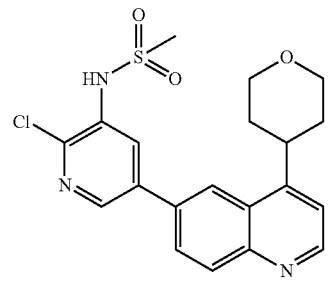 [SMILES: CS(=O)(=O)Nc1cc(-c2ccc3nccc(C4CCOCC4)c3c2)cnc1Cl]

To a solution of N-(2-chloro-5-(4-(3,6-dihydro-2H-pyran-4-yl)quinolin-6-yl)pyridin-3-yl)methanesulfonamide (0.055 g, 0.13 mmol) in (10 mL) under N$_2$ was added platinum (IV) oxide (0.015 g, 0.066 mmol). The reaction mixture was purged with N$_2$ followed by evacuating. This procedure was done 3 times. After last evacuation, a hydrogen balloon was inserted. The reaction was stirred at rt under H$_2$ for 4 h. The reaction mixture was passed through a pad of Celite® (diatomaceous earth). The reaction mixture was then concentrated. The crude product was purified by column chromatography (12 g, 20% to 30% acetone in hexanes) to afford the desired product as an off-white solid (30.0 mg). MS (ESI pos. ion) m/z: calcd for $C_{20}H_{26}ClN_3O_3S$: 417.1; found: 417.9 [M+1]. $^1$H NMR (300 MHz, CHLOROFORM-d) δ ppm 1.85-2.14 (m, 4 H) 3.14 (s, 3 H) 3.55-3.85 (m, 3 H) 4.10-4.29 (m, 2 H) 6.93 (br. s., 1 H) 7.39 (d, J=4.53 Hz, 1 H) 7.92 (dd, J=8.70, 1.97 Hz, 1 H) 8.17-8.37 (m, 3 H) 8.57 (d, J=2.34 Hz, 1 H) 8.94 (d, J=4.53 Hz, 1 H).

Example 115

N-(2-Chloro-5-(4-(tetrahydrothiophen-1,1-dioxide-3-yloxy)quinolin-6-yl)pyridin-3-yl)-4-fluorobenzenesulfonamide

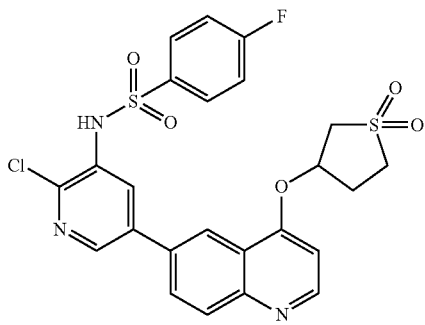 [SMILES: O=S1(=O)CCC(Oc2ccnc3ccc(-c4cnc(Cl)c(NS(=O)(=O)c5ccc(F)cc5)c4)cc23)C1]

To a solution of N-(2-chloro-5-(4-(tetrahydrothiophen-3-yloxy)quinolin-6-yl)pyridin-3-yl)-4-fluorobenzenesulfonamide (0.080 g, 0.16 mmol) in MeOH (12 mL) and water (3 mL) was added sodium periodate (0.099 g, 0.47 mmol). The reaction mixture was heated at 60° C. for 20 h. The reaction mixture was partitioned between water and DCM. The aqueous layer was extracted with DCM (2×10 mL). The combined organic layers were dried over MgSO$_4$ and concentrated. The crude product was purified by column chromatography (12 g, 3% MeOH and 32% EtOAc in DCM) to afford the desired product as a white solid (20.0 mg). MS (ESI pos. ion) m/z: calcd for $C_{24}H_{19}ClFN_3O_5S_2$: 547.0; found: 547.8 [M+1]. $^1$H NMR (300 MHz, CHLOROFORM-d) δ ppm 2.68-2.82 (m, 1 H) 2.87 (br. s., 1 H) 3.27-3.43 (m, 1 H) 3.45-3.64 (m, 3 H) 5.53 (d, J=5.41 Hz, 1 H) 6.78 (d, J=5.26 Hz, 1 H) 7.01-7.13 (m, 1 H) 7.14-7.24 (m, 2 H) 7.82-7.91 (m, 2 H) 7.94 (dd, J=8.77, 2.05 Hz, 1 H) 8.23 (d, J=8.77 Hz, 1 H) 8.36 (dd, J=6.43, 2.05 Hz, 2 H) 8.50 (d, J=2.34 Hz, 1 H) 8.86 (d, J=5.12 Hz, 1 H).

Example 116

N-(2-Chloro-5-(4-(pyridin-3-yl)quinolin-6-yl)pyridin-3-yl)methanesulfonamide

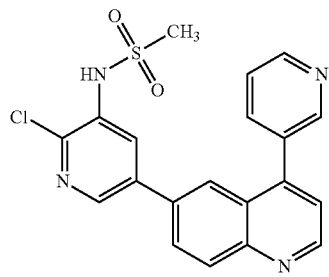 [SMILES: CS(=O)(=O)Nc1cc(-c2ccc3nccc(-c4cccnc4)c3c2)cnc1Cl]

To a 5 mL microwave vial, N-(2-chloro-5-(4-chloroquinolin-6-yl)pyridin-3-yl)methanesulfonamide (0.0500 g, 0.136 mmol, Example 9), 3-(4,4,5,5-tetramethyl-1,3,2-dioxaborolan-2-yl)pyridine (0.0334 g, 0.163 mmol), potassium acetate (0.0333 g, 0.339 mmol) and dichlorobis(di-tert-butylphenylphosphine)palladium(II) (0.0042 g, 0.0068 mmol) were mixed into 1 mL of nBuOH along with 0.1 mL of water. The reaction mixture was stirred at 105° C. for 3 h. The reaction mixture was partitioned between water (10mL)/brine (10 mL) and 25% IPA/CHCl$_3$ (20 mL). The aqueous phase was extracted with 25% IPA/CHCl$_3$ (2×20 mL). The combined organic phases were dried over sodium sulfate, filtered and concentrated in vacuo. The crude product was purified by silica gel column chromatography (eluent: acetone in DCM 20%-70%) to afford an off white solid (0.0286 g) as the desired product. MS (ESI pos. ion) m/z calcd for C$_{20}$H$_{15}$ClN$_4$O$_2$S: 410.1; found 410.9 [M+1]. $^1$H NMR (300 MHz, DMSO-d$_6$) δ ppm 9.85 (s, 1 H) 9.05 (d, J=4.38 Hz, 1 H) 8.86 (d, J=1.75 Hz, 1 H) 8.77 (dd, J=4.82, 1.61 Hz, 1 H) 8.63 (d, J=2.34 Hz, 1 H) 8.24-8.33 (m, 1 H) 8.09-8.24 (m, 3 H) 8.05 (d, J=1.75 Hz, 1 H) 7.59-7.69 (m, 2 H) 3.16 (s, 3 H).

Example 117

N-(5-(4-(Pyridin-3-yl)quinolin-6-yl)-2,3'-bipyridin-3-yl)methanesulfonamide

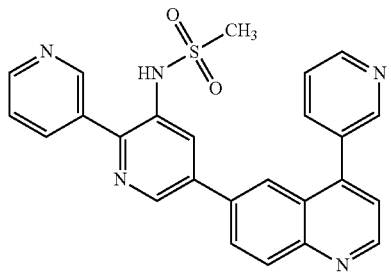 [SMILES: CS(=O)(=O)Nc1cc(-c2ccc3nccc(-c4cccnc4)c3c2)cnc1-c1cccnc1]

This compound was prepared similarly to the procedure described in Example 116, except dichlro[1,1'-bis(diphenylphosphino)ferrocene]palladium(II) dichloromethane adduct, potassium carbonate and 1,4-dioxane were used in place of dichlorobis(di-tert-butylphenylphosphine)palladium(II), potassium acetate and ethanol respectively. MS (ESI pos. ion) m/z calcd for C$_{25}$H$_{19}$N$_5$O$_2$S: 453.1; found 454.0 [M+1].

Example 118

N-(2-Chloro-5-(4-(pyridin-4-yl)quinolin-6-yl)pyridin-3-yl)methanesulfonamide

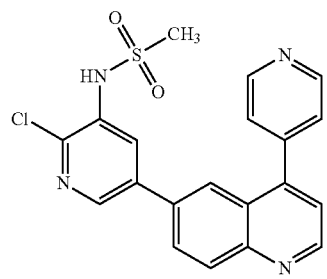 [SMILES: CS(=O)(=O)Nc1cc(-c2ccc3nccc(-c4ccncc4)c3c2)cnc1Cl]

This compound was prepared similarly to the procedure described in Example 116. MS (ESI pos. ion) m/z calcd for C$_{20}$H$_{15}$ClN$_4$O$_2$S: 410.1; found 410.9 [M+1].

Example 119

N-(2-Methoxy-5-(4-morpholinoquinolin-6-yl)pyridin-3-yl)methanesulfonamide (1) N-(5-Bromo-2-methoxypyridin-3-yl)methanesulfonamide. To a 5 mL microwave vial, 5-bromo-3-iodo-2-methoxypyridine (0.317 g, 1.01 mmol, Alfa Aesar, Ward Hill, Mass.), methanesulfonamide (0.100 g, 1.06 mmol), cesium carbonate (0.829 g, 2.54 mmol) and copper(I) iodide (0.0211 g, 0.111 mmol) were mixed into DMF (1 mL). water (0.1 mL) was added and the mixture was heated at 105° C. for 20 h. The reaction mixture was poured into water/Tris-1M HCl pH 7 buffer then 1N HCl was added to bring pH to ~5. The aqueous phase was extracted with EtOAc (3×20 mL). The combined organic phases were washed with saturated aqueous NaCl (40 mL). The organic phase was dried over sodium sulfate, filtered and concentrated in vacuo. The crude product was purified by silica gel column chromatography (eluent: EtOAc in hexanes 0-50%) to afford an off white solid (0.135 g) as the desired product. MS (ESI pos. ion) m/z calcd for $C_7H_9BrN_2O_3S$: 280.0; found 280.8/282.8 [M+1/M+3]. $^1H$ NMR (300 MHz, CHLOROFORM-d). δ ppm 3.04 (s, 3 H) 3.92-4.07 (m, 3 H) 6.74 (br. s., 1H) 7.89 (d, J=2.19 Hz, 1 H) 7.97 (d, J=2.19 Hz, 1 H).

(2) N-(2-methoxy-5-(4-morpholinoquinolin-6-yl)pyridin-3-yl)methanesulfonamide. To a 5 mL microwave reaction tube was added N-(5-bromo-2-methoxypyridin-3-yl)methanesulfonamide (0.0682 g, 0.243 mmol), 4-morpholino-6-(4,4,5,5-tetramethyl-1,3,2-dioxaborolan-2-yl)quinoline (0.1098 g, 0.323 mmol, Example 1, step 3), dichlro[1,1'-bis(diphenylphosphino)ferrocene]palladium(II) dichloromethane adduct (0.0123 g, 0.0151 mmol) and potassium carbonate (0.303 ml, 0.606 mmol) in 1,4-dioxane (2 mL). The mixture was degassed by bubbling nitrogen through for 10 min. The tube was subjected to the microwave irradiation at 100° C. for 10 min. The reaction mixture was partitioned between water (20 mL) and EtOAc (20 mL). The aqueous phase was extracted with EtOAc (2×10 mL). The combined organic phases were washed with saturated aqueous NaCl (50 mL). The organic phase was dried over sodium sulfate, filtered and concentrated in vacuo. The crude product was purified by silica gel column chromatography (eluent: acetone in DCM 0%-75%) to afford a pale yellow solid, which was recrystallized from methanol to afford a white solid (0.0371 g) as the desired product. MS (ESI pos. ion) m/z calcd for $C_{20}H_{22}N_4O_4S$: 414.1; found 414.9 [M+1]. $^1H$ NMR (300 MHz, CHLOROFORM-d) δ ppm 8.77 (d, J=4.97 Hz, 1 H) 8.29 (d, J=2.34 Hz, 1 H) 8.16 (dt, J=8.40, 1.86 Hz, 3 H) 7.87 (dd, J=8.70, 2.12 Hz, 1 H) 6.91 (d, J=4.97 Hz, 1 H) 6.80 (br. s., 1 H) 4.10 (s, 3 H) 3.97-4.06 (m, 4 H) 3.24-3.33 (m, 4 H) 3.07 (s, 3 H).

Example 120

N-(2-Methoxy-5-(4-(pyridin-4-yl)quinolin-6-yl)pyridin-3-yl)methanesulfonamide

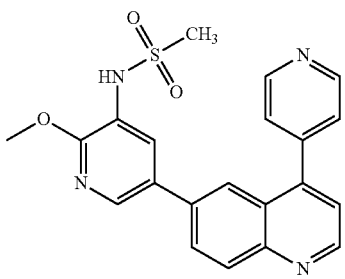 [SMILES: COc1ncc(-c2ccc3nccc(-c4ccncc4)c3c2)cc1NS(C)(=O)=O]

This compound was prepared similarly to the procedure described in Example 116. MS (ESI pos. ion) m/z calcd for $C_{21}H_{18}N_4O_3S$: 406.1; found 406.9 [M+1].

Example 121

N-(2-Chloro-5-(3-(pyridin-4-yl)quinoxalin-6-yl)pyridin-3-yl)-4-fluorobenzenesulfonamide

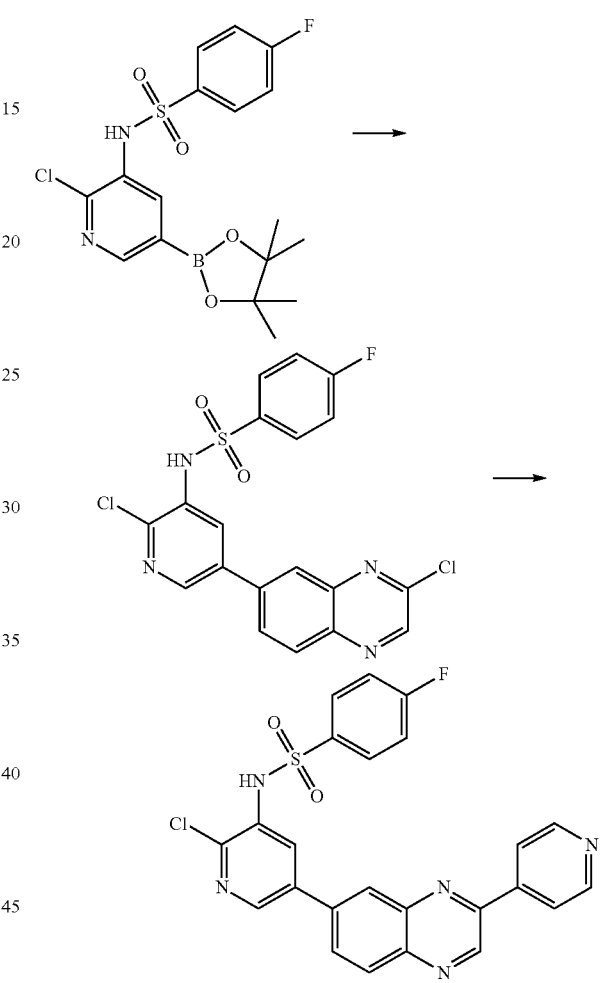

N-(2-Chloro-5-(3-chloroquinoxalin-6-yl)pyridin-3-yl)-4-fluorobenzenesulfonamide: To a 5 mL microwave vial, 7-bromo-2-chloroquinoxaline (0.100 g, 0.410 mmol), N-(2-chloro-5-(4,4,5,5-tetramethyl-1,3,2-dioxaborolan-2-yl)pyridin-3-yl)-4-fluorobenzenesulfonamide (0.189 g, 0.457 mmol), dichlorobis(di-tert-butylphenylphosphine)palladium (II) (0.0138 g, 0.0222 mmol) and potassium carbonate (0.513 ml, 1.03 mmol) were mixed into 1,4-dioxane (4 mL). The mixture was degassed by bubbling nitrogen through for 5 min. The reaction mixture was stirred at 90° C. for 1.5 h. The reaction mixture was partitioned between water (20 mL) and EtOAc (20 mL). The aqueous phase was extracted with EtOAc (2×20 mL). The combined organic phases were washed with saturated aqueous NaCl (40 mL). The organic phase was dried over sodium sulfate, filtered and concentrated in vacuo. Upon addition of DCM, precipitate came out and it was collected via filtration to afford a white solid (0.0746 g) as the desired product. The filtrate was purified by silica gel column chromatography (eluent: EtOAc in hexanes 0%-50%) to afford another 0.0512 g of the product. The combine yield was 0.1258 g. MS (ESI pos. ion) m/z calcd for $C_{19}H_{11}C_{12}FN_4O_2S$: 448.0; found 448.8 [M+1]. $^1$H NMR (300 MHz, DMSO-$d_6$) δ ppm 7.38-7.50 (m, 2 H) 7.79-7.89 (m, 2 H) 8.18-8.35 (m, 3 H) 8.40 (d, J=1.75 Hz, 1 H) 8.80 (d, J=2.34 Hz, 1 H) 9.05 (s, 1 H) 10.56 (br. s., 1 H).

N-(2-Chloro-5-(3-(pyridin-4-yl)quinoxalin-6-yl)pyridin-3-yl)-4-fluorobenzenesulfonamide: To a 5 mL microwave vial, N-(2-chloro-5-(3-chloroquinoxalin-6-yl)pyridin-3-yl)-4-fluorobenzenesulfonamide (0.106 g, 0.236 mmol), pyridine-4-ylboronic acid (0.0430 g, 0.350 mmol), dichlorobis(di-tert-butylphenylphosphine)palladium(II) (0.0111 g, 0.0178 mmol), potassium acetate (0.0581 g, 0.592 mmol) and water (0.300 ml, 16.7 mmol) were mixed into (4 mL). The mixture was degassed by bubbling nitrogen through for 5 min. The reaction mixture was stirred at 90° C. for 6 h, then at 110° C. for 1.5 h. The reaction mixture was partitioned between Tris-1M HCl pH 7 buffer (20 mL) and EtOAc (20 mL). The aqueous phase was extracted with EtOAc (20 mL). The combined organic phases were washed with saturated aqueous NaCl (40 mL). The organic phase was dried over sodium sulfate, filtered and concentrated in vacuo. The crude product was purified by silica gel column chromatography (eluent: acetone in DCM 0%-50%) to afford a light yellow solid (0.0662 g) as the desired product. MS (ESI pos. ion) m/z calcd for $C_{24}H_{15}ClFN_5O_2S$: 491.1; found 491.9 [M+1]. $^1$H NMR (300 MHz, CHLOROFORM-d) δ ppm 7.06-7.23 (m, 3 H) 7.82-7.92 (m, 2 H) 8.01 (dd, J=8.77, 2.05 Hz, 1 H) 8.14 (dd, J=4.53, 1.61 Hz, 2 H) 8.31 (d, J=8.77 Hz, 1 H) 8.40 (t, J=1.83 Hz, 1 H) 8.57 (d, J=2.34 Hz, 1 H) 8.89 (dd, J=4.68, 1.46 Hz, 2 H) 9.42 (s, 1 H).

Example 122

N'-(2-Chloro-5-(4-(4-morpholinyl)-6-quinolinyl)-3-pyridinyl)-N,N-dimethylsulfamide

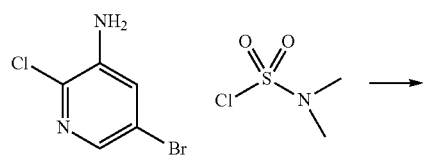

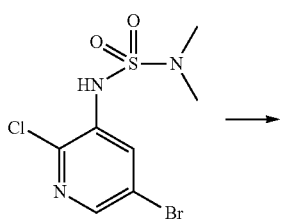

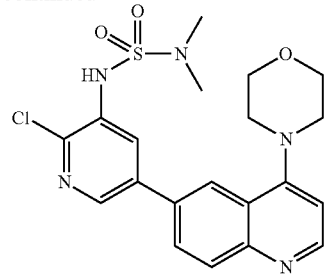

(1) N'-(5-bromo-2-chloropyridin-3-yl)-N,N-dimethylsulfonamide. To a microwave vial equipped with a magnetic stirbar was added 5-bromo-2-chloropyridin-3-amine (0.300 g, 1.4 mmol), Pyridine (3.0 mL, 36 mmol), DMAP (0.053 g, 0.43 mmol) and dimethylsulfamoyl chloride (0.77 mL, 7.2 mmol) (Aldrich, St. Louis, Mo.). The vial was capped, then placed into a CEM Microwave for 15 minutes at 140° C., while 100 Watts of energy was supplied via Powermax® (simultaneous heating while cooling technology). The progress of the reaction was monitored by LC/MS, which showed mostly desired product. The mixture was added to a round-bottom flask, then diluted with 1:1 dichloromethane/ethyl acetate (20 mL) and stirred 5 minutes. The DCM/EtOAc mixture was decanted into a round-bottom flask, while the insoluble dark pyridine residues remained in the flask. This process was repeated three times. The combined organic washes were concentrated in-vacuo. The crude product was purified by ISCO Silica-Gel Chromatography (Teledyne ISCO, Lincoln, Nebr.) (80 gram column), in a gradient of 0-10% EtOAc/DCM over 30 minutes to give N-(5-bromo-2-chloropyridin-3-yl)-N,N-dimethylsulfonamide (0.250 g, 55% yield) as a yellow solid. MS (ESI pos. ion) m/z: Calcd for $C_7H_9BrClN_3O_2S$: 314.5; found: 315.9 (M+1). $^1$H NMR (400 MHz, DMSO-d6) δ ppm 2.75 (s, 6H), 8.04 (d, J=2.01 Hz, 1H), 8.39 (d, J=2.01 Hz, 1H), 10.00 (s, 1H).

(2) N'-(2-chloro-5-(4-(4-morpholinyl)-6-quinolinyl)-3-pyridinyl)-N,N-dimethylsulfamide. To a microwave vial equipped with a stirbar and charged with 4-morpholinoquinolin-6-ylboronic acid (0.30 g, 1.1 mmol), cesium carbonate (0.93 g, 2.9 mmol), PdCl$_2$(dppf)-DCM (0.14 g, 0.17 mmol), N-(5-bromo-2-chloropyridin-3-yl)N,N-dimethylsulfonamide (0.300 g, 0.95 mmol) in THF (3 mL) was added water (1 mL). The vial was capped and placed into CEM Microwave for 12 minutes at 100° C., while 100 Watts of energy was supplied via Powermax® (Simultaneous heating while cooling technology). The progress of the reaction was monitored by LC/MS, which showed desired material in the mixture. The organic layer was collected by extracting the Water with DCM (3×25 mL) and brine solution. The combined organics was dried over sodium sulfate, filtered, and concentrated in-vacuo. The crude was purified by ISCO Silica-Gel Chromatography (Teledyne ISCO, Lincoln, Nebr.) (80 gram column) in a gradient of 0-8% isopropyl alcohol/DCM over 30 minutes. The fractions with desired material were combined and concentrated. The solid was diluted with ethyl ether (20 mL), then placed into a sonicator (to remove excess isopropyl alcohol) for 15 minutes. The solid was collected and placed into a fine-fritted funnel The solid was allowed to dry overnight under a nitrogen blanket to give the title compound (0.050 g, 12% yield) as a yellow solid. MS (ESI pos. ion) m/z: Calcd for $C_{20}H_{22}ClN_5O_3S$: 447.9; found: 449.1 (M+1). $^1$H NMR (400 MHz, DMSO-d6) δ ppm 2.79 (s, 6H), 3.25 (s, 4H), 3.90 (s, 4H), 7.08 (s, 1H), 8.08 (d, J=6.46 Hz, 2H), 8.24 (d, J=9.98 Hz, 2H), 8.68 (s, 2H), 10.00 (s, 1H).

Example 123

N'-(2-Chloro-5-(4-(4-morpholinyl)-6-quinolinyl)-3-pyridinyl)-N-(2-methoxyethyl)-N-methylsulfamide

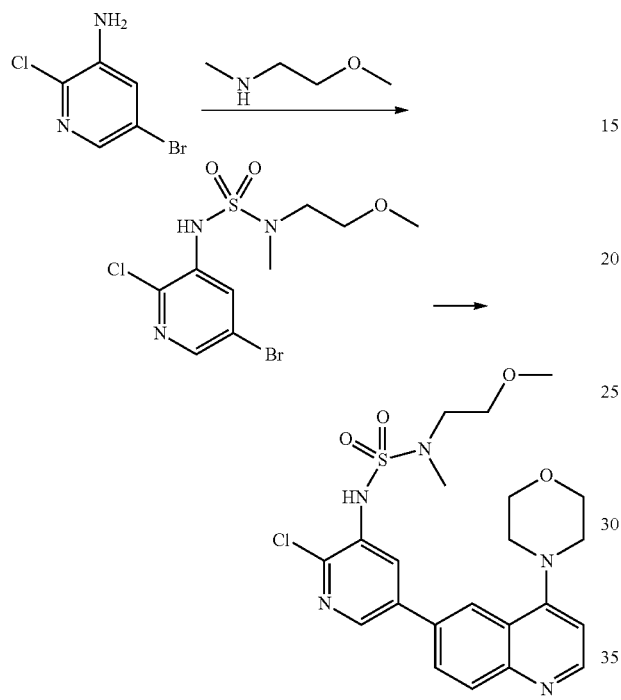

(1) N'-(5-bromo-2-chloro-3-pyridinyl)-N-(2-methoxyethyl)-N-methylsulfamide. To a 100-mL round-bottomed flask was added 5-bromo-2-chloropyridin-3-amine (0.400 g, 1.928 mmol) and N-(2-methoxyethyl)methylamine (0.207 mL, 1.928 mmol) in pyridine (4 mL). To the stirred reaction mixture, DMAP (0.059 g, 0.482 mmol) was added, then chilled the mixture to −30° C. in a dry ice/acetone bath. Then a cold solution (−40° C.) of sulfuryl chloride (0.172 mL, 2.121 mmol) was added slowly via cannulation into the mixture. After the addition, the ice bath was removed and the mixture was allowed to stir under inert atmosphere overnight. The progress of the reaction was monitored by LC/MS, which showed the desired material and some starting material. The reaction mixture was diluted with ethyl acetate (50 mL) and allowed to stir for 20 min. The organic layer was separated and the solid was dissolved into DCM (1.5 mL) and stirred. Ethyl acetate (20 mL) was added to the mixture and allowed to stir for 10 minutes. The combined organics were concentrated in-vacuo. The crude material was absorbed onto a plug of silica gel and purified by chromatography through a Redi-Sep pre-packed silica gel column (120 g), eluting with a gradient of 1% to 50% EtOAc in $CH_2CL_2$ over 37 minutes, to provide N'-(5-bromo-2-chloro-3-pyridinyl)-N-(2-methoxyethyl)-N-methylsulfamide (0.397 g, 1.107 mmol, 57.4% yield) as a tan oil. MS (ESI pos. ion) m/z: Calcd for $C_9H_{13}BrClN_3O_3S$: 356.9; found: 357.9 (M+1). $^1$H NMR (400 MHz, CHLOROFORM-d) δ ppm 2.97 (s, 3 H) 3.44-3.50 (m, 4 H) 3.60-3.65 (m, 4 H) 7.75 (s, 1 H) 8.13 (s, 2 H).

(2). N'-(2-chloro-5-(4-(4-morpholinyl)-6-quinolinyl)-3-pyridinyl)-N-(2-methoxyethyl)-N-methylsulfamide. To a microwave vial equipped with a stirbar and charged with 4-morpholinoquinolin-6-ylboronic acid (0.11 g, 0.42 mmol), cesium carbonate (0.34 g, 1.0 mmol), $PdCl_2$(dppf)-DCM (0.051 g, 0.063 mmol), N'-(5-bromo-2-chloro-3-pyridinyl)-N-(2-methoxyethyl)-N-methylsulfamide (0.125 g, 0.35 mmol) in THF (3 mL) was added water (0.5 mL). The vial was capped and placed into CEM Microwave for 12 minutes at 100° C., while 100 Watts of energy was supplied via Powermax® (Simultaneous heating while cooling technology). The progress of the reaction was monitored by LC/MS, which showed desired material in the mixture. The mixture was poured into a round-bottom flask equipped with a stirbar and diluted with DCM, Water and brine solution. The aqueous layer was extracted with DCM (3×25 mL). The combined organics were dried over sodium sulfate, filtered, and concentrated in-vacuo. The crude was purified by ISCO Silica-Gel Chromatography (Teledyne ISCO, Lincoln, Nebr.) (40 gram column) in a gradient of 1-10% IPA/DCM over 20 minutes. The fractions with desired material were combined and concentrated. The crude residue was triturated with ethyl ether and hexanes to give N'-(2-chloro-5-(4-(4-morpholinyl)-6-quinolinyl)-3-pyridinyl)-N-(2-methoxyethyl)-N-methylsulfamide (0.075 g, 44% yield) as a light-yellow crystalline solid. MS (ESI pos. ion) m/z: Calcd for $C_{22}H_{26}ClN_5O_4S$: 491.9; found: 493.0 (M+1). $^1$H NMR (400 MHz, DMSO-d) δ ppm 2.86 (s, 3 H) 3.11 (s, 3 H) 3.25 (d, J=4.11 Hz, 4 H) 3.33 (d, J=5.09 Hz, 2 H) 3.42 (t, J=5.38 Hz, 2 H) 3.86-3.94 (m, 4 H) 7.08 (d, J=4.89 Hz, 1 H) 8.04-8.12 (m, 2 H) 8.24 (dd, J=10.76, 1.76 Hz, 2 H) 8.67 (d, J=2.15 Hz, 1 H) 8.76 (d, J=5.09 Hz, 1 H) 9.90 (s, 1 H).

Example 124

N-(2-chloro-5-(4-morpholinoquinolin-6-yl)pyridin-3-yl)morpholine-4-sulfonamide

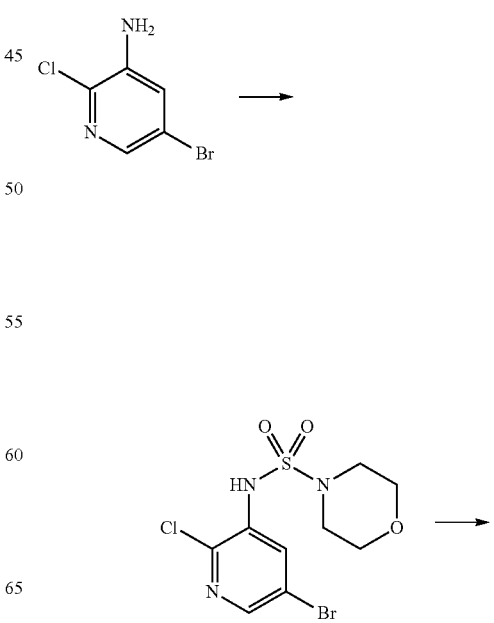

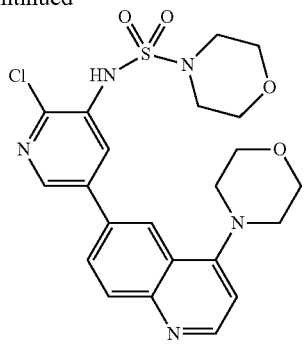

(1) N-(5-bromo-2-chloropyridin-3-yl)morpholine-4-sulfonamide. To a 50 mL round-bottom flask equipped with a stir bar and charged with 5-bromo-2-chloropyridin-3-amine (0.863 g, 4.2 mmol) in pyridine (5 mL), was added DMAP (0.13 g, 1.0 mmol) and morpholine (0.36 mL, 4.2 mmol). The mixture was chilled to −30° C. in a dry ice/acetone bath. Then sulfuryl chloride (0.36 mL, 4.6 mmol) was added dropwise into the mixture while stirring. After the addition, the ice bath was removed and the mixture was allowed to stir under inert atmosphere overnight. The progress of the reaction was monitored by LC/MS, which showed the desired product mass. The mixture was diluted with water (10 mL), DCM (10 mL) and saturated sodium bicarbonate (5 mL). The aqueous layer was extracted with DCM (3×20 mL). The combined organics were dried over sodium sulfate, filtered, and concentrated in-vacuo. The crude was dissolved in DCM and purified by ISCO Silica-Gel Chromatography (Teledyne ISCO, Lincoln, Nebr.) (80 gram column) in a gradient of 1-50% EtOAc/DCM over 30 minutes. The fractions with desired material were combined and concentrated to give N-(5-bromo-2-chloropyridin-3-yl)morpholine-4-sulfonamide (0.550 g, 37% yield) as a tan crystalline solid. MS (ESI pos. ion) m/z: Calcd for $C_9H_{11}BrClN_3O_3S$: 356.6; found: 357.8 (M+1). $^1H$ NMR (400 MHz, DMSO-d) δ ppm 3.07-3.12 (m, 4 H) 3.58-3.62 (m, 4 H) 8.07 (d, 8.07 (d, J=2.15 Hz, 1 H) 8.42 (d, J=2.35 Hz, 1 H) 10.19 (s, 1 H).

(2) N-(2-chloro-5-(4-morpholinoquinolin-6-yl)pyridin-3-yl)morpholine-4-sulfonamide. To a microwave vial equipped with a stirbar and charged with 4-morpholinoquinolin-6-yl-boronic acid (0.11 g, 0.42 mmol), cesium carbonate (0.34 g, 1.1 mmol), $PdCl_2$(dppf)-DCM (0.052 g, 0.063 mmol), N-(5-bromo-2-chloropyridin-3-yl)morpholine-4-sulfonamide (0.125 g, 0.35 mmol) in THF (3 mL) was added water (0.5 mL). The vial was capped and placed into CEM Microwave for 12 minutes at 100° C., while 100 Watts of energy was supplied via Powermax® (Simultaneous heating while cooling technology). The progress of the reaction was monitored by LC/MS, which showed desired material in the mixture. The mixture was diluted with DCM (5 mL) and then filtered. The crude material was purified by ISCO Silica-Gel Chromatography (Teledyne ISCO, Lincoln, Nebr.) (40 gram column) in a gradient of 1-10% IPA/DCM over 20 minutes. The fractions with desired material were combined and concentrated.

The crude residue was recrystalized from ethyl ether and hexanes to give N-(2-chloro-5-(4-morpholinoquinolin-6-yl)pyridin-3-yl)morpholine-4-sulfonamide (0.070 g, 41% yield) as an off-white crystalline solid. MS (ESI pos. ion) m/z: Calcd for $C_{22}H_{24}ClN_5O_4S$: 489.9; found: 491.0 (M+1). $^1H$ NMR (300 MHz, DMSO-d) δ ppm 1.04 (d, J=6.14 Hz, 4 H) 3.14 (s, 4 H) 3.62 (s, 4 H) 3.90 (s, 4 H) 7.08 (d, J=4.97 Hz, 1 H) 8.03-8.13 (m, 2 H) 8.27 (d, J=1.90 Hz, 2 H) 8.68 (d, J=1.75 Hz, 1 H) 8.75 (d, J=4.82 Hz, 1 H).

Example 125

N'-(2-chloro-5-(4-chloro-6-quinolinyl)-3-pyridinyl)-N,N-dimethylsulfamide

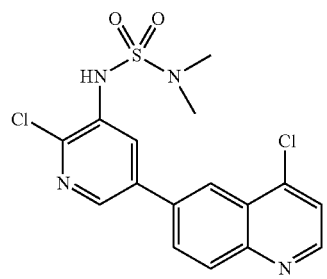 [SMILES: CN(C)S(=O)(=O)Nc1cc(-c2ccc3nccc(Cl)c3c2)cnc1Cl]

N'-(2-chloro-5-(4-chloro-6-quinolinyl)-3-pyridinyl)-N,N-dimethylsulfamide. To a microwave vial equipped with a stirbar was charged with 4-chloro-6-(4,4,5,5-tetramethyl-1,3,2-dioxaborolan-2-yl)quinoline (0.044 g, 0.15 mmol), cesium carbonate (0.12 g, 0.38 mmol), $PdCl_2$(dppf)-DCM (0.019 g, 0.023 mmol), N'-(5-bromo-2-chloropyridin-3-yl)-N,N-dimethylsulfonamide (0.040 g, 0.13 mmol) in THF (3 mL) was added water (0.5 mL). The vial was capped and placed into CEM Microwave for 10 minutes at 100° C., while 100 Watts of energy was supplied via Powermax® (Simultaneous heating while cooling technology). The progress of the reaction was monitored by LC/MS, which showed desired material in the mixture. The crude organic layer was extracted from the aqueous layer with DCM (3×20 mL). The combined organics were dried over sodium sulfate, filtered, and concentrated in-vacuo. The crude was purified by Silica-Gel Chromatography (SiliCycle-High Performance 40 gram column) (Teledyne ISCO, Lincoln, Nebr.), in a gradient of 5-50% EtOAc/DCM over 35 minutes. Combined fractions with desired material, then concentrated in-vacuo. The material was rinsed with ethyl-ether and collected by filtration to give N'-(2-chloro-5-(4-chloro-6-quinolinyl)-3-pyridinyl)-N,N-dimethylsulfamide (0.014 g, 28% yield) as a tan crystalline solid. MS (ESI pos. ion) m/z: Calcd for $C_{16}H_{14}Cl_2N_4O_2S$: 397.2; found: 398.9 (M+1). $^1H$ NMR (400 MHz, DMSO-d6)

δ ppm 2.80 (s, 6 H) 7.86 (d, J=4.30 Hz, 1 H) 8.23 (s, 1 H) 8.26 (d, J=12.91 Hz, 2 H) 8.43 (s, 1 H) 8.75 (s, 1 H) 8.90 (d, J=4.30 Hz, 1 H) 9.94 (s, 1 H).

Example 126

N'-(2-chloro-5-(4-((2-methoxyethyl)(methyl)amino)-6-quinolinyl)-3-pyridinyl)-N-(2-methoxyethyl)-N-methylsulfamide

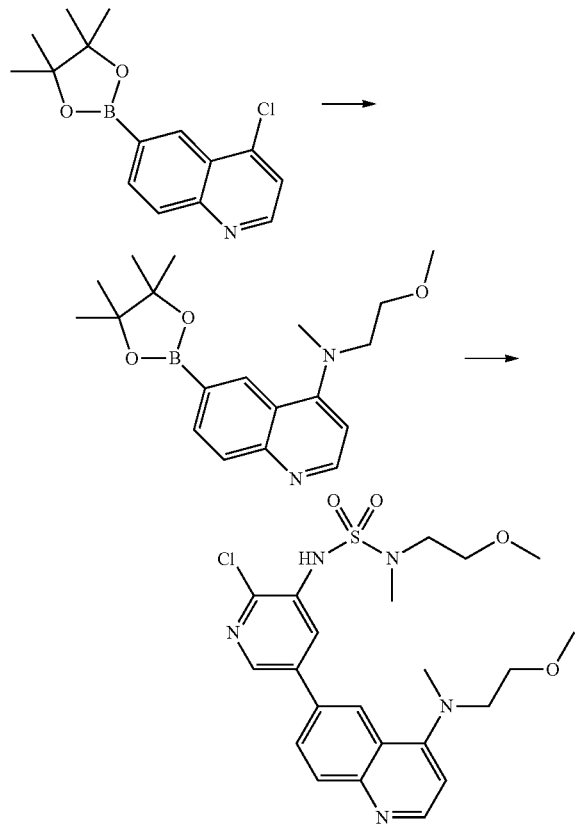

(1) N-(2-methoxyethyl)-N-methyl-6-(4,4,5,5-tetramethyl-1,3,2-dioxaborolan-2-yl)quinolin-4-amine. To a microwave vial equipped with a stirbar, was added 4-chloro-6-(4,4,5,5-tetramethyl-1,3,2-dioxaborolan-2-yl)quinoline (0.300 g, 1.0 mmol) and ethanol (1.5 mL). Then N-(2-methoxyethyl)methylamine (TCI America, Wellesley, Mass.) (1.1 mL, 10 mmol) and HCl (0.0031 mL, 0.10 mmol) was added into the mixture. The mixture was placed into a CEM Microwave for 10 minutes at 100° C., while 60 Watts of energy was supplied via Powermax® (Simultaneous heating while cooling technology). The progress of the reaction was monitored by LC/MS, which showed an 80/20 mixture of desired boronic ester and boronic acid (m/z=261) material. The mixture was transferred to a round-bottom and the mixture was concentrated in-vacuo. The oil was diluted with DCM and water. The organic layer was collected by extracting the water with DCM (3×25 mL). The combined organics were dried over sodium sulfate, filtered, and concentrated in-vacuo to give N-(2-methoxyethyl)-N-methyl-6-(4,4,5,5-tetramethyl-1,3,2-dioxaborolan-2-yl)quinolin-4-amine (0.330 g, 93% yield) with 20% boronic acid as a tan oil. MS (ESI pos. ion) m/z: Calcd for $C_{19}H_{22}BN_2O_3$: 342.2; found: 343.1 (M+1). $^1$H NMR (400 MHz, CHLOROFORM-d) δ ppm 1.39 (d, J=10.37 Hz, 12 H) 3.09 (s, 4 H) 3.30-3.43 (m, 4 H) 3.58 (t, J=5.77 Hz, 2 H) 3.75 (t, J=5.87 Hz, 2 H) 6.82 (d, J=5.09 Hz, 1 H) 7.27 (s, 1 H) 7.50 (d, 2 H) 8.00 (s, 1 H) 8.04-8.16 (m, 2 H) 8.64-8.68 (m, 2 H) 8.72 (s, 1 H) 8.80 (d, J=4.69 1 H). (Mixtures of boronic ester and boronic acid).

(2) N'-(2-chloro-5-(4-((2-methoxyethyl)(methyl)amino)-6-quinolinyl)-3-pyridinyl)-N-(2-methoxyethyl)-N-methylsulfamide. To a microwave vial equipped with a stirbar and charged with N-(2-methoxyethyl)-N-methyl-6-(4,4,5,5-tetramethyl-1,3,2-dioxaborolan-2-yl)quinolin-4-amine (0.14 g, 0.42 mmol), cesium carbonate (0.34 g, 1.0 mmol), PdCl$_2$(dppf)-DCM (0.051 g, 0.063 mmol), N'-(5-bromo-2-chloro-3-pyridinyl)-N-(2-methoxyethyl)-N-methylsulfamide (0.125 g, 0.35 mmol) in THF (3 mL) was added water (0.5 mL). The vial was capped and placed into CEM Microwave for 10 minutes at 100° C., while 100Watts of energy was supplied via Powermax® (Simultaneous heating while cooling technology). The progress of the reaction was monitored by LC/MS, which showed desired material in the mixture. The mixture was diluted with DCM, water and brine solution. The organic layer was collected by extracting the aqueous with DCM (3×25 mL). The combined organics were dried over sodium sulfate, filtered, and concentrated in-vacuo. The crude was purified by ISCO Silica-Gel Chromatography (40 gram column) (Teledyne ISCO, Lincoln, Nebr.) in a gradient of 1-10% IPA/DCM over 20 minutes. The fractions with desired material were combined and concentrated. The material was rinsed with ethyl ether, concentrated in-vacuo, and then placed under high-vacuum to give N'-(2-chloro-5-(4-((2-methoxyethyl)(methyl)amino)-6-quinolinyl)-3-pyridinyl)-N-(2-methoxyethyl)-N-methylsulfamide (0.040 g, 23% yield) as a light-yellow amorphous solid. MS (ESI pos. ion) m/z: Calcd for $C_{22}H_{28}ClN_5O_4S$: 494.0; found: 495.0 (M+1). $^1$H NMR (400 MHz, DMSO-d) δ ppm 2.83 (s, 3 H) 3.01 (s, 3 H) 3.14 (s, 3 H) 3.41 (t, J=5.48 Hz, 6 H) 3.50 (t, J=4.99 Hz, 3 H) 3.73 (t, J=5.09 Hz, 2 H) 7.03 (d, 1 H) 7.98-8.06 (m, 2 H) 8.23 (d, 1 H) 8.61 (m, 2 H) 8.64 (s, 1 H).

Example 127

N-(2-Chloro-5-(2,3-dihydrobenzo[b][1,4]dioxin-6-yl)pyridin-3-yl)-4-methoxybenzenesulfonamide

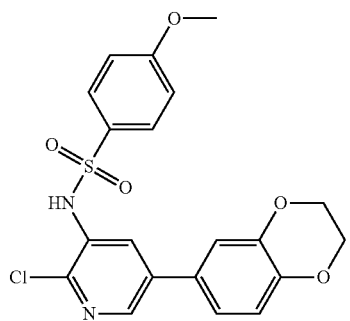 [SMILES: COc1ccc(S(=O)(=O)Nc2cc(-c3ccc4c(c3)OCCO4)cnc2Cl)cc1]

A 15 mL sealed pressure tube was charged with N-(5-bromo-2-chloropyridin-3-yl)-4-methoxybenzenesulfonamide (190 mg, 0.503 mmol), 2,3-dihydrobenzo[b][1,4]dioxin-6-ylboronic acid (100 mg, 0.553 mmol) in EtOH (1.5 ml). Pd(PPh$_3$)$_4$ (29 mg, 0.025 mmol) was added, followed by sodium carbonate (2M, 0.629 mL). The tube was purged with argon, backfilled with argon, sealed and stirred at 85° C. for 1.5 hours. The crude was partitioned between water and methylene chloride and extracted with methylene chloride (3×, 10 ml). The combined organics were dried over Na$_2$SO$_4$, filtered and concentrated in vacuo. The solid was purified by ISCO with a 20-50% gradient of EtOAc in hexanes to afford desired product. MS (ESI pos. ion) m/z calcd for C$_{20}$H$_{12}$ClN$_2$O$_5$S: 432.8; found 433.3 $^1$H NMR (400 MHz, DMSO-d$_6$) δ ppm 3.83 (s, 3 H), 4.30 (s, 4 H), 6.99 (d, J=8.3 Hz, 1 H), 7.06-7.15 (m, 4 H), 7.61-7.72 (m, 2 H), 7.78 (d, J=2.3 Hz, 1 H), 8.47 (s, 1 H), 10.21 (s, 1 H).

Example 128

N-(2-Chloro-5-(2,3-dihydrobenzo[b][1,4]dioxin-6-yl)pyridin-3-yl)-4-fluorobenzenesulfonamide

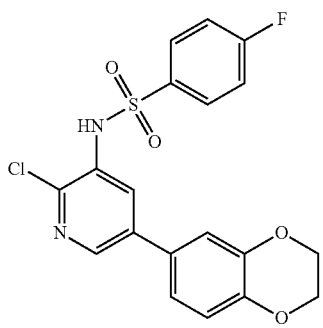 [SMILES: O=S(=O)(Nc1cc(-c2ccc3c(c2)OCCO3)cnc1Cl)c1ccc(F)cc1]

To a 50 mL round-bottomed flask was added N-(2-chloro-5-(4,4,5,5-tetramethyl-1,3,2-dioxaborolan-2-yl)pyridin-3-yl)-4-fluorobenzenesulfonamide (62 mg, 150 μmol), 1-bromo-3,4-(ethylenedioxy)benzene (32 mg, 150 μmol, Aldrich, St. Louis, Mo.), dichloro 1,1'-bis(diphenylphosphino)ferrocene palladium (II) (12 mg, 15 μmol), Cesium carbonate (98 mg, 300 μmol), dioxane (1 mL), water (0.2 mL). The reaction mixture was stirred at 100° C. for 1 h. The mixture was cooled down to room temperature. The reaction mixture was diluted with saturated NH$_4$Cl (5 mL) and extracted with EtOAc (2×30 mL). The organic extract was washed with saturated NaCl (10 mL), dried over Na$_2$SO$_4$, filtered and concentrated in vacuo and the residue was purified by silica gel chromatography, eluting with 30% EtOAc/hexanes to give N-(2-chloro-5-(2,3-dihydrobenzo[b][1,4]dioxin-6-yl)pyridin-3-yl)-4-fluorobenzenesulfonamide (51 mg, 81% yield). MS (EI, pos.) calcd for C$_{19}$H$_{14}$ClFN$_2$O$_4$S: 420.0; found 420.9. $^1$H NMR (300 MHz, CHLOROFORM-d) δ ppm 4.32 (s, 4 H) 6.88-7.09 (m, 4 H) 7.09-7.21 (m, 2 H) 7.74-7.87 (m, 2 H) 8.12 (d, J=2.19 Hz, 1 H) 8.30 (d, J=2.34 Hz, 1 H).

Example 129

N-(2-Chloro-5-(3-oxo-3,4-dihydro-2H-benzo[b][1,4]oxazin-6-yl)pyridin-3-yl)-4-fluorobenzenesulfonamide

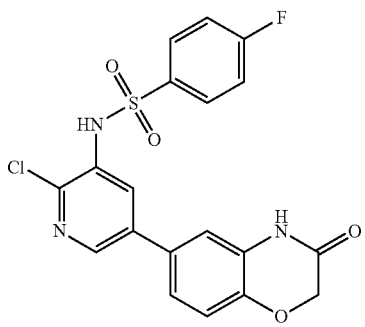 [SMILES: O=C1COc2ccc(-c3cnc(Cl)c(NS(=O)(=O)c4ccc(F)cc4)c3)cc2N1]

To a 15-mL pressure tube was added N-(2-chloro-5-(4,4,5,5-tetramethyl-1,3,2-dioxaborolan-2-yl)pyridin-3-yl)-4-fluorobenzenesulfonamide (0.15 g, 0.37 mmol), 6-bromo-2H-benzo[b][1,4]oxazin-3(4H)-one (Aldrich, St Louis, Mo.) (0.10 g, 0.44 mmol), sodium carbonate (0.12 g, 1.1 mmol), tetrakis(triphenylphosphine)palladium 0.021 g, 0.018 mmol) (Strem Chemicals, Newburyport, Mass.), EtOH (1.5 mL), and water (0.5 mL). The tube was sealed, purged with argon for several minutes, and the reaction mixture was heated at 90° C. for 12 h. The reaction mixture was diluted with water and extracted with EtOAc (2×). The combined organic phases were washed with water, brine, dried over Na$_2$SO$_4$, filtered, and concentrated in vacuo. The crude material was absorbed onto a plug of silica gel and purified by chromatography through a Redi-Sep pre-packed silica gel column (12 g) eluting with a gradient 2 to 5% MeOH in DCM, to provide crude N-(2-chloro-5-(3-oxo-3,4-dihydro-2H-benzo[b][1,4]oxazin-6-yl)pyridin-3-yl)-4-fluorobenzenesulfonamide. Purification by reverse-phase preparative HPLC using a Phenomenex Gemini column (Phenomenex, Torrance, Calif.), (10 micron, C18, 100 Å, 150×30 mm) 0.1% TFA in CH$_3$CN/H$_2$O, gradient 30% to 100% over 18 min to provide the product as TFA salt. Basification with saturated NaHCO$_3$, extraction with EtOAc, provided the title compound as an off-white solid. MS (ESI pos. ion) m/z calcd for C$_{19}$H$_{13}$ClFN$_3$O$_4$S: 433.0; found 433.7. 1H NMR (400 MHz, DMSO-d$_6$) δ ppm 4.64 (s, 2 H) 7.08 (d, J=8.41 Hz, 1 H) 7.14 (d, J=1.76 Hz, 1 H) 7.23 (d, J=8.61 Hz, 1 H) 7.43 (t, J=8.80 Hz, 2 H) 7.72-7.90 (m, 3 H) 8.42 (br. s., 1 H) 10.48 (br. s., 1 H) 10.84 (s, 1 H).

Example 130

N-(2-chloro-5-(3-oxo-4-phenyl-3,4-dihydroquinoxalin-6-yl)pyridin-3-yl)dimethylaminosulfonamide

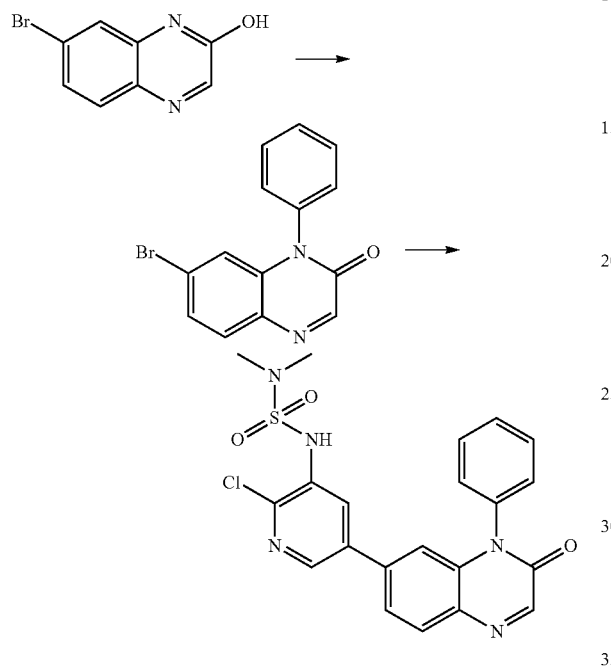

(1) 7-bromo-1-phenylquinoxalin-2(1 H)-one. To a 25 mL round-bottomed flask was added 7-bromoquinoxalin-2-ol (0.090 g, 0.400 mmol), phenylboronic acid (0.073 g, 0.600 mmol), copper (II) acetate (7.26 mg, 0.040 mmol), triethylamine (0.111 mL, 0.800 mmol), and DCM (3 mL). The resulting mixture was stirred at rt, opened to the air, for 20 h. The reaction mixture was partitioned between water and DCM. The aqueous layer was extracted with DCM (2×10 mL). The combined organic layers were dried over $MgSO_4$ and concentrated. The crude product was purified by column chromatography (40 g, 10% to 20% EtOAc in hexanes) to afford the desired product as a red solid (65.0 mg). MS (ESI pos. ion) m/z: calcd for $C_{14}H_9BrN_2O$: 299.9; found: 301.8/302.8 [M+1/M+3]. $^1$H NMR (300 MHz, CHLOROFORM-d) δ ppm 3.50 (d, J=5.26 Hz, 1 H) 6.86 (s, 1 H) 7.31 (br. s., 1 H) 7.45 (d, J=7.31 Hz, 1 H) 7.58-7.71 (m, 3 H) 7.78 (d, J=8.48 Hz, 1 H) 8.39 (s, 1 H).

(2) N-(2-chloro-5-(3-oxo-4-phenyl-3,4-dihydroquinoxalin-6-yl)pyridin-2-yl)dimethylaminosulfonamide. To a 5 mL microwave tube was added N-(2-chloro-5-(4,4,5,5-tetramethyl-1,3,2-dioxaborolan-2-yl)pyridin-3-yl)dimethylaminosulfonamide (0.079 g, 0.219 mmol), 7-bromo-1-phenylquinoxalin-2(1H)-one (0.060 g, 0.199 mmol), 1,1'-bis(diphenylphosphino)ferrocene]dichloride palladium(II) (0.015 g, 0.020 mmol), sodium carbonate (0.249 mL, 0.498 mmol), and dioxane (3 mL). The resulting mixture was sealed and subject to microwave heating at 110° C. for 20 min. The reaction mixture was partitioned between pH 7 buffer (1M Tris-HCl) and DCM. The aqueous layer was extracted with DCM (2×10 mL). The combined organic layers were dried over $MgSO_4$ and concentrated. The crude product was purified by column chromatography (12 g, 3% MeOH and 32% EtOAc in DCM) to afford the desired product as a light yellow solid (65.0 mg). MS (ESI pos. ion) m/z: calcd for $C_{21}H_{18}ClN_5O_3S$: 455.1; found: 455.8 [M+1]. $^1$H NMR (300 MHz, CHLOROFORM-d) δ ppm 2.80 (s, 6 H) 6.76-6.86 (m, 2 H) 7.35 (d, J=7.16 Hz, 2 H) 7.53 (d, J=8.33 Hz, 1 H) 7.58-7.72 (m, 3 H) 7.94 (s, 1 H) 8.04 (d, J=8.18 Hz, 1 H) 8.20 (s, 1 H) 8.45 (s, 1 H).

Example 131

N-(2-chloro-5-(3-oxo-4-phenyl-3,4-dihydroquinoxalin-6-yl)pyridin-3-yl) 2-methoxy-N-methylethanaminosulfonamide

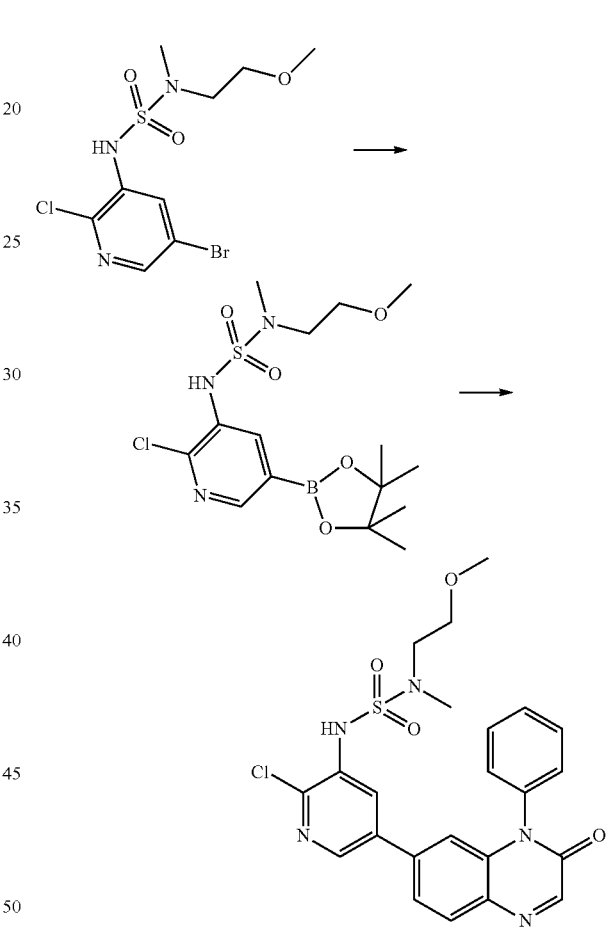

(1) N-(2-chloro-5-(4,4,5,5-tetramethyl-1,3,2-dioxaborolan-2-yl)pyridin-3-yl) 2-methoxy-N-methylethanaminosulfonamide. To a 25 mL microwave tube was added N-(5-bromo-2-chloropyridin-3-yl)2-methoxy-N-methylethanaminosulfonamide (0.500 g, 1.394 mmol), bis(pinacolato)diboron (0.425 g, 1.673 mmol), 1,1'-bis(diphenylphosphino)ferrocene]dichloride palladium(II) (0.102 g, 0.139 mmol), potassium acetate (0.274 g, 2.79 mmol), and dioxane (10 mL). The resulting mixture was sealed and underwent microwave heating at 110° C. for 20 min. The reaction mixture was partitioned between pH 7 buffer (1M Tris-HCl) and DCM. The aqueous layer was extracted with DCM (2×15 mL). The combined organic layers were dried over $MgSO_4$ and concentrated. Hexanes (20 mL) was added into the dried crude product and stirred for 1 h. The supernatant was removed by decanting and this process was repeated one more time to remove excess bis(pinacolato)diboron. The product was dried under vacuum to give a dark brownish liquid (510 mg). This product was used as is for the next step.

(2) N-(2-chloro-5-(3-oxo-4-phenyl-3,4-dihydroquinoxalin-6-yl)pyridin-3-yl) 2-methoxy-N-methylethanaminosulfonamide. To a 5 mL microwave tube was added 7-bromo-1-phenylquinoxalin-2(1H)-one (0.080 g, 0.266 mmol), N-(2-chloro-5-(4,4,5,5-tetramethyl-1,3,2-dioxaborolan-2-yl) pyridin-3-yl) 2-methoxy-N-methylethanaminosulfonamide (0.129 g, 0.319 mmol), 1,1'-bis(diphenylphosphino)ferrocene]dichloride palladium(II) (0.019 g, 0.027 mmol), sodium carbonate (0.332 mL, 0.664 mmol), and dioxane (3 mL). The resulting mixture was sealed and underwent microwave heating at 110° C. for 20 min. The reaction mixture was partitioned between pH 7 buffer (1M Tris-HCl) and DCM. The aqueous layer was extracted with DCM (2×10 mL). The combined organic layers were dried over MgSO$_4$ and concentrated. The crude product was purified by column chromatography (12 g, 3% MeOH in DCM) to afford the desired product as a brown solid (47.0 mg). MS (ESI pos. ion) m/z: calcd for $C_{23}H_{22}ClN_5O_4S$: 499.1; found: 499.8 [M+1]. $^1$H NMR (300 MHz, CHLOROFORM-d) δ ppm 2.94 (s, 3 H) 3.41 (s, 3 H) 3.58 (br. s., 4 H) 6.85 (s, 1 H) 7.34 (d, J=7.31 Hz, 2 H) 7.54 (d, J=8.48 Hz, 1 H) 7.58-7.75 (m, 4 H) 7.97-8.07 (m, 2 H) 8.11 (s, 1 H) 8.44 (s, 1 H).

Example 132

N-(2-chloro-5-(4-(6-methoxypyridin-3-yl)-3-oxo-3,4-dihydroquinoxalin-6-yl)pyridin-3-yl)dimethylaminosulfonamide

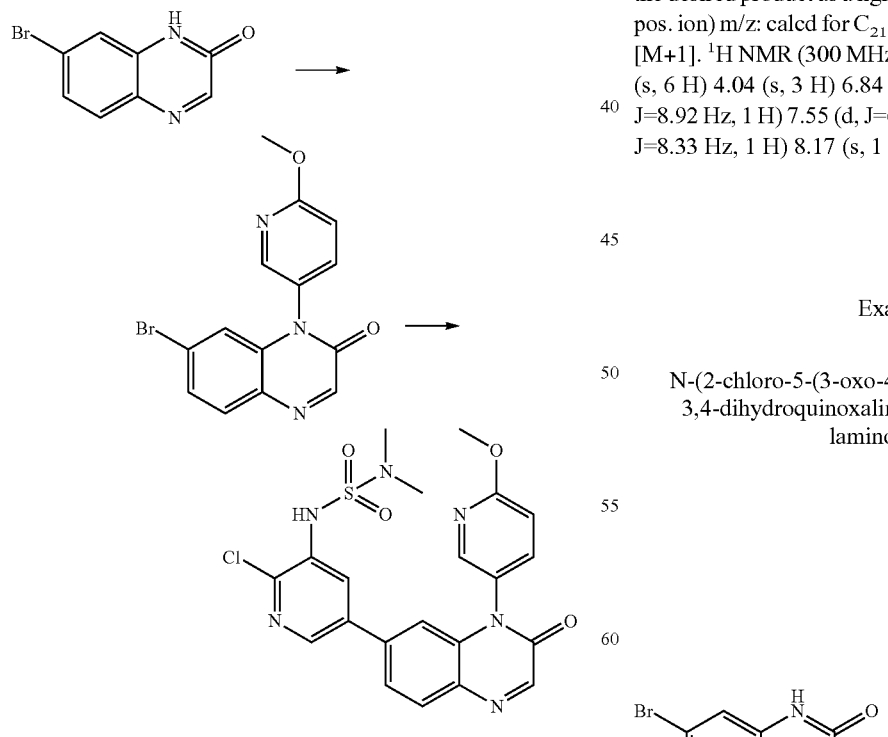

(1) 7-bromo-1-(6-methoxypyridin-3-yl)quinoxalin-2 (1H)-one. To a 25 mL round bottom flask was added 7-bromoquinoxalin-2-ol (0.100 g, 0.444 mmol), 6-methoxypyridin-3-ylboronic acid (0.102 g, 0.667 mmol), copper (II) acetate (8.07 mg, 0.044 mmol), triethylamine (0.124 mL, 0.889 mmol), and DCM (3 mL). The resulting mixture was stirred at rt opened to the air for 20 h. The reaction mixture was partitioned between water and DCM. The aqueous layer was extracted with DCM (2×10 mL). The combined organic layers were dried over MgSO$_4$ and concentrated. The crude product was purified by column chromatography (40 g, 10% to 20% acetone in hexanes) to afford the desired product as a red solid (30.0 mg). MS (ESI pos. ion) m/z: calcd for $C_{14}H_{10}BrN_3O$: 331.0; found: 331.8/333.8 [M+1/M+3]. $^1$H NMR (300 MHz, CHLOROFORM-d) δ ppm 4.05 (s, 3 H) 6.94 (s, 1 H) 7.01 (d, J=8.92 Hz, 1 H) 7.43-7.56 (m, 2 H) 7.79 (d, J=8.18 Hz, 1 H) 8.12 (br. s., 1 H) 8.38 (s, 1 H).

(2) N-(2-chloro-5-(4-(6-methoxypyridin-3-yl)-3-oxo-3,4-dihydroquinoxalin-6-yl)pyridin-3-yl)dimethylaminosulfonamide. To a 5 mL microwave tube was added N-(2-chloro-5-(4,4,5,5-tetramethyl-1,3,2-dioxaborolan-2-yl)pyridin-3-yl)dimethylaminosulfonamide (0.033 g, 0.090 mmol), 7-bromo-1-(6-methoxypyridin-3-yl)quinoxalin-2(1H)-one (0.030 g, 0.090 mmol), 1,1'-bis(diphenylphosphino)ferrocene]dichloride palladium(II) (6.61 mg, 9.03 μmol), sodium carbonate (0.249 mL, 0.498 mmol), and dioxane (3 mL). The resulting mixture was sealed and heated under microwave at 110° C. for 20 min. The reaction mixture was partitioned between pH 7 buffer (1M Tris-HCl) and DCM. The aqueous layer was extracted with DCM (2×10 mL). The combined organic layers were dried over MgSO$_4$ and concentrated. The crude product was purified by column chromatography (12 g, 4% MeOH and 32% EtOAc in DCM) to afford the desired product as a light yellow solid (15.0 mg). MS (ESI pos. ion) m/z: calcd for $C_{21}H_{19}ClN_6O_4S$: 486.1; found: 486.8 [M+1]. $^1$H NMR (300 MHz, CHLOROFORM-d) δ ppm 2.83 (s, 6 H) 4.04 (s, 3 H) 6.84 (br. s., 1 H) 6.89 (s, 1 H) 7.01 (d, J=8.92 Hz, 1 H) 7.55 (d, J=6.72 Hz, 1 H) 7.97 (s, 1 H) 8.05 (d, J=8.33 Hz, 1 H) 8.17 (s, 1 H) 8.23 (s, 1 H) 8.44 (s, 1).

Example 133

N-(2-chloro-5-(3-oxo-4-(3-(trifluoromethyl)phenyl)-3,4-dihydroquinoxalin-6-yl)pyridin-3-yl)dimethylaminosulfonamide

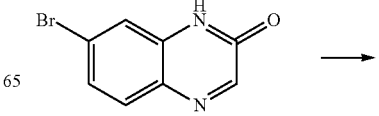

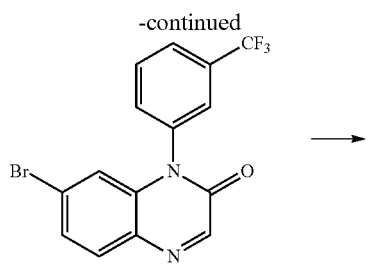

(1) 7-bromo-1-(3-(trifluoromethyl)phenyl)quinoxalin-2 (1H)-one. To a 25 mL round bottom flask was added 7-bromoquinoxalin-2-ol (0.200 g, 0.889 mmol), 3-(trifluoromethyl)phenylboronic acid (0.253 g, 1.333 mmol), copper (II) acetate (0.016 g, 0.089 mmol), triethylamine (0.248 mL, 1.777 mmol), and DCM (5 mL). The resulting mixture was stirred at rt opened to the air for 20 h. The reaction mixture was partitioned between water and DCM. The aqueous layer was extracted with DCM (2×10 mL). The combined organic layers were dried over MgSO$_4$ and concentrated. The crude product was purified by column chromatography (40 g, 10% to 20% EtOAc in hexanes) to afford the desired product as a red solid (30.0 mg). MS (ESI pos. ion) m/z: calcd for C$_{15}$H$_8$BrF$_3$N$_2$O: 367.9; found: 368.8/370.8 [M+1/M+3]. $^1$H NMR (300 MHz, CHLOROFORM-d) δ ppm 6.80 (s, 1 H) 7.51 (t, J=8.99 Hz, 2 H) 7.60 (s, 1 H) 7.75-7.86 (m, 2 H) 7.86-7.93 (m, 1 H) 8.39 (s, 1 H).

(2) N-(2-chloro-5-(3-oxo-4-(3-(trifluoromethyl)phenyl)-3,4-dihydroquinoxalin-6-yl)pyridin-3-yl)dimethylaminosulfonamide. To a 5 mL microwave tube was added 7-bromo-1-(3-(trifluoromethyl)phenyl)quinoxalin-2(1H)-one (0.080 g, 0.217 mmol), N-(2-chloro-5-(4,4,5,5-tetramethyl-1,3,2-dioxaborolan-2-yl)pyridin-3-yl)dimethylaminosulfonamide (0.086 g, 0.238 mmol), 1,1'-bis(diphenylphosphino)ferrocene]dichloride palladium(II) (0.016 g, 0.022 mmol), sodium carbonate (0.271 mL, 0.542 mmol), and dioxane (3 mL). The resulting mixture was sealed and heater under microwave at 110° C. for 20 min. The reaction mixture was partitioned between pH 7 buffer (1M Tris-HCl) and DCM. The aqueous layer was extracted with DCM (2×10 mL). The combined organic layers were dried over MgSO$_4$ and concentrated. The crude product was purified by column chromatography (40 g, 3% 2 M NH$_3$ in MeOH and 32% EtOAc in DCM) to afford the desired product as a light yellow solid (75.0 mg). MS (ESI pos. ion) m/z: calcd for C$_{22}$H$_{17}$ClF$_3$N$_5$O$_3$S: 523.1; found: 523.8 [M+1]. $^1$H NMR (300 MHz, CHLOROFORM-d) δ ppm 2.79 (s, 6 H) 6.75 (s, 1 H) 6.81 (br. s., 1 H) 7.57 (t, J=7.97 Hz, 2 H) 7.65 (s, 1 H) 7.78-7.92 (m, 2 H) 7.95 (s, 1 H) 8.07 (d, J=8.48 Hz, 1 H) 8.19 (s, 1 H) 8.45 (s, 1 H).

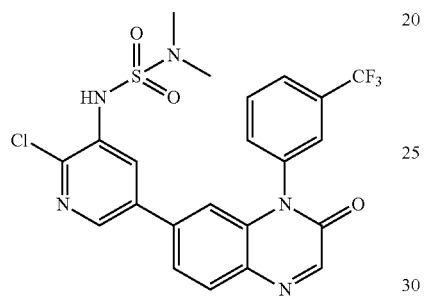

Example 134

N-(2-Chloro-5-(3-oxo-4-(3-(trifluoromethyl)phenyl)-3,4-dihydroquinoxalin-6-yl)pyridin-3-yl) 2-methoxy-N-methylethanamino sulfonamide

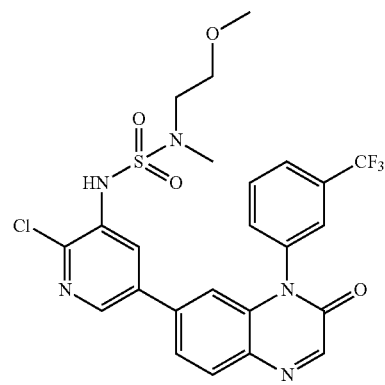 [SMILES: COCCN(C)S(=O)(=O)Nc1cc(-c2ccc3ncc(=O)n(-c4cccc(C(F)(F)F)c4)c3c2)cnc1Cl]

To a 5 mL microwave tube was added 7-bromo-1-(3-(trifluoromethyl)phenyl)quinoxalin-2(1H)-one (0.090 g, 0.244 mmol), N-(2-chloro-5-(4,4,5,5-tetramethyl-1,3,2-dioxaborolan-2-yl)pyridin-3-yl) 2-methoxy-N-methylethanaminosulfonamide (0.119 g, 0.293 mmol), 1,1'-bis(diphenylphosphino)ferrocene]dichloride palladium(II) (0.018 g, 0.024 mmol), sodium carbonate (0.305 mL, 0.610 mmol), and dioxane (3 mL). The resulting mixture was sealed and heated under microwave at 110° C. for 20 min. The reaction was partitioned between pH 7 buffer (1M Tris-HCl) and DCM. The aqueous layer was extracted with DCM (2×10 mL). The combined organic layers were dried over MgSO$_4$ and concentrated. The crude product was purified by column chromatography (12 g, 4% MeOH and 32% EtOAc in DCM) to afford the desired product as a brown solid (40.0 mg). MS (ESI pos. ion) m/z: calcd for C$_{24}$H$_{21}$ClF$_3$N$_5$O$_4$S: 567.1; found: 567.8 [M+1]. $^1$H NMR (300 MHz, CHLOROFORM-d) δ ppm 2.94 (s, 3 H) 3.42 (s, 3 H) 3.60 (s, 4 H) 6.77 (s, 1 H)

7.57 (d, J=8.18 Hz, 2 H) 7.65 (s, 1 H) 7.71-7.83 (m, 2 H) 7.87 (t, J=7.82 Hz, 1 H) 7.98-8.08 (m, 2 H) 8.10 (s, 1 H) 8.44 (s, 1 H).

Example 135

N-(2-Chloro-5-(7,8-dihydro-1,6-naphthyridin-6(5H)-yl)pyridin-3-yl)-4-fluorobenzenesulfonamide

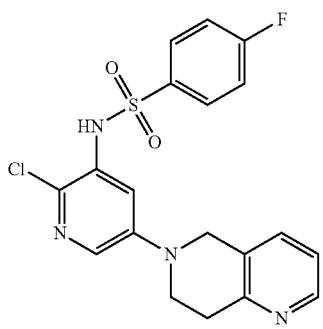 [SMILES: O=S(=O)(Nc1cc(N2CCc3ncccc3C2)cnc1Cl)c1ccc(F)cc1]

A 25-mL round bottomed flask was charged with 4,5-bis(diphenylphosphino)-9,9-dimethyl-9H-xanthene (44 mg, 76 µmol) (Strem Chemicals, Newburyport, Mass.), Pd$_2$(dba)$_3$ (23 mg, 25 µmol) (Strem Chemicals, Newburyport, Mass.), and toluene (2 mL). The flask was closed and the reaction mixture was purged with nitrogen for 5 min, and then stirred at room temperature for 10 min. To this flask, a suspension of N-(5-bromo-2-chloropyridin-3-yl)-4-fluorobenzenesulfonamide (0.18 g, 0.51 mmol), 5,6,7,8-tetrahydro-1,6-naphthyridine (0.07 g, 0.51 mmol) (J & W Pharmlab, Levittown, Pa.) (previously free based by using MP-carbonate resin), NaO(t-Bu) (0.15 g, 1.52 mmol) in t-BuOH (2 mL) was added. The reaction mixture was stirred at 100° C. for 16 h under a nitrogen atmosphere. After cooling to room temperature, the reaction mixture was diluted with EtOAc, washed with citric acid (10%), water, brine, dried over Na$_2$SO$_4$, filtered, and concentrated in vacuo. The crude material was absorbed onto a plug of silica gel and purified first by silica gel column chromatography using a Redi-Sep pre-packed silica gel column (12 g) and eluting with a gradient 1 to 4% MeOH in DCM. Second purification by reverse-phase preparative HPLC using a Phenomenex Gemini column, (10 micron, C18, 100 Å, 150×30 mm) 0.1% TFA in CH$_3$CN/H$_2$O, gradient 10% to 90% over 16 min to provide N-(2-chloro-5-(7,8-dihydro-1,6-naphthyridin-6(5H)-yl)pyridin-3-yl)-4-fluorobenzenesulfonamide as a TFA salt. Basification with satd NaHCO$_3$, extraction with EtOAc, provided the title compound as a white solid. MS (ESI pos. ion) m/z calcd for C$_{19}$H$_{16}$ClFN$_4$O$_2$S: 418.1; found 419.0. 1H NMR (400 MHz, DMSO-d$_6$) δ ppm 2.98 (t, J=5.97 Hz, 2 H) 3.64 (t, J=5.97 Hz, 2 H) 4.43 (s, 2 H) 7.18-7.30 (m, 2 H) 7.42 (t, J=8.80 Hz, 2 H) 7.63 (d, J=7.83 Hz, 1 H) 7.78 (dd, J=8.80, 5.28 Hz, 2 H) 8.03 (d, J=2.74 Hz, 1 H) 8.39 (d, J=4.50 Hz, 1 H) 10.18 (s, 1 H).

Example 136

N'-(2-Chloro-5-(4-(4-morpholinyl)-7,8-dihydro-1,6-naphthyridin-6(5H)-yl)-3-pyridinyl)-N,N-dimethylsulfamide

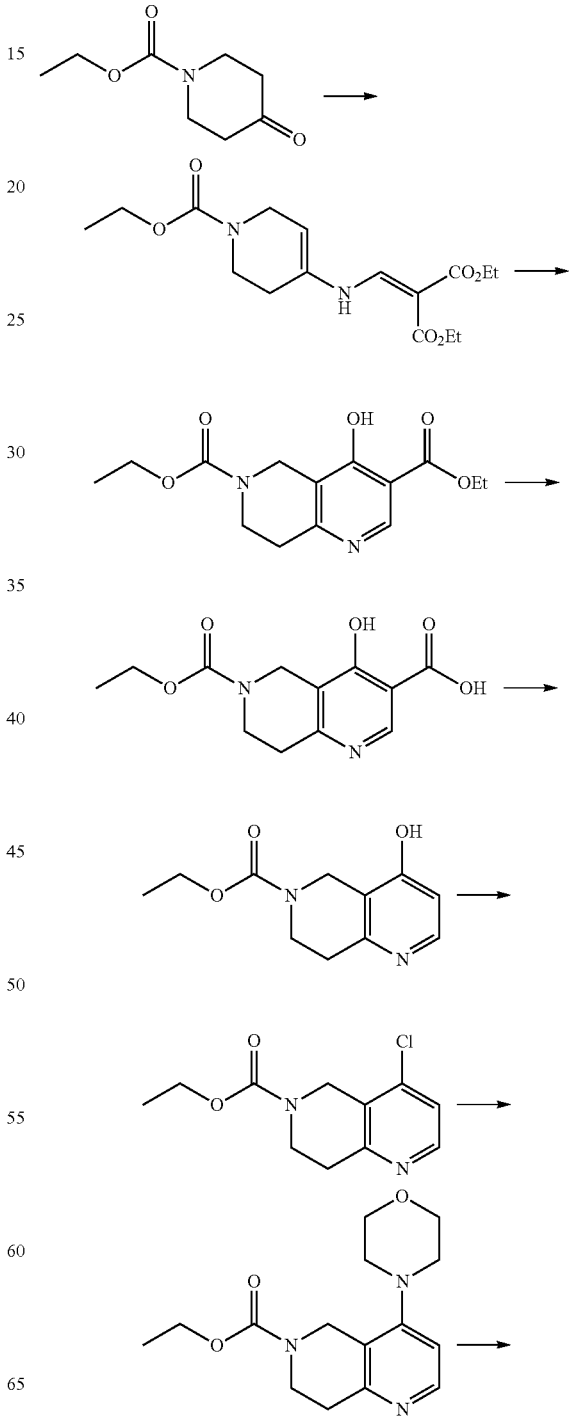

-continued

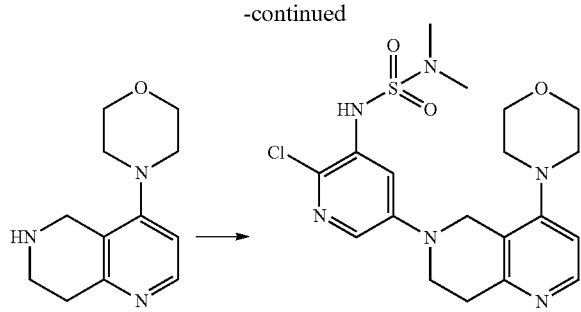

(1) 2-((1-(ethoxycarbonyl)-1,2,3,6-tetrahydropyridin-4-ylamino)methylene)malonate. A mixture of 1-carbethoxy-4-piperidone (10.0 mL, 66.3 mmol), 4-methylbenzenesulfonic acid hydrate (0.60 g, 3.15 mmol), and diethyl 2-(aminomethylene)malonate (4.65 g, 24.84 mmol) in toluene (50 mL) in a 150 mL RBF equipped with a Dean-Stark trap was heated to 135° C. under nitrogen overnight. The reaction mixture was cooled and concentrated. The oil was purified on silica gel using acetone-hexane (1:9-4:6). The product fraction was collected and concentrated to yellow oil that was contaminated by the ketone starting material. This material was used directly in the next step.

$^1$H NMR (400 MHz, CHLOROFORM-d) δ ppm 1.22-1.41 (m, 9 H) 2.35 (br. s., 2 H) 3.68 (t, J=5.58 Hz, 2 H) 4.06 (d, J=1.76 Hz, 2 H) 4.11-4.32 (m, 6 H) 5.33-5.43 (m, 1 H) 8.14 (d, J=13.89 Hz, 1 H) 10.60 (br. s., 1 H)

(2) Diethyl 4-oxo-4,5,7,8-tetrahydro-1,6-naphthyridine-3,6(1H)-dicarboxylate. A mixture of diethyl 2-((1-(ethoxycarbonyl)-1,2,3,6-tetrahydropyridin-4-ylamino)methylene)malonate (7.0 g, 20.57 mmol) in diphenyl ether (80 mL, 503 mmol) containing sodium sulfate (7.0 g, 49.3 mmol) was briefly purged with argon and then heated under nitrogen from 170 to 250° C. in a heating mantle for a total of 65 min. The cooled mixture was filtered and washed with DCM containing 10% MeOH. The combined washings was concentrated and loaded to silica gel. The diphenyl ether was eluted with DCM. The product fraction was eluted with DCM containing 1-7% MeOH. The desired product was collected and concentrated. This residue was triturated with ether-hexane (1:1) several times to yield a brown solid (2.0 g, 27% over two steps). $^1$H NMR (400 MHz, CHLOROFORM-d) δ ppm 1.30 (t, J=7.14 Hz, 4 H) 1.44 (t, J=7.14 Hz, 3 H) 2.92-3.04 (m, 2 H) 3.78 (t, J=5.38 Hz, 2 H) 4.21 (q, J=7.11 Hz, 2 H) 4.46 (q, J=7.04 Hz, 2 H) 4.60 (s, 2 H) 8.80 (s, 1 H) 11.39 (br. s., 1 H)

(3) 6-(ethoxycarbonyl)-4-oxo-1,4,5,6,7,8-hexahydro-1,6-naphthyridine-3-carboxylic acid. To a mixture of diethyl 4-oxo-4,5,7,8-tetrahydro-1,6-naphthyridine-3,6(1H)-dicarboxylate (2.0 g, 6.80 mmol) in THF (10 mL) and water (10 mL) was added NaOH (5.0 mL, 25.00 mmol). The resulting orange solution was stirred at 80° C. for 1 h. The reaction mixture was cooled to rt. HCl (5N, 6 mL) was added and the THF was evaporated. The resulting slurry was filtered and washed with water to give a yellow solid (1.0 g). LCMS (ES, pos.): calcd for $C_{12}H_{14}N_2O_5$: 266.1; found: 267.1 (M+1). $^1$H NMR (400 MHz, DMSO-d$_6$) δ ppm 1.21 (t, J=7.04 Hz, 3 H) 2.81 (t, J=5.77 Hz, 2 H) 3.65 (t, J=5.77 Hz, 2 H) 4.09 (q, J=7.17 Hz, 2 H) 4.33 (s, 2 H) 8.54 (s, 1 H) 13.11 (br. s., 2 H).

(4) Ethyl 4-oxo-4,5,7,8-tetrahydro-1,6-naphthyridine-6(1H)-carboxylate. A mixture of 6-(ethoxycarbonyl)-4-oxo-1,4,5,6,7,8-hexahydro-1,6-naphthyridine-3-carboxylic acid (1.0 g, 3.76 mmol) in diphenyl ether (40 mL) was heated to 265° C. under nitrogen for 50 min total. The hot solution was cooled to rt and was diluted with hexane (40 mL) and filtered.

The solid was washed with hexanes several time to yield an off-white powder (0.60 g). LCMS (ES, pos.): calcd for $C_{11}H_{14}N_2O_3$: 222.2; found: 223.2 (M+1). $^1$H NMR (400 MHz, CHLOROFORM-d) δ ppm 1.27 (t, J=7.04 Hz, 3 H) 2.83 (t, J=5.28 Hz, 2 H) 3.74 (t, J=5.67 Hz, 2 H) 4.17 (q, J=7.04 Hz, 2 H) 4.44 (s, 2 H) 6.30 (d, J=7.24 Hz, 1 H) 7.58 (d, J=7.04 Hz, 1 H) 12.73 (br. s., 1 H).

(5) ethyl 4-chloro-7,8-dihydro-1,6-naphthyridine-6(5H)-carboxylate. A mixture of ethyl 4-oxo-4,5,7,8-tetrahydro-1,6-naphthyridine-6(1H)-carboxylate (0.5 g, 2.250 mmol) and POCl$_3$ (5.0 mL, 53.6 mmol) in DCM (5 mL) was heated to 100° C. for 3 h. The mixture was cooled to rt. Benzene (20 mL) was added. The mixture was mixed with toluene and evaporated to dryness. The residue was partitioned between DCM and saturated aqueous NaHCO$_3$. The organic layer was dried over MgSO4. The solution was filtered and concentrated in vacuo to give a yellow oil (0.36). LCMS (ES, pos.): calcd for $C_{11}H_{13}ClN_2O_2$: 240.1; found: 241.1 (M+1). $^1$H NMR (400 MHz, CHLOROFORM-d) δ ppm 1.31 (t, J=7.14 Hz, 3 H) 3.03 (t, J=5.48 Hz, 2 H) 3.81 (t, J=5.58 Hz, 2 H) 4.22 (q, J=7.11 Hz, 2 H) 4.66 (br. s., 2 H) 7.21 (d, J=5.28 Hz, 1 H) 8.34 (d, J=5.09 Hz, 1 H).

(6) ethyl 4-morpholino-7,8-dihydro-1,6-naphthyridine-6(5H)-carboxylate. A mixture of ethyl 4-chloro-7,8-dihydro-1,6-naphthyridine-6(5H)-carboxylate (0.36 g, 1.496 mmol) and morpholine (0.50 mL, 5.74 mmol) in BuOH (5 mL) was heated to 100° C. under nitrogen. Three more batches of morpholine were added over 48 h period. The mixture was cooled to rt. EtOAc (20 mL) was added. The slurry was filtered and the white solid was washed with EtOAc. The combined filtrate was concentrated and purified on silica gel with EtOAc containing 1-5% [(2N NH3)-MeOH] to give a light yellow oil (0.40 g). LCMS (ES, pos.): calcd for $C_{11}H_{13}ClN_2O_2$: 240.1; found: 241.1 (M+1). $^1$H NMR (400 MHz, CHLOROFORM-d) δ ppm 1.29 (td, J=7.04, 3.33 Hz, 3 H) 2.92-3.00 (m, 4 H) 3.00-3.07 (m, 2 H) 3.72-3.81 (m, 2 H) 3.82-3.92 (m, 4 H) 4.18 (qd, J=7.04, 3.52 Hz, 2 H) 4.57 (br. s., 2 H) 6.77 (dd, J=5.38, 2.64 Hz, 1 H) 8.34 (t, J=4.69 Hz, 1 H).

(7) 4-(5,6,7,8-tetrahydro-1,6-naphthyridin-4-yl)morpholine. To a mixture of ethyl 4-morpholino-7,8-dihydro-1,6-naphthyridine-6(5 H)-carboxylate (400 mg, 1.373 mmol) in MeOH (2 mL) and water (10 mL) was added KOH (300 mg, 5.35 mmol). The mixture was heated to 100° C. for 9 h. The mixture was cooled and to this HCl (5N, 1.05 mL) was added slowly. The resulting mixture was loaded on an acidic silica (Varian Meg Bond Elut SCX) catridge (5 g), washed with MeOH, and then eluted with (2N) NH$_3$ in MeOH. The product was isolated as a white solid (240 mg). $^1$H NMR (400 MHz, MeOH) δ ppm 2.96 (t, J=6.16 Hz, 2 H) 2.99-3.09 (m, 4 H) 3.21 (t, J=6.26 Hz, 2 H) 3.80-3.89 (m, 4 H) 3.92 (s, 2 H) 6.90 (d, J=5.48 Hz, 1 H) 8.24 (d, J=5.67 Hz, 1 H).

(8) N'-(2-chloro-5-(4-(4-morpholinyl)-7,8-dihydro-1,6-naphthyridin-6(5H)-yl)-3-pyridinyl)-N,N-dimethylsulfamide. A mixture of xantphos (36 mg, 0.062 mmol) and Pd$_2$dba$_3$ (30 mg, 0.033 mmol) in toluene (5 mL) was degassed with nitrogen for 10 min. To this dark orange mixture was added 4-(5,6,7,8-tetrahydro-1,6-naphthyridin-4-yl)morpholine (120 mg, 0.547 mmol), N-(5-bromo-2-chloropyridin-3-yl)-N', N'-dimethylsulfone (520 mg, 0.661 mmol), and sodium tert-butoxide (360 mg, 3.75 mmol). After additional 5 min, the orange mixture was placed under nitrogen and heated to 100° C. for 20 h. The mixture was cooled to rt and treated with aqueous citric acid until pH reached 5-6. The mixture was extracted with CHCl$_3$ containing 5% $^i$PrOH (3×). The organic layer was dried over MgSO$_4$ and concentrated. The residue was purified on silica gel [5% MeOH in DCM to 5% MeOH+5% (2N NH$_3$ in MeOH) in DCM]. The product was further purified on silica gel with 0-5% (2N NH$_3$ in MeOH) in DCM. The resulting foam was triturated with hot 2:1 hexane-acetone affording the desired product as a yellow powder (160 mg). LCMS (ES, pos.): calcd for C$_{19}$H$_{25}$ClN$_6$O$_3$S:452.1; found: 453.1(M+1). $^1$H NMR (400 MHz, DMSO-d$_6$) δ ppm 2.67 (s, 6 H) 2.91-3.01 (m, 6 H) 3.71 (t, J=6.26 Hz, 2 H) 3.76-3.83 (m, 1 H) 3.77-3.84 (m, 4 H) 4.36 (s, 2 H) 6.87 (d, J=5.48 Hz, 1 H) 7.39 (d, J=2.74 Hz, 1 H) 7.96 (d, J=2.74 Hz, 1 H) 8.25 (d, J=5.48 Hz, 1 H) 9.51 (br. s., 1 H).

Example 137

N-(2-chloro-5-(5-oxo-1,6-naphthyridin-6(5H)-yl)-3-pyridinyl)-4-fluorobenzenesulfonamide

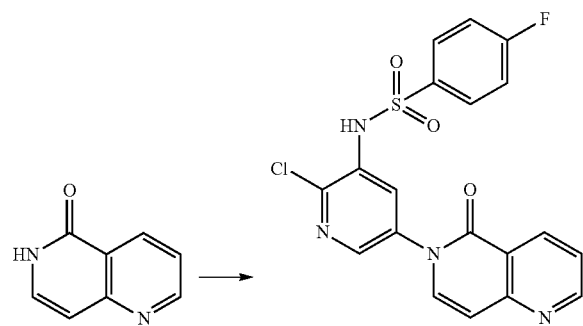 [SMILES: O=c1[nH]ccc2ncccc12 ; O=c1c2cccnc2ccn1-c1cnc(Cl)c(NS(=O)(=O)c2ccc(F)cc2)c1]

A mixture of N-(2-chloro-5-(4,4,5,5-tetramethyl-1,3,2-dioxaborolan-2-yl)pyridin-3-yl)-4-fluorobenzenesulfonamide (618 mg, 1.499 mmol), 1,6-naphthyridin-5(6H)-one (PrincetonBio, Monmouth Junction, N.J., 146 mg, 0.999 mmol), copper (II) acetate (363 mg, 1.998 mmol), DBU (0.301 mL, 1.998 mmol) in DMSO (4 mL) in a microwave tube equipped with a magnetic stirring bar was irradiated at 100° C. for 15 min in a CEM microwave (J. Comb. Chem. 2008, 10, 358-360). The mixture was diluted with water (10 mL) and acidified with HCl (5 N) to pH ~5. After agitating at rt overnight, the slurry was filtered and the solid was washed with water. The solid was washed with DCM (3×), acetone (3×), and MeOH (2×) to remove the less polar fraction. The resulting solid was dissolved in hot DMSO (6 mL) and filtered. The mother liquid was diluted with water (6 mL) and the resulting slurry was filtered and washed with water. The solid was dissolved in DMSO and purified by reverse-phase preparative HPLC (Phenomenex Luna column, 5 micron, C8(2), 100 Å, 150×21.2 mm, 0.1% TFA in CH$_3$CN/H$_2$O, gradient 5% to 90% over 10 min) The product fraction was concentrated, and neutralized with NaHCO$_3$. The slurry was filtered and washed with water to provide N-(2-chloro-5-(5-oxo-1,6-naphthyridin-6(5H)-yl)pyridin-3-yl)-4-fluorobenzenesulfonamide (37 mg, 0.086 mmol, 8.60% yield) as an off-white powder.

LCMS (ES, pos.): calcd for C$_{19}$H$_{12}$ClFN$_4$O$_3$S: 430.0; found: 430.9 (M+1)

$^1$H NMR (400 MHz, DMSO-d$_6$) δ ppm 6.84 (d, J=7.63 Hz, 1 H) 7.44 (t, J=8.80 Hz, 3 H) 7.60 (dd, J=8.12, 4.60 Hz, 1 H) 7.78 (d, J=7.63 Hz, 1 H) 7.85 (dd, J=8.71, 5.18 Hz, 2 H) 8.03 (d, J=2.35 Hz, 1 H) 8.46 (d, J=2.15 Hz, 1 H) 8.59 (d, J=8.02 Hz, 1 H) 8.99 (d, J=3.72 Hz, 1 H) 10.60 (br. s., 1 H).

The following assays can be used to determine the degree of activity of individual compounds as PI3 kinase and/or mTOR inhibitors.

Recombinant Expression of PI3K Enzymes

Full length p110 subunits of PI3K α, β and δ, N-terminally labeled with polyHis tag, can be co-expressed with p85 with Baculo virus expression vectors in sf9 insect cells. P110/p85 heterodimers can be purified by sequential Ni-NTA, Q-HP, Superdex-100 chromatography. Purified α, β and δ isozymes can be stored at –20° C. in 20 mM Tris, pH 8, 0.2M NaCl, 50% glycerol, 5 mM DTT, 2 mM Na cholate. Truncated PI3Kγ, residues 114-1102, N-terminally labeled with poly-His tag, can be expressed with Baculo virus in Hi5 insect cells. The γ isozyme can be purified by sequential Ni-NTA, Superdex-200, Q-HP chromatography. The γ isozyme can be stored frozen at –80° C. in NaH$_2$PO$_4$, pH 8, 0.2M NaCl, 1% ethylene glycol, 2 mM β-mercaptoethanol.

|  | Alpha | Beta | Delta | Gamma |
| --- | --- | --- | --- | --- |
| 50 mM Tris | pH 8 | pH 7.5 | pH 7.5 | pH 8 |
| MgCl2 | 15 mM | 10 mM | 10 mM | 15 mM |
| Na cholate | 2 mM | 1 mM | 0.5 mM | 2 mM |
| DTT | 2 mM | 1 mM | 1 mM | 2 mM |
| ATP | 1 uM | 0.5 uM | 0.5 uM | 1 uM |
| PIP2 | none | 2.5 uM | 2.5 uM | none |
| time | 1 hr | 2 hr | 2 hr | 1 hr |
| [Enzyme] | 15 nM | 40 nM | 15 nM | 50 nM |

In Vitro PI3 Kinase Enzyme Assays (PI3K Atploss)

PI3K enzyme assays (alpha, beta, delta and gamma) can be performed in 25 μL with the above final concentrations of components in white polyproplyene plates. Phosphatidyl inositol phosphoacceptor, PtdIns(4,5)P$_2$ (eg. P4508) can be obtained from Echelon Biosciences, Salt Lake City, Utah. The ATPase activity of the alpha and gamma isozymes may not be greatly stimulated by PtdIns(4,5)P$_2$ under these conditions, it can be omitted from the assay of these isozymes. Test compounds can be dissolved in DMSO and diluted with three-fold serial dilutions. The compound in DMSO (1 μL) may be added per test well, and the inhibition relative to reactions containing no compound, with and without enzyme can be determined After assay incubation at RT, the reaction can be stopped and residual ATP can be determined by addition of an equal volume of a commercial ATP bioluminescence kit (Perkin Elmer EasyLite, Perkin Elmer, Waltham, Mass.) according to the manufacturer's instructions, and detected using an Analyst GT luminometer.

Activity data for the compounds tested in the PI3K enzyme assays is provided in Table 1 under the column heading ATP Loss (PI3Kα) or ATP Loss (PI3Kβ).

Cell-Based Phospho-Akt Ser473 Assay (HCT116 Cell)

This assay determines the ability of a compound to inhibit the phosphorylation of Serine 472 in Akt using a MSD based sandwich immunoassay (Meso Scale Detection, Meso Scale Discovery (MSD), Gaithersburg, Md.). HCT 116 human colon carcinoma cell lines can be grown in McCoy's 5A growth medium (GIBCO, Carlsbad, Calif.) containing 10% FBS (GIBCO, Carlsbad, Calif.) and X1 Penicillin-streptomycin-glutamine (GIBCO, Carlsbad, Calif.). Prior to the assay, cells can be detached from the culture flask with trypsin, and re-suspended in complete media to give a final concentration of 1.6×10$^5$ cells per mL. Aliquots (100 μl) of the HCT116 cell suspension can be seeded into each well of a 96 well tissue culture plate to give a final density of 16,000 cells per well. Cells can then be incubated overnight at 37° C.

The following day the cells can be treated with serially diluted test compounds and incubated for 2 hours at 37° C. The culture media on the HCT 116 cells can be replaced with 189 µL McCoys media, supplemented with 0.1% BSA (ICN Biomedicals, Inc., Costa Mesa, Calif.). Compounds can be prepared as either 10 mM or 0.5 mM stock solutions in DMSO, and serially diluted 3 fold in a 10-point dose-response curve to give final concentrations that are 200-fold greater than the desired final test concentration. Aliquots (1 µL) of serially-diluted compounds can be transferred to 96 well tissue culture plates containing the HCT 116 cells. As a minimum response control, each plate can contain wells having a final concentration of 2.5 µM of a potent PI3K inhibitor which had previously been shown to completely inhibit Akt phosphorylation at this test concentration. As a maximum response control, wells can contain 0.5% DMSO in place of compound. The plates can be mixed at 700 rpm for 2 min to ensure even distribution of the test compound and incubated for 2 hours at 37° C. Cells can then be stimulated with insulin-like growth factor 1 (Sigma, St Louis, Mo.) at final concentration of 100 ng/ml for 15 minutes at 37° C. The media can then be removed and the cells treated with 80 µL cell-lysis buffer (MSD) containing a cocktail of protease and phosphatase inhibitors for one hour at 4° C.

25 µL Cell lysate can then be transferred to pre-blocked MSD assay plates pre-coated with a capture antibody specific for Akt and the plates can be incubated for 2 hours at room temperature. The cell lysates can then be removed and plates can then be washed four times with 200 µl per well of Tris wash buffer (500 mM Tris, PH 7.5, 1.5 M NaCl, 0.2% Tween-20). Subsequently cells can be incubated for 1 hour at room temperature with a 25 µL solution containing the detection antibody, anti-phospho Akt (Ser 473) labeled with an electrochemiluminescent compound (Meso Scale Discovery SULPHO-TAG™ label, MSD, Gaithersburg, Md.). The detection antibody can be removed and plates can then be washed four times with 200 µL per well of Tris wash buffer. An aliquot of 150 µL of diluted MSD read buffer can then be applied to each well, and the electrochemiluminescent signal can be measured using a MSD SECTOR™ plate reader (Meso Scale Discovery, Gaithersburg, Md.). This instrument measures the intensity of emitted light to determine a quantitative measure of phosphorylated Akt in each well. The dose-response data obtained with each compound can be analyzed and the $IC_{50}$ inhibition of Akt phosphorylation at Ser473 can be calculated.

Activity data for the compounds tested in the PI3K cell based Akt assay is provided in Table 1 under the column heading HCT116 Cell.

In Vitro PI3K Alphascreen® Assay

The PI3K AlphaScreen® assay (PerkinElmer, Waltham, Mass.) measures the activity of a panel of four phosphoinositide 3-kinases: PI3Kα, PI3Kβ, PI3Kγ, and PI3Kδ. Each of these enzymes phosphorylates the 3'-hydroxyl group on phosphatidylinositiol (4,5)-bisphosphate ($PIP_2$) to produce phosphatidylinositol (3,4,5)-trisphosphate ($PIP_3$). This phosphorylation activity is measured using a GST-tagged $PIP_3$ binding protein (Echelon Biosciences, Salt Lake City, Utah), an anti-GST-tagged Acceptor bead, and streptavidin-Donor bead. The interaction of biotinylated-$PIP_3$ analog ($IP_4$) and the $PIP_3$ binding protein brings both Acceptor and Donor beads together producing, upon excitation of the Donor beads at 680 nm, a singlet oxygen species leading to the luminescent AlphaScreen® signal. When $PIP_3$ is produced via phophorylation of PIP2 by a PI3K, PIP3 competes with biotinylated-$PIP_3$ analog ($IP_4$) for binding to the $PIP_3$ binding protein. In the absence of this interaction, proximity of the Donor and Acceptor beads is decreased, producing a loss of luminescent signal which is inversely proportional to PI3K activity. An inhibitor reduces activity of the enzyme, resulting in less $PIP_3$ production and greater luminescence.

The enzyme reaction buffer is made using sterile water (Baxter, Deerfield, Ill.) and 50 mM Tris HCl pH 7, 14 mM $MgCl_2$, 2 mM sodium cholate, and 100 mM NaCl. 2 mM DTT is added fresh the day of the experiment. The AlphaScreen® reaction buffer is made using sterile water and 10 mM Tris HCl pH 7.5, 150 mM NaCl, 0.10% Tween 20, and 30 mM EDTA. 1 mM DTT is added fresh the day of the experiment.

The source plates for this assay are 384-well Greiner clear polypropylene plates containing test compounds at 5mM and diluted 1:2 over 22 points. Columns 23 and 24 contain only DMSO as these are designated for positive and negative controls. Source plates are replicated into 384-well Optiplates (PerkinElmer, Waltham, Mass.), 0.5 µL/well, to make assay-ready plates.

The different PI3K isoforms are each diluted in enzyme reaction buffer to 2× working solutions. PI3Kα is diluted to 1.6 nM, PI3Kβ is diluted to 0.8 nM, PI3Kγ is diluted to 15 nM, and PI3Kδ is diluted to 1.6nM. Two different 2× substrate solutions are made in enzyme reaction buffer. In one solution, PI(4,5)P2 (Echelon Biosciences, Salt Lake City, Utah) is diluted to 10 µM and ATP is diluted to 20 µM. This solution is used in the assays testing PI3Kα and PI3Kβ. In a second solution, PI(4,5)P2 is diluted to 10 µM and ATP is diluted to 8 µM. This solution used in the assays testing PI3Kγ and PI3Kδ.

The AlphaScreen® reaction solutions are made using beads from the anti-GST AlphaScreen® kit (PerkinElmer, Waltham, Mass.). Two solutions are made in Alphascreen reaction buffer to 4× working concentrations. In one solution, biotinylated-$IP_4$ (Echelon Biosciences, Salt Lake City, Utah) is diluted to 40 nM and streptavidin-Donor Beads are diluted to 80 µg/mL. In the second solution, $PIP_3$-binding protein (Echelon Biosciences, Salt Lake City, Utah) is diluted to 40 nM and anti-GST-Acceptor Beads are diluted to 80 µg/mL. 10 µL/well of enzyme reaction buffer is added to Column 24 of the assay ready plates in place of enzyme. This is done for plates in the PI3Kα, β, and 67 assays.

Using a 384-well dispensing Multidrop (Titertek, Huntsville, Ala.), 10 µL/well of 2× enzyme (PI3Kα, β, δ) is added to Columns 1-23 of the appropriate assay ready plates (for PI3Kγ 10 µL is added to Columns 1-24). 10 µL/well of the appropriate substrate solution (the solution with 20 µM ATP for PI3Kα and β assays, and the solution with 8 µM ATP for PI3Kγ and δ assays) is then added to Columns 1-24 of the plates. Plates are then incubated at room temperature for 20 minutes.

In the dark, 10 µL/well of the Donor Bead solution is added to Columns 1-24 of the plates to quench the enzyme reaction. The plates are incubated at room temperature for 30 minutes. Still in the dark, 10 µL/well of the Acceptor Bead solution is also added to Columns 1-24 of the plates. The plates are then incubated in the dark for 1.5 hours. The plates are read on an Envision Multilabel Plate Reader (PerkinElmer, Waltham, Mass.) with a 680 nm excitation filter and a 520-620 nm emission filter.

Activity data for the compounds tested in the assay is provided in Table 2 under the column heading PI3Kα AlphaScreen®.

pAkt Alphascreen (U87 Cell)

The pAkt AlphaScreen® assay (PerkinElmer, Waltham, Mass.) determines whether there is phosphorylation of Akt at Serine 473 by recruitment of a phosphospecific antibody. This assay was performed using U87 MG cells. The U87 growth media consists of MEM (Gibco, Carlsbad, Calif.) supplemented with 10% FBS (Gibco,), 1× Non-Essential Amino Acids (Gibco,) and 1× Penicillin/Streptomycin/Glutamine (Gibco). The cells were maintained weekly using 0.05% Trypsin (Gibco) and replated in 150 mm TC-Treated Culture Dishes (Corning, Corning, N.Y.).

The first day of the assay, the adherent cells were trypsinized, media was added to the loose cells and cells were mixed to a homogenous mixture. 0.5 ml of the homogenous mixture was counted on the Beckman Coulter® Vi-CELL™ XR (Fullerton, Calif.). 50 frames of cells were counted and the number of viable cells was determined. The cells were then diluted to 0.25 million cells per ml, and centrifuged at 200 rcf for 5 minutes. The media was removed and the cells were reconstituted in fresh media for plating. The cells were plated at 20 µl per well on the PerkinElmer® FlexDrop PLUS in Low Volume 384 Well White Tissue Culture Plates (Corning) with a final cell density of 5K cells per well. The plates were incubated overnight at 37° Celsius, 5% $CO_2$.

On the second day, the compound plates were prepared, the cells were treated with compound and the pAkt reaction mix was added to the cell lysate. 384 well compound plates were prepared containing 1 µl of compound per well starting at 5 mM and diluted 1:2 across the row, resulting in a 22 well serial dilution. 39 µl of growth media was added to the compound plate in rows 1-22 using the PerkinElmer® FlexDrop PLUS resulting in a DMSO concentration of 2.5%. The cell plates and diluted compound plates were put onto the VELOCITY11™ VPREP™ 384 ST where the compound plate was mixed and 5 µl of serially diluted compound and controls was added to the cell plate. The final concentration of the compounds was 25 µM serially diluted to 11.9 pM in 0.5% DMSO. The cell plates were then incubated with compound for two hours at 37° Celsius, 5% $CO_2$. After two hours, the media in the cell plates was aspirated using the BioTek® ELx405HT plate washer (Winooski, Vt.) removing the majority of media and compound without disturbing the adherent U87 cells. The following assay reagents are components of the SureFire® Akt (Ser 473) Phosphorylation 50K Point Kit (TGR BioSciences, Adelaide, Austalia) and an IgG Detection Kit (PerkinElmer, Waltham, Mass.). 5 µl of 1× Lysis Buffer was added to each well using the PerkinElmer® FlexDrop PLUS. The plates were then incubated at room temperature on a shaker for ten minutes. The AlphaScreen® reaction was prepared under low light conditions (subdued or green light) including p-Akt (Ser 473) Reaction Buffer, Dilution Buffer, Activation Buffer, Acceptor Beads and Donor Beads at a ratio of 40:20:10:1:1 respectively. The AlphaScreen® reaction was added to the cell lysate at 6 µl per well using the PerkinElmer® FlexDrop PLUS. The plates were placed in a humid environment to reduce edge effects and incubated overnight at room temperature with restricted air flow in the dark.

On the final day of the experiment, the plates were read on the PerkinElmer® EnVision™ 2103 Multilable Reader using the standard AlphaScreen® readout. The POC is calculated and the data is analyzed to report the $IC_{50}$ IP for pAkt at Serine 473.

Activity data for the compounds tested in the PI3K cell based Akt assay is provided in Table 2 under the column heading U87

The compounds of the present invention may inhibit mTOR, PI3K or both. The assay below can be used to determine if a compound inhibits mTOR. Thus, one aspect of the present invention concerns compounds that inhibit PI3K and mTOR. In another aspect, the present invention concerns compounds that primarily inhibit mTOR. In another aspect, the present invention concerns compounds that primarily inhibit PI3K. The present invention also contemplates the use of such compounds for the treatment of the diseases and conditions, such as cancer, disclosed herein.

In Vitro mTOR Assay

The Invitrogen (Carlsbad, Calif.) mammalian target of rapamycin (mTOR) Lanthascreen assay can be used to quantitate mTOR kinase activity in an in vitro setting. Active mTOR phosphorylates eukaryotic translation initiation factor 4E binding protein 1 (4E-BP1) on residue threonine 46. This phosphorylation event can be detected with a phospho-specific terbium (Tb) labeled Ab, in turn bringing the Tb label in close proximity to the GFP tagged 4E-BP1 and allowing for time-resolved fluorescence resonance energy transfer (TR-FRET), which correlates 4E-BP1 phosphorylation levels with mTOR kinase activity.

Enzyme reaction buffer can be prepared in deionized water containing 50 mM HEPES (pH 7.5), 0.01% Polysorbate 20, 1 mM EGTA, and 10 mM $MnCl_2$.

Dilutions of the compound to be tested can be prepared in 96-well polypropylene plates (Fisher Scientific, Waltham, Mass.). One row represents a 10-point dose of compound diluted 1:3 in enzyme reaction buffer and 20% dimethyl sulfoxide (DMSO). The top concentration for all compounds is 36 µM. Wells 6 and 12 can serve as the no compound (DMSO only) and high compound controls.

An mTOR substrate solution can prepared in enzyme reaction buffer containing 1600 nM green fluorescent protein tagged eukaryotic translation initiation factor 4E binding protein 1 (GFP-4E-BP1) (Invitrogen, Carlsbad, Calif.) and 28 uM adenosine triphosphate (ATP) (Calbiochem, Gibbstown, N.J.).

mTOR enzyme (Invitrogen, Carlsbad, Calif.) can be diluted in enzyme reaction buffer to a working concentration of 100 ng/mL.

The enzyme assay can be run in 384 well low volume assay plates (Corning, Corning, N.Y.). 2.5 uL of substrate solution containing GFP-4E-BP1 and ATP can be added to appropriate wells in the assay plate followed by 2.5 µL of compound dilutions. 5 µL of appropriately diluted mTOR enzyme can be added and the reaction allowed to proceed for 1 hour at room temperature. Final reagent concentrations in the enzyme assay are 50 ng/mL mTOR, 400 nM GFP-4E-BP1, and 7 µM ATP.

The enzyme assay can be terminated upon the addition of 10 µL of 20 mM EDTA and 4 nM Tb-labeled anti-phospho-4E-BP1 [T46] antibody (Invitrogen, Carlsbad, Calif.). The assay plate can then be incubated at room temperature for 1 hour and results read on a Tecan Safire II plate reader (Tecan, Männedorf, Switzerland).

TABLE 1

| Example no. | IUPAC name | ATP Loss (PI3Kα) $IC_{50}$ µM (Avg) | ATP Loss (PI3Kβ) $IC_{50}$ µM (Avg) | HCT116 Cell $IC_{50}$ µM (Avg) |
|---|---|---|---|---|
| 1 | N-(2-chloro-5-(4-(4-morpholinyl)-6-quinolinyl)-3-pyridinyl)-4-fluorobenzenesulfonamide | 0.0055 | 0.0174 | 0.0174 |

TABLE 1-continued

| | | | | |
|---|---|---|---|---|
| 2 | N-(2-chloro-5-(4-chloro-6-quinolinyl)-3-pyridinyl)-4-fluorobenzenesulfonamide | 0.0062 | 0.0093 | 0.1090 |
| 3 | tert-butyl (2-((6-(6-chloro-5-(((4-fluorophenyl)sulfonyl)amino)-3-pyridinyl)-4-quinolinyl)oxy)ethyl)carbamate | 0.0678 | 0.6823 | 1.6602 |
| 4 | N-(2-chloro-5-(3-methoxy-6-quinolinyl)-3-pyridinyl)-4-fluorobenzenesulfonamide | 0.0162 | 0.0253 | 0.1857 |
| 5 | N-(2-chloro-5-(4-phenoxy-6-quinolinyl)-3-pyridinyl)methanesulfonamide | 0.2549 | 0.1051 | 1.1422 |
| 6 | N-(2-chloro-5-(6-quinoxalinyl)-3-pyridinyl)-4-fluorobenzenesulfonamide | 0.0081 | 0.0254 | 1.5896 |
| 7 | N-(2-chloro-5-(6-quinolinyl)-3-pyridinyl)-4-fluorobenzenesulfonamide | 0.0099 | 0.0277 | 1.3045 |
| 8 | N-(2-chloro-5-(4-methoxy-6-quinolinyl)-3-pyridinyl)-4-fluorobenzenesulfonamide | 0.0127 | 0.0147 | 0.2217 |
| 9 | N-(2-chloro-5-(4-chloro-6-quinolinyl)-3-pyridinyl)methanesulfonamide | 0.0142 | 0.0520 | 2.0588 |
| 10 | N-(2-chloro-5-(3-methoxy-6-quinolinyl)-3-pyridinyl)methanesulfonamide | 0.0424 | 0.1657 | 0.3477 |
| 11 | N-(2-chloro-5-(4-(4-morpholinyl)-6-quinolinyl)-3-pyridinyl)methanesulfonamide | 0.0458 | 0.1557 | 0.0501 |
| 12 | N-(2-chloro-5-(6-quinolinyl)-3-pyridinyl)methanesulfonamide | 0.0689 | 0.3652 | 2.6490 |
| 13 | 2-chloro-N,N-dimethyl-5-(6-quinolinyl)-3-pyridinamine | 1.1157 | 40 | ND |
| 14 | (2-chloro-5-(4-(4-morpholinyl)-6-quinolinyl)-3-pyridinyl)methanol | 1.1288 | 5.4228 | ND |
| 15 | (2-chloro-5-(4-(4-morpholinyl)-6-quinolinyl)-3-pyridinyl)methyl acetate | 1.3861 | 3.6650 | ND |
| 16 | 1-(2-chloro-5-(4-(4-morpholinyl)-6-quinolinyl)-3-pyridinyl)methanamine | 3.5346 | 26.6752 | ND |
| 17 | N-((2-chloro-5-(4-(4-morpholinyl)-6-quinolinyl)-3-pyridinyl)methyl)-2,2-dimethylpropanamide | 3.1131 | 27.4351 | ND |
| 18 | N-(2-chloro-5-(7-quinolinyl)-3-pyridinyl)-4-fluorobenzenesulfonamide | 1.9657 | 7.7049 | ND |
| 19 | 2-chloro-5-(4-(4-morpholinyl)-6-quinolinyl)-3-pyridinol | 0.0258 | 0.6439 | 0.3113 |
| 20 | N-(2-chloro-5-(3-(4-morpholinyl)-6-quinoxalinyl)-3-pyridinyl)-4-fluorobenzenesulfonamide | 0.0030 | 0.0189 | 0.0062 |
| 21 | N-(2-chloro-5-(3-(4-(1-methylethyl)-1-piperazinyl)-6-quinoxalinyl)-3-pyridinyl)-4-fluorobenzenesulfonamide | 0.0054 | 0.0096 | 0.0115 |
| 22 | N-(2-chloro-5-(3-hydroxy-6-quinolinyl)-3-pyridinyl)-4-fluorobenzenesulfonamide | 0.0114 | 0.0552 | 0.6542 |
| 23 | N-(2-chloro-5-(4-hydroxy-6-quinolinyl)-3-pyridinyl)-4-fluorobenzenesulfonamide | 0.5886 | 1.6179 | ND |
| 24 | N-(2-chloro-5-(4-(1-piperidinyl)-6-quinolinyl)-3-pyridinyl)-4-fluorobenzenesulfonamide | 0.0028 | 0.0184 | 0.1590 |
| 25 | N-(2-chloro-5-(4-(4-(1-methylethyl)-1-piperazinyl)-6-quinolinyl)-3-pyridinyl)-4-fluorobenzenesulfonamide | 0.0092 | 0.0119 | 0.0189 |
| 26 | N-(2-chloro-5-(4-(3-hydroxy-1-pyrrolidinyl)-6-quinolinyl)-3-pyridinyl)-4-fluorobenzenesulfonamide | 0.0111 | 0.0778 | 2.9647 |

TABLE 1-continued

| | | | | |
|---|---|---|---|---|
| 27 | N-(2-chloro-5-(4-(4-hydroxy-1-piperidinyl)-6-quinolinyl)-3-pyridinyl)-4-fluorobenzenesulfonamide | 0.0041 | 0.0126 | 0.1757 |
| 28 | N-(5-(4-(4-benzyl-1-piperazinyl)-6-quinolinyl)-2-chloro-3-pyridinyl)-4-fluorobenzenesulfonamide | 0.0062 | 0.0339 | ND |
| 29 | N-(2-chloro-5-(4-(4-(1-phenylethyl)-1-piperazinyl)-6-quinolinyl)-3-pyridinyl)-4-fluorobenzenesulfonamide | 0.0069 | 0.0449 | 0.3454 |
| 30 | N-(2-chloro-5-(4-(2,6-dimethyl-4-morpholinyl)-6-quinolinyl)-3-pyridinyl)-4-fluorobenzenesulfonamide | 0.0041 | 0.0302 | 0.0228 |
| 31 | N-(2-chloro-5-(4-(2-methoxyethoxy)-6-quinolinyl)-3-pyridinyl)-4-fluorobenzenesulfonamide | 0.0075 | 0.0144 | 0.0252 |
| 32 | N-(2-chloro-5-(4-(4-morpholinyl)-6-quinolinyl)-3-pyridinyl)-2-fluorobenzenesulfonamide | 0.0050 | 0.0248 | 0.0117 |
| 33 | 2-chloro-N-(2-chloro-5-(4-(4-morpholinyl)-6-quinolinyl)-3-pyridinyl)benzenesulfonamide | 0.0041 | 0.0219 | 0.0063 |
| 34 | 2,6-dichloro-N-(2-chloro-5-(4-(4-morpholinyl)-6-quinolinyl)-3-pyridinyl)benzenesulfonamide | 0.0065 | 0.0359 | 0.0376 |
| 35 | N-(2-chloro-5-(4-(2-methoxy-3-pyridinyl)-6-quinolinyl)-3-pyridinyl)-4-fluorobenzenesulfonamide | 0.0077 | 0.0212 | 0.0548 |
| 36 | N-(2-chloro-5-(4-phenyl-6-quinolinyl)-3-pyridinyl)-4-fluorobenzenesulfonamide | 0.0071 | 0.0149 | 0.0914 |
| 37 | N-(2-chloro-5-(6-cinnolinyl)-3-pyridinyl)-4-fluorobenzenesulfonamide | 0.0783 | 0.2120 | ND |
| 38 | N-(2-chloro-5-(6-isoquinolinyl)-3-pyridinyl)-4-fluorobenzenesulfonamide | 0.7399 | 40 | ND |
| 39 | N-(2-chloro-5-(5-phthalazinyl)-3-pyridinyl)-4-fluorobenzenesulfonamide | 1.8989 | 4.1211 | ND |
| 40 | N-(2-chloro-5-(6-phthalazinyl)-3-pyridinyl)-4-fluorobenzenesulfonamide | 0.8995 | 0.6976 | ND |
| 41 | N-(2-chloro-5-(1,5-naphthyridin-2-yl)-3-pyridinyl)-4-fluorobenzenesulfonamide | 0.0134 | 0.0597 | 0.6294 |
| 42 | N-(2-chloro-5-(1,5-naphthyridin-4-yl)-3-pyridinyl)-4-fluorobenzenesulfonamide | 0.0875 | 0.6197 | 1.7274 |
| 43 | N-(5-(2-amino-3-oxo-3,4-dihydro-6-quinoxalinyl)-2-chloro-3-pyridinyl)-4-fluorobenzenesulfonamide | 0.0169 | 0.0648 | 5.0374 |
| 44 | N-(2-chloro-5-(1,8-naphthyridin-3-yl)-3-pyridinyl)-4-fluorobenzenesulfonamide | 2.8438 | 5.6101 | ND |
| 45 | N-(6-(6-chloro-5-(((4-methoxyphenyl)sulfonyl)amino)-3-pyridinyl)-2-quinolinyl)acetamide | 0.0192 | 0.0597 | 0.0646 |
| 46 | N-(5-(2-amino-6-quinolinyl)-2-chloro-3-pyridinyl)-4-methoxybenzenesulfonamide | 0.1361 | 0.1799 | 0.1077 |
| 47 | N-(2-chloro-5-(6-quinolinyl)-3-pyridinyl)-4-methoxybenzenesulfonamide | 0.0417 | 0.0249 | 0.5264 |

TABLE 1-continued

| | | | | |
|---|---|---|---|---|
| 48 | N-(2-chloro-5-(2-(methylamino)-6-quinolinyl)-3-pyridinyl)-4-methoxybenzenesulfonamide | 0.0954 | 2.4907 | ND |
| 49 | N-(2-chloro-5-(4-(dimethylamino)-6-quinolinyl)-3-pyridinyl)-4-methoxybenzenesulfonamide | 0.0074 | 0.0151 | 0.2732 |
| 50 | N-(2-chloro-5-(4-(4-methoxy-1-piperidinyl)-6-quinolinyl)-3-pyridinyl)-4-methoxybenzenesulfonamide | 0.0030 | 0.0366 | 0.1072 |
| 51 | 2-chloro-N,N-dimethyl-5-(4-(4-morpholinyl)-6-quinolinyl)-3-pyridinamine | 0.1793 | 2.4625 | ND |
| 52 | 2-chloro-5-(4-chloro-6-quinolinyl)-N,N-dimethyl-3-pyridinamine | 0.4302 | 2.2401 | ND |
| 53 | 2-chloro-N,N-dimethyl-5-(4-(4-(1-phenylethyl)-1-piperazinyl)-6-quinolinyl)-3-pyridinamine | 0.2945 | 4.2210 | ND |
| 54 | N-(2-chloro-5-(3-(1-piperidinyl)-6-quinoxalinyl)-3-pyridinyl)-4-fluorobenzenesulfonamide | 0.0027 | 0.0842 | 0.1410 |
| 55 | N-(2-chloro-5-(3-((2-methoxyethyl)(methyl)amino)-6-quinoxalinyl)-3-pyridinyl)-4-fluorobenzenesulfonamide | 0.0027 | 0.0207 | 0.0640 |
| 56 | N-(5-(3-(4-acetyl-1-piperazinyl)-6-quinoxalinyl)-2-chloro-3-pyridinyl)-4-fluorobenzenesulfonamide | 0.0057 | 0.0318 | 0.0236 |
| 57 | N-(2-chloro-5-(3-((2-phenoxyethyl)amino)-6-quinoxalinyl)-3-pyridinyl)-4-fluorobenzenesulfonamide | 0.0022 | 0.0079 | 0.0451 |
| 58 | N-(2-chloro-5-(3-(4,4-difluoro-1-piperidinyl)-6-quinoxalinyl)-3-pyridinyl)-4-fluorobenzenesulfonamide | 0.0034 | 0.0824 | 0.0635 |
| 59 | tert-butyl 3-(((7-(6-chloro-5-(((4-fluorophenyl)sulfonyl)amino)-3-pyridinyl)-2-quinoxalinyl)amino)methyl)-1-piperidinecarboxylate | 0.0031 | 0.0225 | 0.1357 |
| 60 | N-(2-chloro-5-(3-((1-(4-fluorophenyl)ethyl)amino)-6-quinoxalinyl)-3-pyridinyl)-4-fluorobenzenesulfonamide | 0.0103 | 0.0436 | 0.5693 |
| 61 | N-(2-chloro-5-(3-((2-(1-piperidinyl)ethyl)amino)-6-quinoxalinyl)-3-pyridinyl)-4-fluorobenzenesulfonamide | 0.0073 | 0.0155 | 0.0515 |
| 62 | N-(5-(3-(3-azabicyclo[3.2.2]non-3-yl)-6-quinoxalinyl)-2-chloro-3-pyridinyl)-4-fluorobenzenesulfonamide | 0.0059 | 0.3429 | 0.2631 |
| 63 | N-(2-chloro-5-(3-((4-methoxybenzyl)amino)-6-quinoxalinyl)-3-pyridinyl)-4-fluorobenzenesulfonamide | 0.0056 | 0.0502 | 0.1576 |
| 64 | N-(2-chloro-5-(3-((2-phenylethyl)amino)-6-quinoxalinyl)-3-pyridinyl)-4-fluorobenzenesulfonamide | 0.0074 | 0.0597 | 0.1883 |
| 65 | N-(5-(3-(benzyl(methyl)amino)-6-quinoxalinyl)-2-chloro-3-pyridinyl)-4-fluorobenzenesulfonamide | 0.0039 | 0.0303 | 0.2792 |
| 66 | N-(2-chloro-5-(3-(3-methoxy-1-piperidinyl)-6-quinoxalinyl)-3-pyridinyl)-4-fluorobenzenesulfonamide | 0.0027 | 0.0300 | 0.0405 |

TABLE 1-continued

| | | | | |
|---|---|---|---|---|
| 67 | N-(2-chloro-5-(3-(2,6-dimethyl-4-morpholinyl)-6-quinoxalinyl)-3-pyridinyl)-4-fluorobenzenesulfonamide | 0.0029 | 0.0648 | 0.0203 |
| 68 | N-(2-chloro-5-(3-(2-(methoxymethyl)-1-pyrrolidinyl)-6-quinoxalinyl)-3-pyridinyl)-4-fluorobenzenesulfonamide | 0.0081 | 0.0358 | 0.0434 |
| 69 | N-(2-chloro-5-(3-(4-methoxy-1-piperidinyl)-6-quinoxalinyl)-3-pyridinyl)-4-fluorobenzenesulfonamide | 0.0051 | 0.0344 | 0.0526 |
| 70 | N-(2-chloro-5-(3-((cyclohexylmethyl)amino)-6-quinoxalinyl)-3-pyridinyl)-4-fluorobenzenesulfonamide | 0.0045 | 0.0532 | 0.1507 |
| 71 | N-(2-chloro-5-(3-((cyanomethyl)(methyl)amino)-6-quinoxalinyl)-3-pyridinyl)-4-fluorobenzenesulfonamide | 0.0188 | 0.0934 | 0.0893 |
| 72 | N-(2-chloro-5-(3-(1-piperazinyl)-6-quinoxalinyl)-3-pyridinyl)-4-fluorobenzenesulfonamide | 0.0049 | 0.0100 | 0.0168 |
| 73 | N-(2-chloro-5-(3-((2-methoxyethyl)amino)-6-quinoxalinyl)-3-pyridinyl)-4-fluorobenzenesulfonamide | 0.0029 | 0.0334 | 0.0595 |
| 74 | N-(2-chloro-5-(3-((3-piperidinylmethyl)amino)-6-quinoxalinyl)-3-pyridinyl)-4-fluorobenzenesulfonamide | 0.0192 | 0.0463 | 2.6292 |
| 75 | N-(2-chloro-5-(1,7-naphthyridin-6-yl)pyridin-3-yl)-4-fluorobenzenesulfonamide | ND | ND | ND |
| 76 | N-(2-chloro-5-(8-methoxy-1,7-naphthyridin-6-yl)pyridin-3-yl)-4-fluorobenzenesulfonamide | ND | ND | 0.8056 |

| Example no. | PI3Kα AlphaScreen® $K_i$ (μM) (Avg) | mTOR $IC_{50}$ (μM) (Avg) | U87 $IC_{50}$ (μM) (Avg) |
|---|---|---|---|
| 77 | 0.0184 | 0.0677 | 1.9290 |
| 78 | 0.0276 | 0.0117 | 0.1934 |
| 79 | 0.0823 | 0.3635 | 2.8350 |
| 80 | 0.0294 | 0.3894 | 0.7036 |
| 81 | 0.3682 | 2.7441 | 2.7145 |
| 82 | 0.0052 | 0.0167 | 0.3639 |
| 83 | 0.0136 | 0.0821 | 0.7577 |
| 84 | 0.0225 | 0.0487 | 0.2894 |
| 85 | 0.0158 | 0.0621 | 1.6618 |
| 86 | 0.0160 | 0.1618 | 0.6667 |
| 87 | 0.0332 | 0.2949 | 1.4183 |
| 88 | 0.1608 | 1.7709 | 6.8388 |
| 89 | 0.0025 | 0.0039 | 0.0223 |
| 90 | 0.0107 | 0.0044 | 0.0484 |
| 91 | 0.0033 | 0.0053 | 0.0750 |
| 92 | 0.0028 | 0.0283 | 0.0840 |
| 93 | 0.0008 | 0.0016 | 0.0119 |
| 94 | 0.0013 | 0.0006 | 0.0053 |
| 95 | 0.0058 | 0.1112 | ND |
| 96 | 0.0068 | 0.0110 | 0.0375 |
| 97 | 0.0086 | 0.1106 | ND |
| 98 | 0.0889 | 1.1578 | ND |
| 99 | 0.1215 | 2.3929 | ND |
| 100 | 0.0012 | 0.0400 | ND |
| 101 | 0.0027 | 0.0036 | 0.0762 |
| 102 | 0.0013 | 0.0153 | 0.0641 |
| 103 | 0.0032 | 0.0102 | 0.0556 |
| 104 | 0.0083 | 0.0058 | 0.0284 |
| 105 | 0.0015 | 0.0015 | 0.0085 |
| 106 | 0.0019 | 0.0034 | 0.0259 |
| 107 | 0.0017 | 0.0040 | 0.0198 |
| 108 | 0.0023 | 0.0079 | 0.3061 |
| 109 | 0.0032 | 0.0137 | 0.0214 |

TABLE 1-continued

| | | | |
|---|---|---|---|
| 110 | 0.0063 | 0.0051 | 0.0141 |
| 111 | 0.0030 | 0.0028 | 0.0261 |
| 112 | 0.0021 | 0.0021 | 0.0091 |
| 113 | 0.0016 | 0.0146 | 0.0444 |
| 114 | ND | 0.0063 | 0.0254 |
| 115 | ND | 0.0126 | 0.1944 |
| 116 | 0.0013 | 0.0029 | 0.0190 |
| 117 | 0.0053 | 0.0015 | 0.2547 |
| 118 | 0.0011 | 0.0012 | 0.01267 |
| 119 | 0.0047 | 0.0176 | 0.0448 |
| 120 | 0.0035 | 0.0048 | 0.0147 |
| 121 | 0.0011 | 0.0057 | 0.0310 |
| 122 | 0.0065 | 0.0182 | 0.0163 |
| 123 | 0.0054 | 0.0169 | 0.0370 |
| 124 | 0.0046 | 0.0143 | 0.0399 |
| 125 | 0.0033 | 0.0077 | 0.7230 |
| 126 | 0.0801 | 0.1342 | 0.6691 |
| 127 | 0.0273 | 0.0651 | ND |
| 128 | 0.0333 | 0.0527 | 20.4163 |
| 129 | 0.0858 | ND | ND |
| 130 | 0.0025 | 0.0012 | 0.0087 |
| 131 | 0.0032 | 0.0076 | 0.0092 |
| 132 | 0.0022 | 0.0023 | 0.0408 |
| 133 | 0.0023 | 0.0005 | 0.0094 |
| 134 | 0.0185 | 0.0042 | 0.0283 |
| 135 | 0.0638 | 0.2182 | ND |
| 136 | 0.1108 | 0.0650 | 0.2887 |
| 137 | 0.5482 | ND | 2.9827 |

ND = not determined

It is noted that if an assay is run more than once the number above represents an average of the results from each experiment.

What is claimed is:

1. A compound of Formula I

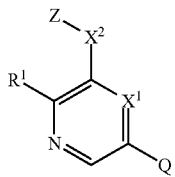

I or a pharmaceutically acceptable salt thereof,
wherein Q is a ring

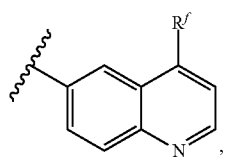

wherein the ring has 0, 1, 2, or 3 substituents on carbon atoms that are independently selected from R;

$X^1$ is N or CR;

$R^1$ is halo, —$CF_3$, —$C_{1-6}$alkyl, —$C_{2-6}$alkenyl, —$C_{2-6}$alkynyl, —$OC_{1-6}$alkyl, or —CN, wherein the —$C_{1-6}$alkyl, —$C_{2-6}$alkenyl, or —$C_{2-6}$alkynyl are substituted by 0, 1 or 2 substituents independently selected from —$C_{1-8}$alkyl, —$C_{2-6}$alkenyl, —$C_{2-6}$alkynyl, $C_{1-4}$haloalkyl, halo, —CN, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)2$R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$, —N$R^aC_{2-6}$alkylO$R^a$, or a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, wherein the ring is further substituted by 0, 1, 2 or 3 substituents independently selected from $C_{1-8}$alkyl, —$C_{2-6}$alkenyl, —$C_{2-6}$alkynyl, $C_{1-4}$haloalkyl, halo, —CN, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ or —N$R^aC_{2-6}$alkylO$R^a$;

$X^2$ is —N($R^a$)S(=O)$_2$(C$R^aR^a$)$_n$—, —N($R^a$)C(=O)(C$R^aR^a$)$_n$—, —O(C$R^aR^a$)$_n$—, —(C$R^aR^a$)$_n$O—, —(C$R^aR^a$)$_n$S(=O)$_m$—, —(C$R^aR^a$)$_n$N($R^a$)—, —N($R^a$)(C$R^aR^a$)$_n$—, —S(O)$_m$(C$R^aR^a$)$_n$—, —S(=O)$_2$N($R^a$)(C$R^aR^a$)$_n$—, —N($R^a$)C(=O)O(C$R^aR^a$)$_n$—, —N($R^a$)C(=O)N$R^a$(C$R^aR^a$)$_n$—, —N($R^a$)C(=N$R^a$)N$R^a$(C$R^aR^a$)$_n$—, —OC(=O)N$R^a$(C$R^aR^a$)$_n$—, or —N($R^a$)S(=O)$_2$N$R^a$(C$R^aR^a$)$_n$—;

Z is hydrogen, —$C_{1-6}$alkyl, —$C_{2-6}$alkenyl, —$C_{2-6}$alkynyl, —C(=O)$R^a$, or a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, wherein the —$C_{1-6}$alkyl, —$C_{2-6}$alkenyl, —$C_{2-6}$alkynyl, or ring are substituted by 0, 1 or 2 or 3 substituents independently selected from $C_{1-8}$alkyl, —$C_{2-6}$alkenyl, —$C_{2-6}$alkynyl, $C_{1-4}$haloalkyl, halo, —CN, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ or —N$R^aC_{2-6}$alkylO$R^a$;

each R is independently hydrogen, $C_{1-4}$haloalkyl, halo, —CN, nitro, —C(=O)N$R^aR^a$, —C(=O)$R^b$, —C(=O)O$R^b$, —C(=N$R^a$)N$R^aR^a$, —O$R^a$, —OC(=O)$R^b$, —OC(=O)N$R^aR^a$, —O—$C_{1-6}$alkylN($R^a$)C(=O)O$R^b$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$, —N$R^aC_{2-6}$alkylO$R^a$, —$C_{1-6}$alkyl, —$C_{2-6}$alkenyl, —$C_{2-6}$alkynyl, or a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, wherein the —$C_{1-6}$alkyl, —$C_{2-6}$alkenyl, —$C_{2-6}$alkynyl, or ring are substituted by 0, 1, 2 or 3 substituents independently selected from $C_{1-8}$alkyl, —$C_{2-6}$alkenyl, —$C_{2-6}$alkynyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$, —N$R^aC_{2-6}$alkylO$R^a$, —N($R^a$)(C$R^aR^a$)$_n$—Y, —(C$R^1R^a$)$_n$Y, or —(C$R^aR^a$)$_n$O$R^a$;

each $R^f$ is independently, $C_{1-4}$haloalkyl, halo, —CN, nitro, —C(=O)N$R^aR^a$, —C(=O)$R^b$, —C(=O)O$R^b$, —C(=N$R^a$)N$R^aR^a$, —O$R^a$, —OC(=O)$R^b$, —OC(=O)N$R^aR^a$, —O—$C_{1-6}$alkylN($R^a$)C(=O)O$R^b$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$, —N$R^aC_{2-6}$alkylO$R^a$, —$C_{1-6}$alkyl, —$C_{2-6}$alkenyl, —$C_{2-6}$alkynyl, wherein the —$C_{1-6}$alkyl, —$C_{2-6}$alkenyl, —$C_{2-6}$alkynyl are substituted by 0, 1, 2 or 3 substituents independently selected from $C_{1-8}$alkyl, —$C_{2-6}$alkenyl, —$C_{2-6}$alkynyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O) O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$, —N$R^aC_{2-6}$alkylO$R^a$, —N($R^a$)(C$R^aR^a$)$_n$—Y, —(C$R^1R^a$)$_n$Y, or —(C$R^aR^a$)$_n$O$R^a$;

Y is a saturated, partially saturated or unsaturated 5-, 6- or 7-membered monocyclic ring or 6-, 7-, 8-, 9-, or 10-membered bicylcic ring containing 0, 1, 2, 3 or 4 heteroatoms independently selected from N, O and S, which is substituted with 0, 1, or 2 substitutents independently selected from $C_{1-8}$alkyl, —$C_{2-6}$alkenyl, —$C_{2-6}$ alkynyl, $C_{1-4}$haloalkyl, halo, —CN, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ or —N$R^aC_{2-6}$alkylO$R^a$;

each $R^a$ is independently hydrogen or $R^b$;

each $R^b$ is independently phenyl, benzyl or $C_{1-6}$alkyl, wherein the phenyl, benzyl or $C_{1-6}$alkyl is substituted by 0, 1, 2 or 3 substituents independently selected from halo, $C_{1-4}$alkyl, $C_{1-3}$haloalkyl, —O$C_{1-4}$alkyl, —NH$_2$, —CN, —NH$C_{1-4}$alkyl, or —N($C_{1-4}$alkyl)$_2$;

each n is independently 0, 1, 2, or 3; and each m is independently 0, 1, or 2.

2. A compound of claim 1, or a pharmaceutically acceptable salt thereof, wherein $R^1$ is halo or —CF$_3$.

3. A compound of claim 1, or a pharmaceutically acceptable salt thereof, wherein $R^1$ is chlorine.

4. A compound of claim 1, or a pharmaceutically acceptable salt thereof, wherein $X^1$ is CH.

5. A compound of claim 1, or a pharmaceutically acceptable salt thereof, wherein $X^2$ is —NHSO$_2$— or —N(CH$_3$)SO$_2$—.

6. A compound of claim 1, or a pharmaceutically acceptable salt thereof, wherein Z is phenyl or phenyl substituted with halo or —OCH$_3$.

7. A compound of claim 1, or a pharmaceutically acceptable salt thereof, wherein $R^1$ is Cl; $X^1$ is CH; $X^2$ is —NHSO$_2$— and Z is fluorophenyl.

8. A pharmaceutical composition comprising:
A) a compound in accordance with claim 1, or a pharmaceutically acceptable salt thereof, and
B) a pharmaceutically acceptable excipient.

9. A compound, or a pharmaceutically acceptable salt thereof, selected from:

N-(2-chloro-5-(4-chloro-6-quinolinyl)-3-pyridinyl)-4-fluorobenzenesulfonamide;

tert-butyl (2-((6-(6-chloro-5-(((4- fluorophenyl)sulfonyl)amino)-3-pyridinyl)-4-quinolinyl)oxy)ethyl)carbamate;

N-(2-chloro-5-(4-phenoxy-6-quinolinyl)-3-pyridinyl)methanesulfonamide;

N-(2-chloro-5-(4-methoxy-6-quinolinyl)-3-pyridinyl)-4-fluorobenzenesulfonamide;

N-(2-chloro-5-(4-chloro-6-quinolinyl)-3-pyridinyl)methanesulfonamide;

N-(2chloro-5-(4-hydroxy-6-quinolinyl)-3-pyridinyl)-4-fluorbenzenesulfonamide;

N-(2-chloro-5-(4-(2-methoxyethoxy)-6-quinolinyl)-3-pyridinyl)-4-fluorobenzenesulfonamide;

N-(2-chloro-5-(4-(dimethylamino)-6-quinolinyl)-3-pyridinyl)-4-methoxybenzenesulfonamide;

2-chloro-5-(4-chloro-6-quinolinyl)-N,N-dimethyl-3-pyridinamine;

N-(2-chloro-5-(4-(((5-cyclopropyl-1,2,4-oxadiazol-3-yl)methyl)(ethyl)amino)-6-quinolinyl)-3-pyridinyl)methanesulfonamide;

N-(2-chloro-5-(4-((2-cyanoethyl)(ethyl)amino)-6-quinolinyl)-3-pyridinyl)methanesulfonamide;

N-(2-chloro-5-(4-((2-methoxy-2-methylpropyl)amino)-6-quinolinyl)-3-pyridinyl)methanesulfonamide;

N-(2-chloro-5-(4-((3-fluorobenzyl)(methyl)amino)-6-quinolinyl)-3-pyridinyl)methanesulfonamide;

N-(2-chloro-5-(4-((2,5-dimethoxybenzyl)amino)-6-quinolinyl)-3-pyridinyl)methanesulfonamide;

N-(2-chloro-5-(4-(4-piperidinylamino)-6-quinolinyl)-3-pyridinyl)methanesulfonamide;

N-(2-chloro-5-(4-(dimethylamino)-6-quinolinyl)-3-pyridinyl)-4-fluorobenzenesulfonamide;

N-(2-chloro-5-(4-((2-methoxyethyl)amino)-6-quinolinyl)-3-pyridinyl)-4-fluorobenzenesulfonamide;

N-(2-chloro-5-(4-((2-methoxy-1-methylethyl)amino)-6-quinolinyl)-3-pyridinyl)-4-fluorobenzenesulfonamide;

N-(2-chloro-5-(4-(tetrahydro-2H-thiopyran-4-ylmethoxy)-6-quinolinyl)-3-pyridinyl)-4-fluorobenzenesulfonamide;

N-(2-chloro-5-(4-(tetrahydro-3-thiophenyloxy)-6-quinolinyl)-3-pyridinyl)-4-fluorobenzenesulfonamide;

N-(2-chloro-5-(4-((tetrahydro-2H-thiopyran-1,1-dioxide-4-yl)methoxy)quinolin-6-yl)pyridin-3-yl)-4-fluorobenzenesulfonamide;

N-(2-chloro-5-(4-(tetrahydrothiophen-1,1-dioxide-3-yloxy)quinolin-6-yl)pyridin-3-yl)-4-fluorobenzenesulfonamide;

N'-(2-chloro-5-(4-chloro-6-quinolinyl)-3-pyridinyl)-N,N-dimethylsulfamide; or

N'-(2-chloro-5-(4((2-methoxyethyl)(methyl)amino)-6-quinolinyl)-3-pyridinyl)-N-(2-methoxyethyl)-N-methylsulfamide.

\* \* \* \* \*